(12) United States Patent
Sikorski et al.

(10) Patent No.: US 6,482,862 B1
(45) Date of Patent: Nov. 19, 2002

(54) METHOD OF USING SUBSTITUTED N-BENZYL-N-PHENYL AMINOALCOHOLS FOR INHIBITING CHOLESTERYL ESTER TRANSFER PROTEIN ACTIVITY

(75) Inventors: James A. Sikorski, Des Peres; Richard C. Durley, Chesterfield; Mark A. Massa, Ballwin; Jane L. Wang, Wildwood; Deborah A. Mischke, Defiance; Barry L. Parnas, University City; Melvin L. Rueppel, St. Louis, all of MO (US)

(73) Assignee: G.D. Searle & Co., St. Louis, MO (US)

( * ) Notice: Subject to any disclaimer, the term of this patent is extended or adjusted under 35 U.S.C. 154(b) by 0 days.

(21) Appl. No.: 09/470,046

(22) Filed: Dec. 20, 1999

(51) Int. Cl.[7] .............................................. A61K 31/133

(52) U.S. Cl. ..................... 514/654; 514/237.8; 514/351; 514/417; 514/471; 514/655; 564/374; 564/383; 564/389; 564/390

(58) Field of Search ................................. 564/389, 390, 564/374, 383; 514/655, 654

(56) References Cited

PUBLICATIONS

Pruecher et al., Bioorganic & Medicinal Chemistry Letters, vol. 2, No. 2, pp. 165–170, 1992.*
Pruecher et al., Chemical Abstracts, vol. 119:225867, 1993.*

* cited by examiner

Primary Examiner—Richard L. Raymond
(74) Attorney, Agent, or Firm—J. Timothy Keane

(57) ABSTRACT

The invention relates to use of substituted aromatic polycyclic tertiary-heteroalkylamine compounds as inhibitors of cholesteryl ester transfer protein (CETP; plasma lipid transfer protein-I) and compounds, compositions and methods for treating atherosclerosis and other coronary artery diseases. Preferred substituted aromatic polycyclic tertiary-heteroalkylamine compounds are substituted N-benzyl-N-phenyl aminoalcohols. A preferred specific N-benzyl-N-phenyl aminoalcohol is the compound:

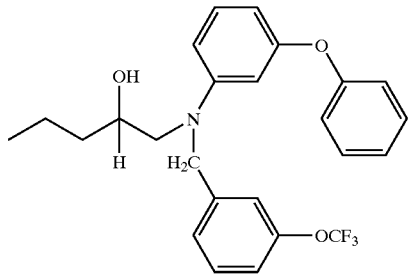

9 Claims, No Drawings

US 6,482,862 B1

METHOD OF USING SUBSTITUTED N-BENZYL-N-PHENYL AMINOALCOHOLS FOR INHIBITING CHOLESTERYL ESTER TRANSFER PROTEIN ACTIVITY

FIELD OF THE INVENTION

This invention is in the field of treating cardiovascular disease, and specifically relates to compounds, compositions and methods for treating atherosclerosis and other coronary artery disease. More particularly, the invention relates to substituted aromatic policyclic tertiay-heteroalkylamine compounds that inhibit cholesteryl ester transfer protein (CETP), also known as plasma lipid transfer protein-I.

BACKGROUND OF THE INVENTION

Numerous studies have demonstrated that a low plasma concentration of high density lipoprotein (HDL) cholesterol is a powerful risk factor for the development of atherosclerosis (Barter and Rye, *Atherosclerosis*, 121, 1–12 (1996)). HDL is one of the major classes of lipoproteins that function in the transport of lipids through the blood. The major lipids found associated with HDL include cholesterol, cholesteryl ester, triglycerides, phospholipids and fatty acids. The other classes of lipoproteins found in the blood are low density lipoprotein (LDL) and very low density lipoprotein (VLDL). Since low levels of HDL cholesterol increase the risk of atherosclerosis, methods for elevating plasma HDL cholesterol would be therapeutically beneficial for the treatment of atherosclerosis and other diseases associated with accumulation of lipid in the blood vessels. These diseases include, but are not limited to, coronary heart disease, peripheral vascular disease, and stroke.

Atherosclerosis underlies most coronary artery disease (CAD), a major cause of morbidity and mortality in modern society. High LDL cholesterol (above 180 mg/dl) and low HDL cholesterol (below 35 mg/dl) have been shown to be important contributors to the development of atherosclerosis. Other diseases, such as peripheral vascular disease, stroke, and hypercholesterolaemia are negatively affected by adverse HDL/LDL ratios. Inhibition of CETP by the subject compounds is shown to effectively modify plasma HDL/LDL ratios, and to check the progress and/or formation of these diseases.

CETP is a plasma protein that facilitates the movement of cholesteryl esters and triglycerides between the various lipoproteins in the blood (Tall, *J. Lipid Res.*, 34, 1255–74 (1993)). The movement of cholesteryl ester from HDL to LDL by CETP has the effect of lowering HDL cholesterol. It therefore follows that inhibition of CETP should lead to elevation of plasma HDL cholesterol and lowering of plasma LDL cholesterol, thereby providing a therapeutically beneficial plasma lipid profile (McCarthy, *Medicinal Res. Revs.*, 13, 139–59 (1993); Sitori, *Pharmac. Ther.*, 67,443–47 (1995)). This exact phenomenon was first demonstrated by Swenson et al., (*J. Biol. Chem.*, 264, 14318 (1989)) with the use of a monoclonal antibody that specifically inhibited CETP. In rabbits, the antibody caused an elevation of the plasma HDL cholesterol and a decrease in LDL cholesterol. Son et al. (*Biochim. Biophys. Acta* 795, 743–480 (1984)), Morton et al. (*J. Lipid Res.* 35, 836–847 (1994)) and Tollefson et al. (*Am. J. Physiol.*, 255, (Endocrinol. Metab. 18, E894–E902 (1988))) describe proteins from human plasma that inhibit CETP. U.S. Pat. No. 5,519,001, issued to Kushwaha et al., describes a 36 amino acid peptide derived from baboon apo C-1 that inhibits CETP activity. Cho et al. (*Biochim. Biophys. Acta* 1391, 133–144 (1998)) describe a peptide from hog plasma that inhibits human CETP. Bonin et al. (*J. Peptide Res.*, 51, 216–225 (1998)) disclose a decapeptide inhibitor of CETP. A depsipeptide fungal metabolite is disclosed as a CETP inhibitor by Hedge et al. in *Bioorg. Med. Chem. Lett.*, 8, 1277–80 (1998).

There have been several reports of non-peptidic compounds that act as CETP inhibitors. Barrett et al. (*J. Am. Chem. Soc.*, 188, 7863–63 (1996)) and Kuo et al. (*J. Am. Chem. Soc.*, 117, 10629–34 (1995)) describe cyclopropane-containing CETP inhibitors. Pietzonka et al. (*Bioorg. Med. Chem. Lett*, 6, 1951–54 (1996)) describe phosphonate-containing analogs of cholesteryl ester as CETP inhibitors. Coval et al. (*Bioorg. Med. Chem. Lett.*, 5, 605–610 (1995)) describe Wiedendiol-A and -B, and related sesquiterpene compounds as CETP inhibitors. Japanese Patent Application No. 10287662-A describes polycyclic, non-amine containing, polyhydroxylic natural compounds possessing CETP inhibition properties. Lee et al. (*J. Antibiotics*, 49, 693–96 (1996)) describe CETP inhibitors derived from an insect fungus. Busch et al. (*Lipids*, 25, 216–220, (1990)) describe cholesteryl acetyl bromide as a CETP inhibitor. Morton and Zilversmit (*J. Lipid Res.*, 35, 836–47 (1982)) describe that p-chloromercuriphenyl sulfonate, p-hydroxymercuribenzoate and ethyl mercurithiosalicylate inhibit CETP. Connolly et al. (*Biochem. Biophys. Res. Comm.* 223, 4247 (1996)) describe other cysteine modification reagents as CETP inhibitors. Xia et al. describe 1,3,5-triazines as CETP inhibitors (*Bioorg. Med. Chem. Lett.*, 6, 919–22 (1996)). Bisgaier et al. (*Lipids*, 29, 811–8 (1994)) describe 4-phenyl-5-tridecyl4H-1,2,4-triazole-thiol as a CETP inhibitor. Oomura et al. disclose non-peptidic tetracyclic and hexacyclic phenols as CETP inhibitors in Japanese Patent Application No. 10287662. In WO Patent Application No. 09914204, Sikorski describes 1,2,4-triazolylthiols useful as chlolesteryl ester transfer protein inhibitors.

Some substituted heteroalkylamine compounds are known. In European Patent Application No. 796846, Schmidt et al. describe 2-aryl-substituted pyridines as cholesteryl ester transfer protein inhibitors useful as cardiovascular agents. One substitutent at C3 of the pyridine ring can be an hydroxyalkyl group. In European Patent Application No. 801060, Dow and Wright describe heterocyclic derivatives substituted with an aldehyde addition product of an alkylamine to afford 1-hydroxy-1-amines. These are reported to be β3-adrenergic receptor agonists useful for treating diabetes and other disorders. In Great Britain Patent Application No. 2305665, Fisher et al. disclose 3-agonist secondary amino alcohol substituted pyridine derivatives useful for treating several disorders including cholesterol levels and artherosclerotic diseases. In European Patent Application No. 818448, Schmidt et al. describe tetrahydroquinoline derivatives as chlolesteryl ester transfer protein inhibitors. European Patent Application No. 818197, Schmek et al. describe pyridines with fused heterocycles as cholesteryl ester transfer protein inhibitors. Brandes et al. in German Patent Application No. 19627430 describe bicyclic condensed pyridine derivatives as cholesteryl ester transfer protein inhibitors. In WO Patent Application No. 09839299, Muller-Gliemann et al. describe quinoline derivatives as cholesteryl ester transfer protein inhibitors. U.S. Pat. No. 2,700,686, issued to Dickey and Towne, describes N-(2-haloalkyl-2-hydroxyethyl)amines in which the amine is further substituted with either 1 to 2 aliphatic groups or one aromatic group and one aliphatic group. U.S. Pat. No. 2,700,686 further describes a process to prepare the N-(2- haloalkyl-2-hydroxyethyl)amines by reacting halogenated-1,2-epoxyalkanes with the corresponding aliphatic amines and N-alkylanilines and their use as dye intermediates.

SUMMARY OF THE INVENTION

The present invention provides compounds that can be used to inhibit cholesteryl ester transfer protein (CETP) activity and that have the general structure:

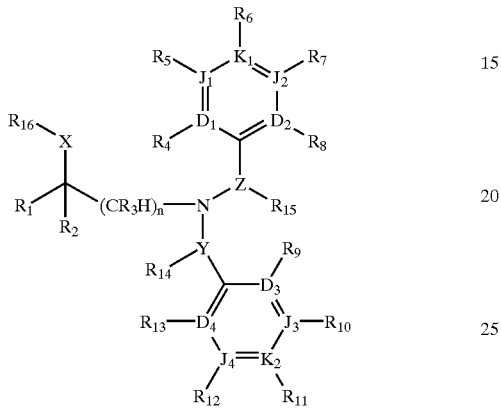

In another aspect, the present invention includes pharmaceutical compositions comprising a pharmaceutically effective amount of the compounds of this invention and a pharmaceutically acceptable carrier.

In another aspect, this invention relates to methods of using these inhibitors as therapeutic agents in humans to inhibit cholesteryl ester transfer protein (CETP) activity, thereby decreasing the concentrations of low density lipoprotein (LDL) and raising the level of high density lipoprotein (HDL), resulting in a therapeutically beneficial plasma lipid profile. The compounds and methods of this invention can also be used to treat dyslipidemia (hypoalphalipoproteinemia), hyperlipoproteinaemia (chylomicronemia and hyperapobetalipoproteinemia), peripheral vascular disease, hypercholesterolaemia, atherosclerosis, coronary artery disease and other CETP-mediated disorders. The compounds can also be used in prophylactic treatment of subjects who are at risk of developing such disorders. The compounds can be used to lower the risk of atherosclerosis. The compounds of this invention would be also useful in prevention of cerebral vascular accident (CVA) or stroke. Besides being useful for human treatment, these compounds are also useful for veterinary treatment of companion animals, exotic animals and farm animals such as primates, rabbits, pigs, horses, and the like.

DESCRIPTION OF THE INVENTION

The present invention relates to a class of compounds comprising substituted aromatic policyclic tertiary-heteroalkylamines which are beneficial in the therapeutic and prophylactic treatment of coronary artery disease as given in Formula VII-H (also referred to herein as generic substituted aromatic polycyclic tertiary 2-heteroalkyl-amines):

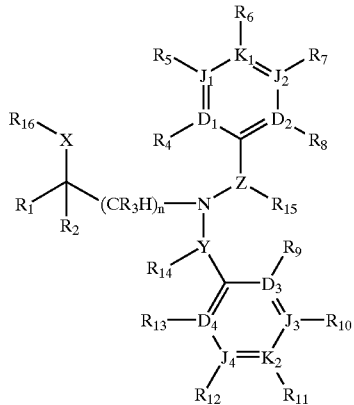

or a pharmaceutically acceptable salt thereof, wherein;

n is an integer selected from 0 through 5;

$R_1$ is selected from the group consisting of hydrido, hydroxyalkyl, alkyl, alkenyl, cycloalkyl, cycloalkenyl, cycloalkylalkyl, cycloalkenylalkyl, alkoxyalkyl, aryl, aralkyl, aryloxyalkyl, heteroaryloxyalkyl, perhaloaryl, perhaloaralkyl, perhaloaryloxyalkyl, heteroaryl, heteroaralkyl, heterocyclylalkyl, monocarboalkoxyalkyl, dicarboalkoxyalkyl, monocyanoalkyl, dicyanoalkyl, carboalkoxycyanoalkyl, carboxy, carboxyalkyl, carboalkoxy, carboxamide, carboxamidoalkyl, carboaralkoxy;

X is selected from the group consisting of O, H, F, S, S(O), NH, N(OH), N(alkyl), and N(alkoxy);

$R_{16}$ is selected from the group consisting of hydrido and a spacer selected from the group consisting of a covalent single bond and a linear spacer moiety having from 1 through 4 contiguous atoms linked to the point of bonding of an aromatic substituent selected from the group consisting of $R_4$, $R_8$, $R_9$, $R_{13}$, $R_{14}$, and $R_{15}$ to form a heterocyclyl ring having from 5 through 10 contiguous members with the proviso there is no $R_{16}$ wherein X is H or F;

$D_1$, $D_2$, $J_1$, $J_2$ and $K_1$ are independently selected from the group consisting of C, N, O, S and a covalent bond with the provisos that no more than one of $D_1$, $D_2$, $J_1$, $J_2$ and $K_1$ is a covalent bond, no more than one of $D_1$, $D_2$, $J_1$, $J_2$ and $K_1$ is O, no more than one of $D_1$, $D_2$, $J_1$, $J_2$ and $K_1$ is S, on $D_1$, $D_2$, $J_1$, $J_2$ and $K_1$ must be a covalent bond when two of $D_1$, $D_2$, $J_1$, $J_2$ and $K_1$ are O and S, and no more than four of $D_1$, $D_2$, $J_1$, $J_2$ and $K_1$ are N;

$D_3$, $D_4$, $J_3$, $J_4$ and $K_2$ are independently selected from the group consisting of C, N, O, S and a covalent bond with the provisos that no more than one of $D_3$, $D_4$, $J_3$, $J_4$ and $K_2$ is a covalent bond, no more than one of $D_3$, $D_4$, $J_3$, $J_4$ and $K_2$ is O, no more than one of $D_3$, $D_4$, $J_3$, $J_4$ and $K_2$ is S, on $D_3$, $D_4$, $J_3$, $J_4$ and $K_2$ must be a covalent bond when two of $D_3$, $D_4$, $J_3$, $J_4$ and $K_2$ are O and S, and no more than four of $D_3$, $D_4$, $J_3$, $J_4$ and $K_2$ are N;

$R_2$ is selected from the group consisting of hydrido, hydroxyalkyl, alkyl, alkenyl, alkynyl, aryl, aralkyl, aralkoxyalkyl, aryloxyalkyl, alkoxyalkyl, heteroaryloxyalkyl, heteroaralkoxyalkyl, alkenyloxyalkyl, alkylthioalkyl, aralkylthioalkyl, arylthioalkyl, cycloalkyl, cycloalkylalkyl, cycloalkylalkenyl, cycloalkenyl, cycloalkenylalkyl, perhaloaryl, perhaloaralkyl, perhaloaryloxyalkyl, heteroaryl, heteroarylalkyl, heteroarylthioalkyl, heteroaralkylthioalkyl, monocarboalkoxyalkyl, dicarboalkoxyalkyl, monocyanoalkyl, dicyanoalkyl, carboalkoxycyanoalkyl, alkylsulfinyl, alkylsulfonyl, alkylsulfinylalkyl, alkylsulfonylalkyl, haloalkylsulfinyl, haloalkylsulfonyl, arylsulfinyl, arylsulfinylalkyl, arylsulfonyl, arylsulfonylalkyl, aralkylsulfinyl, aralkylsulfonyl, cycloalkylsulfinyl, cycloalkylsulfonyl, cycloalkylsulfinylalkyl, cycloalkylsufonylalkyl, heteroarylsulfonylalkyl, heteroarylsulfinyl, heteroarylsulfonyl, heteroarylsulfinylalkyl, aralkylsulfinylalkyl, aralkylsulfonylalkyl, carboxy, carboxyalkyl, carboalkoxy, carboxamide, carboxamidoalkyl, carboaralkoxy, dialkoxyphosphono, diaralkoxyphosphono, dialkoxyphosphonoalkyl, diaralkoxyphosphonoalkyl;

$R_2$ and $R_3$ can be taken together to form a linear spacer moiety selected from the group consisting of a covalent single bond and a moiety having from 1 through 6 contiguous atoms to form a ring selected from the group consisting of a cycloalkyl having from 3 through 8 contiguous members, a cycloalkenyl having from 5 through 8 contiguous members, and a heterocyclyl having from 4 through 8 contiguous members;

$R_3$ is selected from the group consisting of hydrido, hydroxy, halo, cyano, aryloxy, hydroxyalkyl, amino, alkylamino, dialkylamino, acyl, sulfhydryl, acylamido, alkoxy, alkylthio, arylthio, alkyl, alkenyl, alkynyl, aryl, aralkyl, aryloxyalkyl, alkoxyalkyl, heteroarylthio, aralkylthio, aralkoxyalkyl, alkylsulfinylalkyl, alkylsulfonylalkyl, aroyl, heteroaroyl, aralkylthioalkyl, heteroaralkylthioalkyl, heteroaryloxyalkyl, alkenyloxyalkyl, alkylthioalkyl, arylthioalkyl, cycloalkyl, cycloalkylalkyl, cycloalkylalkenyl, cycloalkenyl, cycloalkenylalkyl, haloalkyl, haloalkenyl, halocycloalkyl, halocycloalkenyl, haloalkoxy, haloalkoxyalkyl, haloalkenyloxyalkyl, halocycloalkoxy, halocycloalkoxyalkyl, halocycloalkenyloxyalkyl, perhaloaryl, perhaloaralkyl, perhaloaryloxyalkyl, heteroaryl, heteroarylalkyl, heteroarylthioalkyl, monocarboalkoxyalkyl, dicarboalkoxyalkyl, monocyanoalkyl, dicyanoalkyl, carboalkoxycyanoalkyl, alkylsulfinyl, alkylsulfonyl, haloalkylsulfinyl, haloalkylsulfonyl, arylsulfinyl, arylsulfinylalkyl, arylsulfonyl, arylsulfonylalkyl, aralkylsulfinyl, aralkylsulfonyl, cycloalkylsulfinyl, cycloalkylsulfonyl, cycloalkylsulfinylalkyl, cycloalkylsufonylalkyl, heteroarylsulfonylalkyl, heteroarylsulfinyl, heteroarylsulfonyl, heteroarylsulfinylalkyl, aralkylsulfinylalkyl, aralkylsulfonylalkyl, carboxy, carboxyalkyl, carboalkoxy, carboxamide, carboxamidoalkyl, carboaralkoxy, dialkoxyphosphono, diaralkoxyphosphono, dialkoxyphosphonoalkyl, and diaralkoxyphosphonoalkyl;

Y is selected from a group consisting of a covalent single bond, $(C(R_{14})_2)_q$ wherein q is an integer selected from 1 through 4 and $(CH(R_{14}))_g$—W—$(CH(R_{14}))_p$ wherein g and p are integers independently selected from 0 through 2;

$R_{14}$ is independently selected from the group consisting of hydrido, hydroxy, halo, cyano, aryloxy, amino, alkylamino, dialkylamino, hydroxyalkyl, acyl, aroyl, heteroaroyl, heteroaryloxyalkyl, sulfhydryl, acylamido, alkoxy, alkylthio, arylthio, alkyl, alkenyl, alkynyl, aryl, aralkyl, aryloxyalkyl, aralkoxyalkylalkoxy, alkylsulfinylalkyl, alkylsulfonylalkyl, aralkylthioalkyl, heteroaralkoxythioalkyl, alkoxyalkyl, heteroaryloxyalkyl, alkenyloxyalkyl, alkylthioalkyl, arylthioalkyl, cycloalkyl, cycloalkylalkyl, cycloalkylalkenyl, cycloalkenyl, cycloalkenylalkyl, haloalkyl, haloalkenyl, halocycloalkyl, halocycloalkenyl, haloalkoxy, haloalkoxyalkyl, haloalkenyloxyalkyl, halocycloalkoxy, halocycloalkoxyalkyl, halocycloalkenyloxyalkyl, perhaloaryl, perhaloaralkyl, perhaloaryloxyalkyl, heteroaryl, heteroarylalkyl, heteroarylthioalkyl, heteroaralkylthioalkyl, monocarboalkoxyalkyl, dicarboalkoxyalkyl, monocyanoalkyl, dicyanoalkyl, carboalkoxycyanoalkyl, alkylsulfinyl, alkylsulfonyl, haloalkylsulfinyl, haloalkylsulfonyl, arylsulfinyl, arylsulfinylalkyl, arylsulfonyl, arylsulfonylalkyl, aralkylsulfinyl, aralkylsulfonyl, cycloalkylsulfinyl, cycloalkylsulfonyl, cycloalkylsulfinylalkyl, cycloalkylsufonylalkyl, heteroarylsulfonylalkyl, heteroarylsulfinyl, heteroarylsulfonyl, heteroarylsulfinylalkyl, aralkylsulfinylalkyl, aralkylsulfonylalkyl, carboxy, carboxyalkyl, carboalkoxy, carboxamide, carboxamidoalkyl, carboaralkoxy, dialkoxyphosphono, diaralkoxyphosphono, dialkoxyphosphonoalkyl, diaralkoxyphosphonoalkyl, a spacer selected from a moiety having a chain length of 3 to 6 atoms connected to the point of bonding selected from the group consisting of $R_9$ and $R_{13}$ to form a ring selected from the group consisting of a cycloalkenyl ring having from 5 through 8 contiguous members and a heterocyclyl ring having from 5 through 8 contiguous members, and a spacer selected from a moiety having a chain length of 2 to 5 atoms connected to the point of bonding selected from the group consisting of $R_4$ and $R_8$ to form a heterocyclyl having from 5 through 8 contiguous members with the proviso that, when Y is a covalent bond, an $R_{14}$ substituent is not attached to Y;

$R_{14}$ and $R_{15}$ are taken together to form a spacer selected from a moiety having a chain length of 2 to 5 atoms to form a heterocyclyl ring having from 5 through 8 contiguous members;

W is selected from the group consisting of O, C(O), C(S), C(O)N($R_{14}$), C(S)N($R_{14}$), ($R_{14}$)NC(O), ($R_{14}$)NC(S), S, S(O), S(O)$_2$, S(O)$_2$N($R_{14}$, ($R_{14}$)NS(O)$_2$, and N($R_{14}$) with the proviso that $R_{14}$ is selected from other than halo and cyano;

Z is independently selected from a group consisting of a covalent single bond, $(C(R_{15})_2)_q$ wherein q is an integer selected from 1 through 4, $(CH(R_{15}))_j$—W—$(CH(R_{15}))_k$ wherein j and k are integers independently selected from 0 through 2 with the proviso that, when Z is a covalent single bond, an $R_{15}$ substituent is not attached to Z;

$R_{15}$ is independently selected, when Z is $(C(R_{15})_2)_q$ wherein q is an integer selected from 1 through 4, from the group consisting of hydrido, hydroxy, halo, cyano, aryloxy, amino, alkylamino, dialkylamino, hydroxyalkyl, acyl, aroyl, heteroaroyl, heteroaryloxyalkyl, sulfhydryl, acylamido, alkoxy, alkylthio, arylthio, alkyl, alkenyl, alkynyl, aryl, aralkyl, aryloxyalkyl, aralkoxyalkyl, alkylsulfinylalkyl, alkylsulfonylalkyl, aralkylthioalkyl, heteroaralkylthioalkyl, alkoxyalkyl, heteroaryloxyalkyl, alkenyloxyalkyl, alkylthioalkyl, arylthioalkyl, cycloalkyl, cycloalkylalkyl, cycloalkylalkenyl, cycloalkenyl, cycloalkenylalkyl, haloalkyl, haloalkenyl, halocycloalkyl, halocycloalkenyl, haloalkoxy, haloalkoxyalkyl, haloalkenyloxyalkyl, halocycloalkoxy, halocycloalkoxyalkyl, halocycloalkenyloxyalkyl, perhaloaryl, perhaloaralkyl, perhaloaryloxyalkyl, heteroaryl, heteroarylalkyl, heteroarylthioalkyl, heteroaralkylthioalkyl, monocarboalkoxyalkyl, dicarboalkoxyalkyl, monocyanoalkyl, dicyanoalkyl, carboalkoxycyanoalkyl, alkylsulfinyl, alkylsulfonyl, haloalkylsulfinyl, haloalkylsulfonyl, arylsulfinyl, arylsulfinylalkyl, arylsulfonyl, arylsulfonylalkyl, aralkylsulfinyl, aralkylsulfonyl, cycloalkylsulfinyl, cycloalkylsulfonyl, cycloalkylsulfinylalkyl, cycloalkylsufonylalkyl, heteroarylsulfonylalkyl, heteroarylsulfinyl, heteroarylsulfonyl, heteroarylsulfinylalkyl, aralkylsulfinylalkyl, aralkylsulfonylalkyl, carboxy, carboxyalkyl, carboalkoxy, carboxamide, carboxamidoalkyl, carboaralkoxy, dialkoxyphosphono, diaralkoxyphosphono, dialkoxyphosphonoalkyl, diaralkoxyphosphonoalkyl, a spacer selected from a moiety having a chain length of 3 to 6 atoms connected to the point of bonding selected from the group consisting of $R_4$ and $R_8$ to form a ring selected from the group consisting of a cycloalkenyl ring having from 5 through 8 contiguous members and a heterocyclyl ring having from 5 through 8 contiguous members, and a spacer selected from a moiety having a chain length of 2 to 5 atoms connected to the point of bonding selected from the group consisting of $R_9$ and $R_{13}$ to form a heterocyclyl having from 5 through 8 contiguous members;

$R_{15}$ can be independently selected, when Z is $(CH(R_{15}))_j$—W—$(CH(R_{15}))_k$ wherein j and k are integers independently selected from 0 through 2, from the group consisting of hydrido, halo, cyano, aryloxy, carboxyl, acyl, aroyl, heteroaroyl, hydroxyalkyl, heteroaryloxyalkyl, acylamido, alkoxy, alkylthio, arylthio, alkyl, alkenyl, alkynyl, aryl, aralkyl, aryloxyalkyl, alkoxyalkyl, heteroaryloxyalkyl, aralkoxyalkyl, heteroaralkoxyalkyl, alkylsulfonylalkyl, alkylsulfinylalkyl, alkenyloxyalkyl, alkylthioalkyl, arylthioalkyl, cycloalkyl, cycloalkylalkyl, cycloalkylalkenyl, cycloalkenyl, cycloalkenylalkyl, haloalkyl, haloalkenyl, halocycloalkyl, halocycloalkenyl, haloalkoxy, haloalkoxyalkyl, haloalkenyloxyalkyl, halocycloalkoxy, halocycloalkoxyalkyl, halocycloalkenyloxyalkyl, perhaloaryl, perhaloaralkyl, perhaloaryloxyalkyl, heteroaryl, heteroarylalkyl, heteroarylthioalkyl, heteroaralkylthioalkyl, monocarboalkoxyalkyl, dicarboalkoxyalkyl, monocyanoalkyl, dicyanoalkyl, carboalkoxycyanoalkyl, alkylsulfinyl, alkylsulfonyl, haloalkylsulfinyl, haloalkylsulfonyl, arylsulfinyl, arylsulfinylalkyl, arylsulfonyl, arylsulfonylalkyl, aralkylsulfinyl, aralkylsulfonyl, cycloalkylsulfinyl, cycloalkylsulfonyl, cycloalkylsulfinylalkyl, cycloalkylsufonylalkyl, heteroarylsulfonylalkyl, heteroarylsulfinyl, heteroarylsulfonyl, heteroarylsulfinylalkyl, aralkylsulfinylalkyl, aralkylsulfonylalkyl, carboxyalkyl, carboalkoxy, carboxamide, carboxamidoalkyl, carboaralkoxy, dialkoxyphosphonoalkyl, diaralkoxyphosphonoalkyl, a spacer selected from a linear moiety having a chain length of 3 to 6 atoms connected to the point of bonding selected from the group consisting of $R_4$ and $R_8$ to form a ring selected from the group consisting of a cycloalkenyl ring having from 5 through 8 contiguous members and a heterocyclyl ring having from 5 through 8 contiguous members, and a spacer selected from a linear moiety having a chain length of 2 to 5 atoms connected to the point of bonding selected from the group consisting of $R_9$ and $R_{13}$ to form a heterocyclyl ring having from 5 through 8 contiguous members;

$R_4$, $R_5$, $R_6$, $R_7$, $R_8$, $R_9$, $R_{10}$, $R_{11}$, $R_{12}$, and $R_{13}$ are independently selected from the group consisting of perhaloaryloxy, alkanoylalkyl, alkanoylalkoxy, alkanoyloxy, N-aryl-N-alkylamino, heterocyclylalkoxy, heterocyclylthio, hydroxyalkoxy, carboxamidoalkoxy, alkoxycarbonylalkoxy, alkoxycarbonylalkenyloxy, aralkanoylalkoxy, aralkenoyl, N-alkylcarboxamido, N-haloalkylcarboxamido, N-cycloalkylcarboxamido, N-arylcarboxamidoalkoxy, cycloalkylcarbonyl, cyanoalkoxy, heterocyclylcarbonyl, hydrido, carboxy, heteroaralkylthio, heteroaralkoxy, cycloalkylamino, acylalkyl, acylalkoxy, aroylalkoxy, heterocyclyloxy, aralkylaryl, aralkyl, aralkenyl, aralkynyl, heterocyclyl, perhaloaralkyl, aralkylsulfonyl, aralkylsulfonylalkyl, aralkylsulfinyl, aralkylsulfinylalkyl, halocycloalkyl, halocycloalkenyl, cycloalkylsulfinyl, cycloalkylsulfinylalkyl, cycloalkylsulfonyl, cycloalkylsulfonylalkyl, heteroarylamino, N-heteroarylamino-N-alkylamino, heteroarylaminoalkyl, haloalkylthio, alkanoyloxy, alkoxy, alkoxyalkyl, haloalkoxylalkyl, heteroaralkoxy, cycloalkoxy, cycloalkenyloxy, cycloalkoxyalkyl, cycloalkylalkoxy, cycloalkenyloxyalkyl, cycloalkylenedioxy, halocycloalkoxy, halocycloalkoxyalkyl, halocycloalkenyloxy, halocycloalkenyloxyalkyl, hydroxy, amino, thio, nitro, lower alkylamino, alkylthio, alkylthioalkyl, arylamino, aralkylamino, arylthio, arylthioalkyl, heteroaralkoxyalkyl, alkylsulfinyl, alkylsulfinylalkyl, arylsulfinylalkyl, arylsulfonylalkyl, heteroarylsulfinylalkyl, heteroarylsulfonylalkyl, alkylsulfonyl, alkylsulfonylalkyl, haloalkylsulfinylalkyl, haloalkylsulfonylalkyl, alkylsulfonamido, alkylaminosulfonyl, amidosulfonyl, monoalkyl amidosulfonyl, dialkyl amidosulfonyl, monoarylamidosulfonyl, arylsulfonamido, diarylamidosulfonyl, monoalkyl monoaryl amidosulfonyl, arylsulfinyl, arylsulfonyl, heteroarylthio, heteroarylsulfinyl, heteroarylsulfonyl, heterocyclylsulfonyl, heterocyclylthio, alkanoyl, alkenoyl, aroyl, heteroaroyl, aralkanoyl, heteroaralkanoyl, haloalkanoyl, alkyl, alkenyl, alkynyl, alkenyloxy, alkenyloxyalky, alkylenedioxy, haloalkylenedioxy, cycloalkyl, cycloalkylalkanoyl, cycloalkenyl, lower cycloalkylalkyl, lower cycloalkenylalkyl, halo, haloalkyl, haloalkenyl, haloalkoxy, hydroxyhaloalkyl, hydroxyaralkyl, hydroxyalkyl, hydoxyheteroaralkyl, haloalkoxyalkyl, aryl, heteroaralkynyl, aryloxy, aralkoxy, aryloxyalkyl, saturated heterocyclyl, partially saturated heterocyclyl, heteroaryl, heteroaryloxy, heteroaryloxyalkyl, arylalkenyl, heteroarylalkenyl, carboxyalkyl, carboalkoxy, alkoxycarboxamido, alkylamidocarbonylamido, arylamidocarbonylamido, carboalkoxyalkyl, carboalkoxyalkenyl, carboaralkoxy, carboxamido, carboxamidoalkyl, cyano, carbohaloalkoxy, phosphono, phosphonoalkyl, diaralkoxyphosphono, and diaralkoxyphosphonoalkyl with the provisos that $R_5$ and $R_{10}$ are independently selected from other than hydrido, and $R_4$, $R_5$, $R_6$, $R_7$, $R_8$, $R_9$, $R_{10}$, $R_{11}$, $R_{12}$, and $R_{13}$ are each independently selected to maintain the tetravalent nature of carbon, trivalent nature of nitrogen, the divalent nature of sulfur, and the divalent nature of oxygen;

$R_4$ and $R_5$, $R_5$ and $R_6$, $R_6$ and $R_7$, $R_7$ and $R_8$, $R_9$ and $R_{10}$, $R_{10}$ and $R_{11}$, $R_{11}$ and $R_{12}$, and $R_{12}$ and $R_{13}$ can be independently selected to form spacer pairs wherein a spacer pair is taken together to form a linear moiety having from 3 through 6 contiguous atoms connecting the points of bonding of said spacer pair members to form a ring selected from the group consisting of a cycloalkenyl ring having 5 through 8 contiguous members, a partially saturated heterocyclyl ring having 5 through 8 contiguous members, a heteroaryl ring having 5 through 6 contiguous members, and an aryl with the provisos that no more than one of the group consisting of spacer pairs $R_4$ and $R_5$, $R_5$ and $R_6$, $R_6$ and $R_7$, and $R_7$ and $R_8$, is used at the same time and that no more than one of the group consisting of spacer pairs $R_9$ and $R_{10}$, $R_{10}$ and $R_{11}$, $R_{11}$ and $R_{12}$, and $R_{12}$ and $R_{13}$ is used at the same time;

$R_4$ and $R_9$, $R_4$ and $R_{13}$, $R_8$ and $R_9$, and $R_8$ and $R_{13}$ can be independently selected to form a spacer pair wherein said spacer pair is taken together to form a linear moiety wherein said linear moiety forms a ring selected from the group consisting of a partially saturated heterocyclyl ring having from 5 through 8 contiguous members and a heteroaryl ring having from 5 through 6 contiguous members with the proviso that no more than one of the group consisting of spacer pairs $R_4$ and $R_9$, $R_4$ and $R_{13}$, $R_8$ and $R_9$, and $R_8$ and $R_{13}$ is used at the same time.

In another embodiment of compounds of Formula VII-H, $D_1$, $D_2$, $J_1$, $J_2$ and $K_1$ are each carbon with the proviso that at least one of $D_3$, $D_4$, $J_3$, $J_4$ and $K_2$ is selected from the group consisting of O, S, and N, wherein $D_3$, $D_4$, $J_3$, $J_4$ and $K_2$ are independently selected from the group consisting of C, N, O, S and covalent bond with the provisos that no more than one of $D_3$, $D_4$, $J_3$, $J_4$ and $K_2$ is a covalent bond, no more than one of $D_3$, $D_4$, $J_3$, $J_4$ and $K_2$ is O, no more than one of $D_3$, $D_4$, $J_3$, $J_4$ and $K_2$ is S, one of $D_3$, $D_4$, $J_3$, $J_4$ and $K_2$ must be a covalent bond when two of $D_3$, $D_4$, $J_3$, $J_4$ and $K_2$ are O and S, and no more than four of $D_3$, $D_4$, $J_3$, $J_4$ and $K_2$ are N;

$D_1$, $D_2$, $J_1$, $J_2$ and $K_1$ can be selected from the group consisting of C, O, S, N and covalent bond with the provisos that $D_3$, $D_4$, $J_3$, $J_4$ and $K_2$ are each carbon and at least one of $D_1$, $D_2$, $J_1$, $J_2$ and $K_1$ is selected from the group consisting of O, S, and N wherein, when $D_1$, $D_2$, $J_1$, $J_2$ and $K_1$ are selected from the group consisting of C, O, S, covalent bond, and N, no more than one of $D_1$, $D_2$, $J_1$, $J_2$ and $K_1$ is a covalent bond, no more than one of $D_1$, $D_2$, $J_1$, $J_2$ and $K_1$ is O, no more than one of $D_1$, $D_2$, $J^3$, $J_2$ and $K_1$ is S, on $D_1$, $D_2$, $J_1$, $J_2$ and $K_1$ must be a covalent bond when two of $D_1$, $D_2$, $J_1$, $J_2$ and $K_1$ are O and S, and no more than four of $D_1$, $D_2$, $J_1$, $J_2$ and $K_1$ are N;

n is an integer selected from 0 through 4;

X is selected from the group consisting of O, H, F, S, S(O), NH, N(OH), N(alkyl), and N(alkoxy);

$R_{16}$ is selected from the group consisting of hydrido and a spacer selected from the group consisting of a covalent single bond and a linear spacer moiety having a chain length of 1 to 4 atoms linked to the point of bonding of any aromatic substituent selected from the group consisting of $R_4$, $R_8$, $R_9$, and $R_{13}$ to form a heterocyclyl ring having from 5 through 10 contiguous members;

$R_1$ is selected from the group consisting of hydrido, hydroxyalkyl, alkyl, alkenyl, cycloalkyl, cycloalkenyl, cycloalkylalkyl, cycloalkenylalkyl, alkoxyalkyl, aryl, aralkyl, aryloxyalkyl, heteroaryloxyalkyl, heteroaralkoxyalkyl, perhaloaryl, perhaloaralkyl, perhaloaryloxyalkyl, heteroaryl, heteroaralkyl, heterocyclylalkyl, monocarboalkoxyalkyl, monocyanoalkyl, carboxy, carboxyalkyl, carboalkoxy, carboxamido, carboxamidoalkyl, and carboaralkoxy;

$R_2$ is selected from the group consisting of hydrido, hydroxyalkyl, alkyl, alkenyl, alkynyl, aryl, aralkyl, aralkoxyalkyl, aryloxyalkyl, alkoxyalkyl, heteroaryloxyalkyl, alkenyloxyalkyl, cycloalkyl, cycloalkylalkyl, cycloalkylalkenyl, cycloalkenyl, cycloalkenylalkyl, perhaloaryl, perhaloaralkyl, perhaloaryloxyalkyl, heteroaryl, heteroaralkyl, monocarboalkoxyalkyl, monocyanoalkyl, carboxy, carboxyalkyl, carboalkoxy, carboxamide, carboxamidoalkyl, and carboaralkoxy;

$R_3$ is selected from the group consisting of hydrido, hydroxy, cyano, aryl, aralkyl, acyl, alkoxy, alkyl, alkenyl, alkoxyalkyl, heteroaryl, heteroaralkyl, alkenyloxyalkyl, haloalkyl, haloalkenyl, haloalkoxy, haloalkoxyalkyl, haloalkenyloxyalkyl, cycloalkyl, cycloalkenyl, cycloalkylalkyl, and cycloalkenylalkyl;

Y is selected from the group consisting of covalent single bond and $(C(R_{14})_2)_q$ wherein q is an integer selected from 1 through 2;

$R_{14}$ is selected from the group consisting of hydrido, hydroxy, cyano, hydroxyalkyl, acyl, alkoxy, alkyl, alkenyl, alkynyl, alkoxyalkyl, haloalkyl, haloalkenyl, haloalkoxy, haloalkoxyalkyl, haloalkenyloxyalkyl, monocarboalkoxyalkyl, monocyanoalkyl, dicyanoalkyl, carboalkoxycyanoalkyl, carboalkoxy, carboxamide, carboxamidoalkyl;

Z is selected from the group consisting of covalent single bond, $(C(R_{15})_2)_q$ wherein q is an integer selected from 1 through 2, and $(CH(R_{15}))_j$—W—$(CH(R_{15}))_k$ wherein j and k are integers independently selected from 0 through 2;

W is selected from the group consisting of O, C(O), C(S), C(O)N($R_{14}$), C(S)N($R_{14}$), ($R_{14}$)NC(O), ($R_{14}$)NC(S), S, S(O), S(O)$_2$, S(O)$_2$N($R_{14}$), ($R_{14}$)NS(O)$_2$, and N($R_{14}$) with the proviso that $R_{14}$ is other than cyano;

$R_{15}$ is selected from the group consisting of hydrido, cyano, hydroxyalkyl, acyl, alkoxy, alkyl, alkenyl, alkynyl, alkoxyalkyl, haloalkyl, haloalkenyl, haloalkoxy, haloalkoxyalkyl, haloalkenyloxyalkyl, monocarboalkoxyalkyl, monocyanoalkyl, dicyanoalkyl, carboalkoxycyanoalkyl, carboalkoxy, carboxamide, and carboxamidoalkyl;

$R_4$, $R_8$, $R_9$, and $R_{13}$ are independently selected from the group consisting of hydrido, halo, haloalkyl, and alkyl;

$R_5$, $R_6$, $R_7$, $R_{10}$, $R_{11}$, and $R_{12}$ are independently selected from the group consisting of perhaloaryloxy, alkanoylalkyl, alkanoylalkoxy, alkanoyloxy, N-aryl-N-alkylamino, heterocyclylalkoxy, heterocyclylthio, hydroxyalkoxy, carboxamidoalkoxy, alkoxycarbonylalkoxy, alkoxycarbonylalkenyloxy, aralkanoylalkoxy, aralkenoyl, N-alkylcarboxamido, N-haloalkylcarboxamido, N-cycloalkylcarboxamido, N-arylcarboxamidoalkoxy, cycloalkylcarbonyl, cyanoalkoxy, heterocyclylcarbonyl, hydrido, carboxy, heteroaralkylthio, heteroaralkoxy, cycloalkylamino, acylalkyl, acylalkoxy, aroylalkoxy, heterocyclyloxy, aralkylaryl, aralkyl, aralkenyl, aralkynyl, heterocyclyl, perhaloaralkyl, aralkylsulfonyl, aralkylsulfonylalkyl, aralkylsulfinyl, aralkylsulfinylalkyl, halocycloalkyl, halocycloalkenyl, cycloalkylsulfinyl, cycloalkylsulfinylalkyl, cycloalkylsulfonyl, cycloalkylsulfonylalkyl, heteroarylamino, N-heteroarylamino-N-alkylamino, heteroarylaminoalkyl, haloalkylthio, alkanoyloxy, alkoxy, alkoxyalkyl, haloalkoxylalkyl, heteroaralkoxy, cycloalkoxy, cycloalkenyloxy, cycloalkoxyalkyl, cycloalkylalkoxy, cycloalkenyloxyalkyl, cycloalkylenedioxy, halocycloalkoxy, halocycloalkoxyalkyl, halocycloalkenyloxy, halocycloalkenyloxyalkyl, hydroxy, amino, thio, nitro, lower alkylamino, alkylthio, alkylthioalkyl, arylamino, aralkylamino, arylthio, arylthioalkyl, heteroaralkoxyalkyl, alkylsulfinyl, alkylsulfinylalkyl, arylsulfinylalkyl, arylsulfonylalkyl, heteroarylsulfinylalkyl, heteroarylsulfonylalkyl, alkylsulfonyl, alkylsulfonylalkyl, haloalkylsulfinylalkyl, haloalkylsulfonylalkyl, alkylsulfonamido, alkylaminosulfonyl, amidosulfonyl, monoalkyl amidosulfonyl, dialkyl amidosulfonyl, monoarylamidosulfonyl, arylsulfonamido, diarylamidosulfonyl, monoalkyl monoaryl amidosulfonyl, arylsulfinyl, arylsulfonyl, heteroarylthio, heteroarylsulfinyl, heteroarylsulfonyl, heterocyclylsulfonyl, heterocyclylthio, alkanoyl, alkenoyl, aroyl, heteroaroyl, aralkanoyl, heteroaralkanoyl, haloalkanoyl, alkyl, alkenyl, alkynyl, alkenyloxy, alkenyloxyalky, alkylenedioxy, haloalkylenedioxy, cycloalkyl, cycloalkylalkanoyl, cycloalkenyl, lower cycloalkylalkyl, lower cycloalkenylalkyl, halo, haloalkyl, haloalkenyl, haloalkoxy, hydroxyhaloalkyl, hydroxyaralkyl, hydroxyalkyl, hydoxyheteroaralkyl, haloalkoxyalkyl, aryl, heteroaralkynyl, aryloxy, aralkoxy, aryloxyalkyl, saturated heterocyclyl, partially saturated heterocyclyl, heteroaryl, heteroaryloxy, heteroaryloxyalkyl, heteroaralkyl, arylalkenyl, heteroarylalkenyl, carboxyalkyl, carboalkoxy, alkoxycarboxamido, alkylamidocarbonylamido, arylamidocarbonylamido, carboalkoxyalkyl, carboalkoxyalkenyl, carboaralkoxy, carboxamido, carboxamidoalkyl, cyano, carbohaloalkoxy, phosphono, phosphonoalkyl, diaralkoxyphosphono, and diaralkoxyphosphonoalkyl with the proviso that $R_5$ and $R_{10}$ are independently selected from other than hydrido;

$R_4$ and $R_5$, $R_5$ and $R_6$, $R_6$ and $R_7$, $R_7$ and $R_8$, $R_9$ and $R_{10}$, $R_{10}$ and $R_{11}$, $R_{11}$ and $R_{12}$, and $R_{12}$ and $R_{13}$ are independently selected to form spacer pairs wherein a spacer pair is taken together to form a linear moiety having from 3 through 6 contiguous atoms connecting the points of bonding of said spacer pair members to form a ring selected from the group consisting of a cycloalkenyl ring having 5 through 8 contiguous members, a partially saturated heterocyclyl ring having 5 through 8 contiguous members, a heteroaryl ring having 5 through 6 contiguous members, and an aryl with the provisos that no more than one of the group consisting of spacer pairs $R_4$ and $R_5$, $R_5$ and $R_6$, $R_6$ and $R_7$, and $R_7$ and $R_8$, is used at the same time and that no more than one of the group consisting of spacer pairs $R_9$ and $R_{10}$, $R_{10}$ and $R_{11}$, $R_{11}$ and $R_{12}$, and $R_{12}$ and $R_{13}$ is used at the same time.

In a preferred embodiment of compounds of Formula VII-H, $D_1$, $D_2$, $J_1$, $J_2$ and $K_1$ are each carbon with the proviso that at least one of $D_3$, $D_4$, $J_3$, $J_4$ and $K_2$ is selected from the group consisting of O, S, and N, wherein $D_3$, $D_4$, $J_3$, $J_4$ and $K_2$ are independently selected from the group consisting of C, N, O, S and covalent bond with the provisos that no more than one of $D_3$, $D_4$, $J_3$, $J_4$ and $K_2$ is a covalent bond, no more than one of $D_3$, $D_4$, $J_3$, $J_4$ and $K_2$ is O, no more than one of $D_3$, $D_4$, $J_3$, $J_4$ and $K_2$ is S, one of $D_3$, $D_4$, $J_3$, $J_4$ and $K_2$ must be a covalent bond when two of $D_3$, $D_4$, $J_3$, $J_4$ and $K_2$ are O and S, and no more than four of $D_3$, $D_4$, $J_3$, $J_4$ and $K_2$ are N;

$D_1$, $D_2$, $J_1$, $J_2$ and $K_1$ are selected from the group consisting of C, O, S, N and covalent bond with the provisos that $D_3$, $D_4$, $J_3$, $J_4$ and $K_2$ are each carbon and at least one of $D_1$, $D_2$, $J_1$, $J_2$ and $K_1$ is selected from the group consisting of O, S, and N wherein, when $D_1$, $D_2$, $J_1$, $J_2$ and $K_1$ are selected from the group consisting of C, O, S, covalent bond, and N, no more than one of $D_1$, $D_2$, $J_1$, $J_2$ and $K_1$ is a covalent bond, no more than one of $D_1$, $D_2$, $J_1$, $J_2$ and $K_1$ is O, no more than one of $D_1$, $D_2$, $J_1$, $J_2$ and $K_1$ is S, one of $D_1$, $D_2$, $J_1$, $J_2$ and $K_1$ must be a covalent bond when two of $D_1$, $D_2$, $J_1$, $J_2$ and $K_1$ are O and S, and no more than four of $D_1$, $D_2$, $J_1$, $J_2$ and $K_1$ are N;

n is an integer selected from 1 and 2;

X is oxy;

$R_{16}$ is hydrido;

$R_1$ is selected from the group consisting of hydrido, alkyl, alkenyl, cycloalkyl, cycloalkenyl, cycloalkylalkyl, cycloalkenylalkyl, alkoxyalkyl, aryl, aralkyl, perhaloaryl, perhaloaralkyl, heteroaryl, heteroaralkyl, and carboalkoxy;

$R_2$ is selected from the group consisting of hydrido, alkyl, alkenyl, hydroxyalkyl, aryl, aralkyl, alkoxyalkyl, heteroaryloxyalkyl, heteroaralkoxyalkyl, cycloalkyl, cycloalkylalkyl, cycloalkenyl, cycloalkenylalkyl, perhaloaryl, perhaloaralkyl, heteroaryl, carboalkoxy, and heteroaralkyl;

$R_3$ is selected from the group consisting of hydrido, hydroxy, cyano, aryl, aralkyl, acyl, alkoxy, alkyl, alkenyl, alkoxyalkyl, heteroaryl, heteroaralkyl, alkenyloxyalkyl, haloalkyl, haloalkenyl, haloalkoxy, haloalkoxyalkyl, haloalkenyloxyalkyl, cycloalkyl, cycloalkenyl, cycloalkylalkyl, and cycloalkenylalkyl;

Y is selected from the group consisting of a covalent single bond and alkylene;

Z is selected from the group consisting of a covalent single bond and alkylene;

$R_{14}$ is selected from the group consisting of hydrido, alkyl, and haloalkyl;

$R_{15}$ is selected from the group consisting of hydrido, alkyl, and haloalkyl;

$R_4$, $R_8$, $R_9$, and $R_{13}$ are independently selected from the group consisting of hydrido and halo;

$R_5$, $R_6$, $R_7$, $R_{10}$, $R_{11}$, and $R_{12}$ are independently selected from the group consisting of perhaloaryloxy, N-aryl-N-alkylamino, heterocyclylalkoxy, heterocyclylthio, hydroxyalkoxy, carboxamidoalkoxy, alkoxycarbonylalkoxy, alkoxycarbonylalkenyloxy, aralkanoylalkoxy, aralkenoyl, N-arylcarboxamidoalkoxy, cycloalkylcarbonyl, cyanoalkoxy, heterocyclylcarbonyl, hydrido, alkyl, halo, haloalkyl, haloalkoxy, aryl, alkylthio, arylamino, arylthio, aroyl, arylsulfonyl, aryloxy, aralkoxy, heteroaryloxy, alkoxy, aralkyl, cycloalkoxy, cycloalkylalkoxy, cycloalkylalkanoyl, heteroaryl, cycloalkyl, haloalkylthio, hydroxyhaloalkyl, heteroaralkoxy, heterocyclyloxy, aralkylaryl, heteroaryloxyalkyl, heteroarylthio, and heteroarylsulfonyl with the proviso that $R_5$ and $R_{10}$ are independently selected from other than hydrido.

In a more preferred embodiment of compounds of Formula VII-H, $D_1$, $D_2$, $J_1$, $J_2$ and $K_1$ are each carbon;

$D_3$, $D_4$, $J_3$, $J_4$ and $K_2$ are independently selected from the group consisting of C, N, O, S and covalent bond to form a heteroaryl ring selected from the group consisting of 2-thienyl, 3-thienyl, 2-furyl, 3-furyl, 2-pyrrolyl, 3-pyrrolyl, 2-imidazolyl, 4-imidazolyl, 3-pyrazolyl, 4-pyrazolyl, 2-thiazolyl, 3-isoxazolyl, 5-isoxazolyl, 2-pyridyl, 3-pyridyl, 4-pyridyl, 2-pyrazinyl, 2-pyrimidinyl, 4-pyrimidinyl, 5-pyrimidinyl, 3-pyridazinyl, 4-pyridazinyl, and 1,3,5-triazin-2-yl, wherein a ring carbon atom adjacent to the carbon atom at the point of attachment may be optionally substituted with $R_9$ or $R_{13}$, a ring carbon atom adjacent to the $R_9$ position and two atoms from the point of attachment may be substituted with $R_{10}$, a ring carbon atom adjacent to the $R_{13}$ position and two atoms from the point of attachment may be substituted with $R_{12}$, and a ring carbon atom three atoms from the point of attachment and adjacent to the $R_{10}$ and $R_{12}$ positions may be substituted with $R_{11}$;

n is the integer 1;

X is oxy;

$R_{16}$ is hydrido;

$R_1$ is selected from the group consisting of hydrido, C2–C4 alkyl, C2–C4 alkenyl, cycloalkyl, cycloalkylalkyl, aryl, aralkyl, perhaloaryl, perhaloaralkyl, heteroaryl, and heteroaralkyl;

$R_2$ is selected from the group consisting of hydrido, C1–C2 alkyl, C2 alkenyl, hydroxyalkyl, aryl, aralkyl, perhaloaryl, perhaloaralkyl, heteroaryl, and heteroaralkyl;

$R_3$ is selected from the group consisting of hydrido, alkyl, cycloalkyl, cycloalkylmethyl, and haloalkyl;

Y is alkylene;

Z is covalent single bond;

$R_{14}$ is hydrido;

$R_4$, $R_8$, $R_9$, and $R_{13}$ are independently selected from the group consisting of hydrido and halo;

$R_5$, $R_6$, $R_7$, $R_{10}$, $R_{11}$, and $R_{12}$ are independently selected from the group consisting of perhaloaryloxy, N-aryl-N-alkylamino, heterocyclylalkoxy, heterocyclylthio, hydroxyalkoxy, aralkanoylalkoxy, aralkenoyl, cycloalkylcarbonyl, cyanoalkoxy, heterocyclylcarbonyl, hydrido, alkyl, halo, haloalkyl, haloalkoxy, aryl, alkylthio, arylamino, arylthio, aroyl, arylsulfonyl, aryloxy, aralkoxy, heteroaryloxy, alkoxy, aralkyl, cycloalkoxy, cycloalkylalkoxy, cycloalkylalkanoyl, heteroaryl, cycloalkyl, haloalkylthio, hydroxyhaloalkyl, heteroaralkoxy, and heteroaryloxyalkyl with the proviso that $R_5$ and $R_{10}$ are independently selected from other than hydrido.

In another more preferred embodiment of compounds of Formula VII-H, $D_3$, $D_4$, $J_3$, $J_4$ and $K_2$ are each carbon;

$D_1$, $D_2$, $J_1$, $J_2$ and $K_1$ are independently selected from the group consisting of C, N, O, S and a covalent bond to form a heteroaryl ring selected from the group consisting of 2-thienyl, 3-thienyl, 2-furyl, 3-furyl, 2-pyrrolyl, 3-pyrrolyl, 2-imidazolyl, 4-imidazolyl, 3-pyrazolyl, 4-pyrazolyl, 2-thiazolyl, 3-isoxazolyl, 5-isoxazolyl, 2-pyridyl, 3-pyridyl, 4pyridyl, 2-pyrazinyl, 2-pyrimidinyl, 4-pyrimidinyl, 5-pyrimidinyl, 3-pyridazinyl, 4-pyridazinyl, and 1,3,5-triazin-2-yl, wherein a ring carbon atom adjacent to the carbon atom at the point of attachment may be optionally substituted with $R_4$ or $R_8$, a ring carbon atom adjacent to the $R_4$ position and two atoms from the point of attachment may be substituted with $R_5$, a ring carbon atom adjacent to the $R_8$ position and two atoms from the point of attachment may be substituted with $R_7$, and a ring carbon atom three atoms from the point of attachment and adjacent to the $R_5$ and $R_7$ positions may be substituted with $R_6$;

n is the integer 1;

X is oxy;

$R_{16}$ is hydrido;

$R_1$ is selected from the group consisting of hydrido, C2–C4 alkyl, C2–C4 alkenyl, cycloalkyl, cycloalkylalkyl, aryl, aralkyl, perhaloaryl, perhaloaralkyl, heteroaryl, and heteroaralkyl;

$R_2$ is selected from the group consisting of hydrido, C1–C2 alkyl, C2 alkenyl, hydroxyalkyl, aryl, aralkyl, perhaloaryl, perhaloaralkyl, heteroaryl, and heteroaralkyl;

$R_3$ is selected from the group consisting of hydrido, alkyl, cycloalkyl, cycloalkylmethyl, and haloalkyl;

Y is alkylene;

Z is covalent single bond;

$R_{14}$ is hydrido;

$R_4$, $R_8$, $R_9$, and $R_{13}$ are independently selected from the group consisting of hydrido and halo;

$R_5$, $R_6$, $R_7$, $R_{10}$, $R_{11}$, and $R_{12}$ are independently selected from the group consisting of perhaloaryloxy, N-aryl-N-alkylamino, heterocyclylalkoxy, heterocyclylthio, hydroxyalkoxy, aralkanoylalkoxy, aralkenoyl, cycloalkylcarbonyl, cyanoalkoxy, heterocyclylcarbonyl, hydrido, alkyl, halo, haloalkyl, haloalkoxy, aryl, alkylthio, arylamino, arylthio, aroyl, arylsulfonyl, aryloxy, aralkoxy, heteroaryloxy, alkoxy, aralkyl, cycloalkoxy, cycloalkylalkoxy, cycloalkylalkanoyl, heteroaryl, cycloalkyl, haloalkylthio, hydroxyhaloalkyl, heteroaralkoxy, and heteroaryloxyalkyl with the proviso that $R_5$ and $R_{10}$ are independently selected from other than hydrido.

In a more preferred more specific embodiment of compounds of Formula VII-H, $D_1$, $D_2$, $J_1$, $J_2$ and $K_1$ are each carbon;

$D_3$, $D_4$, $J_3$, $J_4$ and $K_2$ are independently selected from the group consisting of C, N, O, S and covalent bond to form a heteroaryl ring selected from the group consisting of 2-thienyl, 3-thienyl, 2-furyl, 3-furyl, 2-pyrrolyl, 3-pyrrolyl, 2-imidazolyl, 4-imidazolyl, 3-pyrazolyl, 4-pyrazolyl, 2-thiazolyl, 3-isoxazolyl, 5-isoxazolyl, 2-pyridyl, 3-pyridyl, 4-pyridyl, 2-pyrazinyl, 2-pyrimidinyl, 4-pyrimidinyl, 5-pyrimidinyl, 3-pyridazinyl, 4-pyridazinyl, and 1,3,5-triazin-2-yl, wherein a ring carbon atom adjacent to the carbon atom at the point of attachment may be optionally substituted with $R_9$ or $R_{13}$, a ring carbon atom adjacent to the $R_9$ position and two atoms from the point of attachment may be substituted with $R_{10}$, a ring carbon atom adjacent to the $R_{13}$ position and two atoms from the point of attachment may be substituted with $R_{12}$, and a ring carbon atom three atoms from the point of attachment and adjacent to the $R_{10}$ and $R_{12}$ positions may be substituted with $R_{11}$;

n is the integer 1;

X is oxy;

$R_1$ is selected from the group consisting of hydrido, isopropyl, propyl, benzyl, cyclopropyl, cyclopropylmethyl, phenyl, 3-trifluoromethylphenyl, and 4-trifluoromethylphenyl;

$R_{16}$ is hydrido;

$R_2$ is selected from the group consisting of hydrido, methyl, ethyl, and hydroxymethyl;

$R_3$ is hydrido;

Y is methylene;

Z is covalent single bond;

$R_4$, $R_8$, $R_9$, and $R_{13}$ are independently selected from the group consisting of hydrido and fluoro;

$R_5$ is selected from the group consisting of 5-bromo-2-fluorophenoxy, 4-chloro-3-ethylphenoxy, 2,3-dichlorophenoxy, 3,4-dichlorophenoxy, 3-difluoromethoxyphenoxy, 3,5-dimethylphenoxy, 3,4-dimethylphenoxy, 3-ethylphenoxy, 3-ethyl-5-methylphenoxy, 4-fluoro-3-methylphenoxy, 4-fluorophenoxy, 3-isopropylphenoxy, 3-methylphenoxy, 3-pentafluoroethylphenoxy, 3-tert-butylphenoxy, 3-(1,1,2,2-tetrafluoroethoxy)phenoxy, 2-(5,6,7,8-tetrahydronaphthyloxy), 3-trifluoromethoxybenzyloxy, 3-trifluoromethoxyphenoxy, 3-trifluoromethylbenzyloxy, and 3-trifluoromethylthiophenoxy;

$R_{10}$ is selected from the group consisting of cyclopentyl, 1,1,2,2-tetrafluoroethoxy, 2-furyl, 1,1-bis-trifluoromethyl-1-hydroxymethyl, pentafluoroethyl, trifluoromethoxy, trifluoromethyl, and trifluoromethylthio;

$R_6$ and $R_{11}$ are independently selected from the group consisting of fluoro and hydrido;

$R_7$ and $R_{12}$ are independently selected from the group consisting of hydrido and fluoro.

In another more preferred specific embodiment of compounds of Formula VII-H, $D_3$, $D_4$, $J_3$, $J_4$ and $K_2$ are each carbon;

$D_1$, $D_2$, $J_1$, $J_2$ and $K_1$ are independently selected from the group consisting of C, N, O, S and a covalent bond to form a heteroaryl ring selected from the group consisting of 2-thienyl, 3-thienyl, 2-furyl, 3-furyl, 2-pyrrolyl, 3-pyrrolyl, 2-imidazolyl, 4-imidazolyl, 3-pyrazolyl, 4-pyrazolyl, 2-thiazolyl, 3-isoxazolyl, 5-isoxazolyl, 2-pyridyl, 3-pyridyl, 4-pyridyl, 2-pyrazinyl, 2-pyrimidinyl, 4-pyrimidinyl, 5-pyrimidinyl, 3-pyridazinyl, 4-pyridazinyl, and 1,3,5-triazin-2-yl, wherein a ring carbon atom adjacent to the carbon atom at the point of attachment may be optionally substituted with $R_4$ or $R_8$, a ring carbon atom adjacent to the $R_4$ position and two atoms from the point of attachment may be substituted with $R_5$, a ring carbon atom adjacent to the $R_8$ position and two atoms from the point of attachment may be substituted with $R_7$, and a ring carbon atom three atoms from the point of attachment and adjacent to the $R_5$ and $R_7$ positions may be substituted with $R_6$;

n is the integer 1;

X is oxy;

$R_1$ is selected from the group consisting of hydrido, isopropyl, propyl, benzyl, cyclopropyl, cyclopropylmethyl, phenyl, 3-trifluoromethylphenyl, and 4-trifluoromethylphenyl;

$R_{16}$ is hydrido;

$R_2$ is selected from the group consisting of hydrido, methyl, ethyl, and hydroxymethyl;

$R_3$ is hydrido;

Y is methylene;

Z is covalent single bond;

$R_4$, $R_8$, $R_9$, and $R_{13}$ are independently selected from the group consisting of hydrido and fluoro;

$R_5$ is selected from the group consisting of 5-bromo-2-fluorophenoxy, 4-chloro-3-ethylphenoxy, 2,3-dichlorophenoxy, 3,4-dichlorophenoxy, 3-difluoromethoxyphenoxy, 3,5-dimethylphenoxy, 3,4-dimethylphenoxy, 3-ethylphenoxy, 3-ethyl-5-methylphenoxy, 4-fluoro-3-methylphenoxy, 4-fluorophenoxy, 3-isopropylphenoxy, 3-methylphenoxy, 3-pentafluoroethylphenoxy, 3-tert-butylphenoxy, 3-(1,1,2,2-tetrafluoroethoxy)phenoxy, 2-(5,6,7,8-tetrahydronaphthyloxy), 3-trifluoromethoxybenzyloxy, 3-trifluoromethoxyphenoxy, 3-trifluoromethylbenzyloxy, and 3-trifluoromethylthiophenoxy;

$R_{10}$ is selected from the group consisting of cyclopentyl, 1,1,2,2-tetrafluoroethoxy, 2-furyl, 1,1-bis-trifluoromethyl-1-hydroxymethyl, pentafluoroethyl, trifluoromethoxy, trifluoromethyl, and trifluoromethylthio;

$R_6$ and $R_{11}$ are independently selected from the group consisting of fluoro and hydrido;

$R_7$ and $R_{12}$ are independently selected from the group consisting of hydrido and fluoro.

In a preferred embodiment of compounds of Formula VII-H, the compounds correspond to the Formula VII (also referred to herein as generic phenyl tertiary 2-heteroalkylamines):

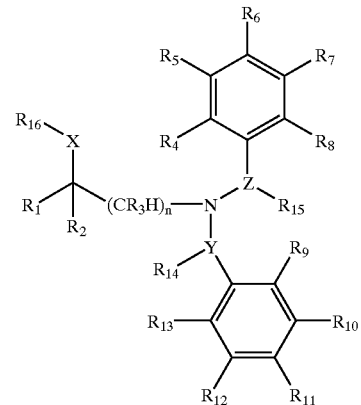

(VII)

or a pharmaceutically acceptable salt thereof, wherein;

n is an integer selected from 0 through 4;

X is selected from the group consisting of O, H, F, S, S(O), NH, N(OH), N(alkyl), and N(alkoxy) with the proviso that there is no $R_{16}$ when X is selected from H or F;

$R_{16}$ is selected from the group consisting of hydrido and a spacer selected from the group consisting of a covalent single bond and a linear spacer moiety having a chain length of 1 to 4 atoms linked to the point of bonding of any aromatic substituent selected from the group consisting of $R_4$, $R_8$, $R_9$, and $R_{13}$ to form a heterocyclyl ring having from 5 through 10 contiguous members;

$R_1$ is selected from the group consisting of hydrido, hydroxyalkyl, alkyl, alkenyl, cycloalkyl, cycloalkenyl, cycloalkylalkyl, cycloalkenylalkyl, alkoxyalkyl, aryl, aralkyl, aryloxyalkyl, heteroaryloxyalkyl, heteroaralkoxyalkyl, perhaloaryl, perhaloaralkyl, perhaloaryloxyalkyl, heteroaryl, heteroaralkyl, heterocyclylalkyl, monocarboalkoxyalkyl, monocyanoalkyl, carboxy, carboxyalkyl, carboalkoxy, carboxamido, carboxamidoalkyl, and carboaralkoxy;

$R_2$ is selected from the group consisting of hydrido, hydroxyalkyl, alkyl, alkenyl, alkynyl, aryl, aralkyl, aralkoxyalkyl, aryloxyalkyl, alkoxyalkyl, heteroaryloxyalkyl, alkenyloxyalkyl, cycloalkyl, cycloalkylalkyl, cycloalkylalkenyl, cycloalkenyl, cycloalkenylalkyl, perhaloaryl, perhaloaralkyl, perhaloaryloxyalkyl, heteroaryl, heteroaralkyl, monocarboalkoxyalkyl, monocyanoalkyl, carboxy, carboxyalkyl, carboalkoxy, carboxamide, carboxamidoalkyl, and carboaralkoxy;

$R_3$ is selected from the group consisting of hydrido, hydroxy, cyano, aryl, aralkyl, acyl, alkoxy, alkyl, alkenyl, alkoxyalkyl, heteroaryl, heteroaralkyl, alkenyloxyalkyl, haloalkyl, haloalkenyl, haloalkoxy, haloalkoxyalkyl, haloalkenyloxyalkyl, cycloalkyl, cycloalkenyl, cycloalkylalkyl, and cycloalkenylalkyl;

Y is selected from the group consisting of covalent single bond and $(C(R_{14})_2)_q$ wherein q is an integer selected from 1 through 2;

$R_{14}$ is selected from the group consisting of hydrido, hydroxy, cyano, hydroxyalkyl, acyl, alkoxy, alkyl, alkenyl, alkynyl, alkoxyalkyl, haloalkyl, haloalkenyl, haloalkoxy, haloalkoxyalkyl, haloalkenyloxyalkyl, monocarboalkoxyalkyl, monocyanoalkyl, dicyanoalkyl, carboalkoxycyanoalkyl, carboalkoxy, carboxamide, carboxamidoalkyl;

Z is selected from the group consisting of covalent single bond, $(C(R_{15})_2)_q$ wherein q is an integer selected from 1 through 2, and $(CH(R_{15}))_j$—W—$(CH(R_{15}))_k$ wherein j and k are integers independently selected from 0 through 2;

W is selected from the group consisting of O, C(O), C(S), C(O)N($R_{14}$), C(S)N($R_{14}$), ($R_{14}$)NC(O), ($R_{14}$)NC(S), S, S(O), S(O)$_2$, S(O)$_2$N($R_{14}$), ($R_{14}$)NS(O)$_2$, and N($R_{14}$) with the proviso that $R_{14}$ is other than cyano;

$R_{15}$ is selected from the group consisting of hydrido, cyano, hydroxyalkyl, acyl, alkoxy, alkyl, alkenyl, alkynyl, alkoxyalkyl, haloalkyl, haloalkenyl, haloalkoxy, haloalkoxyalkyl, haloalkenyloxyalkyl, monocarboalkoxyalkyl, monocyanoalkyl, dicyanoalkyl, carboalkoxycyanoalkyl, carboalkoxy, carboxamide, and carboxamidoalkyl;

$R_4$, $R_8$, $R_9$, and $R_{13}$ are independently selected from the group consisting of hydrido, halo, haloalkyl, and alkyl;

$R_5$, $R_6$, $R_7$, $R_{10}$, $R_{11}$, and $R_{12}$ are independently selected from the group consisting of perhaloaryloxy, alkanoylalkyl, alkanoylalkoxy, alkanoyloxy, N-aryl-N-alkylamino, heterocyclylalkoxy, heterocyclylthio, hydroxyalkoxy, carboxamidoalkoxy, alkoxycarbonylalkoxy, alkoxycarbonylalkenyloxy, aralkanoylalkoxy, aralkenoyl, N-alkylcarboxamido, N-haloalkylcarboxamido, N-cycloalkylcarboxamido, N-arylcarboxamidoalkoxy, cycloalkylcarbonyl, cyanoalkoxy, heterocyclylcarbonyl, hydrido, carboxy, heteroaralkylthio, heteroaralkoxy, cycloalkylamino, acylalkyl, acylalkoxy, aroylalkoxy, heterocyclyloxy, aralkylaryl, aralkyl, aralkenyl, aralkynyl, heterocyclyl, perhaloaralkyl, aralkylsulfonyl, aralkylsulfonylalkyl, aralkylsulfinyl, aralkylsulfinylalkyl, halocycloalkyl, halocycloalkenyl, cycloalkylsulfinyl, cycloalkylsulfinylalkyl, cycloalkylsulfonyl, cycloalkylsulfonylalkyl, heteroarylamino, N-heteroarylamino-N-alkylamino, heteroarylaminoalkyl, haloalkylthio, alkanoyloxy, alkoxy, alkoxyalkyl, haloalkoxyalkyl, heteroaralkoxy, cycloalkoxy, cycloalkenyloxy, cycloalkoxyalkyl, cycloalkylalkoxy, cycloalkenyloxyalkyl, cycloalkylenedioxy, halocycloalkoxy, halocycloalkoxyalkyl, halocycloalkenyloxy, halocycloalkenyloxyalkyl, hydroxy, amino, thio, nitro, lower alkylamino, alkylthio, alkylthioalkyl, arylamino, aralkylamino, arylthio, arylthioalkyl, heteroaralkoxyalkyl, alkylsulfinyl, alkylsulfinylalkyl, arylsulfinylalkyl, arylsulfonylalkyl, heteroarylsulfinylalkyl, heteroarylsulfonylalkyl, alkylsulfonyl, alkylsulfonylalkyl, haloalkylsulfinylalkyl, haloalkylsulfonylalkyl, alkylsulfonamido, alkylaminosulfonyl, amidosulfonyl, monoalkyl amidosulfonyl, dialkyl amidosulfonyl, monoarylamidosulfonyl, arylsulfonamido, diarylamidosulfonyl, monoalkyl monoaryl amidosulfonyl, arylsulfinyl, arylsulfonyl, heteroarylthio, heteroarylsulfinyl, heteroarylsulfonyl, heterocyclylsulfonyl, heterocyclylthio, alkanoyl, alkenoyl, aroyl, heteroaroyl, aralkanoyl, heteroaralkanoyl, haloalkanoyl, alkyl, alkenyl, alkynyl, alkenyloxy, alkenyloxyalky, alkylenedioxy, haloalkylenedioxy, cycloalkyl, cycloalkylalkanoyl, cycloalkenyl, lower cycloalkylalkyl, lower cycloalkenylalkyl, halo, haloalkyl, haloalkenyl, haloalkoxy, hydroxyhaloalkyl, hydroxyaralkyl, hydroxyalkyl, hydoxyheteroaralkyl, haloalkoxyalkyl, aryl, heteroaralkynyl, aryloxy, aralkoxy, aryloxyalkyl, saturated heterocyclyl, partially saturated heterocyclyl, heteroaryl, heteroaryloxy, heteroaryloxyalkyl, heteroaralkyl, arylalkenyl, heteroarylalkenyl, carboxyalkyl, carboalkoxy, alkoxycarboxamido, alkylamidocarbonylamido, arylamidocarbonylamido, carboalkoxyalkyl, carboalkoxyalkenyl, carboaralkoxy, carboxamido, carboxamidoalkyl, cyano, carbohaloalkoxy, phosphono, phosphonoalkyl, diaralkoxyphosphono, and diaralkoxyphosphonoalkyl with the proviso that $R_5$ and $R_{10}$ are independently selected from other than hydrido;

$R_4$ and $R_5$, $R_5$ and $R_6$, $R_6$ and $R_7$, $R_7$ and $R_8$, $R_9$ and $R_{10}$, $R_{10}$ and $R_{11}$, $R_{11}$ and $R_{12}$, and $R_{12}$ and $R_{13}$ are independently selected to form spacer pairs wherein a spacer pair is taken together to form a linear moiety having from 3 through 6 contiguous atoms connecting the points of bonding of said spacer pair members to form a ring selected from the group consisting of a cycloalkenyl ring having 5 through 8 contiguous members, a partially saturated heterocyclyl ring having 5 through 8 contiguous members, a heteroaryl ring having 5 through 6 contiguous members, and an aryl with the provisos that no more than one of the group consisting of spacer pairs $R_4$ and $R_5$, $R_5$ and $R_6$, $R_6$ and $R_7$, and $R_7$ and $R_8$, is used at the same time and that no more than one of the group consisting of spacer pairs $R_9$ and $R_{10}$, $R_{10}$ and $R_{11}$, $R_{11}$ and $R_{12}$, and $R_{12}$ and $R_{13}$ is used at the same time.

In a preferred embodiment of compounds of Formula VII, compounds have the Formula VII-2:

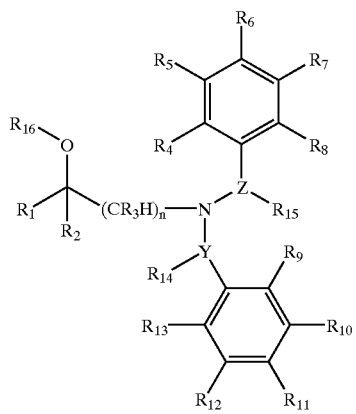

(VII-2)

wherein;

n is an integer selected from 1 through 2;

$R_{16}$ is hydrido;

$R_1$ is selected from the group consisting of hydrido, alkyl, alkenyl, cycloalkyl, cycloalkenyl, cycloalkylalkyl, cycloalkenylalkyl, alkoxyalkyl, aryl, aralkyl, perhaloaryl, perhaloaralkyl, heteroaryl, heteroaralkyl, and carboalkoxy; $R_2$ is selected from the group consisting of hydrido, alkyl, alkenyl, hydroxyalkyl, aryl, aralkyl, alkoxyalkyl, heteroaryloxyalkyl, heteroaralkoxyalkyl, cycloalkyl, cycloalkylalkyl, cycloalkenyl, cycloalkenylalkyl, perhaloaryl, perhaloaralkyl, heteroaryl, carboalkoxy, and heteroaralkyl;

$R_3$ is selected from the group consisting of hydrido, hydroxy, cyano, aryl, aralkyl, acyl, alkoxy, alkyl, alkenyl, alkoxyalkyl, heteroaryl, heteroaralkyl, alkenyloxyalkyl, haloalkyl, haloalkenyl, haloalkoxy, haloalkoxyalkyl, haloalkenyloxyalkyl, cycloalkyl, cycloalkenyl, cycloalkylalkyl, and cycloalkenylalkyl;

Y is selected from the group consisting of a covalent single bond and alkylene;

Z is selected from the group consisting of a covalent single bond and alkylene;

$R_{14}$ is selected from the group consisting of hydrido, alkyl, and haloalkyl;

$R_{15}$ is selected from the group consisting of hydrido, alkyl, and haloalkyl;

$R_4$, $R_8$, $R_9$, and $R_{13}$ are independently selected from the group consisting of hydrido and halo;

$R_5$, $R_6$, $R_7$, $R_{10}$, $R_{11}$, and $R_{12}$ are independently selected from the group consisting of perhaloaryloxy, N-aryl-N-alkylamino, heterocyclylalkoxy, heterocyclylthio, hydroxyalkoxy, carboxamidoalkoxy, alkoxycarbonylalkoxy, alkoxycarbonylalkenyloxy, aralkanoylalkoxy, aralkenoyl, N-arylcarboxamidoalkoxy, cycloalkylcarbonyl, cyanoalkoxy, heterocyclylcarbonyl, hydrido, alkyl, halo, haloalkyl, haloalkoxy, aryl, alkylthio, arylamino, arylthio, aroyl, arylsulfonyl, aryloxy, aralkoxy, heteroaryloxy, alkoxy, aralkyl, cycloalkoxy, cycloalkylalkoxy, cycloalkylalkanoyl, heteroaryl, cycloalkyl, haloalkylthio, hydroxyhaloalkyl, heteroaralkoxy, heterocyclyloxy, aralkylaryl, heteroaryloxyalkyl, heteroarylthio, and heteroarylsulfonyl with the proviso that $R_5$ and $R_{10}$ are independently selected from other than hydrido.

In a more preferred embodiment of compounds of Formula VII-2, n is the integer 1;

$R_{16}$ is hydrido;

$R_1$ is selected from the group consisting of hydrido, C2–C4 alkyl, C2–C4 alkenyl, cycloalkyl, cycloalkylalkyl, aryl, aralkyl, perhaloaryl, perhaloaralkyl, heteroaryl, and heteroaralkyl;

$R_2$ is selected from the group consisting of hydrido, C1–C2 alkyl, C2 alkenyl, hydroxyalkyl, aryl, aralkyl, perhaloaryl, perhaloaralkyl, heteroaryl, and heteroaralkyl;

$R_3$ is selected from the group consisting of hydrido, alkyl, cycloalkyl, cycloalkylmethyl, and haloalkyl;

Y is alkylene;

Z is covalent single bond;

$R_{14}$ is hydrido;

$R_4$, $R_8$, $R_9$, and $R_{13}$ are independently selected from the group consisting of hydrido and halo;

$R_5$, $R_6$, $R_7$, $R_{10}$, $R_{11}$, and $R_{12}$ are independently selected from the group consisting of perhaloaryloxy, N-aryl-N-alkylamino, heterocyclylalkoxy, heterocyclylthio, hydroxyalkoxy, aralkanoylalkoxy, aralkenoyl, cycloalkylcarbonyl, cyanoalkoxy, heterocyclylcarbonyl, hydrido, alkyl, halo, haloalkyl, haloalkoxy, aryl, alkylthio, arylamino, arylthio, aroyl, arylsulfonyl, aryloxy, aralkoxy, heteroaryloxy, alkoxy, aralkyl, cycloalkoxy, cycloalkylalkoxy, cycloalkylalkanoyl, heteroaryl, cycloalkyl, haloalkylthio, hydroxyhaloalkyl, heteroaralkoxy, and heteroaryloxyalkyl with the proviso that $R_5$ and $R_{10}$ are independently selected from other than hydrido.

In a specific preferred embodiment of compounds of Formula VII-2, n is the integer 1;

$R_{16}$ is hydrido;

$R_1$ is selected from the group consisting of hydrido, methyl, isopropyl, isobutyl, propyl, hexyl, benzyl, phenyl, 4-trifluoromethylphenyl, methoxycarbonyl, vinyl, methoxymethyl, cyclopropyl, cyclopropylmethyl, 3-trifluoromethylphenyl, and 4-trifluoromethylcyclohexyl;

$R_2$ is selected from the group consisting of hydrido, methyl, ethyl, hydroxymethyl, 1-hydroxyethyl, propyl, butyl, hexyl, vinyl, phenyl, methoxycarbonyl, benzyl, 3-trifluoromethylphenyl, and 4-trifluoromethylphenyl;

$R_3$ is selected from the group consisting of hydrido, methyl, ethyl, propyl, cyclopropyl, cyclopropylmethyl, cyclobutyl, cyclobutylmethyl, cyclopentyl, cyclopentylmethyl, cyclohexyl, cyclohexylmethyl, phenyl, 4-trifluoromethylphenyl, trifluoromethyl, chloromethyl, fluoromethyl, difluoromethyl, chlorodifluoromethyl, pentafluoroethyl, 2,2,3,3,3-pentafluoropropyl, heptafluoropropyl, pentafluorophenyl, and 3-trifluoromethylphenyl;

Y is selected from the group consisting of methylene, ethylene, and ethylidene;

Z is covalent single bond;

$R_4$, $R_8$, $R_9$, and $R_{13}$ are independently selected from the group consisting of hydrido and fluoro;

$R_5$ and $R_{10}$ are independently selected from the group consisting of 4-aminophenoxy, benzoyl, benzyl, benzyloxy, 5-bromo-2-fluorophenoxy, 4-bromo-3-fluorophenoxy, 4-bromo-2-nitrophenoxy, 3-bromobenzyloxy, 4-bromobenzyloxy, 4-bromophenoxy, 5-bromopyrid-2-yloxy, 4-butoxyphenoxy, chloro, 3-chlorobenzyl, 2-chlorophenoxy, 4-chlorophenoxy, 4-chloro-3-ethylphenoxy, 3-chloro-4-fluorobenzyl, 3-chloro-4-fluorophenyl, 3-chloro-2-fluorobenzyloxy, 3-chlorobenzyloxy, 4-chlorobenzyloxy, 4-chloro-3-methylphenoxy, 2-chloro4-fluorophenoxy, 4-chloro-2-fluorophenoxy, 4-chlorophenoxy, 3-chloro-4ethylphenoxy, 3-chloro-4-methylphenoxy, 3-chloro-4-fluorophenoxy, 4-chloro-3-fluorophenoxy, 4-chlorophenylamino, 5-chloropyrid-3-yloxy, 2-cyanopyrid-3-yloxy, 4-cyanophenoxy, cyclobutoxy, cyclobutyl, cyclohexoxy, cyclohexylmethoxy, cyclopentoxy, cyclopentyl, cyclopentylcarbonyl, cyclopropyl, cyclopropylmethoxy, cyclopropoxy, 2,3-dichlorophenoxy, 2,4-dichlorophenoxy, 2,4-dichlorophenyl, 3,5-dichlorophenyl, 3,5-dichlorobenzyl, 3,4-dichlorophenoxy, 3,4-difluorophenoxy, 2,3-difluorobenzyloxy, 2,4-difluorobenzyloxy, 3,4-difluorobenzyloxy, 2,5-difluorobenzyloxy, 3,5-difluorophenoxy, 3,4-difluorophenyl, 3,5-difluorobenzyloxy, 4-difluoromethoxybenzyloxy, 2,3-difluorophenoxy, 2,4-difluorophenoxy, 2,5-difluorophenoxy, 3,5-dimethoxyphenoxy, 3-dimethylaminophenoxy, 3,5-dimethylphenoxy, 3,4-dimethylphenoxy, 3,4-dimethylbenzyl, 3,4-dimethylbenzyloxy, 3,5-dimethylbenzyloxy, 2,2-dimethylpropoxy, 1,3-dioxan-2-yl, 1,4-dioxan-2-yl, 1,3-dioxolan-2-yl, ethoxy, 4-ethoxyphenoxy, 4-ethylbenzyloxy, 3-ethylphenoxy, 4-ethylaminophenoxy, 3-ethyl-5-methylphenoxy, fluoro, 4-fluoro-3-methylbenzyl, 4-fluoro-3-methylphenyl, 4-fluoro-3-methylbenzoyl, 4-fluorobenzyloxy, 2-fluoro-3-methylphenoxy, 3-fluoro-4-methylphenoxy, 3-fluorophenoxy, 3-fluoro-2-nitrophenoxy, 2-fluoro-3-trifluoromethylbenzyloxy, 3-fluoro-5-trifluoromethylbenzyloxy, 4-fluoro-2-trifluoromethylbenzyloxy, 4-fluoro-3-trifluoromethylbenzyloxy, 2-fluorophenoxy, 4-fluorophenoxy, 2-fluoro-3-trifluoromethylphenoxy, 2-fluorobenzyloxy, 4-fluorophenylamino, 2-fluoro-4-trifluoromethylphenoxy, 4-fluoropyrid-2-yloxy, 2-furyl, 3-furyl, heptafluoropropyl, 1,1,1,3,3,3-hexafluoropropyl, 2-hydroxy-3,3,3-trifluoropropoxy, 3-iodobenzyloxy, isobutyl, isobutylamino, isobutoxy, 3-isoxazolyl, 4-isoxazolyl, 5-isoxazolyl, isopropoxy, isopropyl, 4-isopropylbenzyloxy, 3-isopropylphenoxy, 4-isopropylphenoxy, isopropylthio, 4-isopropyl-3-methylphenoxy, 3-isothiazolyl, 4-isothiazolyl, 5-isothiazolyl, 3-methoxybenzyl, 4-methoxycarbonylbutoxy, 3-methoxycarbonylprop-2-enyloxy, 4-methoxyphenyl, 3-methoxyphenylamino, 4-methoxyphenylamino, 3-methylbenzyloxy, 4-methylbenzyloxy, 3-methylphenoxy, 3-methyltmethylthiophenoxy, 4-methylphenoxy, 1-methylpropoxy, 2-methylpyrid-5-yloxy, 4-methylthiophenoxy, 2-naphthyloxy, 2-nitrophenoxy, 4-nitrophenoxy, 3-nitrophenyl, 4-nitrophenylthio, 2-oxazolyl, 4-oxazolyl, 5-oxazolyl, pentafluoroethyl, pentafluoroethylthio, 2,2,3,3,3-pentafluoropropyl, 1,1,3,3,3-pentafluoropropyl, 1,1,2,2,3-pentafluoropropyl, phenoxy, phenylamino, 1-phenylethoxy, phenylsulfonyl, 4-propanoylphenoxy, propoxy, 4-propylphenoxy, 4-propoxyphenoxy, thiophen-3-yl, sec-butyl, 4-sec-butylphenoxy, tert-butoxy, 3-tert-butylphenoxy, 4-tert-butylphenoxy, 1,1,2,2-tetrafluoroethoxy, tetrahydrofuran-2-yl, 2-(5,6,7,8-tetrahydronaphthyloxy), thiazol-2-yl, thiazol-4-yl, thiazol-5-yl, thiophen-2-yl, 2,3,5-trifluorobenzyloxy, 2,2,2-trifluoroethoxy, 2,2,2-trifluoroethyl, 3,3,3-trifluoro-2-hydroxypropyl, trifluoromethoxy, 3-trifluoromethoxybenzyloxy, 4-trifluoromethoxybenzyloxy, 3-trifluoromethoxyphenoxy, 4-trifluoromethoxyphenoxy, trifluoromethyl, 3-trifluoromethylbenzyloxy, 4-trifluoromethylbenzyloxy, 2,4-bis-trifluoromethylbenzyloxy, 1,1-bis-trifluoromethyl-1-hydroxymethyl, 3-trifluoromethylbenzyl, 3,5-bis-trifluoromethylbenzyloxy, 4-trifluoromethylphenoxy, 3-trifluoromethylphenoxy, 3-trifluoromethylphenyl, 3-trifluoromethylthiobenzyloxy, 4-trifluoromethylthiobenzyloxy, 2,3,4-trifluorophenoxy, 2,3,4-trifluorophenyl, 2,3,5-trifluorophenoxy, 3,4,5-trimethylphenoxy, 3-difluoromethoxyphenoxy, 3-pentafluoroethylphenoxy, 3-(1,1,2,2-tetrafluoroethoxy)phenoxy, 3-trifluoromethylthiophenoxy, and trifluoromethylthio;

$R_6$ and $R_{11}$ are independently selected from the group consisting of chloro, fluoro, hydrido, pentafluoroethyl, 1,1,2,2-tetrafluoroethoxy, trifluoromethyl, and trifluoromethoxy;

$R_7$ and $R_{12}$ are independently selected from the group consisting of hydrido, fluoro, and trifluoromethyl.

In a more specific more preferred embodiment of compounds of Formula VII-2, n is the integer 1;

$R_{16}$ is hydrido;

$R_1$ is selected from the group consisting of hydrido, isopropyl, isobutyl, propyl, benzyl, cyclopropyl, cyclopropylmethyl, phenyl, and 4-trifluoromethylphenyl;

$R_2$ is selected from the group consisting of hydrido, methyl, ethyl, hydroxymethyl, 1-hydroxyethyl, propyl, phenyl, benzyl, 3-trifluoromethylphenyl, and 4-trifluoromethylphenyl;

$R_3$ is selected from the group consisting of hydrido, methyl, trifluoromethyl, difluoromethyl, chlorodifluoromethyl, cyclopropyl, cyclopropylmethyl, 3-trifluoromethylphenyl, and 4-trifluoromethylphenyl;

Y is methylene;

Z is a covalent single bond;

$R_4$, $R_8$, $R_9$, and $R_{13}$ are independently selected from the group consisting of hydrido and fluoro;

$R_5$ and $R_{10}$ are independently selected from the group consisting of benzyloxy, 5-bromo-2-fluorophenoxy, 4-bromo-3-fluorophenoxy, 3-bromobenzyloxy, 4-bromophenoxy, 4-butoxyphenoxy, 3-chlorobenzyloxy, 2-chlorophenoxy, 4-chloro-3-ethylphenoxy, 4-chloro-3-methylphenoxy, 2-chloro-4-fluorophenoxy, 4-chloro-2-fluorophenoxy, 4-chlorophenoxy, 3-chloro-4-ethylphenoxy, 3-chloro-4-methylphenoxy, 3-chloro-4-fluorophenoxy, 4-chloro-3-fluorophenoxy, 4-chlorophenylamino, 5-chloropyrid-3-yloxy, cyclobutoxy, cyclobutyl, cyclohexylmethoxy, cyclopentoxy, cyclopentyl, cyclopentylcarbonyl, cyclopropylmethoxy, 2,3-dichlorophenoxy, 2,4-dichlorophenoxy, 2,4-dichlorophenyl, 3,5-dichlorophenyl, 3,5-dichlorobenzyl, 3,4-dichlorophenoxy, 3,4-difluorophenoxy, 2,3-difluorobenzyloxy, 3,5-difluorobenzyloxy, difluoromethoxy, 3,5-difluorophenoxy, 3,4-difluorophenyl, 2,3-difluorophenoxy, 2,4-difluorophenoxy, 2,5-difluorophenoxy, 3,5-dimethoxyphenoxy, 3-dimethylaminophenoxy, 3,4-dimethylbenzyloxy, 3,5-dimethylbenzyloxy, 3,5-dimethylphenoxy, 3,4-dimethylphenoxy, 1,3-dioxolan-2-yl, 3-ethylbenzyloxy, 3-ethylphenoxy, 4-ethylaminophenoxy, 3-ethyl-5-methylphenoxy, 4-fluoro-3-methylbenzyl, 4-fluorobenzyloxy, 2-fluoro-3-methylphenoxy, 3-fluoro-4-methylphenoxy, 3-fluorophenoxy, 3-fluoro-2-nitrophenoxy, 2-fluoro-3-trifluoromethylbenzyloxy, 3-fluoro-5-trifluoromethylbenzyloxy, 2-fluorophenoxy, 4-fluorophenoxy, 2-fluoro-3-trifluoromethylphenoxy, 2-fluorobenzyloxy, 4-fluorophenylamino, 2-fluoro-4-trifluoromethylphenoxy, 2-furyl, 3-furyl, heptafluoropropyl, 1,1,1,3,3,3-hexafluoropropyl, 2-hydroxy-3,3,3-trifluoropropoxy, isobutoxy, isobutyl, 3-isoxazolyl, 4-isoxazolyl, 5-isoxazolyl, isopropoxy, 3-isopropylbenzyloxy, 3-isopropylphenoxy, isopropylthio, 4-isopropyl-3-methylphenoxy, 3-isothiazolyl, 4-isothiazolyl, 5-isothiazolyl, 3-methoxybenzyl, 4-methoxyphenylamino, 3-methylbenzyloxy, 4-methylbenxyloxy, 3-methylphenoxy, 3-methylmethylthiophenoxy, 4-methylphenoxy, 1-methylpropoxy, 2-methylpyrid-5-yloxy, 4-methylthiophenoxy, 2-naphthyloxy, 2-nitrophenoxy, 4-nitrophenoxy, 3-nitrophenyl, 2-oxazolyl, 4-oxazolyl, 5-oxazolyl, pentafluoroethyl, pentafluoroethylthio, 2,2,3,3,3-pentafluoropropyl, 1,1,3,3,3-pentafluoropropyl, 1,1,2,2,3-pentafluoropropyl, phenoxy, phenylamino, 1-phenylethoxy, 4-propylphenoxy, 4-propoxyphenoxy, thiophen-3-yl, tert-butoxy, 3-tert-butylphenoxy, 4-tert-butylphenoxy, 1,1,2,2-tetrafluoroethoxy, tetrahydrofuran-2-yl, 2-(5,6,7,8-tetrahydronaphthyloxy), thiazol-2-yl, thiazol-4-yl, thiazol-5-yl, thiophen-2-yl, 2,2,2-trifluoroethoxy, 2,2,2-trifluoroethyl, 3,3,3-trifluoro-2-hydroxypropyl, trifluoromethoxy, 3-trifluoromethoxybenzyloxy, 4-trifluoromethoxybenzyloxy, 4-trifluoromethoxyphenoxy, 3-trifluoromethoxyphenoxy, trifluoromethyl, 3-trifluoromethylbenzyloxy, 1,1-bis-trifluoromethyl-1-hydroxymethyl, 3-trifluoromethylbenzyl, 3,5-bis-trifluoromethylbenzyloxy, 4-trifluoromethylphenoxy, 3-trifluoromethylphenoxy, 3-trifluoromethylphenyl, 2,3,4-trifluorophenoxy, 2,3,5-trifluorophenoxy, 3,4,5-trimethylphenoxy, 3-difluoromethoxyphenoxy, 3-pentafluoroethylphenoxy, 3-(1,1,2,2-tetrafluoroethoxy)phenoxy, 3-trifluoromethylthiophenoxy, 3-trifluoromethylthiobenzyloxy, and trifluoromethylthio;

$R_6$ and $R_{11}$ are independently selected from the group consisting of chloro, fluoro, hydrido, pentafluoroethyl, 1,1,2,2-tetrafluoroethoxy, and trifluoromethyl;

$R_7$ and $R_{12}$ are independently selected from the group consisting of hydrido, fluoro, and trifluoromethyl.

In a specific even more preferred embodiment of compounds of Formula VII-2, n is the integer 1;

$R_{16}$ is hydrido;

$R_1$ is selected from the group consisting of hydrido, isopropyl, propyl, benzyl, cyclopropyl, cyclopropylmethyl, phenyl, 3-trifluoromethylphenyl, and 4-trifluoromethylphenyl;

$R_2$ is selected from the group consisting of hydrido, methyl, ethyl, and hydroxymethyl;

$R_3$ is hydrido;

Y is methylene;

Z is covalent single bond;

$R_4$, $R_8$, $R_9$, and $R_{13}$ are independently selected from the group consisting of hydrido and fluoro;

$R_5$ is selected from the group consisting of 5-bromo-2-fluorophenoxy, 4-chloro-3-ethylphenoxy, 2,3-dichlorophenoxy, 3,4-dichlorophenoxy, 3-difluoromethoxyphenoxy, 3,5-dimethylphenoxy, 3,5-dimethylphenoxy, 3-ethylphenoxy, 3-ethyl-5-methylphenoxy, 4-fluoro-3-methylphenoxy, 4-fluorophenoxy, 3-isopropylphenoxy, 3-methylphenoxy, 3-pentafluoroethylphenoxy, 3-tert-butylphenoxy, 3-(1,1,2,2-tetrafluoroethoxy)phenoxy, 2-(5,6,7,8-tetrahydronaphthyloxy), 3-trifluoromethoxybenzyloxy, 3-trifluoromethoxyphenoxy, 3-trifluoromethylbenzyloxy, and 3-trifluoromethylthiophenoxy;

$R_{10}$ is selected from the group consisting of cyclopentyl, 1,1,2,2-tetrafluoroethoxy, 2-furyl, 1,1-bis-trifluoromethyl-1-hydroxymethyl, pentafluoroethyl, trifluoromethoxy, trifluoromethyl, and trifluoromethylthio;

$R_6$ and $R_{11}$ are independently selected from the group consisting of fluoro and hydrido;

$R_7$ and $R_{12}$ are independently selected from the group consisting of hydrido and fluoro.

In another embodiment of compounds of Formula VII, compounds have the formula Cyclo-VII:

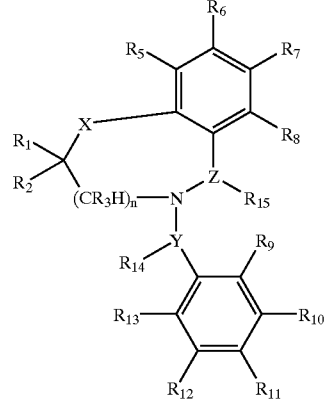

(Cyclo-VII)

wherein;

n is the integer 1;

X is selected from the group consisting of O, NH, and S;

$R_{16}$ is taken together with $R_4$, $R_8$, $R_9$, or $R_{13}$ to form a spacer selected from the group consisting of a covalent single bond, $CH_2$, $CH(CH_3)$, $CF_2$, $C(O)$, $C(S)$, and $SO_2$;

$R_1$ is selected from the group consisting of hydrido, methyl, isopropyl, propyl, isobutyl, hexyl, benzyl, cyclopropyl, cyclopropylmethyl, phenyl, 4-trifluoromethylphenyl, methoxycarbonyl, vinyl, ethoxycarbonylmethyl, methoxymethyl, 3-trifluoromethylphenyl, and 4-trifluoromethylcyclohexyl;

$R_2$ is selected from the group consisting of hydrido, methyl, ethyl, hydroxymethyl, propyl, butyl, hexyl, vinyl, phenyl, methoxycarbonyl, benzyl, 3-trifluoromethylphenyl, and 4-trifluoromethylphenyl;

$R_3$ is selected from the group consisting of hydrido, methyl, ethyl, propyl, cyclopropyl, cyclopropylmethyl, cyclobutyl, cyclobutylmethyl, cyclopentyl, cyclopentylmethyl, cyclohexyl, cyclohexylmethyl, phenyl, 4-trifluoromethylphenyl, trifluoromethyl, chloromethyl, fluoromethyl, difluoromethyl, chlorodifluoromethyl, pentafluoroethyl, 2,2,3,3,3-pentafluoropropyl, heptafluoropropyl, pentafluorophenyl, and 3-trifluoromethylphenyl;

Y is selected from the group consisting of methylene, ethylene, and ethylidene;

Z is covalent single bond;

$R_4$, $R_8$, $R_9$, and $R_{13}$ are independently selected from the group consisting of hydrido and fluoro;

$R_5$ and $R_{10}$ are independently selected from the group consisting of 4-aminophenoxy, benzoyl, benzyl, benzyloxy, 5-bromo-2-fluorophenoxy, 4-bromo-3-fluorophenoxy, 4-bromo-2-nitrophenoxy, 3-bromobenzyloxy, 4-bromobenzyloxy, 4-bromophenoxy, 5-bromopyrid-2-yloxy, 4-butoxyphenoxy, chloro, 3-chlorobenzyl, 2-chlorophenoxy, 4-chlorophenoxy, 4-chloro-3-ethylphenoxy, 3-chloro-4-fluorobenzyl, 3-chloro-4-fluorophenyl, 3-chloro-2-fluorobenzyloxy, 3-chlorobenzyloxy, 4-chlorobenzyloxy, 4-chloro-3-methylphenoxy, 2-chloro-4-fluorophenoxy, 4-chloro-2-fluorophenoxy, 4-chlorophenoxy, 3-chloro-4-ethylphenoxy, 3-chloro-4-methylphenoxy, 3-chloro-4-fluorophenoxy, 4-chloro-3-fluorophenoxy, 4-chlorophenylamino, 5-chloropyrid-3-yloxy, 2-cyanopyrid-3-yloxy, 4-cyanophenoxy, cyclobutoxy, cyclobutyl, cyclohexoxy, cyclohexylmethoxy, cyclopentoxy, cyclopentyl, cyclopentylcarbonyl, cyclopropyl, cyclopropylmethoxy, cyclopropoxy, 2,3-dichlorophenoxy, 2,4-dichlorophenoxy, 2,4-dichlorophenyl, 3,5-dichlorophenyl, 3,5-dichlorobenzyl, 3,4-dichlorophenoxy, 3,4-difluorophenoxy, 2,3-difluorobenzyloxy, 2,4-difluorobenzyloxy, 3,4-difluorobenzyloxy, 2,5-difluorobenzyloxy, 3,5-difluorophenoxy, 3,4-difluorophenyl, 3,5-difluorobenzyloxy, 4-difluoromethoxybenzyloxy, 2,3-difluorophenoxy, 2,4-difluorophenoxy, 2,5-difluorophenoxy, 3,5-dimethoxyphenoxy, 3-dimethylaminophenoxy, 3,5-dimethylphenoxy, 3,4-dimethylphenoxy, 3,4-dimethylbenzyl, 3,4-dimethylbenzyloxy, 3,5-dimethylbenzyloxy, 2,2-dimethylpropoxy, 1,3-dioxan-2-yl, 1,4-dioxan-2-yl, 1,3-dioxolan-2-yl, ethoxy, 4-ethoxyphenoxy, 4-ethylbenzyloxy, 3-ethylphenoxy, 4-ethylaminophenoxy, 3-ethyl-5-methylphenoxy, fluoro, 4-fluoro-3-methylbenzyl, 4-fluoro-3-methylphenyl, 4-fluoro-3-methylbenzoyl, 4-fluorobenzyloxy, 2-fluoro-3-methylphenoxy, 3-fluoro-4-methylphenoxy, 3-fluorophenoxy, 3-fluoro-2-nitrophenoxy, 2-fluoro-3-trifluoromethylbenzyloxy, 3-fluoro-5-trifluoromethylbenzyloxy, 4-fluoro-2-trifluoromethylbenzyloxy, 4-fluoro-3-trifluoromethylbenzyloxy, 2-fluorophenoxy, 4-fluorophenoxy, 2-fluoro-3-trifluoromethylphenoxy, 2-fluorobenzyloxy, 4-fluorophenylamino, 2-fluoro-4-trifluoromethylphenoxy, 4-fluoropyrid-2-yloxy, 2-furyl, 3-furyl, heptafluoropropyl, 1,1,1,3,3,3-hexafluoropropyl, 2-hydroxy-3,3,3-trifluoropropoxy, 3-iodobenzyloxy, isobutyl, isobutylamino, isobutoxy, 3-isoxazolyl, 4-isoxazolyl, 5-isoxazolyl, isopropoxy, isopropyl, 4-isopropylbenzyloxy, 3-isopropylphenoxy, 4-isopropylphenoxy, isopropylthio, 4-isopropyl-3-methylphenoxy, 3-isothiazolyl, 4-isothiazolyl, 5-isothiazolyl, 3-methoxybenzyl, 4-methoxycarbonylbutoxy, 3-methoxycarbonylprop-2-enyloxy, 4-methoxyphenyl, 3-methoxyphenylamino, 4-methoxyphenylamino, 3-methylbenzyloxy, 4-methylbenzyloxy, 3-methylphenoxy, 3-methyl-methylthiophenoxy, 4-methylphenoxy, 1-methylpropoxy, 2-methylpyrid-5-yloxy, 4-methylthiophenoxy, 2-naphthyloxy, 2-nitrophenoxy, 4-nitrophenoxy, 3-nitrophenyl, 4-nitrophenylthio, 2-oxazolyl, 4-oxazolyl, 5-oxazolyl, pentafluoroethyl, pentafluoroethylthio, 2,2,3,3,3-pentafluoropropyl, 1,1,3,3,3-pentafluoropropyl, 1,1,2,2,3-pentafluoropropyl, phenoxy, phenylamino, 1-phenylethoxy, phenylsulfonyl, 4-propanoylphenoxy, propoxy, 4-propylphenoxy, 4-propoxyphenoxy, thiophen-3-yl, sec-butyl, 4-sec-butylphenoxy,tert-butoxy, 3-tert-butylphenoxy, 4-tert-butylphenoxy, 1,1,2,2-tetrafluoroethoxy, tetrahydrofuran-2-yl, 2-(5,6,7,8-tetrahydronaphthyloxy), thiazol-2-yl, thiazol-4-yl, thiazol-5-yl, thiophen-2-yl, 2,3,5-trifluorobenzyloxy, 2,2,2-trifluoroethoxy, 2,2,2-trifluoroethyl, 3,3,3-trifluoro-2-hydroxypropyl, trifluoromethoxy, 3-trifluoromethoxybenzyloxy, 4-trifluoromethoxybenzyloxy, 3-trifluoromethoxyphenoxy, 4-trifluoromethoxyphenoxy, trifluoromethyl, 3-trifluoromethylbenzyloxy, 4-trifluoromethylbenzyloxy, 2,4-bis-trifluoromethylbenzyloxy, 1,1-bis-trifluoromethyl-1-hydroxymethyl, 3-trifluoromethylbenzyl, 3,5-bis-trifluoromethylbenzyloxy, 4-trifluoromethylphenoxy, 3-trifluoromethylphenoxy, 3-trifluoromethylphenyl, 3-trifluoromethylthiobenzyloxy, 4-trifluoromethylthiobenzyloxy, 2,3,4-trifluorophenoxy, 2,3,4-trifluorophenyl, 2,3,5-trifluorophenoxy, 3,4,5-trimethylphenoxy, 3-difluoromethoxyphenoxy, 3-pentafluoroethylphenoxy, 3-(1,1,2,2-tetrafluoroethoxy)phenoxy, 3-trifluoromethylthiophenoxy, and trifluoromethylthio;

$R_6$ and $R_{11}$ are independently selected from the group consisting of chloro, fluoro, hydrido, pentafluoroethyl, 1,1,2,2-tetrafluoroethoxy, trifluoromethyl, and trifluoromethoxy;

$R_7$ and $R_{12}$ are independently selected from the group consisting of hydrido, fluoro, and trifluoromethyl.

In an embodiment of compounds of Formula Cyclo-VII, n is the integer 1;

X is oxy;

$R_{16}$ is taken together with $R_4$, $R_8$, $R_9$, or $R_{13}$ to form a covalent single bond;

$R_1$ is selected from the group consisting of hydrido, propyl, isopropyl, cyclopropyl, benzyl, phenyl, 4-trifluoromethylphenyl, and 3-trifluoromethylphenyl;

$R_2$ is selected from the group consisting of hydrido, methyl, ethyl, hydroxymethyl, isopropyl, propyl, cyclopropyl, phenyl, methoxycarbonyl, benzyl, 3-trifluoromethylphenyl, and 4-trifluoromethylphenyl;

$R_3$ is selected from the group consisting of hydrido, methyl, cyclopropyl, cyclopropylmethyl, cyclobutyl, cyclobutylmethyl, cyclopentyl, cyclopentylmethyl, cyclohexyl, cyclohexylmethyl, trifluoromethyl, difluoromethyl, chlorodifluoromethyl, 3-trifluoromethylphenyl, and 4-trifluoromethylphenyl;

Y is methylene;

Z is covalent single bond;

$R_4$, $R_8$, $R_9$, and $R_{13}$ are independently selected from the group consisting of hydrido and fluoro;

$R_5$ is selected from the group consisting of 5-bromo-2-fluorophenoxy, 4-chloro-3-ethylphenoxy, 2,3-dichlorophenoxy, 3,4-dichlorophenoxy, 3-difluoromethoxyphenoxy, 3,5-dimethylphenoxy, 3,4-dimethylphenoxy, 3-ethylphenoxy, 3-ethyl-5-methylphenoxy, 4-fluoro-3-methylphenoxy, 4-fluorophenoxy, 3-isopropylphenoxy, 3-methylphenoxy, 3-pentafluoroethylphenoxy, 3-tert-butylphenoxy, 3-(1,1,2,2-tetrafluoroethoxy)phenoxy, 2-(5,6,7,8-tetrahydronaphthyloxy), 3-trifluoromethoxybenzyloxy, 3-trifluoromethoxyphenoxy, 3-trifluoromethylbenzyloxy, and 3-trifluoromethylthiophenoxy;

$R_{10}$ is selected from the group consisting of cyclopentyl, 1,1,2,2-tetrafluoroethoxy, 2-furyl, 1,1-bis-trifluoromethyl-1-hydroxymethyl, pentafluoroethyl, trifluoromethoxy, trifluoromethyl, and trifluoromethylthio;

$R_6$ and $R_{11}$ are independently selected from the group consisting of fluoro and hydrido;

$R_7$ and $R_{12}$ are independently selected from the group consisting of hydrido and fluoro.

In another embodiment of compounds of Formula VII, compounds have the Formula VII-3:

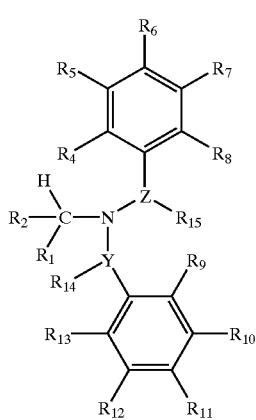

(VII-3)

or a pharmaceutically acceptable salt thereof, wherein:

$R_1$ is selected from the group consisting of hydrido, C2–C4 alkyl, C2–C4 alkenyl, cycloalkyl, cycloakylalkyl, aryl, aralkyl, perhaloaryl, perhaloaralkyl, heteroaryl, and heteroaralkyl;

$R_2$ is hydroxyalkyl;

Y is alkylene;

Z is covalent single bond;

$R_{14}$ is hydrido;

$R_4$, $R_8$, $R_9$, and $R_{13}$ are independently selected from the group consisting of hydrido and halo;

$R_5$, $R_6$, $R_7$, $R_{10}$, $R_{11}$, and $R_{12}$ are independently selected from the group consisting of perhaloaryloxy, N-aryl-N-alkylamino, heterocyclylalkoxy, heterocyclylthio, hydroxyalkoxy, aralkanoylalkoxy, aralkenoyl, cycloalkylcarbonyl, cyanoalkoxy, heterocyclylcarbonyl, hydrido, alkyl, halo, haloalkyl, haloalkoxy, aryl, alkylthio, arylamino, arylthio, aroyl, arylsulfonyl, aryloxy, aralkoxy, heteroaryloxy, alkoxy, aralkyl, cycloalkoxy, cycloalkylalkoxy, cycloalkylalkanoyl, heteroaryl, cycloalkyl, haloalkylthio, hydroxyhaloalkyl, heteroaralkoxy, and heteroaryloxyalkyl.

In an embodiment of compounds of Formula VII-3, $R_1$ is selected from the group consisting of hydrido, methyl, isopropyl, propyl, isobutyl, hexyl, benzyl, cyclopropyl, cyclopropylmethyl, phenyl, 4-trifluoromethylphenyl, methoxycarbonyl, vinyl, ethoxycarbonylmethyl, methoxymethyl, 3-trifluoromethylphenyl, and 4-trifluoromethylcyclohexyl;

$R_2$ is hydroxymethyl, 1-hydroxyethyl, and 1,2-dihydroxyethyl;

Y is methylene;

Z is covalent single bond;

$R_4$, $R_8$, $R_9$, and $R_{13}$ are independently selected from the group consisting of hydrido and fluoro;

$R_5$ is selected from the group consisting of 5-bromo-2-fluorophenoxy, 4-chloro-3-ethylphenoxy, 2,3-dichlorophenoxy, 3,4-dichlorophenoxy, 3-difluoromethoxyphenoxy, 3,5-dimethylphenoxy, 3,4-dimethylphenoxy, 3-ethylphenoxy, 3-ethyl-5-methylphenoxy, 4-fluoro-3-methylphenoxy, 4-fluorophenoxy, 3-isopropylphenoxy, 3-methylphenoxy, 3-pentafluoroethylphenoxy, 3-tert-butylphenoxy, 3-(1,1,2,2-tetrafluoroethoxy)phenoxy, 2-(5,6,7,8-tetrahydronaphthyloxy), 3-trifluoromethoxybenzyloxy, 3-trifluoromethoxyphenoxy, 3-trifluoromethylbenzyloxy, and 3-trifluoromethylthiophenoxy;

$R_{10}$ is selected from the group consisting of cyclopentyl, 1,1,2,2-tetrafluoroethoxy, 2-furyl, 1,1-bis-trifluoromethyl-1-hydroxymethyl, pentafluoroethyl, trifluoromethoxy, trifluoromethyl, and trifluoromethylthio;

$R_6$ and $R_{11}$ are independently selected from the group consisting of fluoro and hydrido;

$R_7$ and $R_{12}$ are independently selected from the group consisting of hydrido and fluoro.

In another embodiment of compounds of Formula VII, compounds have the Formula VII-4:

(VII-4)

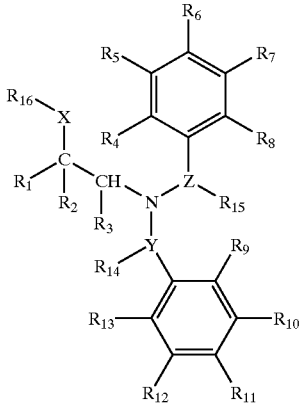

wherein;

X is oxy;

$R_1$ is selected from the group consisting of hydrido, alkyl, alkenyl, cycloalkyl, cycloalkenyl, cycloalkylalkyl, cycloalkenylalkyl, alkoxyalkyl, aryl, aralkyl, perhaloaryl, perhaloaralkyl, heteroaryl, heteroaralkyl, and carboalkoxy;

$R_{16}$ is hydrido;

$R_2$ and $R_3$ are taken together to form a linear spacer moiety selected from the group consisting of a covalent single bond and a moiety having from 1 through 6 contiguous atoms to form a ring selected from the group consisting of a cycloalkyl having from 3 through 8 contiguous members, a cycloalkenyl having from 5 through 8 contiguous members, and a heterocyclyl having from 4 through 8 contiguous members;

Y is selected from the group consisting of a covalent single bond and C1–C2 alkylene;

Z is selected from the group consisting of a covalent single bond and C1–C2 alkylene;

$R_{14}$ is selected from the group consisting of hydrido, alkyl, and haloalkyl;

$R_{15}$ is selected from the group consisting of hydrido, alkyl, and haloalkyl;

$R_4$, $R_8$, $R_9$, and $R_{13}$ are independently selected from the group consisting of hydrido and halo;

$R_5$, $R_6$, $R_7$, $R_{10}$, $R_{11}$, and $R_{12}$ are independently selected from the group consisting of perhaloaryloxy, N-aryl-N-alkylamino, heterocyclylalkoxy, heterocyclylthio, hydroxyalkoxy, carboxamidoalkoxy, alkoxycarbonylalkoxy, alkoxycarbonylalkenyloxy, aralkanoylalkoxy, aralkenoyl, N-arylcarboxamidoalkoxy, cycloalkylcarbonyl, cyanoalkoxy, heterocyclylcarbonyl, hydrido, alkyl, halo, haloalkyl, haloalkoxy, aryl, alkylthio, arylamino, arylthio, aroyl, arylsulfonyl, aryloxy, aralkoxy, heteroaryloxy, alkoxy, aralkyl, cycloalkoxy, cycloalkylalkoxy, cycloalkylalkanoyl, heteroaryl, cycloalkyl, haloalkylthio, hydroxyhaloalkyl, heteroaralkoxy, heterocyclyloxy, aralkylaryl, heteroaryloxyalkyl, heteroarylthio, and heteroarylsulfonyl.

In an embodiment of compounds of Formula VII-4,

X is oxy;

$R_{16}$ is hydrido;

$R_1$ is selected from the group consisting of hydrido, methyl, propyl, isopropyl, isobutyl, cyclopropyl, cyclopropylmethyl, benzyl, phenyl, 4-trifluoromethylphenyl, methoxycarbonyl, vinyl, ethoxycarbonylmethyl, methoxymethyl, and 4-trifluoromethylcyclohexyl;

$R_2$ and $R_3$ spacer pair is selected from the group consisting of —$CH_2SCH_2$—, —$CH_2OCH_2$—, —$CH_2CH(R_{17})$—, —$CH=C(R_{17})$—, —$CH_2S(O)_2CH_2$—, —$CH_2CH_2CH(R_{17})$—, —$CH_2CH(R_{17})CH_2$—, —$CH_2CH=C(R_{17})$—, —$CH(R_{17})CH=CH$—, —$CH_2C(R_{17})=CH$—, —$CH(R_{17})C(O)N(R_{17})$—, —$C(O)N(R_{17})CH(R_{17})$—, —$CH(R_{17})C(O)NHCH_2$—, —$CH_2C(O)NHCH(R_{17})$—, —$CH(R_{17})CH(R_{17})C(O)NH$—, —$C(O)NHCH(R_{17})CH(R_{17})$—, —$CH_2CH(R_{17})CH_2CH_2$—, —$CH(R_{17})CH_2CH_2CH_2$—, —$CH_2CH=CHCH_2$—, —$CH=CHCH_2CH_2$—, —$CH=CHCH=CH$—, —$CH_2CH_2CH_2CH_2CH_2$—, —$CH_2CH_2CH=CHCH_2$—, —$(CH_2)_2O$—, —$(CH_2CHR_{17})O$—, —$(CF_2)_2O$—, —$SCH_2CH_2$—, —$S(O)CH_2CH_2$—, —$CH_2S(O)CH_2$—, —$CH_2S(O)CH_2CH_2$—, —$S(O)_2CH_2$—, —$CH_2N(R_{17})O$—, —$CH_2CH_2C(O)$—, —$CH_2C(O)NR_{17}$—, and —$CH_2NR_{17}CH_2$— wherein $R_{17}$ is selected from the group consisting of H, $CH_3$, $OCH_3$, $CF_3$, $CH_2CH_3$, F, Cl, $CH_2OH$, and OH;

Y is selected from the group consisting of methylene, ethylene, and ethylidene;

Z is covalent single bond;

$R_4$, $R_8$, $R_9$, and $R_{13}$ are independently selected from the group consisting of hydrido and fluoro;

$R_5$ and $R_{10}$ are independently selected from the group consisting of 4-aminophenoxy, benzoyl, benzyl, benzyloxy, 5-bromo-2-fluorophenoxy, 4-bromo-3-fluorophenoxy, 4-bromo-2-nitrophenoxy, 3-bromobenzyloxy, 4-bromobenzyloxy, 4-bromophenoxy, 5-bromopyrid-2-yloxy, 4-butoxyphenoxy, chloro, 3-chlorobenzyl, 2-chlorophenoxy, 4-chlorophenoxy, 4-chloro-3-ethylphenoxy, 3-chloro-4-fluorobenzyl, 3-chloro-4-fluorophenyl, 3-chloro-2-fluorobenzyloxy, 3-chlorobenzyloxy, 4-chlorobenzyloxy, 4-chloro-3-methylphenoxy, 2-chloro-4-fluorophenoxy, 4-chloro-2-fluorophenoxy, 4-chlorophenoxy, 3-chloro-4-ethylphenoxy, 3-chloro-4-methylphenoxy, 3-chloro-4-fluorophenoxy, 4-chloro-3-fluorophenoxy, 4-chlorophenylamino, 5-chloropyrid-3-yloxy, 2-cyanopyrid-3-yloxy, 4-cyanophenoxy, cyclobutoxy, cyclobutyl, cyclohexoxy, cyclohexylmethoxy, cyclopentoxy, cyclopentyl, cyclopentylcarbonyl, cyclopropyl, cyclopropylmethoxy, cyclopropoxy, 2,3-dichlorophenoxy, 2,4-dichlorophenoxy, 2,4-dichlorophenyl, 3,5-dichlorophenyl, 3,5-dichlorobenzyl, 3,4-dichlorophenoxy, 3,4-difluorophenoxy, 2,3-difluorobenzyloxy, 2,4-difluorobenzyloxy, 3,4-difluorobenzyloxy, 2,5-difluorobenzyloxy, 3,5-difluorophenoxy, 3,4-difluorophenyl, 3,5-difluorobenzyloxy, 4-difluoromethoxybenzyloxy, 2,3-difluorophenoxy, 2,4-difluorophenoxy, 2,5-difluorophenoxy, 3,5-dimethoxyphenoxy, 3-dimethylaminophenoxy, 3,5-dimethylphenoxy, 3,4-dimethylphenoxy, 3,5-dimethylbenzyl, 3,4-dimethylbenzyloxy, 3,5-dimethylbenzyloxy, 2,2-dimethylpropoxy, 1,3-dioxan-2-yl, 1,4-dioxan-2-yl, 1,3-dioxolan-2-yl, ethoxy, 4-ethoxyphenoxy, 4-ethylbenzyloxy, 3-ethylphenoxy, 4-ethylaminophenoxy, 3-ethyl-5-methylphenoxy, fluoro, 4-fluoro-3-methylbenzyl, 4-fluoro-3- methylphenyl, 4-fluoro-3-methylbenzoyl, 4-fluorobenzyloxy, 2-fluoro-3-methylphenoxy, 3-fluorotmethylphenoxy, 3-fluorophenoxy, 3-fluoro-2-nitrophenoxy, 2-fluoro-3-trifluoromethylbenzyloxy, 3-fluoro-5-trifluoromethylbenzyloxy, 4-fluoro-2-trifluoromethylbenzyloxy, 4-fluoro-3-trifluoromethylbenzyloxy, 2-fluorophenoxy, 4-fluorophenoxy, 2-fluoro-3-trifluoromethylphenoxy, 2-fluorobenzyloxy, 4-fluorophenylamino, 2-fluoro-4-trifluoromethylphenoxy, 4-fluoropyrid-2-yloxy, 2-furyl, 3-furyl, heptafluoropropyl, 1,1,1,3,3,3-hexafluoropropyl, 2-hydroxy-3,3,3-trifluoropropoxy, 3-iodobenzyloxy, isobutyl, isobutylamino, isobutoxy, 3-isoxazolyl, 4-isoxazolyl, 5-isoxazolyl, isopropoxy, isopropyl, 4-isopropylbenzyloxy, 3-isopropylphenoxy, 4-isopropylphenoxy, isopropylthio, 4-isopropyl-3-methylphenoxy, 3-isothiazolyl, 4-isothiazolyl, 5-isothiazolyl, 3-methoxybenzyl, 4-methoxycarbonylbutoxy, 3-methoxycarbonylprop-2-enyloxy, 4-methoxyphenyl, 3-methoxyphenylamino, 4-methoxyphenylamino, 3-methylbenzyloxy, 4-methylbenzyloxy, 3-methylphenoxy, 3-methyl-4-methylthiophenoxy, 4-methylphenoxy, 1-methylpropoxy, 2-methylpyrid-5-yloxy, 4-methylthiophenoxy, 2-naphthyloxy, 2-nitrophenoxy, 4-nitrophenoxy, 3-nitrophenyl, 4-nitrophenylthio, 2-oxazolyl, 4-oxazolyl, 5-oxazolyl, pentafluoroethyl, pentafluoroethylthio, 2,2,3,3,3-pentafluoropropyl, 1,1,3,3,3-pentafluoropropyl, 1,1,2,2,3-pentafluoropropyl, phenoxy, phenylamino, 1-phenylethoxy, phenylsulfonyl, 4-propanoylphenoxy, propoxy, 4-propylphenoxy, 4-propoxyphenoxy, thiophen-3-yl, sec-butyl, 4sec-butylphenoxy,tert-butoxy, 3-tert-butylphenoxy, 4-tert-butylphenoxy, 1,1,2,2-tetrafluoroethoxy, tetrahydrofuran-2-yl, 2-(5,6,7,8-tetrahydronaphthyloxy), thiazol-2-yl, thiazol-4-yl, thiazol-5-yl, thiophen-2-yl, 2,3,5-trifluorobenzyloxy, 2,2,2-trifluoroethoxy, 2,2,2-trifluoroethyl, 3,3,3-trifluoro-2-hydroxypropyl, trifluoromethoxy, 3-trifluoromethoxybenzyloxy, 4-trifluoromethoxybenzyloxy, 3-trifluoromethoxyphenoxy, 4-trifluoromethoxyphenoxy, trifluoromethyl, 3-trifluoromethylbenzyloxy, 4-trifluoromethylbenzyloxy, 2,4-bis-trifluoromethylbenzyloxy, 1,1-bis-trifluoromethyl-1-hydroxymethyl, 3-trifluoromethylbenzyl, 3,5-bis-trifluoromethylbenzyloxy, 4-trifluoromethylphenoxy, 3-trifluoromethylphenoxy, 3-trifluoromethylphenyl, 3-trifluoromethylthiobenzyloxy, 4-trifluoromethylthiobenzyloxy, 2,3,4-trifluorophenoxy, 2,3,4-trifluorophenyl, 2,3,5-trifluorophenoxy, 3,4,5-trimethylphenoxy, 3-difluoromethoxyphenoxy, 3-pentafluoroethylphenoxy, 3-(1,1,2,2-tetrafluoroethoxy)phenoxy, 3-trifluoromethylthiophenoxy, and trifluoromethylthio;

$R_6$ and $R_{11}$ are independently selected from the group consisting of chloro, fluoro, hydrido, pentafluoroethyl, 1,1,2,2-tetrafluoroethoxy, trifluoromethyl, and trifluoromethoxy;

$R_7$ and $R_{12}$ are independently selected from the group consisting of hydrido, fluoro, and trifluoromethyl.

DEFINITIONS

The use of generic terms in the description of the compounds are herein defined for clarity.

Standard single letter elemental symbols are used to represent specific types of atoms unless otherwise defined. The symbol "C" represents a carbon atom. The symbol "O" represents an oxygen atom. The symbol "N" represents a nitrogen atom. The symbol "P" represents a phosphorus atom. The symbol "S" represents a sulfur atom. The symbol "H" represents a hydrogen atom. Double letter elemental symbols are used as defined for the elements of the periodical table (i.e., Cl represents chlorine, Se represents selenium, etc.).

As utilized herein, the term "alkyl", either alone or within other terms such as "haloalkyl" and "alkylthio", means an acyclic alkyl radical containing from 1 to about 10, preferably from 1 to about 8 carbon atoms and more preferably 1 to about 6 carbon atoms. Said alkyl radicals may be optionally substituted with groups as defined below. Examples of such radicals include methyl, ethyl, hydroxyethyl, n-propyl, oxopropyl, isopropyl, n-butyl, cyanobutyl, isobutyl, sec-butyl, tert-butyl, pentyl, aminopentyl, iso-amyl, hexyl, octyl and the like.

The term "alkenyl" refers to an unsaturated, acyclic hydrocarbon radical in so much as it contains at least one double bond. Such alkenyl radicals contain from about 2 to about 10 carbon atoms, preferably from about 2 to about 8 carbon atoms and more preferably 2 to about 6 carbon atoms. Said alkenyl radicals may be optionally substituted with groups as defined below. Examples of suitable alkenyl radicals include propenyl, buten-1-yl, isobutenyl, penten-1-yl, 2-2-methylbuten-1-yl, 3-methylbuten-1-yl, hexen-1-yl, 3-hydroxyhexen-1-yl, hepten-1-yl, and octen-1-yl, and the like.

The term "alkynyl" refers to an unsaturated, acyclic hydrocarbon radical in so much as it contains one or more triple bonds, such radicals containing about 2 to about 10 carbon atoms, preferably having from about 2 to about 8 carbon atoms and more preferably having 2 to about 6 carbon atoms. Said alkynyl radicals may be optionally substituted with groups as defined below. Examples of suitable alkynyl radicals include ethynyl, propynyl, hydroxypropynyl, butyn-1-yl, butyn-2-yl, pentyn-1-yl, pentyn-2-yl, 4-methoxypentyn-2-yl, 3-methylbutyn-1-yl, hexyn-1-yl, hexyn-2-yl, hexyn-3-yl, 3,3-dimethylbutyn-1-yl radicals and the like.

The term "hydrido" denotes a single hydrogen atom (H). This hydrido radical may be attached, for example, to an oxygen atom to form a "hydroxyl" radical, one hydrido radical may be attached to a carbon atom to form a "methine" radical (=CH—), or two hydrido radicals may be attached to a carbon atom to form a "methylene" (—CH$_2$—) radical.

The term "carbon" radical denotes a carbon atom without any covalent bonds and capable of forming four covalent bonds.

The term "cyano" radical denotes a carbon radical having three of four covalent bonds shared by a nitrogen atom.

The term "hydroxyalkyl" embraces radicals wherein any one or more of the alkyl carbon atoms is substituted with a hydroxyl as defined above. Specifically embraced are monohydroxyalkyl, dihydroxyalkyl and polyhydroxyalkyl radicals.

The term "alkanoyl" embraces radicals wherein one or more of the terminal alkyl carbon atoms are substituted with one or more carbonyl radicals as defined below. Specifically embraced are monocarbonylalkyl and dicarbonylalkyl radicals. Examples of monocarbonylalkyl radicals include formyl, acetyl, and pentanoyl. Examples of dicarbonylalkyl radicals include oxalyl, malonyl, and succinyl.

The term "alkylene" radical denotes linear or branched radicals having from 1 to about 10 carbon atoms and having attachment points for two or more covalent bonds. Examples of such radicals are methylene, ethylene, ethylidene, methylethylene, and isopropylidene.

The term "alkenylene" radical denotes linear or branched radicals having from 2 to about 10 carbon atoms, at least one double bond, and having attachment points for two or more covalent bonds. Examples of such radicals are 1,1-vinylidene ($CH_2$=C), 1,2-vinylidene (—CH=CH—), and 1,4-butadienyl (—CH=CH—CH=CH—).

The term "halo" means halogens such as fluorine, chlorine, bromine or iodine atoms.

The term "haloalkyl" embraces radicals wherein any one or more of the alkyl carbon atoms is substituted with halo as defined above. Specifically embraced are monohaloalkyl, dihaloalkyl and polyhaloalkyl radicals. A monohaloalkyl radical, for one example, may have either a bromo, chloro or a fluoro atom within the radical. Dihalo radicals may have two or more of the same halo atoms or a combination of different halo radicals and polyhaloalkyl radicals may have more than two of the same halo atoms or a combination of different halo radicals. More preferred haloalkyl radicals are "lower haloalkyl" radicals having one to about six carbon atoms. Examples of such haloalkyl radicals include fluoromethyl, difluoromethyl, trifluoromethyl, chloromethyl, dichloromethyl, trichloromethyl, trifluoroethyl, pentafluoroethyl, heptafluoropropyl, difluorochloromethyl, dichlorofluoromethyl, difluoroethyl, difluoropropyl, dichloroethyl and dichloropropyl.

The term "hydroxyhaloalkyl" embraces radicals wherein any one or more of the haloalkyl carbon atoms is substituted with hydroxy as defined above. Examples of "hydroxyhaloalkyl" radicals include hexafluorohydoxypropyl.

The term "haloalkylene radical" denotes alkylene radicals wherein any one or more of the alkylene carbon atoms is substituted with halo as defined above. Dihalo alkylene radicals may have two or more of the same halo atoms or a combination of different halo radicals and polyhaloalkylene radicals may have more than two of the same halo atoms or a combination of different halo radicals. More preferred haloalkylene radicals are "lower haloalkylene" radicals having one to about six carbon atoms. Examples of "haloalkylene" radicals include difluoromethylene, tetrafluoroethylene, tetrachloroethylene, alkyl substituted monofluoromethylene, and aryl substituted trifluoromethylene.

The term "haloalkenyl" denotes linear or branched radicals having from 1 to about 10 carbon atoms and having one or more double bonds wherein any one or more of the alkenyl carbon atoms is substituted with halo as defined above. Dihaloalkenyl radicals may have two or more of the same halo atoms or a combination of different halo radicals and polyhaloalkenyl radicals may have more than two of the same halo atoms or a combination of different halo radicals.

The terms "alkoxy" and "alkoxyalkyl" embrace linear or branched oxy-containing radicals each having alkyl portions of one to about ten carbon atoms, such as methoxy radical. The term "alkoxyalkyl" also embraces alkyl radicals having one or more alkoxy radicals attached to the alkyl radical, that is, to form monoalkoxyalkyl and dialkoxyalkyl radicals. More preferred alkoxy radicals are "lower alkoxy" radicals having one to six carbon atoms. Examples of such radicals include methoxy, ethoxy, propoxy, butoxy, isopropoxy and tert-butoxy alkyls. The "alkoxy" radicals may be further substituted with one or more halo atoms, such as fluoro, chloro or bromo, to provide "haloalkoxy" and "haloalkoxyalkyl" radicals. Examples of such haloalkoxy radicals include fluoromethoxy, chloromethoxy, trifluoromethoxy, difluoromethoxy, trifluoroethoxy, fluoroethoxy, tetrafluoroethoxy, pentafluoroethoxy, and fluoropropoxy. Examples of such haloalkoxyalkyl radicals include fluoromethoxymethyl, chloromethoxyethyl, trifluoromethoxymethyl, difluoromethoxyethyl, and trifluoroethoxymethyl.

The terms "alkenyloxy" and "alkenyloxyalkyl" embrace linear or branched oxy-containing radicals each having alkenyl portions of two to about ten carbon atoms, such as ethenyloxy or propenyloxy radical. The term "alkenyloxyalkyl" also embraces alkenyl radicals having one or more alkenyloxy radicals attached to the alkyl radical, that is, to form monoalkenyloxyalkyl and dialkenyloxyalkyl radicals. More preferred alkenyloxy radicals are "lower alkenyloxy" radicals having two to six carbon atoms. Examples of such radicals include ethenyloxy, propenyloxy, butenyloxy, and isopropenyloxy alkyls. The "alkenyloxy" radicals may be further substituted with one or more halo atoms, such as fluoro, chloro or bromo, to provide "haloalkenyloxy" radicals. Examples of such radicals include trifluoroethenyloxy, fluoroethenyloxy, difluoroethenyhloxy, and fluoropropenyloxy.

The term "haloalkoxyalkyl" also embraces alkyl radicals having one or more haloalkoxy radicals attached to the alkyl radical, that is, to form monohaloalkoxyalkyl and dihaloalkoxyalkyl radicals. The term "haloalkenyloxy" also embraces oxygen radicals having one or more haloalkenyloxy radicals attached to the oxygen radical, that is, to form monohaloalkenyloxy and dihaloalkenyloxy radicals. The term "haloalkenyloxyalkyl" also embraces alkyl radicals having one or more haloalkenyloxy radicals attached to the alkyl radical, that is, to form monohaloalkenyloxyalkyl and dihaloalkenyloxyalkyl radicals.

The term "alkylenedioxy" radicals denotes alkylene radicals having at least two oxygens bonded to a single alkylene group. Examples of "alkylenedioxy" radicals include methylenedioxy, ethylenedioxy, alkylsubstituted methylenedioxy, and arylsubstituted methylenedioxy. The term "haloalkylenedioxy" radicals denotes haloalkylene radicals having at least two oxy groups bonded to a single haloalkyl group. Examples of "haloalkylenedioxy" radicals include difluoromethylenedioxy, tetrafluoroethylenedioxy, tetrachloroethylenedioxy, alkylsubstituted monofluoromethylenedioxy, and arylsubstituted monofluoromethylenedioxy.

The term "aryl", alone or in combination, means a carbocyclic aromatic system containing one, two or three rings wherein such rings may be attached together in a pendant manner or may be fused. The term "fused" means that a second ring is present (ie, attached or formed) by having two adjacent atoms in common (ie, shared) with the first ring. The term "fused" is equivalent to the term "condensed". The term "aryl" embraces aromatic radicals such as phenyl, naphthyl, tetrahydronaphthyl, indane and biphenyl.

The term "perhaloaryl" embraces aromatic radicals such as phenyl, naphthyl, tetrahydronaphthyl, indane and biphenyl wherein the aryl radical is substituted with 3 or more halo radicals as defined below.

The term "heterocyclyl" embraces saturated, partially saturated and unsaturated heteroatom-containing ring-shaped radicals having from 5 through ring members selected from carbon, nitrogen, sulfur and oxygen, wherein at least one ring atom is a heteroatom. Heterocyclyl radicals may contain one, two or three rings wherein such rings may be attached in a pendant manner or may be fused. Examples of saturated heterocyclic radicals include saturated 3 to 6-membered heteromonocylic group containing 1 to 4 nitrogen atoms[e.g. pyrrolidinyl, imidazolidinyl, piperidino, piperazinyl, etc.]; saturated 3 to 6-membered heteromonocyclic group containing 1 to 2 oxygen atoms and 1 to 3 nitrogen atoms [e.g. morpholinyl, etc.]; saturated 3 to 6-membered heteromonocyclic group containing 1 to 2 sulfur atoms and 1 to 3 nitrogen atoms [e.g., thiazolidinyl, etc.]. Examples of partially saturated heterocyclyl radicals include dihydrothiophene, dihydropyran, dihydrofuran and dihydrothiazole. Examples of unsaturated heterocyclic radicals, also termed "heteroaryl" radicals, include unsaturated 5 to 6 membered heteromonocyclyl group containing 1 to 4 nitrogen atoms, for example, pyrrolyl, pyrrolinyl, imidazolyl, pyrazolyl, 2-pyridyl, 3-pyridyl, 4-pyridyl, pyrimidyl, pyrazinyl, pyridazinyl, triazolyl [e.g., 4H-1,2,4-triazolyl, 1H-1,2,3-triazolyl, 2H-1,2,3-triazolyl, etc.] tetrazolyl [e.g. 1H-tetrazolyl, 2H-tetrazolyl, etc.], etc.; unsaturated condensed heterocyclic group containing 1 to 5 nitrogen atoms, for example, indolyl, isoindolyl, indolizinyl, benzimidazolyl, quinolyl, isoquinolyl, indazolyl, benzotriazolyl, tetrazolopyridazinyl [e.g., tetrazolo [1,5-b] pyridazinyl, etc.], etc.; unsaturated 3 to 6-membered heteromonocyclic group containing an oxygen atom, for example, pyranyl, 2-furyl, 3-furyl, etc.; unsaturated 5 to 6-membered heteromonocyclic group containing a sulfur atom, for example, 2-thienyl, 3-thienyl, etc.; unsaturated 5- to 6-membered heteromonocyclic group containing 1 to 2 oxygen atoms and 1 to 3 nitrogen atoms, for example, oxazolyl, isoxazolyl, oxadiazolyl [e.g., 1,2,4-oxadiazolyl, 1,3,4-oxadiazolyl, 1,2,5-oxadiazolyl, etc.] etc.; unsaturated condensed heterocyclic group containing 1 to 2 oxygen atoms and 1 to 3 nitrogen atoms [e.g. benzoxazolyl, benzoxadiazolyl, etc.]; unsaturated to 6-membered heteromonocyclic group containing 1 to 2 sulfur atoms and 1 to 3 nitrogen atoms, for example, thiazolyl, thiadiazolyl [e.g., 1,2,4-thiadiazolyl, 1,3,4-thiadiazolyl, 1,2,5-thiadiazolyl, etc.] etc.; unsaturated condensed heterocyclic group containing 1 to 2 sulfur atoms and 1 to 3 nitrogen atoms [e.g., benzothiazolyl, benzothiadiazolyl, etc.] and the like. The term also embraces radicals where heterocyclic radicals are fused with aryl radicals. Examples of such fused bicyclic radicals include benzofuran, benzothiophene, and the like. Said "heterocyclyl" group may have 1 to 3 substituents as defined below. Preferred heterocyclic radicals include five to twelve membered fused or unfused radicals. Non-limiting examples of heterocyclic radicals include pyrrolyl, pyridinyl, pyridyloxy, pyrazolyl, triazolyl, pyrimidinyl, pyridazinyl, oxazolyl, thiazolyl, imidazolyl, indolyl, thiophenyl, furanyl, tetrazolyl, 2-pyrrolinyl, 3-pyrrolinyl, pyrrolindinyl, 1,3-dioxolanyl, 2-imidazolinyl, imidazolidinyl, 2-pyrazolinyl, pyrazolidinyl, isoxazolyl, isothiazolyl, 1,2,3-oxadiazolyl, 1,2,3-triazolyl, 1,3,4-thiadiazolyl, 2H-pyranyl, 4H-pyranyl, piperidinyl, 1,4-dioxanyl, morpholinyl, 1,4-dithianyl, thiomorpholinyl, pyrazinyl, piperazinyl, 1,3,5-triazinyl, 1,3,5-trithianyl, benzo(b)thiophenyl, benzimidazoyl, quinolinyl, tetraazolyl, and the like.

The term "sulfonyl", whether used alone or linked to other terms such as alkylsulfonyl, denotes respectively divalent radicals —SO$_2$—. "Alkylsulfonyl", embraces alkyl radicals attached to a sulfonyl radical, where alkyl is defined as above. "Alkylsulfonylalkyl", embraces alkylsulfonyl radicals attached to an alkyl radical, where alkyl is defined as above. "Haloalkylsulfonyl", embraces haloalkyl radicals attached to a sulfonyl radical, where haloalkyl is defined as above. "Haloalkylsulfonylalkyl", embraces haloalkylsulfonyl radicals attached to an alkyl radical, where alkyl is defined as above. The term "aminosulfonyl" denotes an amino radical attached to a sulfonyl radical.

The term "sulfinyl", whether used alone or linked to other terms such as alkylsulfinyl, denotes respectively divalent radicals —S(O)—. "Alkylsulfinyl", embraces alkyl radicals attached to a sulfinyl radical, where alkyl is defined as above. "Alkylsulfinylalkyl", embraces alkylsulfinyl radicals attached to an alkyl radical, where alkyl is defined as above. "Haloalkylsulfinyl", embraces haloalkyl radicals attached to a sulfinyl radical, where haloalkyl is defined as above. "Haloalkylsulfinylalkyl", embraces haloalkylsulfinyl radicals attached to an alkyl radical, where alkyl is defined as above.

The term "aralkyl" embraces aryl-substituted alkyl radicals. Preferable aralkyl radicals are "lower aralkyl" radicals having aryl radicals attached to alkyl radicals having one to six carbon atoms. Examples of such radicals include benzyl, diphenylmethyl, triphenylmethyl, phenylethyl and diphenylethyl. The terms benzyl and phenylmethyl are interchangeable.

The term "heteroaralkyl" embraces heteroaryl-substituted alkyl radicals wherein the heteroaralkyl radical may be additionally substituted with three or more substituents as defined above for aralkyl radicals. The term "perhaloaralkyl" embraces aryl-substituted alkyl radicals wherein the aralkyl radical is substituted with three or more halo radicals as defined above.

The term "aralkylsulfinyl", embraces aralkyl radicals attached to a sulfinyl radical, where aralkyl is defined as above. "Aralkylsulfinylalkyl", embraces aralkylsulfinyl radicals attached to an alkyl radical, where alkyl is defined as above.

The term "aralkylsulfonyl", embraces aralkyl radicals attached to a sulfonyl radical, where aralkyl is defined as above. "Aralkylsulfonylalkyl", embraces aralkylsulfonyl radicals attached to an alkyl radical, where alkyl is defined as above.

The term "cycloalkyl" embraces radicals having three to ten carbon atoms. More preferred cycloalkyl radicals are "lower cycloalkyl" radicals having three to seven carbon atoms. Examples include radicals such as cyclopropyl, cyclobutyl, cyclopentyl, cyclohexyl and cycloheptyl. The term "cycloalkylalkyl" embraces cycloalkyl-substituted alkyl radicals. Preferable cycloalkylalkyl radicals are "lower cycloalkylalkyl" radicals having cycloalkyl radicals attached to alkyl radicals having one to six carbon atoms. Examples of such radicals include cyclohexylhexyl. The term "cycloalkenyl" embraces radicals having three to ten carbon atoms and one or more carbon-carbon double bonds. Preferred cycloalkenyl radicals are "lower cycloalkenyl" radicals having three to seven carbon atoms. Examples include radicals such as cyclobutenyl, cyclopentenyl, cyclohexenyl and cycloheptenyl. The term "halocycloalkyl" embraces radicals wherein any one or more of the cycloalkyl carbon atoms is substituted with halo as defined above. Specifically embraced are monohalocycloalkyl, dihalocycloalkyl and polyhalocycloalkyl radicals. A monohalocycloalkyl radical, for one example, may have either a bromo, chloro or a fluoro atom within the radical. Dihalo radicals may have two or more of the same halo atoms or a combination of different halo radicals and polyhalocycloalkyl radicals may have more than two of the same halo atoms or a combination of different halo radicals. More preferred halocycloalkyl radicals are "lower halocycloalkyl" radicals having three to about eight carbon atoms. Examples of such halocycloalkyl radicals include fluorocyclopropyl, difluorocyclobutyl, trifluorocyclopentyl, tetrafluorocyclohexyl, and dichlorocyclopropyl. The term "halocycloalkenyl" embraces radicals wherein any one or more of the cycloalkenyl carbon atoms is substituted with halo as defined above. Specifically embraced are monohalocycloalkenyl, dihalocycloalkenyl and polyhalocycloalkenyl radicals.

The term "cycloalkoxy" embraces cycloalkyl radicals attached to an oxy radical. Examples of such radicals includes cyclohexoxy and cyclopentoxy. The term "cycloalkoxyalkyl" also embraces alkyl radicals having one or more cycloalkoxy radicals attached to the alkyl radical, that is, to form monocycloalkoxyalkyl and dicycloalkoxyalkyl radicals. Examples of such radicals include cyclohexoxyethyl. The "cycloalkoxy" radicals may be further substituted with one or more halo atoms, such as fluoro, chloro or bromo, to provide "halocycloalkoxy" and "halocycloalkoxyalkyl" radicals.

The term "cycloalkylalkoxy" embraces cycloalkyl radicals attached to an alkoxy radical. Examples of such radicals includes cyclohexylmethoxy and cyclopentylmethoxy.

The term "cycloalkenyloxy" embraces cycloalkenyl radicals attached to an oxy radical. Examples of such radicals includes cyclohexenyloxy and cyclopentenyloxy. The term "cycloalkenyloxyalkyl" also embraces alkyl radicals having one or more cycloalkenyloxy radicals attached to the alkyl radical, that is, to form monocycloalkenyloxyalkyl and dicycloalkenyloxyalkyl radicals. Examples of such radicals include cyclohexenyloxyethyl. The "cycloalkenyloxy" radicals may be further substituted with one or more halo atoms, such as fluoro, chloro or bromo, to provide "halocycloalkenyloxy" and "halocycloalkenyloxyalkyl" radicals.

The term "cycloalkylenedioxy" radicals denotes cycloalkylene radicals having at least two oxygens bonded to a single cycloalkylene group. Examples of "alkylenedioxy" radicals include 1,2-dioxycyclohexylene.

The term "cycloalkylsulfinyl", embraces cycloalkyl radicals attached to a sulfinyl radical, where cycloalkyl is defined as above. "Cycloalkylsulfinylalkyl", embraces cycloalkylsulfinyl radicals attached to an alkyl radical, where alkyl is defined as above. The term "Cycloalkylsulfonyl", embraces cycloalkyl radicals attached to a sulfonyl radical, where cycloalkyl is defined as above. "Cycloalkylsulfonylalkyl", embraces cycloalkylsulfonyl radicals attached to an alkyl radical, where alkyl is defined as above.

The term "cycloalkylalkanoyl" embraces radicals wherein one or more of the cycloalkyl carbon atoms are substituted with one or more carbonyl radicals as defined below. Specifically embraced are monocarbonylcycloalkyl and dicarbonylcycloalkyl radicals. Examples of monocarbonylcycloalkyl radicals include cyclohexylcarbonyl, cyclohexylacetyl, and cyclopentylcarbonyl. Examples of dicarbonylcycloalkyl radicals include 1,2-dicarbonylcyclohexane.

The term "alkylthio" embraces radicals containing a linear or branched alkyl radical, of one to ten carbon atoms, attached to a divalent sulfur atom. More preferred alkylthio radicals are "lower alkylthio" radicals having one to six carbon atoms. An example of "lower alkylthio" is methylthio ($CH_3$—S—). The "alkylthio" radicals may be further substituted with one or more halo atoms, such as fluoro, chloro or bromo, to provide "haloalkylthio" radicals. Examples of such radicals include fluoromethylthio, chloromethylthio, trifluoromethylthio, difluoromethylthio, trifluoroethylthio, fluoroethylthio, tetrafluoroethylthio, pentafluoroethylthio, and fluoropropylthio.

The term "alkyl aryl amino" embraces radicals containing a linear or branched alkyl radical, of one to ten carbon atoms, and one aryl radical both attached to an amino radical. Examples include N-methyl-4-methoxyaniline, N-ethyl-4-methoxyaniline, and N-methyl-4-trifluoromethoxyaniline.

The terms alkylamino denotes "monoalkylamino" and "dialkylamino" containing one or two alkyl radicals, respectively, attached to an amino radical.

The terms arylamino denotes "monoarylamino" and "diarylamino" containing one or two aryl radicals, respectively, attached to an amino radical. Examples of such radicals include N-phenylamino and N-naphthylamino.

The term "aralkylamino", embraces aralkyl radicals attached to an amino radical, where aralkyl is defined as above. The term aralkylamino denotes "monoaralkylamino" and "diaralkylamino" containing one or two aralkyl radicals, respectively, attached to an amino radical. The term aralkylamino further denotes "monoalkyl monoalkylamino" containing one aralkyl radical and one alkyl radical attached to an amino radical.

The term "arylsulfinyl" embraces radicals containing an aryl radical, as defined above, attached to a divalent S(=O) atom. The term "arylsulfinylalkyl" denotes arylsulfinyl radicals attached to a linear or branched alkyl radical, of one to ten carbon atoms.

The term "arylsulfonyl", embraces aryl radicals attached to a sulfonyl radical, where aryl is defined as above. "arylsulfonylalkyl", embraces arylsulfonyl radicals attached to an alkyl radical, where alkyl is defined as above. The term "heteroarylsulfinyl" embraces radicals containing an heteroaryl radical, as defined above, attached to a divalent S(=O) atom. The term "heteroarylsulfinylalkyl" denotes heteroarylsulfinyl radicals attached to a linear or branched alkyl radical, of one to ten carbon atoms. The term "Heteroarylsulfonyl", embraces heteroaryl radicals attached to a sulfonyl radical, where heteroaryl is defined as above. "Heteroarylsulfonylalkyl", embraces heteroarylsulfonyl radicals attached to an alkyl radical, where alkyl is defined as above.

The term "aryloxy" embraces aryl radicals, as defined above, attached to an oxygen atom. Examples of such radicals include phenoxy, 4-chloro-3-ethylphenoxy, 4-chloro-3-methylphenoxy, 3-chloro-4-ethylphenoxy, 3,4-dichlorophenoxy, 4-methylphenoxy, 3-trifluoromethoxyphenoxy, 3-trifluoromethylphenoxy, 4-fluorophenoxy, 3,4-dimethylphenoxy, 5-bromo-2-fluorophenoxy, 4-bromo-3-fluorophenoxy, 4-fluoro-3-methylphenoxy, 5,6,7,8-tetrahydronaphthyloxy, 3-isopropylphenoxy, 3-cyclopropylphenoxy, 3-ethylphenoxy, 4-tert-butylphenoxy, 3-pentafluoroethylphenoxy, and 3-(1,1,2,2-tetrafluoroethoxy)phenoxy.

The term "aroyl" embraces aryl radicals, as defined above, attached to an carbonyl radical as defined above. Examples of such radicals include benzoyl and toluoyl.

The term "aralkanoyl" embraces aralkyl radicals, as defined herein, attached to an carbonyl radical as defined above. Examples of such radicals include, for example, phenylacetyl.

The term "aralkoxy" embraces oxy-containing aralkyl radicals attached through an oxygen atom to other radicals.

More preferred aralkoxy radicals are "lower aralkoxy" radicals having phenyl radicals attached to lower alkoxy radical as described above. Examples of such radicals include benzyloxy, 1-phenylethoxy, 3-trifluoromethoxybenzyloxy, 3-trifluoromethylbenzyloxy, 3,5-difluorobenyloxy, 3-bromobenzyloxy, 4-propylbenzyloxy, 2-fluoro-3-trifluoromethylbenzyloxy, and 2-phenylethoxy.

The term "aryloxyalkyl" embraces aryloxy radicals, as defined above, attached to an alkyl group. Examples of such radicals include phenoxymethyl.

The term "haloaryloxyalkyl" embraces aryloxyalkyl radicals, as defined above, wherein one to five halo radicals are attached to an aryloxy group.

The term "heteroaroyl" embraces heteroaryl radicals, as defined above, attached to an carbonyl radical as defined above. Examples of such radicals include furoyl and nicotinyl.

The term "heteroaralkanoyl" embraces heteroaralkyl radicals, as defined herein, attached to an carbonyl radical as defined above. Examples of such radicals include, for example, pyridylacetyl and furylbutyryl.

The term "heteroaralkoxy" embraces oxy-containing heteroaralkyl radicals attached through an oxygen atom to other radicals. More preferred heteroaralkoxy radicals are "lower heteroaralkoxy" radicals having heteroaryl radicals attached to lower alkoxy radical as described above.

The term "haloheteroaryloxyalkyl" embraces heteroaryloxyalkyl radicals, as defined above, wherein one to four halo radicals are attached to an heteroaryloxy group.

The term "heteroarylamino" embraces heterocyclyl radicals, as defined above, attached to an amino group. Examples of such radicals include pyridylamino.

The term "heteroarylaminoalkyl" embraces heteroarylamino radicals, as defined above, attached to an alkyl group. Examples of such radicals include pyridylmethylamino.

The term "heteroaryloxy" embraces heterocyclyl radicals, as defined above, attached to an oxy group. Examples of such radicals include 2-thiophenyloxy, 2-pyrimidyloxy, 2-pyridyloxy, 3-pyridyloxy, and 4-pyridyloxy.

The term "heteroaryloxyalkyl" embraces heteroaryloxy radicals, as defined above, attached to an alkyl group. Examples of such radicals include 2-pyridyloxymethyl, 3-pyridyloxyethyl, and 4-pyridyloxymethyl.

The term "arylthio" embraces aryl radicals, as defined above, attached to an sulfur atom. Examples of such radicals include phenylthio.

The term "arylthioalkyl" embraces arylthio radicals, as defined above, attached to an alkyl group. Examples of such radicals include phenylthiomethyl.

The term "alkylthioalkyl" embraces alkylthio radicals, as defined above, attached to an alkyl group. Examples of such radicals include methylthiomethyl.

The term "alkoxyalkyl" embraces alkoxy radicals, as defined above, attached to an alkyl group. Examples of such radicals include methoxymethyl.

The term "carbonyl" denotes a carbon radical having two of the four covalent bonds shared with an oxygen atom. The term "carboxy" embraces a hydroxyl radical, as defined above, attached to one of two unshared bonds in a carbonyl group. The term "carboxamide" embraces amino, monoalkylamino, dialkylamino, monocycloalkylamino, alkylcycloalkylamino, and dicycloalkylamino radicals, attached to one of two unshared bonds in a carbonyl group. The term "carboxamidoalkyl" embraces carboxamide radicals, as defined above, attached to an alkyl group. The term "carboxyalkyl" embraces a carboxy radical, as defined above, attached to an alkyl group. The term "carboalkoxy" embraces alkoxy radicals, as defined above, attached to one of two unshared bonds in a carbonyl group. The term "carboaralkoxy" embraces aralkoxy radicals, as defined above, attached to one of two unshared bonds in a carbonyl group. The term "monocarboalkoxyalkyl" embraces one carboalkoxy radical, as defined above, attached to an alkyl group. The term "dicarboalkoxyalkyl" embraces two carboalkoxy radicals, as defined above, attached to an alkylene group. The term "monocyanoalkyl" embraces one cyano radical, as defined above, attached to an alkyl group. The term "dicyanoalkylene" embraces two cyano radicals, as defined above, attached to an alkyl group. The term "carboalkoxycyanoalkyl" embraces one cyano radical, as defined above, attached to an carboalkoxyalkyl group.

The term "acyl", alone or in combination, means a carbonyl or thionocarbonyl group bonded to a radical selected from, for example, hydrido, alkyl, alkenyl, alkynyl, haloalkyl, alkoxy, alkoxyalkyl, haloalkoxy, aryl, heterocyclyl, heteroaryl, alkylsulfinylalkyl, alkylsulfonylalkyl, aralkyl, cycloalkyl, cycloalkylalkyl, cycloalkenyl, alkylthio, arylthio, amino, alkylamino, dialkylamino, aralkoxy, arylthio, and alkylthioalkyl. Examples of "acyl" are formyl, acetyl, benzoyl, trifluoroacetyl, phthaloyl, malonyl, nicotinyl, and the like. The term "haloalkanoyl" embraces one or more halo radicals, as defined herein, attached to an alkanoyl radical as defined above. Examples of such radicals include, for example, chloroacetyl, trifluoroacetyl, bromopropanoyl, and heptafluorobutanoyl. The term "diacyl", alone or in combination, means having two or more carbonyl or thionocarbonyl groups bonded to a radical selected from, for example, alkylene, alkenylene, alkynylene, haloalkylene, alkoxyalkylene, aryl, heterocyclyl, heteroaryl, aralkyl, cycloalkyl, cycloalkylalkyl, and cycloalkenyl. Examples of "diacyl" are phthaloyl, malonyl, succinyl, adipoyl, and the like.

The term "benzylidenyl" radical denotes substituted and unsubstituted benzyl groups having attachment points for two covalent bonds. One attachment point is through the methylene of the benzyl group with the other attachment point through an ortho carbon of the phenyl ring. The methylene group is designated for attached to the lowest numbered position. Examples include the base compound benzylidene of structure:

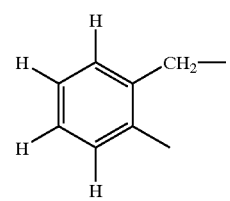

The term "phenoxylidenyl" radical denotes substituted and unsubstituted phenoxy groups having attachment points for two covalent bonds. One attachment point is through the oxy of the phenoxy group with the other attachment point through an ortho carbon of the phenyl ring. The oxy group is designated for attached to the lowest numbered position. Examples include the base compound phenoxylidene of structure:

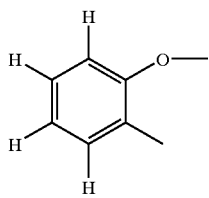

The term "phosphono" embraces a pentavalent phosphorus attached with two covalent bonds to an oxygen radical. The term "dialkoxyphosphono" denotes two alkoxy radicals, as defined above, attached to a phosphono radical with two covalent bonds. The term "diaralkoxyphosphono" denotes two aralkoxy radicals, as defined above, attached to a phosphono radical with two covalent bonds. The term "dialkoxyphosphonoalkyl" denotes dialkoxyphosphono radicals, as defined above, attached to an alkyl radical. The term "diaralkoxyphosphonoalkyl" denotes diaralkoxyphosphono radicals, as defined above, attached to an alkyl radical.

Said "alkyl", "alkenyl", "alkynyl", "alkanoyl", "alkylene", "alkenylene", "benzylidenyl", "phenoxylidenyl", "hydroxyalkyl", "haloalkyl", "haloalkylene", "haloalkenyl", "alkoxy", "alkenyloxy", "alkenyloxyalkyl", "alkoxyalkyl", "aryl", "perhaloaryl", "haloalkoxy", "haloalkoxyalkyl", "haloalkenyloxy", "haloalkenyloxyalkyl", "alkylenedioxy", "haloalkylenedioxy", "heterocyclyl", "heteroaryl", "hydroxyhaloalkyl", "alkylsulfonyl", "haloalkylsulfonyl", "alkylsulfonylalkyl", "haloalkylsulfonylalkyl", "alkylsulfinyl", "alkylsulfinylalkyl", "haloalkylsulfinylalkyl", "aralkyl", "heteroaralkyl", "perhaloaralkyl", "aralkylsulfonyl", "aralkylsulfonylalkyl", "aralkylsulfinyl", "aralkylsulfinylalkyl", "cycloalkyl", "cycloalkylalkanoyl", "cycloalkylalkyl", "cycloalkenyl", "halocycloalkyl", "halocycloalkenyl", "cycloalkylsulfinyl", "cycloalkylsulfinylalkyl", "cycloalkylsulfonyl", "cycloalkylsulfonylalkyl", "cycloalkoxy", "cycloalkoxyalkyl", "cycloalkylalkoxy", "cycloalkenyloxy", "cycloalkenyloxyalkyl", "cycloalkylenedioxy", "halocycloalkoxy", "halocycloalkoxyalkyl", "halocycloalkenyloxy", "halocycloalkenyloxyalkyl", "alkylthio", "haloalkylthio", "alkylsulfinyl", "amino", "oxy", "thio", "alkylamino", "arylamino", "aralkylamino", "arylsulfinyl", "arylsulfinylalkyl", "arylsulfonyl", "arylsulfonylalkyl", "heteroarylsulfinyl", "heteroarylsulfinylalkyl", "heteroarylsulfonyl", "heteroarylsulfonylalkyl", "heteroarylamino", "heteroarylaminoalkyl", "heteroaryloxy", "heteroaryloxylalkyl", "aryloxy", "aroyl", "aralkanoyl", "aralkoxy", "aryloxyalkyl", "haloaryloxyalkyl", "heteroaroyl", "heteroaralkanoyl", "heteroaralkoxy", "heteroaralkoxyalkyl", "arylthio", "arylthioalkyl", "alkoxyalkyl", "acyl" and "diacyl" groups defined above may optionally have 1 to 5 non-hydrido substituents such as perhaloaralkyl, aralkylsulfonyl, aralkylsulfonylalkyl, aralkylsulfinyl, aralkylsulfinylalkyl, halocycloalkyl, halocycloalkenyl, cycloalkylsulfinyl, cycloalkylsulfinylalkyl, cycloalkylsulfonyl, cycloalkylsulfonylalkyl, heteroarylamino, N-heteroarylamino-N-alkylamino, heteroarylaminoalkyl, heteroaryloxy, heteroaryloxylalkyl, haloalkylthio, alkanoyloxy, alkoxy, alkoxyalkyl, haloalkoxyalkyl, heteroaralkoxy, cycloalkoxy, cycloalkenyloxy, cycloalkoxyalkyl, cycloalkylalkoxy, cycloalkenyloxyalkyl, cycloalkylenedioxy, halocycloalkoxy, halocycloalkoxyalkyl, halocycloalkenyloxy, halocycloalkenyloxyalkyl, hydroxy, amino, thio, nitro, lower alkylamino, alkylthio, alkylthioalkyl, arylamino, aralkylamino, arylthio, arylthioalkyl, heteroaralkoxyalkyl, alkylsulfinyl, alkylsulfinylalkyl, arylsulfinylalkyl, arylsulfonylalkyl, heteroarylsulfinylalkyl, heteroarylsulfonylalkyl, alkylsulfonyl, alkylsulfonylalkyl, haloalkylsulfinylalkyl, haloalkylsulfonylalkyl, alkylsulfonamido, alkylaminosulfonyl, amidosulfonyl, monoalkyl amidosulfonyl, dialkyl amidosulfonyl, monoarylamidosulfonyl, arylsulfonamido, diarylamidosulfonyl, monoalkyl monoaryl amidosulfonyl, arylsulfinyl, arylsulfonyl, heteroarylthio, heteroarylsulfinyl, heteroarylsulfonyl, alkanoyl, alkenoyl, aroyl, heteroaroyl, aralkanoyl, heteroaralkanoyl, haloalkanoyl, alkyl, alkenyl, alkynyl, alkenyloxy, alkenyloxyalky, alkylenedioxy, haloalkylenedioxy, cycloalkyl, cycloalkylalkanoyl, cycloalkenyl, lower cycloalkylalkyl, lower cycloalkenylalkyl, halo, haloalkyl, haloalkenyl, haloalkoxy, hydroxyhaloalkyl, hydroxyaralkyl, hydroxyalkyl, hydoxyheteroaralkyl, haloalkoxyalkyl, aryl, aralkyl, aryloxy, aralkoxy, aryloxyalkyl, saturated heterocyclyl, partially saturated heterocyclyl, heteroaryl, heteroaryloxy, heteroaryloxyalkyl, arylalkyl, heteroarylalkyl, arylalkenyl, heteroarylalkenyl, carboxyalkyl, carboalkoxy, alkoxycarbonyl, carboaralkoxy, carboxamido, carboxamidoalkyl, cyano, carbohaloalkoxy, phosphono, phosphonoalkyl, diaralkoxyphosphono, and diaralkoxyphosphonoalkyl.

The term "spacer" can include a covalent bond and a linear moiety having a backbone of 1 to 7 continous atoms. The spacer may have 1 to 7 atoms of a univalent or multi-valent chain. Univalent chains may be constituted, for example, by a radical selected from =C(H)—, =C(R$_{17}$)—, —O—, —S—, —S(O)—, —S(O)$_2$—, —NH—, —N(R$_{17}$)—, —N=, —CH(OH)—, =C(OH)—, —CH(OR$_{17}$)—, =C(OR$_{17}$)—, and —C(O)— wherein R$_{17}$ is selected from alkyl, alkenyl, alkynyl, aryl, heteroaryl, aralkyl, aryloxyalkyl, alkoxyalkyl, alkylthioalkyl, arylthioalkyl, cycloalkyl, cycloalkylalkyl, haloalkyl, haloalkenyl, haloalkoxyalkyl, perhaloaralkyl, heteroarylalkyl, heteroaryloxyalkyl, heteroarylthioalkyl, and heteroarylalkenyl. Multi-valent chains may consist of a straight chain of 1 or 2 or 3 or 4 or 5 or 6 or 7 atoms or a straight chain of 1 or 2 or 3 or 4 or 5 or 6 atoms with a side chain. The chain may be constituted of one or more radicals selected from: lower alkylene, lower alkenyl, —O—, —O—CH$_2$—, —S—CH$_2$—, —CH$_2$CH$_2$—, ethenyl, —CH=CH(OH)—, —OCH$_2$O—, —O(CH$_2$)$_2$O—, —NHCH$_2$—, —OCH(R$_{17}$)O—, —O(CH$_2$CHR$_{17}$)O—, —OCF$_2$O—, —O(CF$_2$)$_2$O—, —S—, —S(O)—, —S(O)$_2$—, —N(H)—, —N(H)O—, —N(R$_{17}$)O—, —N(R$_{17}$)—, —C(O)—, —C(O)NH—, —C(O)NR$_{17}$—, —N=, —OCH$_2$—, —SCH$_2$—, S(O)CH$_2$—, —CH$_2$C(O)—, —CH(OH)—, =C(OH)—, —CH(OR$_{17}$)—, =C(OR$_{17}$)—, S(O)$_2$CH$_2$—, and —NR$_{17}$CH$_2$— and many other radicals defined above or generally known or ascertained by one of skill-in-the art. Side chains may include substituents such as 1 to 5 non-hydrido substituents such as perhaloaralkyl, aralkylsulfonyl, aralkylsulfonylalkyl, aralkylsulfinyl, aralkylsulfinylalkyl, halocycloalkyl, halocycloalkenyl, cycloalkylsulfinyl, cycloalkylsulfinylalkyl, cycloalkylsulfonyl, cycloalkylsulfonylalkyl, heteroarylamino, N-heteroarylamino-N-alkylamino, heteroarylaminoalkyl, heteroaryloxy, heteroaryloxylalkyl, haloalkylthio, alkanoyloxy, alkoxy, alkoxyalkyl, haloalkoxylalkyl, heteroaralkoxy, cycloalkoxy, cycloalkenyloxy, cycloalkoxyalkyl, cycloalkylalkoxy, cycloalkenyloxyalkyl, cycloalkylenedioxy, halocycloalkoxy, halocycloalkoxyalkyl, halocycloalkenyloxy, halocycloalkenyloxyalkyl, hydroxy, amino, thio, nitro, lower alkylamino, alkylthio, alkylthioalkyl, arylamino, aralkylamino, arylthio, arylthioalkyl, heteroaralkoxyalkyl, alkylsulfinyl, alkylsulfinylalkyl, arylsulfinylalkyl, arylsulfonylalkyl, heteroarylsulfinylalkyl, heteroarylsulfonylalkyl, alkylsulfonyl, alkylsulfonylalkyl, haloalkylsulfinylalkyl, haloalkylsulfonylalkyl, alkylsulfonamido, alkylaminosulfonyl, amidosulfonyl, monoalkyl amidosulfonyl, dialkyl amidosulfonyl, monoarylamidosulfonyl, arylsulfonamido, diarylamidosulfonyl, monoalkyl monoaryl amidosulfonyl, arylsulfinyl, arylsulfonyl, heteroarylthio, heteroarylsulfinyl, heteroarylsulfonyl, alkanoyl, alkenoyl, aroyl, heteroaroyl, aralkanoyl, heteroaralkanoyl, haloalkanoyl, alkyl, alkenyl, alkynyl, alkenyloxy, alkenyloxyalky, alkylenedioxy, haloalkylenedioxy, cycloalkyl, cycloalkenyl, lower cycloalkylalkyl, lower cycloalkenylalkyl, halo, haloalkyl, haloalkenyl, haloalkoxy, hydroxyhaloalkyl, hydroxyaralkyl, hydroxyalkyl, hydoxyheteroaralkyl, haloalkoxyalkyl, aryl, aralkyl, aryloxy, aralkoxy, aryloxyalkyl, saturated heterocyclyl, partially saturated heterocyclyl, heteroaryl, heteroaryloxy, heteroaryloxyalkyl, arylalkyl, heteroarylalkyl, arylalkenyl, heteroarylalkenyl, carboxyalkyl, carboalkoxy, carboaralkoxy, carboxamido, carboxamidoalkyl, cyano, carbohaloalkoxy, phosphono, phosphonoalkyl, diaralkoxyphosphono, and diaralkoxyphosphonoalkyl.

Compounds of the present invention can exist in tautomeric, geometric or stereoisomeric forms. The present invention contemplates all such compounds, including cis- and trans-geometric isomers, E- and Z-geometric isomers, R- and S-enantiomers, diastereomers, d-isomers, l-isomers, and mixtures thereof, as falling within the scope of the invention. Pharmaceutically acceptable sales of such tautomeric, geometric or stereoisomeric forms are also included within the invention.

The terms "cis" and "trans" denote a form of geometric isomerism in which two carbon atoms connected by a double bond will each have a hydrogen atom on the same side of the double bond ("cis") or on opposite sides of the double bond ("trans").

Some of the compounds described contain alkenyl groups, and are meant to include both cis and trans or "E" and "Z" geometric forms.

Some of the compounds described contain one or more stereocenters and are meant to include R, S, and mixtures of R and S forms for each stereocenter present.

Some of the compounds described herein may contain one or more ketonic or aldehydic carbonyl groups or combinations thereof alone or as part of a heterocyclic ring system. Such carbonyl groups may exist in part or principally in the "keto" form and in part or principally as one or more "enol" forms of each aldehyde and ketone group present. Compounds of the present invention having aldehydic or ketonic carbonyl groups are meant to include both "keto" and "enol" tautomeric forms.

Some of the compounds described herein may contain one or more amide carbonyl groups or combinations thereof alone or as part of a heterocyclic ring system. Such carbonyl groups may exist in part or principally in the "keto" form and in part or principally as one or more "enol" forms of each amide group present. Compounds of the present invention having amidic carbonyl groups are meant to include both "keto" and "enol" tautomeric forms. Said amide carbonyl groups may be both oxo (C=O) and thiono (C=S) in type.

Some of the compounds described herein may contain one or more imine or enamine groups or combinations thereof. Such groups may exist in part or principally in the "imine" form and in part or principally as one or more "enamine" forms of each group present. Compounds of the present invention having said imine or enamine groups are meant to include both "imine" and "enamine" tautomeric forms.

The following general synthetic sequences are useful in making the present invention. Abbreviations used in the schemes are as follows: "AA" represents amino acids, "BINAP" represents 2,2'-bis(diphenylphosphino)-1,1'-binaphthyl, "Boc" represents tert-butyloxycarbonyl, "BOP" represents benzotriazol-1-yl-oxy-tris-(dimethylamino), "bu" represents butyl, "dba" represents dibenzylideneacetone, "DCC" represents 1,3-dicyclohexylcarbodiimide, "DIBAH" represents diisobutylaluminum hydride, "DIPEA" represents diisopropylethylamine, "DMF" represents dimethylformamide, "DMSO" represents dimethylsulfoxide, "Fmoc" represents 9-fluorenylmethoxycarbonyl, "LDA" represents lithium diisopropylamide, "PHTH" represents a phthaloyl group, "pnZ" represents 4-nitrobenzyloxycarbonyl, "PTC" represents a phase transfer catalyst, "p-TsOH" represents paratoluenesulfonic acid, "TBAF" represents tetrabutylammonium fluoride, "TBTU" represents 2-(1H-benzotriozole-1-yl)-1,1,3,3-tetramethyl uronium tetrafluoroborate, "TEA" represents triethylamine, "TFA" represents trifluoroacetic acid, "THF" represents tetrahydrofuran, "TMS" represents trimethylsilyl, and "Z" represents benzyloxycarbonyl.

PHARMACEUTICAL UTILITY AND COMPOSITION

The present invention comprises a pharmaceutical composition comprising a therapeutically-effective amount of a compound of Formulas VII-H, VII, VII-2, VII-3, VII-4, and Cyclo-VII, in association with at least one pharmaceutically-acceptable carrier, adjuvant or diluent.

The present invention also comprises a treatment and prophylaxis of coronary artery disease and other CETP-mediated disorders in a subject, comprising administering to the subject having such disorder a therapeutically-effective amount of a compound of Formula VII-H:

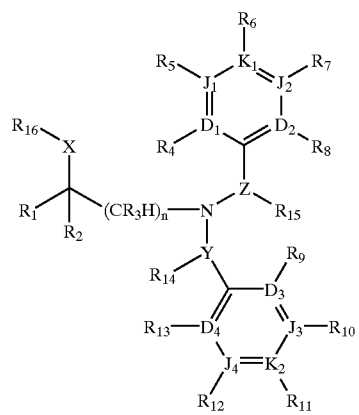

wherein $R_1$, $R_2$, $R_3$, $R_4$, $R_5$, $R_6$, $R_7$, $R_8$, $R_9$, $R_{10}$, $R_{11}$, $R_{12}$, $R_{13}$, $R_{14}$, $R_{15}$, $R_{16}$, X, Y, and Z are as defined above for the compounds of Formula VII-H or a pharmaceutically-acceptable salt thereof.

As a further embodiment, compounds of the present invention of Formulas VII-H, VII, VII-2, VII-3, VII-4, and Cyclo-VII, or a pharmaceutically-acceptable salt thereof as defined above comprise a treatment and prophylaxis of coronary artery disease and other CETP-mediated disorders in a subject, comprising administering to the subject having such disorder a therapeutically-effective amount of compounds of Formulas VII-H, VII, VII-2, VII-3, VII4, and Cyclo-VII, of the present invention or a pharmaceutically-acceptable salt thereof.

Compounds of Formulas VII-H, VII, VII-2, VII-3, VII4, and Cyclo-VII are capable of inhibiting activity of cholesteryl ester transfer protein (CETP), and thus could be used in the manufacture of a medicament, a method for the prophylactic or therapeutic treatment of diseases mediated by CETP, such as peripheral vascular disease, hyperlipidaemia, hypercholesterolemia, and other diseases attributable to either high LDL and low HDL or a combination of both, or a procedure to study the mechanism of action of the cholesteryl ester transfer protein (CETP) to enable the design of better inhibitors. The compounds of Formulas VII-H, VII, VII-2, VII-3, VII-4, and Cyclo-VII would be also useful in prevention of cerebral vascular accident (CVA) or stroke.

Also included in the family of compounds of Formulas VII-H, VII, VII-2, VII-3, VIIA, and Cyclo-VII are the pharmaceutically-acceptable salts thereof. The term "pharmaceutically-acceptable salts" embraces salts commonly used to form alkali metal salts and to form addition salts of free acids or free bases. The nature of the salt is not critical, provided that it is pharmaceutically acceptable. Suitable pharmaceutically-acceptable acid addition salts of compounds of Formula VII-H may be prepared from inorganic acid or from an organic acid. Examples of such inorganic acids are hydrochloric, hydrobromic, hydroiodic, nitric, carbonic, sulfuric and phosphoric acid. Appropriate organic acids may be selected from aliphatic, cycloaliphatic, aromatic, araliphatic, heterocyclic, carboxylic and sulfonic classes of organic acids, examples of which are formic, acetic, propionic, succinic, glycolic, gluconic, lactic, malic, tartaric, citric, ascorbic, glucoronic, maleic, fumaric, pyruvic, aspartic, glutamic, benzoic, anthranilic, mesylic, salicylic, p-hydroxybenzoic, phenylacetic, mandelic, embonic (pamoic), methanesulfonic, ethylsulfonic, benzenesulfonic, sulfanilic, stearic, cyclohexylaminosulfonic, algenic, galacturonic acid. Suitable pharmaceutically-acceptable base addition salts of compounds of Formula VII-H include metallic salts made from aluminum, calcium, lithium, magnesium, potassium, sodium and zinc or organic salts made from N,N'-dibenzylethyleneldiamine, choline, chloroprocaine, diethanolamine, ethylenediamine, meglumine (N-methylglucamine) and procain. All of these salts may be prepared by conventional means from the corresponding compounds of Formulas VII-H, VII, VII-2, VII-3, VII-4, and Cyclo-VII by reacting, for example, the appropriate acid or base with the compounds of Formulas VII-H, VII, VII-2, VII-3, VII4, and Cyclo-VII.

Also embraced within this invention is a class of pharmaceutical compositions comprising the active compounds of Formula VII-H in association with one or more non-toxic, pharmaceutically-acceptable carriers and/or diluents and/or adjuvants (collectively referred to herein as "carrier" materials) and, if desired, other active ingredients. The active compounds of the present invention may be administered by any suitable route, preferably in the form of a pharmaceutical composition adapted to such a route, and in a dose effective for the treatment intended. The active compounds and composition may, for example, be administered orally, intravascularly, intraperitoneally, subcutaneously, intramuscularly or topically.

For oral administration, the pharmaceutical composition may be in the form of, for example, a tablet, capsule, suspension or liquid. The pharmaceutical composition is preferably made in the form of a dosage unit containing a particular amount of the active ingredient. Examples of such dosage units are tablets or capsules. The active ingredient may also be administered by injection as a composition wherein, for example, saline, dextrose or water may be used as a suitable carrier.

The amount of therapeutically active compounds which are administered and the dosage regimen for treating a disease condition with the compounds and/or compositions of this invention depends on a variety of factors, including the age, weight, sex and medical condition of the subject, the severity of the disease, the route and frequency of administration, and the particular compound employed, and thus may vary widely.

The pharmaceutical compositions may contain active ingredients in the range of about 0.1 to 2000 mg, and preferably in the range of about 0.5 to 500 mg. A daily dose of about 0.01 to 100 mg/kg body weight, and preferably between about 0.5 and about 20 mg/kg body weight, may be appropriate. The daily dose can be administered in one to four doses per day.

The compounds may be formulated in topical ointment or cream, or as a suppository, containing the active ingredients in a total amount of, for example, 0.075 to 30% w/w, preferably 0.2 to 20% w/w and most preferably 0.4 to 15% w/w. When formulated in an ointment, the active ingredients may be employed with either paraffinic or a water-miscible ointment base. Alternatively, the active ingredients may be formulated in a cream with an oil-in-water cream base. If desired, the aqueous phase of the cream base may include, for example at least 30% w/w of a polyhydric alcohol such as propylene glycol, butane-1,3-diol, mannitol, sorbitol, glycerol, polyethylene glycol and mixtures thereof. The topical formulation may desirably include a compound which enhances absorption or penetration of the active ingredient through the skin or other affected areas. Examples of such dermal penetration enhancers include dimethylsulfoxide and related analogs. The compounds of this invention can also be administered by a transdermal device. Preferably topical administration will be accomplished using a patch either of the reservoir and porous membrane type or of a solid matrix variety. In either case, the active agent is delivered continuously from the reservoir or microcapsules through a membrane into the active agent permeable adhesive, which is in contact with the skin or mucosa of the recipient. If the active agent is absorbed through the skin, a controlled and predetermined flow of the active agent is administered to the recipient. In the case of microcapsules, the encapsulating agent may also function as the membrane.

The oily phase of the emulsions of this invention may be constituted from known ingredients in a known manner. While the phase may comprise merely an emulsifier, it may comprise a mixture of at least one emulsifier with a fat or an oil or with both a fat and an oil. Preferably, a hydrophilic emulsifier is included together with a lipophilic emulsifier which acts as a stabilizer. It is also preferred to include both an oil and a fat. Together, the emulsifier(s) with or without stabilizer(s) make-up the so-called emulsifying wax, and the wax together with the oil and fat make up the so-called emulsifying ointment base which forms the oily dispersed phase of the cream formulations. Emulsifiers and emulsion stabilizers suitable for use in the formulation of the present invention include Tween 60, Span 80, cetostearyl alcohol, myristyl alcohol, glyceryl monostearate, and sodium lauryl sulfate, among others.

The choice of suitable oils or fats for the formulation is based on achieving the desired cosmetic properties, since the solubility of the active compound in most oils likely to be used in pharmaceutical emulsion formulations is very low. Thus, the cream should preferably be a non-greasy, non-staining and washable product with suitable consistency to avoid leakage from tubes or other containers. Straight or branched chain, mono- or dibasic alkyl esters such as di-isoadipate, isocetyl stearate, propylene glycol diester of coconut fatty acids, isopropyl myristate, decyl oleate, isopropyl palmitate, butyl stearate, 2-ethylhexyl palmitate or a blend of branched chain esters may be used. These may be used alone or in combination depending on the properties required. Alternatively, high melting point lipids such as white soft paraffin and/or liquid paraffin or other mineral oils can be used.

For therapeutic purposes, the active compounds of this combination invention are ordinarily combined with one or more adjuvants appropriate to the indicated route of administration. If administered per os, the compounds may be admixed with lactose, sucrose, starch powder, cellulose esters of alkanoic acids, cellulose alkyl esters, talc, stearic acid, magnesium stearate, magnesium oxide, sodium and calcium salts of phosphoric and sulfuric acids, gelatin, acacia gum, sodium alginate, polyvinylpyrrolidone, and/or polyvinyl alcohol, and then tableted or encapsulated for convenient administration. Such capsules or tablets may contain a controlled-release formulation as may be provided in a dispersion of active compound in hydroxypropylmethyl cellulose. Formulations for parenteral administration may be in the form of aqueous or non-aqueous isotonic sterile injection solutions or suspensions. These solutions and suspensions may be prepared from sterile powders or granules having one or more of the carriers or diluents mentioned for use in the formulations for oral administration. The compounds may be dissolved in water, polyethylene glycol, propylene glycol, ethanol, corn oil, cottonseed oil, peanut oil, sesame oil, benzyl alcohol, sodium chloride, and/or various buffers. Other adjuvants and modes of administration are well and widely known in the pharmaceutical art.

All mentioned references are incorporated by reference as if here written.

Although this invention has been described with respect to specific embodiments, the details of these embodiments are not to be construed as limitations.

GENERAL SYNTHETIC PROCEDURES

The compounds of the present invention can be synthesized, for example, according to the following procedures of Schemes 1 through 15 below, wherein the substituents are as defined for Formulas VII-H, VII, VII-2, VII-3, VII-4, and Cyclo-VII above except where further noted.

Synthetic Scheme 1 shows the preparation of compounds of formula XIIIA-H ("Secondary Heteroaryl Amines") which are intermediates in the preparation of the compounds of the present invention corresponding to Formula VII ("Generic Substituted Polycyclic Aryl tertiary-2-hydroxyalkylamines" and "Isomeric Generic Substituted Polycyclic Aryl tertiary-2-hydroxyalkylamines") and Formula VII-H ("Generic Substituted Polycyclic Heteroaryl tertiary 2-Heteroalkylamines", "Generic Substituted Polycyclic Heteroaryl tertiary-2-hydroxyalkylamines", "Isomeric Generic Substituted Polycyclic Heteroaryl tertiary 2-Heteroalkylamines", or "Isomeric Generic Substituted Polycyclic Heteroaryl tertiary-2-hydroxyalkylamines") wherein the heteroaryl amine (X-AH), Heteroaryl Bromide (XXI-AH), and Heteroaryl Carbonyl (XI-AH) can independently be both aryl and heteroaryl in type. Schemes 1 through 3, taken together, prepare tertiary heteroalkylamine compounds of the present invention by addition of a halogenated, heteroatom (for example, oxygen, sulfur, or nitrogen) containing precursor to a secondary amine to introduce a heteroatom containing alkyl group wherein the two groups making up the secondary amine both are made up of aromatic groups or both groups contain aromatic rings wherein said aromatic rings maybe 0 to 2 aryl rings and 0 to 2 heteroaryl rings.

The "Diheteroaryl Imine" corresponding to Formula XII-AH can be prepared through dehydration techniques generally known in or adaptable from the art by reacting "Heteroaryl Amine" of Formula X-AH with the "Heteroaryl Carbonyl" of Formula XI-AH in Scheme I and subsequent specific examples.

For example, when Z is a covalent bond, methylene, methine substituted with another subsitutent, ethylene, or another substituent as defined in Formula V-H, the two reactants (X-AH and XI-AH) react by refluxing them in an aprotic solvent, such as hexane, toluene, cyclohexane, benzene, and the like, using a Dean-Stark type trap to remove water. After about 2–8 hours or until the removal of water is complete, the aprotic solvent is removed in vacuo to yield the "Diheteroaryl Imine" of Formula XII-AH. Alternately, when Z is an oxygen, the "Diheteroaryl Imine" is an oxime derivative. Oxime type "Diheteroaryl Imine" compounds are readily prepared from the corresponding O-substituted hydroxylamine and the appropriate aldehyde or ketone type "Heteroaryl Carbonyl". Alternately, when Z is a nitrogen, the "Diheteroaryl Imine" is a hydrazone derivative. Hydrazone type "Diheteroaryl Imine" compounds are readily prepared from the corresponding hydrazine and the appropriate aldehyde or ketone type "Heteroaryl Carbonyl". Suitable procedures for forming oxime and hydrazone imines are also described by Shriner, Fuson, and Curtin in The Systematic Identification of Organic Compounds, 5th Edition, John Wiley & Sons, and by Fieser and Fieser in Reagents for Organic Synthesis, Volume 1, John Wiley & Sons, which are incorporated herein by reference.

The "Secondary Heteroaryl Amines" of Formula XIIIA-H can be prepared from the corresponding "Diheteroaryl Imine" of Formula XII-AH in several ways. For example, in one synthetic scheme (Reduction Method-1), which is preferred when Z is a nitrogen, the "Generic Imine" hydrazone of Formula XII-AH is partially or completely dissolved in presence of a lower alcohol containing sufficient organic or mineral acid, as described in WO Patent Application No.9738973, Swiss Patent CH 441366 and U.S. Pat. Nos. 3,359,316 and 3,334,017, which are incorporated herein by reference, and then hydrogenated at 0–100° C., more preferably 20–50° C., and most preferrably between 20–30° C. and pressures of 10–200 psi hydrogen or more preferrably between 50–70 psi hydrogen in the presence of a noble metal catalyst such as In another synthetic scheme (Reduction Method-2), which is preferred when Z is a single bond or carbon, the "Diheteroaryl Imine" of Formula XII-AH is slurried in a lower alcohol such as ethanol, methanol or like solvent at 0–10° C. and solid sodium borohydride is added in batches over 5–10 minutes at 0–10° C. with stirring. The reaction mixture is stirred below 10° C. for 30–90 minutes and then is warmed gradually to 15–30° C. After about 1–10 hours, the mixture is cooled and acid is added until the aqueous layer was just acidic (pH 5–7).

In yet another synthetic scheme (Reduction Method-3), which is preferred when Z is an oxygen, the "Diheteroaryl Imine" oxime of Formula XII-AH is slurried in a lower alcohol solvent at 0–10° C. and acidified to a pH less than 4 and sodium cyanoborohydride is added in batches over 30–90 minutes at 0–20° C. with stirring and addition of a suitable organic or mineral acid to keep the pH at or below 4. The reaction mixture is stirred and warmed gradually to about 20–25° C. After about 1–10 hours, the mixture is cooled and base added until the mixture was just slightly alkaline.

The "Secondary Heteroaryl Amines" of Formula XIII-AH can also be prepared, according to Scheme 1, by an alkylation procedure based on the nucleophilic substitution of bromides by amines. In one synthetic alkylation scheme (Alkylation Method-1), a "Heteroaryl Amine" of Formula X-AH is reacted with a "Heteroaryl Bromide-" of Formula XXIII-AH as described in Vogel's Textbook of Practical Organic Chemistry, Fifth Edition, 1989, pages 902 to 905 and references cited therein all of which are incorporated herein by reference. In an alternate synthetic alkylation scheme exemplified in Scheme 10, a "Heteroaryl Amine" of is reacted with a "Heteroaryl Bromide" in a method employing palladium catalyzed carbon-nitrogen bond formation. Suitable procedures for this conversion are described in Wagaw and Buchwald, J. Org. Chem.(1996), 61, 7240–7241, Wolfe, Wagaw and Buchwald, J. Am. Chem. Soc. (1996), 118, 7215–7216, and Wolfe and Buchwald, Tetrahedron Letters (1997), 38(36), 6359–6362 and references cited therein all of which are incorporated herein by reference.

The "Secondary Heteroaryl Amine" amines, hydroxylamines, and hydrazines, the "Heteroaryl Carbonyl" aldehydes, ketones, hydrazones, and oximes, and "Heteroaryl Bromide" halides, tosylates, mesylates, triflates, and precursor alcohols required to prepare the "Secondary Heteroaryl Amine" compounds are available from commercial sources or can be prepared by one skilled in the art from published procedures. Commercial sources include but are not limited to Aldrich Chemical, TCI-America, Lancaster-Synthesis, Oakwood Products, Acros Organics, and Maybridge Chemical. Disclosed procedures for "Generic Amine" amines, hydroxylamines, and hydrazines include Sheradsky and Nov, J. Chem. Soc., Perkin Trans.1 (1980), (12), 2781–6; Marcoux, Doye, and Buchwald, J. Am. Chem. Soc. (1997), 119, 1053–9; Sternbach and Jamison, Tetrahedron Lett. (1981), 22(35), 33314; U.S. Pat. No. 5,306,718; EP No. 314435; WO No. 9001874; WO No. 9002113; JP No. 05320117; WO No. 9738973; Swiss Patent No. CH 441366; U.S. Pat. Nos. 3,359,316 and 3,334,017; and references cited therein which are incorporated herein by reference.

Synthetic Scheme 2 shows the preparation of the class of compounds of the present invention corresponding to Formula VII ("Generic Substituted Polycyclic Aryl tertiary-2-hydroxyalkylamines") and Formula VII-H (Generic Substituted Polycyclic Heteroaryl tertiary 2-Heteroalkylamines or "Generic Substituted Polycyclic Heteroaryl tertiary-2-hydroxyalkylamines").

Derivatives of "Generic Substituted Polycyclic Aryl tertiary-2-hydroxyalkylamines" or "Generic Substituted Polycyclic Heteroaryl tertiary-2-hydroxyalkylamines", in which the heteroatom (—O—) is attached to an alkyl group removed from the amine by two or more carbons are readily prepared by anion chemistry using the method of Scheme 2. The anion of "Secondary Heteroaryl Amine" amines, hydroxylamines, and hydrazines of Formula XIIIA-H are readily formed by dissolving the specific amine, hydroxylamine, or hydrazine in an aprotic solvent, such as tetrahydrofuran, toluene, ether, dimethylformamide, and dimethylformamide, under anhydrous conditions. The solution is cooled to a temperature between −78 and 0° C., preferably between −78 and −60° C. and the anion formed by the addition of at least one equivalent of a strong, aprotic, non-nucleophilic base such as NaH or n-butyllithium under an inert atmosphere for each acidic group present. Maintaining the temperature between −78 and 0° C., preferably between −78 and −60° C., with suitable cooling, an appropriate alkyl halide, alkyl benzenesulfonate such as a alkyl tosylate, alkyl mesylate, alkyl triflate or similar alkylating reagent of the general structure:

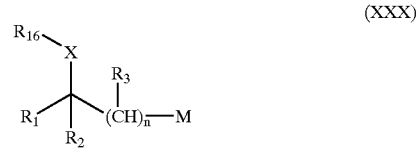

(XXX)

where m is zero, X can be RN, O, and S, and M is a readily displaceable group such as chloride, bromide, iodide, tosylate, triflate, and mesylate. After allowing the reaction mixture to warm to room temperature, the reaction product is added to water, neutralized if necessary, and extracted with a water-immiscible solvent such as diethyl ether or methylene chloride. The combined aprotic solvent extract is washed with saturated brine, dried over drying agent such as anhydrous $MgSO_4$ and concentrated in vacuo to yield crude Formula VII ("Generic Substituted Polycyclic Aryl tertiary-2-hydroxyalkylamines" or Formula VII-H "Generic Substituted Polycyclic Heteroaryl tertiary-2-heteroalkylamines" or "Generic Substituted Polycyclic Heteroaryl tertiary-2-hydroxyalkylamines"). This material is purified, for example, by eluting through silica gel with a medium polar solvent such as ethyl acetate in a non-polar solvent such as hexanes to yield purified Formula VII-H and Formula VII. Products are structurally confirmed by low and high resolution mass spectrometry and NMR.

Compounds of Formula (XXX), which can be used to prepare "Generic Substituted Polycyclic Heteroaryl and Aryl omega tertiary heteroalkylamines" and "Generic Substituted Polycyclic Heteroaryl and Aryl omega tertiary hydroxyalkylamines" compounds are given in Table 2. These reagents can be prepared from the corresponding alcohols. The tosylates are readily obtained by reacting the corresponding alcohol with tosyl chloride using procedures found in House's Modern Synthetic Reactions, Chapter 7, W. A. Benjamin, Inc., Shriner, Fuson, and Curtin in The Systematic Indentification of Organic Compounds, 5th Edition, John Wiley & Sons, and Fieser and Fieser in Reagents for Organic Synthesis, Volume 1, John Wiley & Sons, which are incorporated herein by reference.

A preferred procedure for Formula VII ("Generic Substituted Polycyclic Aryl tertiary-2-hydroxyalkylamines") and Formula VII-H ("Generic Substituted Polycyclic Heteroaryl tertiary-2-hydroxyalkylamines") compounds, exemplified in Tables 3 and 4, is Method A of Scheme 3. Oxirane reagents useful in Method A are exemplified, but not limited to those in Table 1. Formula VII ("Generic Substituted Polycyclic Aryl tertiary-2-hydroxyalkylamines") and Formula VII-H ("Generic Substituted Polycyclic Heteroaryl tertiary-2-hydroxyalkylamines") compounds are prepared by using "Secondary Heteroaryl Amine" amines, hydroxylamines, and hydrazines of Formula XIIIA-H prepared above with oxiranes of the type listed in Table 1 and represented by the general structure:

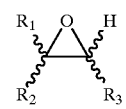

(XX)

In some cases, the oxiranes are prepared by reaction of epoxidation reagents such as MCPBA and similar type reagents readily selectable by a person of skill-in-the-art with alkenes. Fieser and Fieser in Reagents for Organic Synthesis, John Wiley & Sons provides, along with cited references, numerous suitable epoxidation reagents and reaction conditions, which are incorporated herein by reference.

TABLE 1

Structure and Source of Oxiranes, Thiaranes and Aziridine Reagents.

(XX)

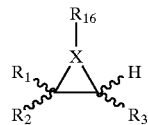

| XX | $R_1$ | $R_2$ | $R_3$ | $R_{16}$ | X |
|---|---|---|---|---|---|
| 1 | $CH_3$ | H | H | none | O |
| 2 | $CH_3CH_2$ | H | H | none | O |
| 3 | $CH_3$ | $CH_3$ | H | none | O |
| 4 | $CH_3CH_2$ | H | H | none | S |
| 5 | $CH_3CH_2CH_2$ | H | H | none | O |
| 6 | $CH_3OCH_2CH_2$ | H | H | none | O |
| 7 | $CH_3CH_2$ | H | H | H | N |
| 8 | $CH_3$ | $CH_3$ | H | none | S |
| 9 | $CH_3$ | H | $CF_3$ | none | O |
| 10 | $CH_3$ | $C_6H_5$ | H | none | O |
| 11 | $CH_3$ | $C_6H_5$ | H | none | S |
| 12 | $CH_3$ | $C_6H_5$ | H | H | N |
| 13 | $CH_3$ | Cyclopropyl | H | none | O |
| 14 | $CH_3$ | Cyclopropyl | H | none | S |
| 15 | $CH_3$ | $(CH_3)_2CH$ | H | none | O |
| 16 | $CH_3$ | $(CH_3)_2CH$ | H | none | S |
| 17 | $CH_3$ | $(CH_3)_2CH$ | H | H | N |
| 18 | $CH_3$ | H | $CH_3$ | none | O |
| 19 | $CH_3$ | $CH_3$ | H | H | N |
| 20 | $CH_3$ | H | $CH_3$ | H | N |
| 21 | $CH_3$ | H | H | Benzyl | N |
| 22 | $CH_3$ | H | H | $CH_3O$ | N |
| 23 | $CH_3$ | H | H | $CH_3$ | N |
| 24 | $CH_3$ | H | H | Benzyloxy | N |
| 25 | $CH_2$=CH | H | H | none | O |
| 26 | $CH_3CH_2CH_2$ | H | H | none | O |
| 27 | $CH_2$=$CHCH_2CH_2$ | H | H | none | O |
| 28 | $CH_3(CH_2)_4CH_2$ | H | H | none | O |
| 29 | $CH_2$=$CH(CH_2)_3CH_2$ | H | H | none | O |
| 30 | $HOCH_2$ | H | H | none | O |
| 31 | $(CH_3)_3COCH_2$ | H | H | none | O |
| 32 | $R_1 + R_2 = (CH_2)_5$ | | H | none | O |
| 33 | H | $R_2 + R_3 = (CH_2)_4$ | | none | O |
| 34 | $CH_3$ | $R_2 + R_3 = (CH_2)_4$ | | none | O |
| 35 | $CH_3$ | $R_2 + R_3 = (CH_2)_4$ | | none | S |
| 36 | H | $R_2 + R_3 = (CH_3)CH(CH_2)_3$ | | none | O |
| 37 | H | $R_2 + R_3 = (CH_3)CH(CH_2)_2$ | | none | O |
| 38 | H | $R_2 + R_3 = CH_2(CH_3)CHCH_2$ | | none | O |
| 39 | $R_1 + R_2 = (CH_2)_6$ | | H | none | O |
| 40 | $CH_3CH_2O_2C$ | H | H | none | O |
| 41 | $CH_3CH_2CH_2CH_2$ | H | H | none | O |

TABLE 1-continued

Structure and Source of Oxiranes, Thiaranes and Aziridine Reagents.

(XX)

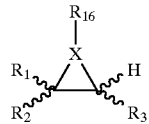

| XX | $R_1$ | $R_2$ | $R_3$ | $R_{16}$ | X |
|---|---|---|---|---|---|
| 42 | $CH_3OCH_2$ | H | H | none | O |
| 43 | $CH_3CH_2CH_2$ | H | H | none | S |
| 44 | $CH_3CH_2OCH_2$ | H | H | H | N |
| 45 | H | $R_2 + R_3 = (CH_2)_2SO_2$ | | none | O |
| 46 | $C_6H_5$ | H | H | none | O |
| 47 | $C_6H_5$ | H | $CH_3$ | none | O |
| 48 | $C_6H_5$ | H | H | H | N |
| 49 | $C_6H_5$ | $CH_3$ | H | none | O |
| 50 | $C_6H_5$ | $CH_3$ | H | none | S |
| 51 | $2\text{-}CH_3C_6H_4$ | H | H | none | O |
| 52 | $3\text{-}CH_3C_6H_4$ | H | H | none | O |
| 53 | $4\text{-}CH_3C_6H_4$ | H | H | none | O |
| 54 | $2\text{-}BrC_6H_4$ | H | H | none | O |
| 55 | $4\text{-}BrC_6H_4$ | H | H | none | O |
| 56 | $2\text{-}ClC_6H_4$ | H | H | none | O |
| 57 | $3\text{-}ClC_6H_4$ | H | H | none | O |
| 58 | $4\text{-}ClC_6H_4$ | H | H | none | O |
| 59 | $2\text{-}CH_3OC_6H_4$ | H | H | none | O |
| 60 | $3\text{-}CH_3OC_6H_4$ | H | H | none | O |
| 61 | $4\text{-}CH_3OC_6H_4$ | H | H | none | O |
| 62 | $3\text{-}CF_3C_6H_4$ | H | H | none | O |
| 63 | $C_6H_5CH_2$ | H | H | none | O |
| 64 | $4F\text{—}C_6H_4$ | H | H | none | O |
| 65 | $4F\text{—}C_6H_4$ | H | $4F\text{—}C_6H_4$ | none | O |
| 66 | $2\text{-}CH_3O\text{-}4\text{-}CH_3O\ C_6H_3$ | H | H | none | O |
| 67 | $3,4\text{-}OCH_2O\text{—}C_6H_3$ | H | H | none | O |
| 68 | $3\text{-}Cl\text{-}4\text{-}Cl\text{—}C_6H_3$ | H | H | none | O |
| 69 | $3\text{-}Cl\text{-}5\text{-}Cl\text{—}C_6H_3$ | H | H | none | O |
| 70 | $C_6H_5OCH_2$ | H | H | none | O |
| 71 | $4Cl\text{—}C_6H_4OCH_2$ | H | H | none | O |
| 72 | $CH_3OC_6H_4OCH_2$ | H | H | none | O |
| 73 | $C_6H_5$ | H | $CO_2\text{—}C_2H_5$ | none | O |
| 74 | 2-Pyridyl | H | H | none | O |

TABLE 2

Structure and Source of Alcohol and Glycol Reagents.

(XXX)

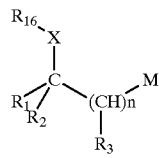

| Reagent Number | $R_1$ | n | M | $R_2$ | $R_3$ | $X\text{-}R_{16}$ |
|---|---|---|---|---|---|---|
| 1A | $CH_3$ | 3 | OTs | H | H | OH |
| 2A | $CH_3CH_2$ | 3 | OTs | H | H | OH |
| 3A | $CH_3CH_2CH_2$ | 3 | OTs | H | H | OH |
| 4A | $CH_3$ | 2 | OTs | H | H | OH |
| 5A | $CH_3CH_2$ | 2 | OTs | H | H | OH |
| 6A | $CH_3CH_2CH_2$ | 2 | OTs | H | H | OH |
| 7A | Phenyl | 3 | OTs | H | H | OH |
| 8A | Benzyl | 3 | OTs | H | H | OH |
| 9A | 2-phenylethyl | 3 | OTs | H | H | OH |
| 10A | Phenyl | 2 | OTs | H | H | OH |

TABLE 2-continued

Structure and Source of Alcohol and Glycol Reagents.

(XXX)

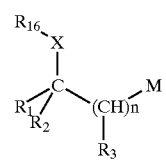

| Reagent Number | $R_1$ | n | M | $R_2$ | $R_3$ | $X\text{-}R_{16}$ |
|---|---|---|---|---|---|---|
| 11A | Benzyl | 2 | OTs | H | H | OH |
| 12A | 2-phenylethyl | 2 | OTs | H | H | OH |
| 13A | $CH_3$ | 4 | OTs | H | H | OH |
| 14A | $CH_3CH_2$ | 4 | OTs | H | H | OH |
| 15A | $CH_3CH_2CH_2$ | 4 | OTs | H | H | OH |
| 16A | $CH_3$ | 3 | OTs | $CH_2OH$ | H | OH |
| 17A | $CH_3CH_2$ | 3 | OTs | $CH_2OH$ | H | OH |
| 18A | H | 3 | OTs | $CH_2OH$ | H | OH |

TABLE 3

Structure of Substituted Phenyl tertiary-omega-Hydroxyalkylamines
(Y is CH; $R_8$, $R_9$, $R_{12}$, $R_{13}$, and $R_{14}$ are each H;
Z is covalent bond and $R_{15}$ is absent).

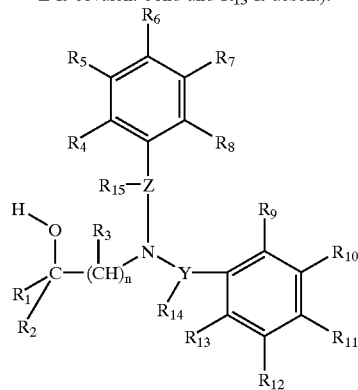

Inhibitor Number
Column 1 +
Column 2

| Reagent | Reagent | $R_1$ | n | $R_2$ | $R_3$ | $R_4$ | $R_5$ | $R_6$ | $R_7$ | $R_{10}$ | $R_{11}$ |
|---|---|---|---|---|---|---|---|---|---|---|---|
| 2A | 1N | $CH_3CH_2$ | 3 | H | H | H | $C_6H_5O$ | H | H | $OCF_2CF_2H$ | H |
| 2A | 2N | $CH_3CH_2$ | 3 | H | H | H | $OCF_3$ | H | H | $OCF_2CF_2H$ | H |
| 2A | 3N | $CH_3CH_2$ | 3 | H | H | F | H | H | F | $OCF_2CF_2H$ | H |
| 2A | 4N | $CH_3CH_2$ | 3 | H | H | H | F | H | H | $OCF_2CF_2H$ | H |
| 2A | 5N | $CH_3CH_2$ | 3 | H | H | H | $C_6H_5O$ | H | H | $OCF_3$ | H |
| 2A | 6N | $CH_3CH_2$ | 3 | H | H | H | $OCF_3$ | H | H | $OCF_3$ | H |
| 2A | 7N | $CH_3CH_2$ | 3 | H | H | H | H | phenyl | H | $OCF_3$ | H |
| 2A | 8N | $CH_3CH_2$ | 3 | H | H | H | phenyl | H | H | $OCF_3$ | H |
| 2A | 9N | $CH_3CH_2$ | 3 | H | H | H | H | H | H | $OCF_3$ | H |
| 2A | 10N | $CH_3CH_2$ | 3 | H | H | H | Br | H | H | $OCF_3$ | H |
| 2A | 11N | $CH_3CH_2$ | 3 | H | H | H | $CF_3$ | F | H | $CF_3$ | H |
| 2A | 12N | $CH_3CH_2$ | 3 | H | H | H | $CH_3$ | H | H | $CF_3$ | H |
| 2A | 13N | $CH_3CH_2$ | 3 | H | H | H | $CF_3$ | H | H | $CF_3$ | H |
| 2A | 14N | $CH_3CH_2$ | 3 | H | H | H | $CH_3$ | H | H | $OCF_3$ | H |
| 2A | 15N | $CH_3CH_2$ | 3 | H | H | H | F | F | H | $OCF_3$ | H |
| 2A | 16N | $CH_3CH_2$ | 3 | H | H | H | Br | H | H | $CF_3$ | H |
| 2A | 17N | $CH_3CH_2$ | 3 | H | H | H | $CF_3$ | F | H | $OCF_3$ | H |
| 2A | 18N | $CH_3CH_2$ | 3 | H | H | H | F | H | H | $OCF_3$ | H |
| 2A | 19N | $CH_3CH_2$ | 3 | H | H | H | Cl | H | H | $OCF_3$ | H |
| 2A | 20N | $CH_3CH_2$ | 3 | H | H | H | F | H | H | $CF_3$ | H |
| 2A | 21N | $CH_3CH_2$ | 3 | H | H | H | F | F | H | $CF_3$ | H |
| 2A | 22N | $CH_3CH_2$ | 3 | H | H | H | Cl | H | H | $CF_3$ | H |
| 2A | 23N | $CH_3CH_2$ | 3 | H | H | H | F | H | H | phenoxy | H |
| 2A | 24N | $CH_3CH_2$ | 3 | H | H | H | $CF_3$ | Cl | H | $CH_3$ | H |
| 2A | 25N | $CH_3CH_2$ | 3 | H | H | H | $CF_3$ | F | H | $CH_3$ | H |
| 2A | 26N | $CH_3CH_2$ | 3 | H | H | H | H | H | H | $CF_3$ | H |
| 2A | 27N | $CH_3CH_2$ | 3 | H | H | F | F | H | H | $CF_3$ | H |
| 2A | 28N | $CH_3CH_2$ | 3 | H | H | H | H | $OCH_3$ | H | $CF_3$ | H |
| 2A | 29N | $CH_3CH_2$ | 3 | H | H | H | F | F | H | $CH_3$ | H |
| 2A | 30N | $CH_3CH_2$ | 3 | H | H | H | $OCH_3$ | H | H | $CH_3$ | H |
| 2A | 31N | $CH_3CH_2$ | 3 | H | H | H | H | $CH_3$ | H | H | H |
| 2A | 32N | $CH_3CH_2$ | 3 | H | H | H | Cl | H | H | H | H |
| 2A | 33N | $CH_3CH_2$ | 3 | H | H | H | F | H | H | F | H |
| 2A | 34N | $CH_3CH_2$ | 3 | H | H | H | H | $OCH_3$ | H | $CH_3$ | H |
| 2A | 35N | $CH_3CH_2$ | 3 | H | H | H | H | H | H | H | H |
| 2A | 36N | $CH_3CH_2$ | 3 | H | H | H | H | $CH_3$ | H | $CH_3$ | H |
| 2A | 37N | $CH_3CH_2$ | 3 | H | H | H | H | Cl | H | H | H |
| 2A | 38N | $CH_3CH_2$ | 3 | H | H | H | F | H | H | 3-$CF_3$-phenoxy | H |
| 2A | 39N | $CH_3CH_2$ | 3 | H | H | H | F | H | H | 4-$CH_3$O-phenoxy | H |
| 2A | 40N | $CH_3CH_2$ | 3 | H | H | H | F | H | H | 4-Cl-phenoxy | H |
| 2A | 41N | $CH_3CH_2$ | 3 | H | H | H | F | H | H | H | H |
| 2A | 42N | $CH_3CH_2$ | 3 | H | H | H | F | H | H | $CH_3$ | H |
| 2A | 43N | $CH_3CH_2$ | 3 | H | H | H | F | H | F | $CH_3$ | H |
| 2A | 44N | $CH_3CH_2$ | 3 | H | H | F | F | H | H | $CH_3$ | H |
| 2A | 45N | $CH_3CH_2$ | 3 | H | H | H | Cl | H | H | $CH_3$ | H |
| 2A | 46N | $CH_3CH_2$ | 3 | H | H | H | $CH_3$ | H | H | $CH_3$ | H |
| 2A | 48N | $CH_3CH_2$ | 3 | H | H | H | H | $CH_3$ | H | $CF_3$ | H |

TABLE 3-continued

Structure of Substituted Phenyl tertiary-omega-Hydroxyalkylamines
(Y is CH; $R_8$, $R_9$, $R_{12}$, $R_{13}$, and $R_{14}$ are each H;
Z is covalent bond and $R_{15}$ is absent).

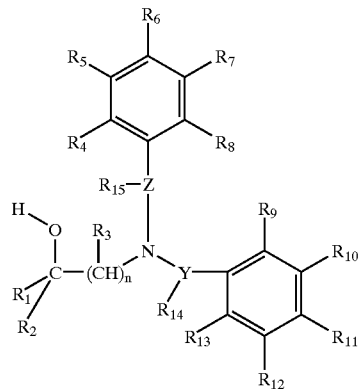

Inhibitor Number
Column 1 +
Column 2

| Reagent | Reagent | $R_1$ | n | $R_2$ | $R_3$ | $R_4$ | $R_5$ | $R_6$ | $R_7$ | $R_{10}$ | $R_{11}$ |
|---|---|---|---|---|---|---|---|---|---|---|---|
| 2A | 51N | $CH_3CH_2$ | 3 | H | H | H | H | $CH_3$ | H | F | H |
| 2A | 52N | $CH_3CH_2$ | 3 | H | H | H | $CF_3$ | H | H | F | H |
| 2A | 53N | $CH_3CH_2$ | 3 | H | H | H | $CF_3$ | H | H | $CH_3$ | H |
| 2A | 54N | $CH_3CH_2$ | 3 | H | H | H | $OCH_3$ | H | H | $CF_3$ | H |
| 2A | 56N | $CH_3CH_2$ | 3 | H | H | H | H | $CH_3$ | H | $CF_3$ | H |
| 2A | 57N | $CH_3CH_2$ | 3 | H | H | H | $C_6H_5O$ | H | H | H | $OCF_3$ |
| 2A | 58N | $CH_3CH_2$ | 3 | H | H | H | H | H | H | H | $OCF_3$ |
| 2A | 59N | $CH_3CH_2$ | 3 | H | H | H | $OCF_3$ | H | H | H | $OCF_3$ |
| 2A | 60N | $CH_3CH_2$ | 3 | H | H | H | $CF_3$ | F | H | H | $CF_3$ |
| 2A | 61N | $CH_3CH_2$ | 3 | H | H | H | H | $OCH_3$ | H | H | $CF_3$ |
| 2A | 62N | $CH_3CH_2$ | 3 | H | H | H | $CH_3$ | H | H | H | $CF_3$ |
| 2A | 63N | $CH_3CH_2$ | 3 | H | H | H | Cl | H | H | H | $CF_3$ |
| 2A | 64N | $CH_3CH_2$ | 3 | H | H | H | $CF_3$ | H | H | H | $OCF_3$ |
| 2A | 65N | $CH_3CH_2$ | 3 | H | H | H | F | H | H | H | $OCF_3$ |
| 2A | 66N | $CH_3CH_2$ | 3 | H | H | H | F | H | F | H | $OCF_3$ |
| 2A | 67N | $CH_3CH_2$ | 3 | H | H | H | Br | H | H | H | $OCF_3$ |
| 2A | 68N | $CH_3CH_2$ | 3 | H | H | H | Cl | H | H | H | $OCF_3$ |
| 2A | 69N | $CH_3CH_2$ | 3 | H | H | H | F | F | H | H | $OCF_3$ |
| 2A | 70N | $CH_3CH_2$ | 3 | H | H | H | F | H | H | H | phenyl |
| 2A | 71N | $CH_3CH_2$ | 3 | H | H | H | $CH_3$ | H | H | H | $OCF_3$ |
| 2A | 72N | $CH_3CH_2$ | 3 | H | H | H | F | F | H | H | $CF_3$ |
| 2A | 73N | $CH_3CH_2$ | 3 | H | H | H | Cl | H | H | H | $CH_3$ |
| 2A | 74N | $CH_3CH_2$ | 3 | H | H | H | $OCH_3$ | H | H | H | $CH_3$ |
| 2A | 75N | $CH_3CH_2$ | 3 | H | H | H | F | H | H | H | $CH_3$ |
| 2A | 76N | $CH_3CH_2$ | 3 | H | H | F | F | H | H | H | $OCF_3$ |
| 2A | 78N | $CH_3CH_2$ | 3 | H | H | H | H | $OCH_3$ | H | H | $CH_3$ |
| 2A | 79N | $CH_3CH_2$ | 3 | H | H | H | H | $CH_3$ | H | H | $CH_3$ |
| 2A | 80N | $CH_3CH_2$ | 3 | H | H | H | $CH_3$ | H | H | H | $CH_3$ |
| 2A | 82N | $CH_3CH_2$ | 3 | H | H | H | F | F | H | H | $CH_3$ |
| 2A | 83N | $CH_3CH_2$ | 3 | H | H | H | F | H | F | H | $CH_3$ |
| 2A | 84N | $CH_3CH_2$ | 3 | H | H | F | F | H | H | H | $CH_3$ |
| 2A | 85N | $CH_3CH_2$ | 3 | H | H | F | $CF_3$ | H | H | H | $CH_3$ |
| 2A | 86N | $CH_3CH_2$ | 3 | H | H | H | H | $CH_3$ | H | H | $CF_3$ |
| 2A | 88N | $CH_3CH_2$ | 3 | H | H | H | $CF_3$ | H | H | H | $CH_3$ |
| 2A | 90N | $CH_3CH_2$ | 3 | H | H | H | H | $CF_3$ | H | H | $CH_3$ |
| 2A | 92N | $CH_3CH_2$ | 3 | H | H | H | $CF_3$ | F | H | H | $CH_3$ |

TABLE 4

Structure of Substituted Phenyl tertiary-omega-Hydroxyalkylamines
(Y and Z are CH; $R_8$, $R_9$, $R_{12}$, $R_{13}$, $R_{14}$, and $R_{15}$ are each H;
Z is covalent $R_{15}$ is absent).

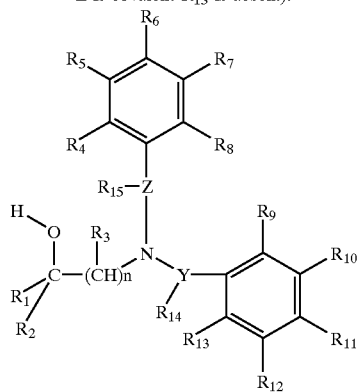

Inhibitor Number
Column 1 +
Column 2

| Reagent | Reagent | $R_1$ | n | $R_2$ | $R_3$ | $R_4$ | $R_5$ | $R_6$ | $R_9$ | $R_{10}$ | $R_{11}$ |
|---|---|---|---|---|---|---|---|---|---|---|---|
| 1A | 1DB | $CH_3$ | 3 | H | H | H | $OCF_3$ | H | H | $OCF_3$ | H |
| 1A | 2DB | $CH_3$ | 3 | H | H | H | Cl | H | H | H | $CF_3$ |
| 1A | 3DB | $CH_3$ | 3 | H | H | H | Br | H | H | $OCF_3$ | H |
| 1A | 4DB | $CH_3$ | 3 | H | H | H | Cl | H | H | $OCF_3$ | H |
| 1A | 5DB | $CH_3$ | 3 | H | H | H | Cl | H | H | $CF_3$ | H |
| 1A | 6DB | $CH_3$ | 3 | H | H | H | H | Cl | H | $CF_3$ | H |
| 1A | 7DB | $CH_3$ | 3 | H | H | H | F | H | H | $OCF_3$ | H |
| 1A | 8DB | $CH_3$ | 3 | H | H | H | H | Cl | H | H | $CF_3$ |
| 1A | 9DB | $CH_3$ | 3 | H | H | H | F | H | H | H | $CF_3$ |
| 1A | 10DB | $CH_3$ | 3 | H | H | H | H | F | H | H | $CF_3$ |
| 1A | 11DB | $CH_3$ | 3 | H | H | F | H | H | H | H | $CF_3$ |
| 1A | 12DB | $CH_3$ | 3 | H | H | H | Cl | H | $CF_3$ | H | H |
| 1A | 13DB | $CH_3$ | 3 | H | H | H | H | Cl | $CF_3$ | H | H |
| 1A | 14DB | $CH_3$ | 3 | H | H | Cl | H | H | $CF_3$ | H | H |
| 1A | 15DB | $CH_3$ | 3 | H | H | H | F | H | $CH_3$ | H | H |
| 1A | 16DB | $CH_3$ | 3 | H | H | H | H | F | H | H | $CH_3$ |
| 1A | 17DB | $CH_3$ | 3 | H | H | H | F | H | H | $CH_3$ | H |
| 1A | 18DB | $CH_3$ | 3 | H | H | F | H | H | $CH_3$ | H | H |
| 1A | 19DB | $CH_3$ | 3 | H | H | H | H | F | H | $CH_3$ | H |
| 1A | 20DB | $CH_3$ | 3 | H | H | F | H | H | H | H | $CH_3$ |
| 1A | 21DB | $CH_3$ | 3 | H | H | F | H | H | H | $CF_3$ | H |
| 1A | 22DB | $CH_3$ | 3 | H | H | Cl | H | H | H | $CF_3$ | H |
| 1A | 23DB | $CH_3$ | 3 | H | H | H | F | H | $CF_3$ | H | H |
| 1A | 24DB | $CH_3$ | 3 | H | H | H | H | F | $CF_3$ | H | H |
| 1A | 25DB | $CH_3$ | 3 | H | H | H | F | H | H | $CF_3$ | H |
| 1A | 26DB | $CH_3$ | 3 | H | H | H | H | F | H | $CF_3$ | H |
| 1A | 27DB | $CH_3$ | 3 | H | H | H | $OCF_3$ | H | H | H | $OCF_3$ |

Formula VII ("Generic Substituted Polycyclic Aryl tertiary-2-heteroalkylamines") and Formula VII-H ("Generic Substituted Polycyclic Heteroaryl tertiary 2-Heteroalkylamines") compounds, wherein the 2-hetero group is an amino, substituted amino, or thiol, can be prepared by using appropriate aziridines and thirranes according to Method A of Scheme 3. Aziridine and thiirane reagents useful in Method A are exemplified, but not limited to those in Table 1. These Formula VII ("Generic Substituted Polycyclic Aryl tertiary 2-heteroalkylamine") and Formula VII-H ("Generic Substituted Polycyclic Heteroaryl tertiary-2-heteroalkylamines") compounds, wherein the 2-hetero group is an amino, substituted amino, or thiol, can be prepared by using "Secondary Heteroaryl Amine" amines, hydroxylamines, and hydrazines of Formula XIIIA-H prepared above with aziridines and thiiranes of the type listed in Table 1 and represented by the general structure:

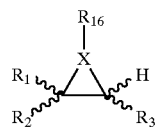

(XX)

wherein X is selected from N and S and $R_{16}$ is hydrogen or another suitable group when X is N.

A mixture of a "Secondary Heteroaryl Amine" amine, hydroxylamine, or hydrazine of Formula XIIIA-H and an oxirane of Formula XX are stirred and heated to 40–90° C. for 5 to 48 hours in a tightly capped or contained reaction vessel. A Lewis acid such as ytterbium triflate in acetonitrile may be added to speed up reaction and improve yield. When a Lewis acid is used, the reaction should be carried out under inert, anhydrous conditions using a blanket of dry nitrogen or argon gas. After cooling to room temperature and testing the reaction mixture for complete reaction by thin layer chromatography or high pressure liquid chromatography (hplc), the reaction product is added to water and extracted with a water immiscible solvent such as diethyl ether or methylene chloride. (Note: If the above analysis indicates that reaction is incomplete, heating should be resumed until complete with the optional addition of more of the oxirane). The combined aprotic solvent extract is washed with saturated brine, dried over drying agent such as anhydrous $MgSO_4$ and concentrated in vacuo to yield crude Formula VII ("Generic Substituted Polycyclic Aryl tertiary 2-hydroxyalkylamine") and Formula VII-H ("Generic Substituted Polycyclic Heteroaryl tertiary-2-hydroxyalkylamine") compounds. This material is purified by eluting through silica gel with 5–40% of a medium polar solvent such as ethyl acetate in a non-polar solvent such as hexanes to yield the Formula VII ("Generic Substituted Polycyclic Aryl tertiary 2-hydroxyalkylamine") and Formula VII-H ("Generic Substituted Polycyclic Heteroaryl tertiary-2-hydroxyalkylamine"). Products are tested for purity by HPLC. If necessary, the Formula VII ("Generic Substituted Polycyclic Aryl tertiary 2-hydroxyalkylamine") and Formula VII-H ("Generic Substituted Polycyclic Heteroaryl tertiary-2-hydroxyalkylamine") compounds are purified by additional chromatography or recrystallization. Products are structurally confirmed by low and high resolution mass spectrometry and NMR. Examples of specific Formula VII ("Generic Substituted Polycyclic Aryl tertiary 2-hydroxyalkylamine") compounds prepared are summarized in the Examples and Example Tables I through 5.

Specific Formula VII ("Generic Substituted Polycyclic Aryl tertiary 2-hydroxyalkylamine") and Formula VII-H ("Generic Substituted Polycyclic Heteroaryl tertiary-2-hydroxyalkylamine") analogs of the "Polycyclic Aryl tertiary-2-hydroxyalkylamine" compounds summarized in the Examples and Example Tables 1 through 5, wherein the hydroxyl or oxy group are replaced with an amino, substituted amino, aza, or thiol, can be prepared by using the appropriate aziridine reagents or thiirane reagents readily by adapting the procedures in the numerous specific Examples and Schemes disclosed in the present invention. Similarly, intermediates, in which the hydroxyl or oxy group of said intermediates are replaced with an amino, substituted amino, aza, or thiol, can be converted using the numerous specific Examples and Schemes disclosed in the present invention to other Formula VII ("Generic Substituted Polycyclic Aryl tertiary 2-hydroxyalkylamine") and Formula VII-H ("Generic Substituted Polycyclic Heteroaryl tertiary-2-hydroxyalkylamine") analogs of the "Polycyclic Aryl tertiary-2-hydroxyalkylamine" compounds.

Formula VII ("Generic Substituted Polycyclic Aryl tertiary-2-hydroxyalkylamines") and Formula VII-H ("Generic Substituted Polycyclic Heteroaryl tertiary-2-hydroxyalkylamines") can further be prepared in an alternate manner to procedures disclosed above and in Schemes 1, 2, and 3. Schemes 9 and 10 detail such procedures to prepare tertiary oxyalkylamine compounds of the present invention by initial formation of an halogenated, oxygen containing primary alkylamine XVL ("Generic Substituted Alkylamine"). Said halogenated, oxygen containing primary alkylamine XVL, formed in Scheme 9, is itself converted to secondary amine VLX-H ("Heteroaryl Alkyl Amine) using procedures disclosed above. Primary alkylamine XVL is first reacted with an aldehydic or ketonic carbonyl compound, XI-AH ("Heteroaryl Carbonyl") with azeotropic distillation to form imines, VL-H ("Heteroaryl Imine"). Said imine VL-H are then reduced with or without prior isolation by Reduction Methods 1, 2 or 3 as disclosed above and in Scheme 1 to yield secondary amines VLX-H ("Heteroaryl Alkyl Amine). Said secondary amine VLX-H can be converted according to Scheme 10 to VII-H ("Generic Substituted Polycyclic Heteroaryl Tertiary 2-hydroxyalkylamines"). Using similar schemes, VLX can be converted to VII ("Generic Substituted Polycyclic Phenyl Tertiary 2-hydroxyalkylamines"). Compounds of this invention in which one aromatic substituent is aryl and the other aromatic substitutent is heteroaryl can be readily prepared by reacting VLX-H with an aryl bromide or aralkyl bromide instead of using an heteroaryl bromide or heteroaralkyl bromide. Similarly, compounds of this invention in which one aromatic substituent is aryl and the other aromatic substitutent is heteroaryl can be readily prepared by reacting the aryl analog of VLX-H with an heteroaryl bromide or heteroaralkyl bromide instead of using an aryl bromide or aralkyl bromide.

Formula VII ("Generic Substituted Polycyclic Aryl tertiary-2-hydroxyalkylamines") and Formula VII-H ("Generic Substituted Polycyclic Heteroaryl tertiary-2-hydroxyalkylamines") can further be prepared in an alternate manner to procedures disclosed above and in Schemes 1, 2, 3, 9, and 10. Schemes 13, 14, and 15 detail alternate procedures to prepare tertiary oxyalkylamine compounds of the present invention by initial formation of an halogenated, oxygen containing secondary alkylamines VLX and VLXX ("Phenyl Alkylamines") and VLXX-O ("Phenyl Oxy Alkylamines"). Said secondary alkylamines VLX and VLXX ("Phenyl Alkylamines") and VLXX-O ("Phenyl Oxy Alkylamines") can be converted according to Schemes 13, 14 and 15 to VII ("Generic Substituted Polycyclic Aryl Tertiary 2-hydroxyalkylamines") and VII-H ("Generic Substituted Polycyclic Heteroaryl Tertiary 2-hydroxyalkylamines") by reaction with appropriate aromatic halides such as aryl bromides and heteroaryl bromides as desired.

Formula VII ("Generic Substituted Polycyclic Aryl tertiary-2-hydroxyalkylamines") and Formula VII-H ("Generic Substituted Polycyclic Heteroaryl tertiary-2-hydroxyalkylamines") can further be prepared in an alternate manner to procedures disclosed above and in Schemes 1, 2, 3, 9, 10, 13, 14, and 15. Another alternate procedure to prepare tertiary oxyalkylamine compounds of the present invention by reacting secondary amine XIIIA-H ("Secondary Heteroaryl Amine") with a diazo ester. The intermediate glycinate tertiary amine can then be reduced, partially reoxidized to an aldehyde, and converted using a perfluoroalkyl trimethylsilyl compound (for example, trifluoromethyl-TMS) to the desired product, VII ("Generic Substituted Polycyclic Aryl Tertiary 2-hydroxyalkylamines") and VII-H ("Generic Substituted Polycyclic Heteroaryl Tertiary 2-hydroxyalkylamines").

A particularly useful procedure to prepare Formula VII ("Generic Substituted Polycyclic Aryl tertiary-2-hydroxyalkylamines") and Formula VII-H (Generic Substituted Polycyclic Heteroaryl tertiary 2-Heteroalkylamines or "Generic Substituted Polycyclic Heteroaryl tertiary-2-hydroxyalkylamines") compounds of the present invention in which the heteroaryl group is directly bonded is disclosed in Schemes 11 and 12. An halogenated, oxygen containing primary alkylamine XVL ("Generic Substituted Alkylamine") formed according to Scheme 9 is itself converted by reaction with LXXI-AH ("Heteroaryl Halide") to afford secondary amine VLXX-H i"Heteroaryl Secondary Amine) using procedures disclosed in Scheme 11 and above.

VLXX-H is converted to VII-H ("Generic Substituted Polycyclic Phenyl Heteroaryl Tertiary 2-hydroxyalkylamine") by alkylation chemistry with an aralkyl bromide or aralkyloxyalkyl bromide using either of two procedures disclosed in Scheme 12. Isolation and purification is effected as disclosed previously.

Formula VII ("Generic Substituted Polycyclic Aryl tertiary-2-hydroxyalkylamines") and Formula VII-H (Generic Substituted Polycyclic Heteroaryl tertiary 2-Heteroalkylamines or "Generic Substituted Polycyclic Heteroaryl tertiary-2-hydroxyalkylamines") can themselves serve as intermediates for conversion to additional compounds of this invention. Compounds of Formula VII-H, Formula VII and the present invention useful as intermediates include those in which the $R_7$ position substituent in Formula VII ("Generic Substituted Polycyclic Aryl tertiary-2-hydroxyalkylamines") is a bromo group, hydroxyl group, sulfhydryl group, bromomethyl or other bromoalkyl groups, nitro group, amino group, methoxy carbonyl or other alkoxy carbonyl groups, cyano group, or acyl groups. Other preferred compounds of Formula VII-H, Formula VII and the present invention useful as intermediates include those in which the $R_{10}$ position substituent in Formula VII is a bromo group, hydroxyl group, sulfhydryl group, bromomethyl or other bromoalkyl groups, nitro group, amino group, methoxy carbonyl or other alkoxy carbonyl groups, cyano group, or acyl groups. Other compounds of Formula VII-H, Formula VII and the present invention useful as intermediates include those in which one or more of $R_6$, $R_7$, $R_{11}$, and $R_{12}$ substituents in Formula VII-H and Formula VII is a bromo group, hydroxyl group, sulfhydryl group, bromomethyl or other bromoalkyl groups, nitro group, amino group, methoxy carbonyl or other alkoxy carbonyl groups, cyano group, or acyl groups.

A 3-bromo substituent at the $R_7$ position in Formula VII ("Generic Substituted Polycyclic 3-Bromoaryl Tertiary 2-hydroxyalkylamine") can be reacted with a phenol to afford 3-phenoxy compounds of the present invention of Formula VII ("Generic Substituted Polycyclic 3-Phenoxyaryl Tertiary 2-Hydroxyalkylamine").

A 3-bromo substituent at the $R_7$ position in Formula VII-H ("Generic Substituted Polycyclic 3-Bromoheteroaryl Tertiary 2-hydroxyalkylamine") can, as shown in Scheme 4, be reacted with a phenol to afford additional compounds of the present invention of Formula VII-H ("Generic Substituted Polycyclic 3-Aryloxyaryl, 3-Heteroaryloxyaryl, 3-Heteroaryloxyheteroaryl, and 3-Aryloxyheteroaryl Tertiary 2-Hydroxyalkylamines").

A 3-bromo substituent at the $R_7$ position in Formula VII ("Generic Substituted Polycyclic 3-Bromoaryl Tertiary 2-hydroxyalkylamine") can, as shown in Scheme 7, be reacted with a phenol to afford additional compounds of the present invention of Formula VII ("Generic Substituted Polycyclic 3-Phenylaryl Tertiary 2-Hydroxyalkylamine").

Conversion of a 3-bromo substituent at the $R_7$ position in Formula VII ("Generic Substituted Polycyclic 3-Bromoaryl Tertiary 2-hydroxyalkylamine") by reaction with a primary or secondary amine can, as shown in Scheme 8, afford additional compounds of the present invention of Formula VII ("Generic Substituted Polycyclic 3-$R_{22}$aminoaryl Tertiary 2-Hydroxyalkylamine").

Conversion of a 3-bromo substituent at the $R_{10}$ position in Formula VII ("Generic Substituted Polycyclic 3-Bromoaryl Tertiary 2-hydroxyalkylamine") by reaction with an aryl borinate can afford additional compounds of the present invention of Formula VII ("Generic Substituted Polycyclic 3-Phenylaryl Tertiary 2-Hydroxyalkylamine").

Conversion of a 3-bromo substituent at the $R_{10}$ position in Formula VII ("Generic Substituted Polycyclic 3-Bromoaryl Tertiary 2-hydroxyalkylamine") by reaction with a heteroaryl dibutyl tin compound can afford additional compounds of the present invention of Formula VII ("Generic Substituted Polycyclic 3-Heteroarylaryl Tertiary 2-Hydroxyalkylamine").

Conversion of a 3-bromomethyl substituent at the $R_7$ position in Formula VII ("Generic Substituted Polycyclic 3-Bromomethylaryl Tertiary 2-hydroxyalkylamine") by reaction with an aryl borinate can afford additional compounds of the present invention of Formula VII ("Generic Substituted Polycyclic 3-Arylmethylaryl Tertiary 2-Hydroxyalkylamine").

Conversion of a 3-hydroxyl substituent at the $R_7$ position in Formula VII-H ("Generic Substituted Polycyclic 3-Hydroxyheteroaryl Tertiary 2-hydroxyalkylamine") by reaction with an aryl bromide or heteroaryl bromide can afford additional compounds of the present invention of Formula VII-H ("Generic Substituted Polycyclic 3-Aryloxyaryl, 3-Heteroaryloxyaryl, 3-Heteroaryloxyheteroaryl, and 3-Aryloxyheteroaryl Tertiary 2-Hydroxyalkylamines").

Conversion of a 3-hydroxyl substituent at the $R_7$ position in Formula VII ("Generic Substituted Polycyclic 3-Hydroxyaryl Tertiary 2-hydroxyalkylamine") by reaction with an aryl bromide can afford, as described Scheme 5, additional compounds of the present invention of Formula VII ("Generic Substituted Polycyclic 3-Phenoxyaryl Tertiary 2-Hydroxyalkylamine").

Conversion of a 3-hydroxyl substituent at the $R_7$ position in Formula VII-H ("Generic Substituted Polycyclic 3-Hydroxyheteroaryl Tertiary 2-hydroxyalkylamine") by reaction with an aralkyl bromide or heteroaralkyl bromide can afford additional compounds of the present invention of Formula VII-H ("Generic Substituted Polycyclic 3-Aralkyloxyaryl, 3-Heteroaralkyloxyaryl, 3-Heteroaralkyloxyheteroaryl, and 3-Aralkyloxyheteroaryl Tertiary 2-Hydroxyalkylamines").

Conversion of a 3-hydroxyl substituent at the $R_7$ position in Formula VII ("Generic Substituted Polycyclic 3-Hydroxyaryl Tertiary 2-hydroxyalkylamine") by reaction with an aralkyl bromide can afford additional compounds of the present invention of Formula VII ("Generic Substituted Polycyclic 3-Aralkyloxyaryl Tertiary 2-Hydroxyalkylamine").

Conversion of a 3-hydroxyl substituent at the $R_7$ position in Formula VII ("Generic Substituted Polycyclic 3-Hydroxyaryl Tertiary 2-hydroxyalkylamine") by reaction with an $R_{17}$-bromide can afford additional compounds of the present invention of Formula VII ("Generic Substituted Polycyclic 3-$R_{17}$-oxyaryl Tertiary 2-Hydroxyalkylamine").

Conversion of a 3-thio substituent at the $R_7$ position in Formula VII ("Generic Substituted Polycyclic 3-thioaryl Tertiary 2-hydroxyalkylamine") by reaction with an $R_{17}$-bromide can afford additional compounds of the present invention of Formula VII ("Generic Substituted Polycyclic 3-$R_{17}$thiaaryl Tertiary 2-Hydroxyalkylamine"). "Generic Substituted Polycyclic 3-$R_{17}$thiaaryl Tertiary 2-Hydroxyalkylamines" can be oxidized to sulfonyl compounds of Formula VII ("Generic Substituted Polycyclic 3-$R_7$sulfonylaryl Tertiary 2-Hydroxyalkylamine").

Conversion of a 3-nitro substituent at the $R_7$ position in Formula VII ("Generic Substituted Polycyclic 3-Nitroaryl Tertiary 2-hydroxyalkylamine") by hydrogenation can afford additional compounds of the present invention of Formula VII ("Generic Substituted Polycyclic 3-Aminoaryl Tertiary 2-Hydroxyalkylamine"). "Generic Substituted Polycyclic 3-Aminoaryl Tertiary 2-Hydroxyalkylamines" can be acylated to acyl amide compounds of Formula VII ("Generic Substituted Polycyclic 3-Acylaminoaryl Tertiary 2-Hydroxyalkylamine").

Conversion of a 3-amino substituent at the $R_7$ position in Formula VII ("Generic Substituted Polycyclic 3-Aminoaryl Tertiary 2-hydroxyalkylamine") by reaction with carbonyl compounds can afford additional compounds of the present invention of Formula VII ("Generic Substituted Polycyclic 3-(Saturated Nitrogen Heterocycl-1yl)aryl Tertiary 2-Hydroxyalkylamine" and "Generic Substituted Polycyclic 3-(Unsaturated Nitrogen Heterocycl-1yl)aryl Tertiary 2-Hydroxyalkylamine").

Conversion of a 3-methoxycarbonyl substituent at the $R_7$ position in Formula VII ("Generic Substituted Polycyclic 3-Carbomethoxyaryl Tertiary 2-hydroxyalkylamine") by reaction with amination reagents can afford additional compounds of the present invention of Formula VII ("Generic Substituted Polycyclic 3-Carboxamidoaryl Tertiary 2-Hydroxyalkylamine").

Conversion of a 3-cyano substituent at the $R_7$ position in Formula VII ("Generic Substituted Polycyclic 3-Cyanoaryl Tertiary 2-hydroxyalkylamine") by reaction with organometallic reagents can afford additional compounds of the present invention of Formula VII ("Generic Substituted Polycyclic 3-Acylaryl Tertiary 2-Hydroxyalkylamine"). Said "Generic Substituted Polycyclic 3-Acylaryl Tertiary 2-Hydroxyalkylamines", can be reduced to hydroxyl compounds of Formula VII ("Generic Substituted Polycyclic 3-Hydroxysubstitutedmethylaryl Tertiary 2-Hydroxyalkylamine").

Conversion of a 3-methoxycarbonyl substituent at the $R_{10}$ position in Formula VII ("Generic Substituted Polycyclic 3-Carbomethoxyaryl Tertiary 2-hydroxyalkylamine") by reaction with amination reagents can afford additional compounds of the present invention of Formula VII ("Generic Substituted Polycyclic 3-Carboxamidoaryl Tertiary 2-Hydroxyalkylamine").

Conversion of a 3-methoxycarbonyl substituent at the $R_{10}$ position in Formula VII ("Generic Substituted Polycyclic 3-Carbomethoxyaryl Tertiary 2-hydroxyalkylamine") by reaction with an organometallic reagent can afford additional compounds of the present invention of Formula VII ("Generic Substituted Polycyclic 3-(bis-$R_{20}$-hydroxymethyl)aryl Tertiary 2-Hydroxyalkylamine").

Conversion of a 3-methoxycarbonyl substituent at the $R_{10}$ position in Formula VII ("Generic Substituted Polycyclic 3-Carbomethoxyaryl Tertiary 2-hydroxyalkylamine") by reaction with lithium aluminum hydride can afford additional compounds of the present invention of Formula VII ("Generic Substituted Polycyclic 3-Hydroxymethylaryl Tertiary 2-Hydroxyalkylamine").

Conversion of a 3-methoxycarbonyl substituent at the $R_{10}$ position in Formula VII ("Generic Substituted Polycyclic 3-Carbomethoxyaryl Tertiary 2-hydroxyalkylamine") by reaction with an alkylation reagent can afford additional compounds of the present invention of Formula VII ("Generic Substituted Polycyclic 3-(bis-$R_{21}$-hydroxymethyl)aryl Tertiary 2-Hydroxyalkylamine").

Conversion of a 3-methoxycarbonyl substituent at the $R_{10}$ position in Formula VII ("Generic Substituted Polycyclic 3-Carbomethoxyaryl Tertiary 2-hydroxyalkylamine") by reaction intially with an amidation reagent and then an $R_{20}$-organometallic reagent can afford additional compounds of the present invention of Formula VII ("Generic Substituted Polycyclic 3-($R_{20}$-carbonyl)aryl Tertiary 2-Hydroxyalkylamine").

Formula VII ("Generic Substituted Polycyclic Aryl tertiary-2-hydroxyalkylamines"), Formula VII-H ("Generic Substituted Polycyclic Heteroaryl tertiary-2-hydroxyalkylamines") and other compounds of this invention possessing hydroxyl, thiol, and amine functional groups can be converted to a wide variety derivatives. The hydroxyl group X, wherein $R_{16}$ is a hydrogen, of compounds of Formulas VII, VII-H, and other compounds of the present invention can be readily converted to esters of carboxylic, sulfonic, carbamic, phosphonic, and phosphoric acids. Acylation to form a carboxylic acid ester is readily effected using a suitable acylating reagent such as an aliphatic acid anhydride or acid chloride. The corresponding aryl and heteroaryl acid anhydrides and acid chlorides can also be used. Such reactions are generally carried out using an amine catalyst such as pyridine in an inert solvent. In like manner, compounds of Formulas VII, VII-H, and Cyclo-VII that have at least one hydroxyl group present in the form of an alcohol or phenol can be acylated to its corresponding esters. Similarly, carbamic acid esters (urethans) can be obtained by reacting any hydroxyl group with isocyanates and carbamoyl chlorides. Sulfonate, phosphonate, and phosphate esters can be prepared using the corresponding acid chloride and similar reagents. Compounds of Formulas VII, VII-H, and Cyclo-VII that have at least one thiol group present can be converted to the corresponding thioesters derivatives analogous to those of alcohols and phenols using the same reagents and comparable reaction conditions. Compounds of Formulas VII, VII-H, and Cyclo-VII that have at least one primary or secondary amine group present can be converted to the corresponding amide derivatives. Amides of carboxylic acids can be prepared using the appropriate acid chloride or anhydrides with reaction conditions analogous to those used with alcohols and phenols. Ureas of the corresponding primary or secondary amine can be prepared using isocyanates directly and carbamoyl chlorides in the presence of an acid scavenger such as triethylamine or pyridine. Sulfonamides can be prepared from the corresponding sulfonyl chloride in the presence of aqueous sodium hydroxide. Suitable procedures and methods for preparing these derivatives can be found in House's Modern Synthetic Reactions, W. A. Benjamin, Inc., Shriner, Fuson, and Curtin in The Systematic Indentification of Organic Compounds, 5th Edition, John Wiley & Sons, and Fieser and Fieser in Reagents for Organic Synthesis, Volume 1, John Wiley & Sons. Reagents of a wide variety that can be used to derivatize hydroxyl, thiol, and amines of compounds of Formulas VII, VII-H, and Cyclo-VII are available from commerical sources or the references cited above, which are incorporated herein by reference.

Formula VII ("Generic Substituted Polycyclic Aryl tertiary-2-hydroxyalkylamines"), Formula VII-H ("Generic Substituted Polycyclic Heteroaryl tertiary-2-hydroxyalkylamines") and other compounds of this invention possessing hydroxyl, thiol, and amine functional groups can be alkylated to a wide variety derivatives. The hydroxyl group X, wherein $R_{16}$ is a hydrogen, of compounds of Formulas VII, VII-H and other compounds of the present invention can be readily converted to ethers. Alkylation to form an ether is readily effected using a suitable alkylating reagent such as an alkyl bromide, alkyl iodide or alkyl sulfonate. The corresponding aralkyl, heteroaralkyl, alkoxyalkyl, aralkyloxyalkyl, and heteroaralkyloxyalkyl bromides, iodides, and sulfonates can also be used. Such reactions are generally carried out using an alkoxide forming reagent such as sodium hydride, potassium t-butoxide, sodium amide, lithium amide, and n-butyl lithium using an inert polar solvent such as DMF, DMSO, THF, and similar, comparable solvents. amine catalyst such as pyridine in an inert solvent. In like manner, compounds of Formulas VII, VII-H, and Cyclo-VII that have at least one hydroxyl group present in the form of an alcohol or phenol can be alkylated to their corresponding ethers. Compounds of Formulas VII, VII-H, and Cyclo-VII that have at least one thiol group present can be converted to the corresponding thioether derivatives analogous to those of alcohols and phenols using the same reagents and comparable reaction conditions. Compounds of Formulas VII, VII-H, and Cyclo-VII that have at least one primary, secondary or tertiary amine group present can be converted to the corresponding quaternary ammonium derivatives. Quaternary ammonium derivatives can be prepared using the appropriate bromides, iodides, and sulfonates analogous to those used with alcohols and phenols. Conditions involve reaction of the amine by warming it with the alkylating reagent with a stoichiometric amount of the amine (i.e., one equivalent with a tertiary amine, two with a secondary, and three with a primary). With primary and secondary amines, two and one equivalents, respectively, of an acid scavenger are used concurrently. Tertiary amines can be prepared from the corresponding primary or secondary amine by reductive alkylation with aldehydes and ketones using reduction methods 1, 2, or 3 as shown in Scheme 1. Suitable procedures and methods for preparing these derivatives can be found in House's Modern Synthetic Reactions, W. A. Benjamin, Inc., Shriner, Fuson, and Curtin in The Systematic Indentification of Organic Compounds, 5th Edition, John Wiley & Sons, and Fieser and Fieser in Reagents for Organic Synthesis, Volume 1, John Wiley & Sons. Perfluoroalkyl derivatives can be prepared as described by DesMarteau in J. Chem. Soc. Chem. Commun. 2241 (1998). Reagents of a wide variety that can be used to derivatize hydroxyl, thiol, and amines of compounds of Formulas VII, VII-H, and Cyclo-VII are available from commerical sources or the references cited above, which are incorporated herein by reference.

Formula VII ("Generic Substituted Polycyclic Aryl tertiary-2-hydroxyalkylamines"), Formula VII-H ("Generic Substituted Polycyclic Heteroaryl tertiary-2-hydroxyalkylamines") and certain other compounds of this invention can be converted, according to Scheme 6, to the corresponding cyclic derivatives represented by the general designation "Tricyclic tertiary-oxyalkylamines" exmplified by Formula Cyclo-VII ("Substituted Tricyclic Phenyl tertiary-2-oxyalkylamines"). The hydroxyl group X, wherein $R_{16}$ is a hydrogen of compounds of Formulas VII and VII-H can be cyclized to corresponding cyclic ethers. Compounds suitable for cyclization will normally have at least one leaving group within 5 to 10 continuous atoms of the hydroxyl group X wherein $R_{16}$ is a hydrogen. Most preferably the leaving group will be within 5 to 7 atoms of the hydroxyl group X so as to form a 5 to 7 membered ring heteroatom containing ring. When the leaving group is part of an aromatic ring system, the leaving group will be preferably in an ortho position. Suitable leaving groups generally include halides, sulfates, sulfonates, trisubsituted amino, disubstituted sulfonium, diazonium, and like, and, in the case of aromatic systems, also includes nitro, alkoxy, aryloxy, heteroaryloxy, and alkylthio. When $X-R_{16}$ is a thiol, amino, or substituted amino, the corresponding analogous sulfur and nitrogen analogs, Cyclo-VII ("Substituted Tricyclic Phenyl tertiary-2-thioalkylamines and tertiary-2-azaalkylamines"), of Formula Cyclo-VII ("Substituted Tricyclic Phenyl tertiary-2-oxyalkylamines") can be obtained.

The cyclization reaction to form "Tricyclic tertiary-oxyalkylamines" can be accomplished by aromatic and aliphatic nucleophilic substitution reactions such as those disclosed in March's Advanced Organic Chemistry, 4th Edition, John Wiley & Sons, especially at pages 293–412 and 649–658 and the references cited therein, which are incorporated herein by reference. Hydroxyl containing suitably substituted compounds can be converted to a cyclic analog by heating a suitably substituted compound under anhydrous conditions in a suitable solvent, such as dimethylformamide, dimethylsulfoxide, N-methylpyrrolidone, tetraglyme, or hexamethylphosphoramide, in the presence of a suitable base such as potassium carbonate, cesium carbonate, sodium hydroxide, potassium tertiary-butoxide, or lithium diisopropylamide. Alternately, sodium amide in anhydrous ammonia solvent can be used. Temperatures in the range of −20° C. to 200° C. can be used for time periods of 30 minutes to more than 24 hours. The preferred temperature can be selected by standard synthetic chemical technique balancing maximum yield, maximum purity, cost, ease of isolation and operation, and time required. Isolation of the "Tricyclic tertiary-oxyalkylamines" can be effected as described above for other tertiary-oxyalkylamines. Representative "Tricyclic tertiary-oxyalkylamines" prepared using the methodology described above are included in Table 5.

Schemes are provided to detail the preparation of a large number examples, to illustrate the present invention, and are not intended to limit the scope thereof. Those skilled in the art will readily understand that known variations of the conditions and processes of the following preparative procedures can be used to prepare these compounds.

TABLE 5

Structure of Substituted Tricyclictertiary-2-oxyalkylamines.

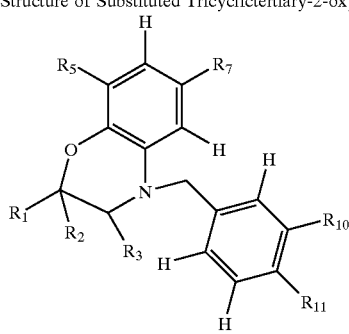

Cyclo-VII

| Cyclized Compound of Inhibitor Number | | $R_1$ | $R_2$ | $R_3$ | $R_5$ | $R_7$ | $R_{10}$ | $R_{11}$ |
|---|---|---|---|---|---|---|---|---|
| 1 | 27N | $CH_3$ | H | H | F | H | $CF_3$ | H |
| 1 | 44N | $CH_3$ | H | H | F | H | $CH_3$ | H |

TABLE 5-continued

Structure of Substituted Tricyclictertiary-2-oxyalkylamines.

Cyclo-VII

| Cyclized Compound of Inhibitor | Number | $R_1$ | $R_2$ | $R_3$ | $R_5$ | $R_7$ | $R_{10}$ | $R_{11}$ |
|---|---|---|---|---|---|---|---|---|
| 1 | 76N | $CH_3$ | H | H | F | H | H | $OCF_3$ |
| 1 | 84N | $CH_3$ | H | H | F | H | H | $CH_3$ |
| 1 | 85N | $CH_3$ | H | H | $CF_3$ | H | H | $CH_3$ |
| 3 | 3N | $CH_3$ | $CH_3$ | H | H | F | $OCF_2CF_2H$ | H |
| 3 | 27N | $CH_3$ | $CH_3$ | H | F | H | $CF_3$ | H |
| 3 | 44N | $CH_3$ | $CH_3$ | H | F | H | $CH_3$ | H |
| 3 | 76N | $CH_3$ | $CH_3$ | H | F | H | H | $OCF_3$ |
| 3 | 84N | $CH_3$ | $CH_3$ | H | F | H | H | $CH_3$ |
| 3 | 85N | $CH_3$ | $CH_3$ | H | $CF_3$ | H | H | $CH_3$ |
| 5 | 3N | $CH_3CH_2CH_2$ | H | H | H | F | $OCF_2CF_2H$ | H |
| 5 | 27N | $CH_3CH_2CH_2$ | H | H | F | H | $CF_3$ | H |
| 5 | 44N | $CH_3CH_2CH_2$ | H | H | F | H | $CH_3$ | H |
| 5 | 76N | $CH_3CH_2CH_2$ | H | H | F | H | H | $OCF_3$ |
| 5 | 84N | $CH_3CH_2CH_2$ | H | H | F | H | H | $CH_3$ |
| 5 | 85N | $CH_3CH_2CH_2$ | H | H | $CF_3$ | H | H | $CH_3$ |
| 6 | 3N | $CH_3OCH_2CH_2$ | H | H | H | F | $OCF_2CF_2H$ | H |
| 6 | 27N | $CH_3OCH_2CH_2$ | H | H | F | H | $CF_3$ | H |
| 6 | 44N | $CH_3OCH_2CH_2$ | H | H | F | H | $CH_3$ | H |
| 6 | 76N | $CH_3OCH_2CH_2$ | H | H | F | H | H | $OCF_3$ |
| 6 | 84N | $CH_3OCH_2CH_2$ | H | H | F | H | H | $CH_3$ |
| 6 | 85N | $CH_3OCH_2CH_2$ | H | H | $CF_3$ | H | H | $CH_3$ |
| 10 | 3N | $CH_3$ | $C_6H_5$ | H | H | F | $OCF_2CF_2H$ | H |
| 10 | 27N | $CH_3$ | $C_6H_5$ | H | F | H | $CF_3$ | H |
| 10 | 44N | $CH_3$ | $C_6H_5$ | H | F | H | $CH_3$ | H |
| 10 | 76N | $CH_3$ | $C_6H_5$ | H | F | H | H | $OCF_3$ |
| 10 | 84N | $CH_3$ | $C_6H_5$ | H | F | H | H | $CH_3$ |
| 10 | 85N | $CH_3$ | $C_6H_5$ | H | $CF_3$ | H | H | $CH_3$ |
| 25 | 3N | $CH_2=CH$ | H | H | H | F | $OCF_2CF_2H$ | H |
| 25 | 27N | $CH_2=CH$ | H | H | F | H | $CF_3$ | H |
| 25 | 44N | $CH_2=CH$ | H | H | F | H | $CH_3$ | H |
| 25 | 76N | $CH_2=CH$ | H | H | F | H | H | $OCF_3$ |
| 25 | 84N | $CH_2=CH$ | H | H | F | H | H | $CH_3$ |
| 25 | 85N | $CH_2=CH$ | H | H | $CF_3$ | H | H | $CH_3$ |
| 30 | 3N | $HOCH_2$ | H | H | H | F | $OCF_2CF_2H$ | H |
| 30 | 27N | $HOCH_2$ | H | H | F | H | $CF_3$ | H |
| 30 | 44N | $HOCH_2$ | H | H | F | H | $CH_3$ | H |
| 30 | 76N | $HOCH_2$ | H | H | F | H | H | $OCF_3$ |
| 30 | 84N | $HOCH_2$ | H | H | F | H | H | $CH_3$ |
| 30 | 85N | $HOCH_2$ | H | H | $CF_3$ | H | H | $CH_3$ |
| 34 | 3N | $CH_3$ | $R_2 + R_3 = (CH_2)_4$ | | H | F | $OCF_2CF_2H$ | H |
| 34 | 27N | $CH_3$ | $R_2 + R_3 = (CH_2)_4$ | | F | H | $CF_3$ | H |
| 34 | 44N | $CH_3$ | $R_2 + R_3 = (CH_2)_4$ | | F | H | $CH_3$ | H |

TABLE 5-continued
Structure of Substituted Tricyclictertiary-2-oxyalkylamines.
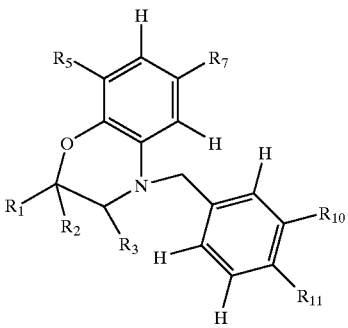
Cyclo-VII
| Cyclized Compound of Inhibitor Number | | $R_1$ | $R_2$ | $R_3$ | $R_5$ | $R_7$ | $R_{10}$ | $R_{11}$ |
|---|---|---|---|---|---|---|---|---|
| 34 | 76N | $CH_3$ | | $R_2 + R_3 =$ $(CH_2)_4$ | F | H | H | $OCF_3$ |
| 34 | 84N | $CH_3$ | | $R_2 + R_3 =$ $(CH_2)_4$ | F | H | H | $CH_3$ |
| 34 | 85N | $CH_3$ | | $R_2 + R_3 =$ $(CH_2)_4$ | $CF_3$ | H | H | $CH_3$ |
| 46 | 3N | $C_6H_5$ | H | H | H | F | O $CF_2CF_2H$ | H |
| 46 | 27N | $C_6H_5$ | H | H | F | H | $CF_3$ | H |
| 46 | 44N | $C_6H_5$ | H | H | F | H | $CH_3$ | H |
| 46 | 76N | $C_6H_5$ | H | H | F | H | H | $OCF_3$ |
| 46 | 84N | $C_6H_5$ | H | H | F | H | H | $CH_3$ |
| 46 | 85N | $C_6H_5$ | H | H | $CF_3$ | H | H | $CH_3$ |
Scheme 1
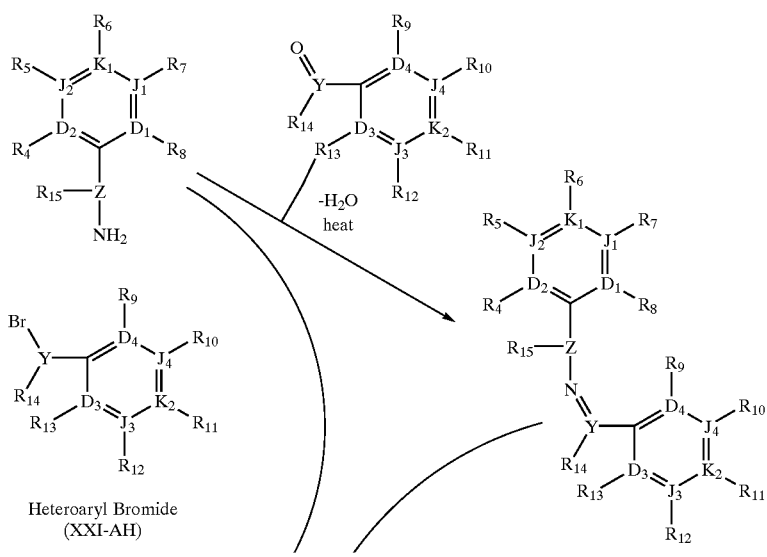

-continued
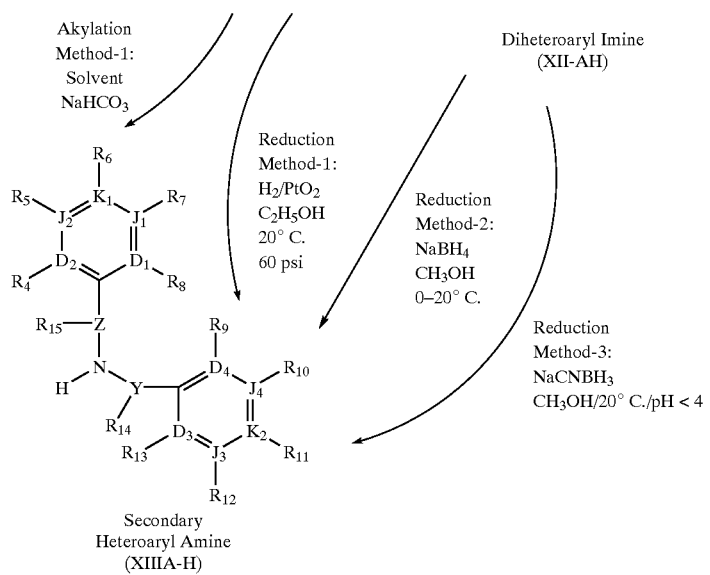
Scheme 2
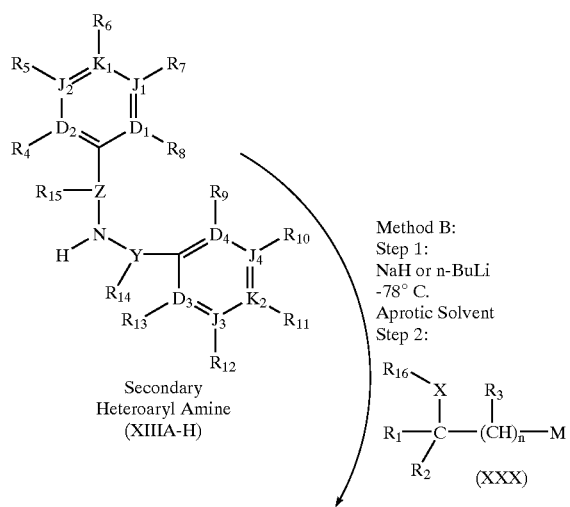
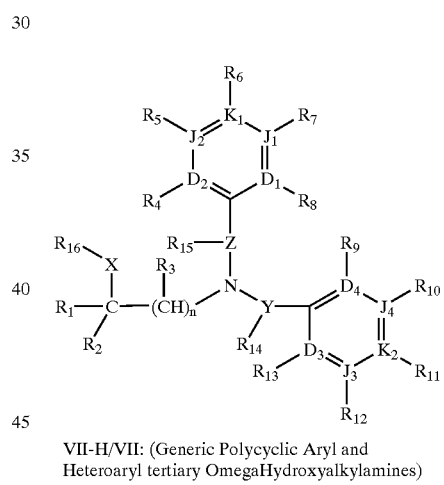
VII-H/VII: (Generic Polycyclic Aryl and Heteroaryl tertiary OmegaHydroxyalkylamines)
Scheme 3
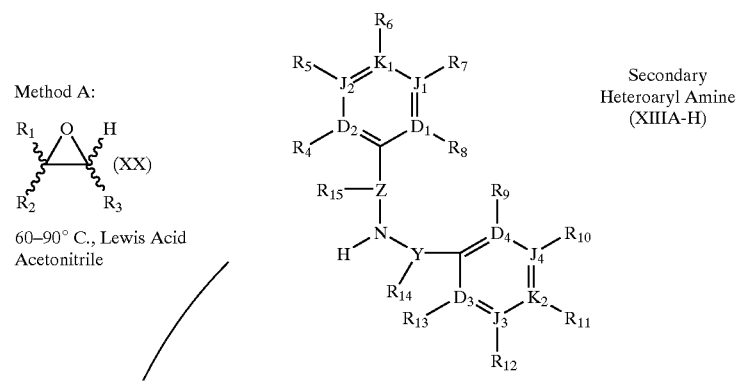

-continued

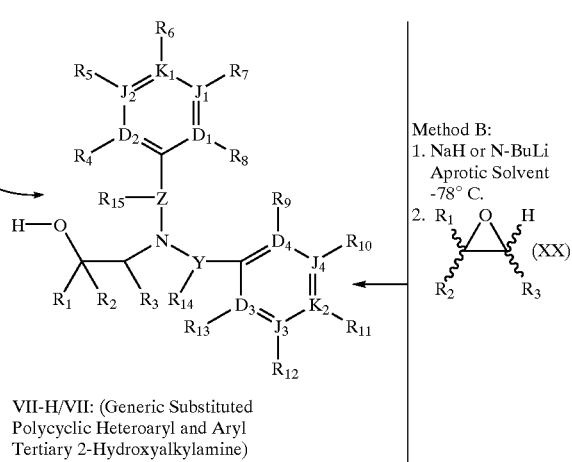

Method B:
1. NaH or N-BuLi
   Aprotic Solvent
   -78° C.
2. $R_1$ (XX) $R_2$ $R_3$ VII-H/VII: (Generic Substituted Polycyclic Heteroaryl and Aryl Tertiary 2-Hydroxyalkylamine)

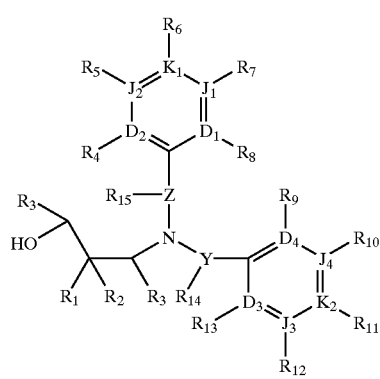

VII-H/VII/VII-3: (Isomeric Generic Substituted Polycyclic Heteroaryl and Aryl Tertiary 2-Hydroxyalkylamine

Scheme 4

VII-H/VII: (Generic Substituted Polycyclic 3-Aryloxyaryl, 3-Heteroaryloxyaryl, 3-Heteroaryloxyheteroaryl, 3-Aryloxyheteroaryl, 3-Arylthioaryl, 3-Heteroarylthioaryl, 3-Heteroarylthioheteroaryl, 3-Arylthioheteroaryl, Tertiary 2-Hydroxyalkylamine)

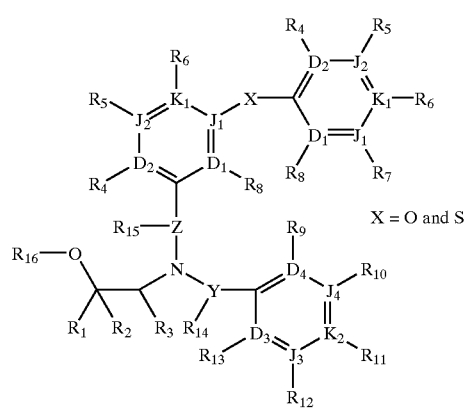

X = O and S

-continued $Cu_2(triflate)_2$·Benzene
2 equivalents of Aryl-OH, Aryl-SH, Heteroaryl-OH, or Heteroaryl-SH
2.5 eqv. $Cs_2CO_3$
2.5 eqv. 1-Napthoic Acid
4A Molecular Sieves
Dimethylacetamide/toluene
105° C./10–14 Days

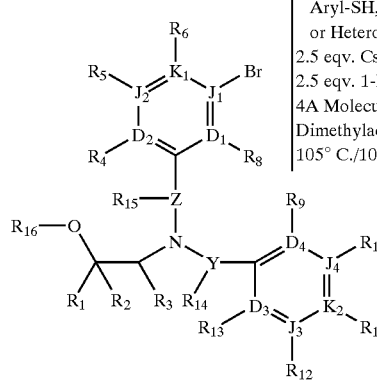

VII-H/VII: (Generic Substituted Polycyclic 3-Bromoheteroaryl and 3-Bromoaryl Tertiary 2-Hydroxyalkylamine)

Scheme 5

VII-H/VII: (Generic Substituted Polycyclic 3-Aryloxyaryl, 3-Heteroaryloxyaryl, 3-Aryloxyheteroaryl, or 3-Heteroaryloxyheteroaryl Tertiary 2-Hydroxyalkylamine)

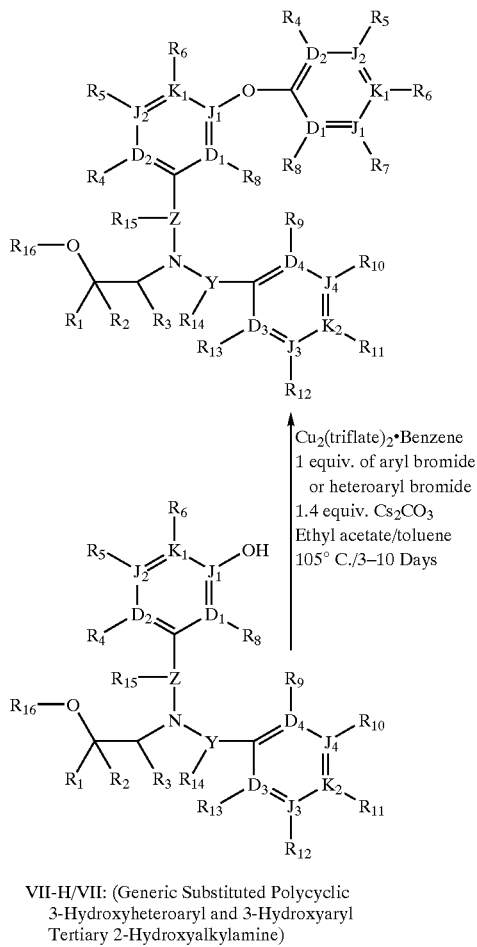

VII-H/VII: (Generic Substituted Polycyclic 3-Hydroxyheteroaryl and 3-Hydroxyaryl Tertiary 2-Hydroxyalkylamine)

Scheme 6

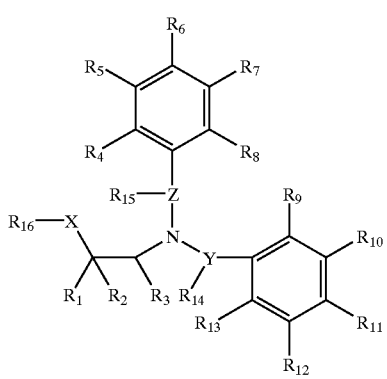

VII-H/VII: (Generic Substituted Polycyclic Aryl Tertiary 2-Hydroxyalkylamine) ($R_{16}$ = H)

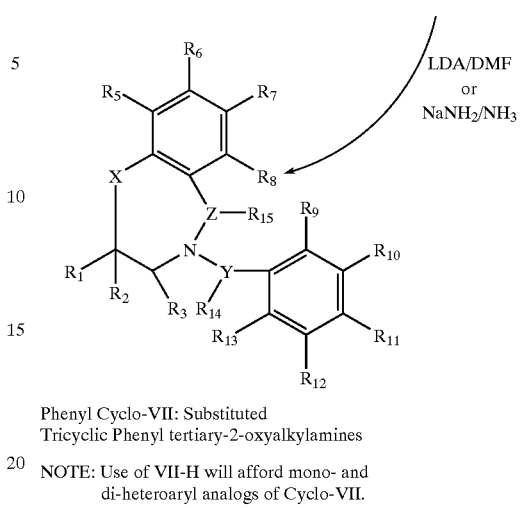

Phenyl Cyclo-VII: Substituted Tricyclic Phenyl tertiary-2-oxyalkylamines

NOTE: Use of VII-H will afford mono- and di-heteroaryl analogs of Cyclo-VII.

Scheme 7

VII: (Generic Substituted Polycyclic 3-Arylaryl Tertiary 2-Hydroxyalkylamine)

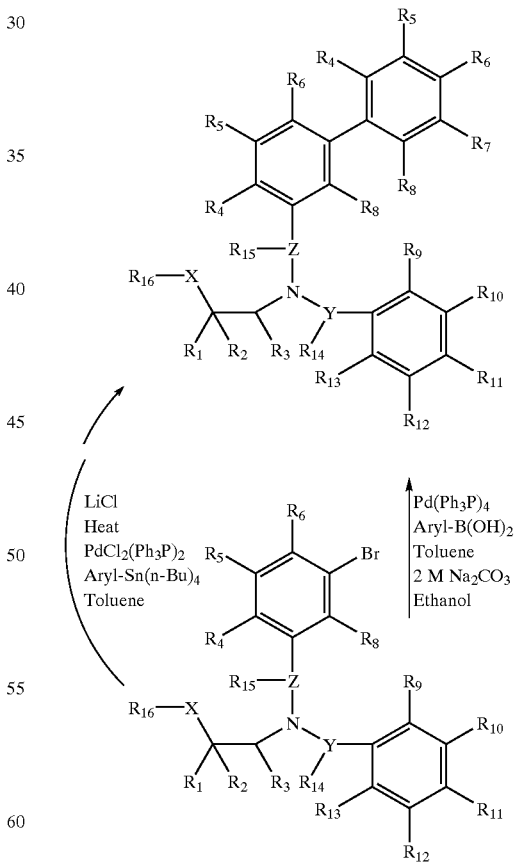

VII: (Generic Substituted Polycyclic 3-Bromoaryl Tertiary 2-Hydroxyalkylamine)

NOTE: Use of Heteroaryl-B(OH)$_2$ will give the heteroarylmethyl analog of VII.

Scheme 8

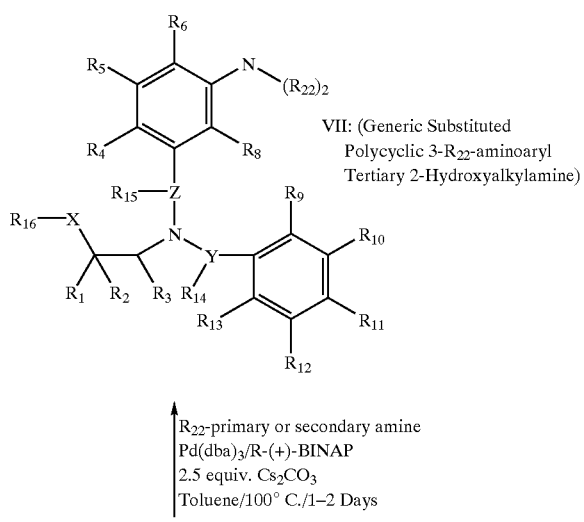

VII: (Generic Substituted Polycyclic 3-$R_{22}$-aminoaryl Tertiary 2-Hydroxyalkylamine)

$R_{22}$-primary or secondary amine
Pd(dba)$_3$/R-(+)-BINAP
2.5 equiv. Cs$_2$CO$_3$
Toluene/100° C./1–2 Days

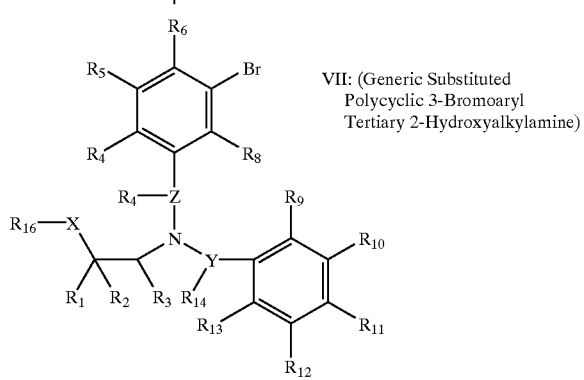

VII: (Generic Substituted Polycyclic 3-Bromoaryl Tertiary 2-Hydroxyalkylamine)

$R_{22}$ is selected independently from any one or two of the following groups: hydrido, hydroxy, aryloxy, alkyl, alkenyl, alkynyl, aryl, aralkyl, aryloxyalkyl, alkoxyalkyl, aralkoxyalkyl, alkkylsulfinylalkyl, haloalkyl, haloalkenyl, halocycloalkyl, halocycloalkoxy, halocycloalkoxyalkyl, arylsufinylaalkyl, arylsulfonylakyl, alkylamino, cycloalkylsulfinylalkyl, cycloalkylsulfonylalkyl, heteroalkylsulfonylalkyl, heteroarylsulfinylalkyl, aralkylsulfinylalkyl, aralkylsulfonylalkyl, hydroxyalkyl, amino, alkoxy, alkylsulfonylalkyl, aralkylthioalkyl, heteroaralkylthioalkyl, heteroaryloalkyl, alkenyloxyalkyl, haloalkoxy, haloalkoxyalkyl, haloalkenyloxyalkyl, heteroaryl, halocycloalkenyloxyalkyl, heteroarylalkyl, halocycloalkenyl, and heteroarylthioalkyl.

Scheme 9

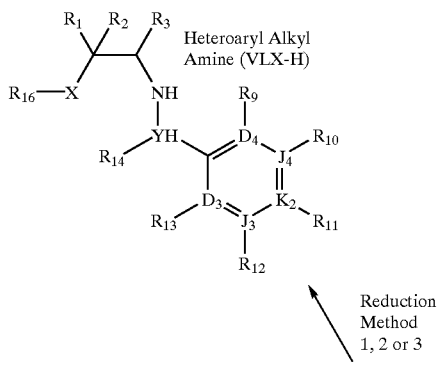

Reduction Method 1, 2 or 3

Heteroaryl Carbonyl (XI-AH) → Heteroaryl Imine (VL-H)

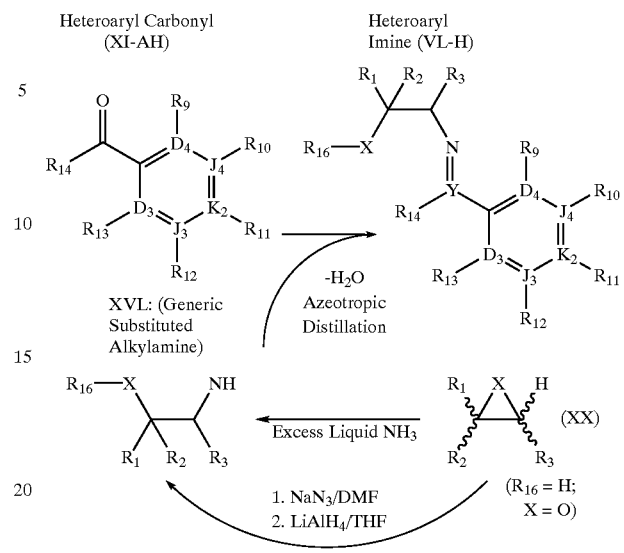

XVL: (Generic Substituted Alkylamine)

-H$_2$O Azeotropic Distillation

Excess Liquid NH$_3$ (XX)
($R_{16}$ = H; X = O)

1. NaN$_3$/DMF
2. LiAlH$_4$/THF

Scheme 10

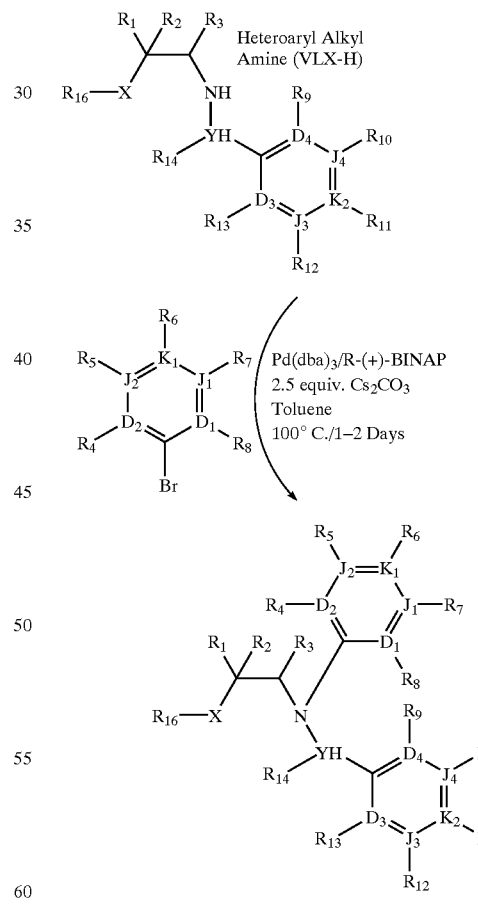

Pd(dba)$_3$/R-(+)-BINAP
2.5 equiv. Cs$_2$CO$_3$
Toluene
100° C./1–2 Days

VII-H: (Generic Substituted Polycyclic Heteroaryl Tertiary 2-hydroxyalkylamine)

NOTE: Use of a heteroaryl alkyl amine with an aryl bromide or an aryl alkyl amine analog of VLX-H with an aryl bromide will afford mono or di aryl analogs of VII-H Scheme 11
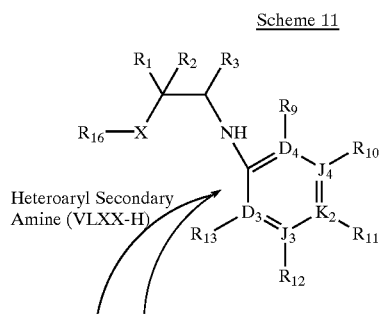
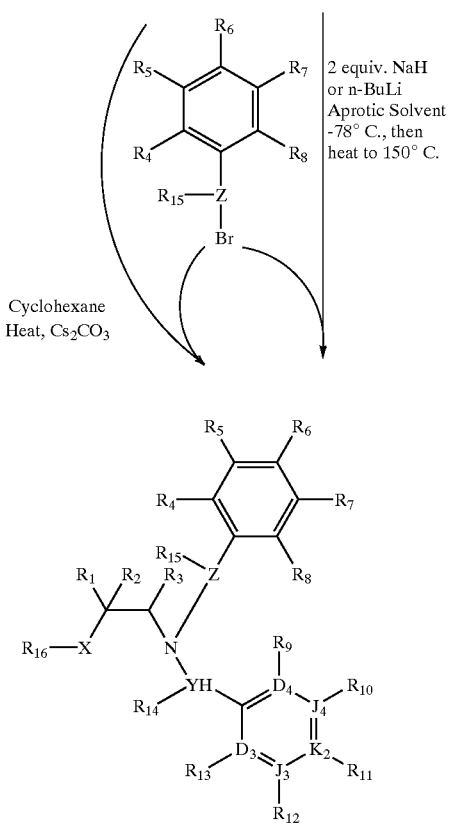
VII-H: (Generic Substituted Polycyclic Aryl Heteroaryl Tertiary 2-hydroxyalkylamine)
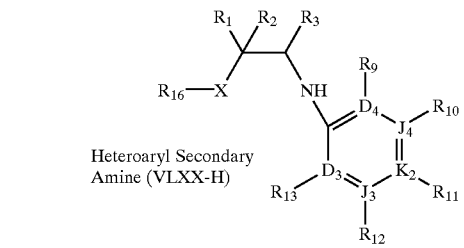
Scheme 12
Scheme 13
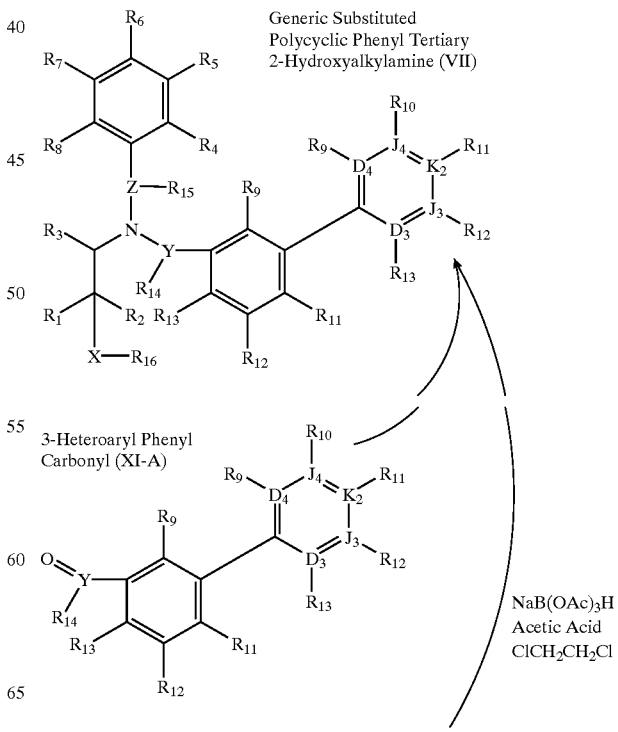

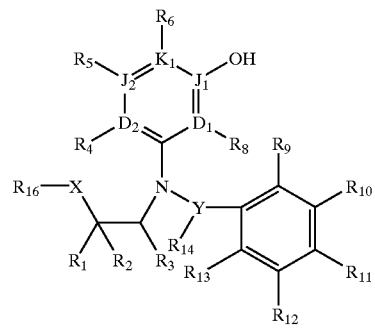

VII-H: (Generic Substituted Polycyclic
Phenyl Heteroaryl Tertiary 2-Hydroxyalkyl-
amine when $R_{16}$-X equals HO) NOTE: Aryl Analogs
(VII) of (VII-H) Can Be Prepared by Starting
with Aryl Bromide Analogs of (LXXI-AH)

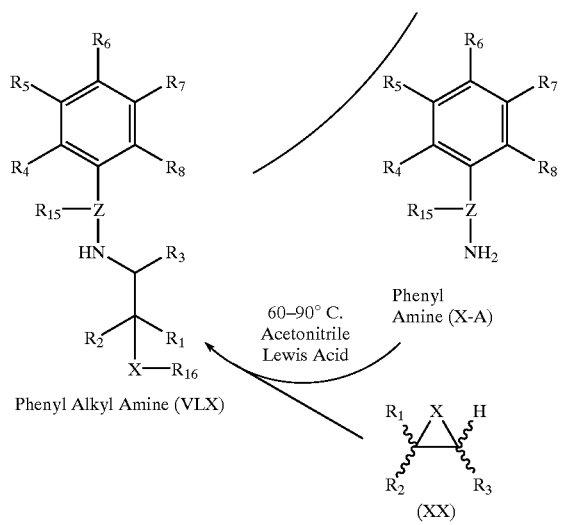

Phenyl Alkyl Amine (VLX)

NOTE: Heteroaryl Analogs Can Be Prepared Using
Heteroaryl Analogs of X-A, VLX, and XI-A.

Scheme 15

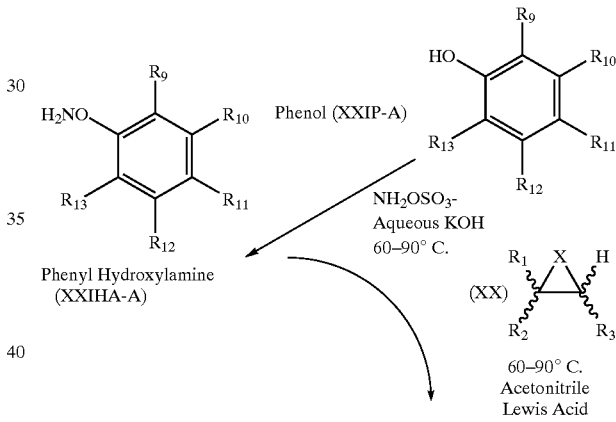

Scheme 14

Method A:

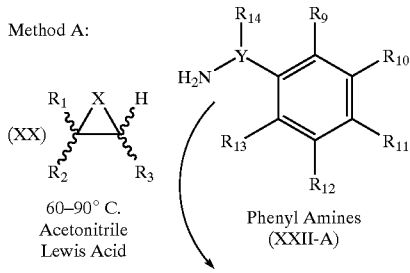

Phenyl Amines
(XXII-A)

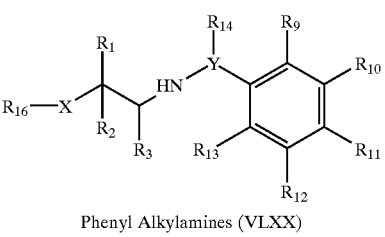

Phenyl Alkylamines (VLXX)

Pd(dba)$_3$/R-(+)-BINAP
2.5 equiv. Cs$_2$CO$_3$
Toluene
100° C./1–20 Days

Heteroaryl Halide
(LXXI-AH)
M = Br or Cl

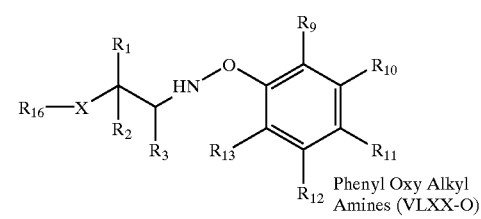

Heteroaryl Halide
(LXXI-AH)
M = Br or Cl

TMS-Cl
TEA

1. Pd(dba)$_3$/R-(+)-BINAP
2.5 equiv. Cs$_2$CO$_3$
Toluene/100° C./1–20 Days
2. Water

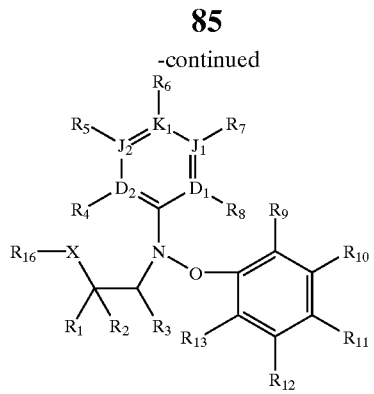

VII-H: (Generic Substituted Polycyclic Phenyl Heteroaryl Tertiary 2-Hydroxyalkylamine when $R_{16}$-X = HO and Y = O) NOTE: Diaryl and Diheteroaryl Analogs Can Be Prepared by Using Aryl Bromide and Heteroaryl-OH, respectively.

The following examples are provided to illustrate the present invention and are not intended to limit the scope thereof. Without further elaboration, it is believed that one skilled in the art can, using the preceding descriptions, utilize the present invention to its fullest extent. Therefore the following preferred specific embodiments are to be construed as merely illustrative and not limitative of the remainder of the disclosure in any way whatsoever. Compounds containing multiple variations of the structural modifications illustrated in the preceding schemes or the following Examples are also contemplated. Those skilled in the art will readily understand that known variations of the conditions and processes of the following preparative procedures can be used to prepare these compounds.

One skilled in the art may use these generic methods to prepare the following specific examples, which have been or may be properly characterized by $^1$H NMR and mass spectrometry. These compounds also may be formed in vivo.

The following examples contain detailed descriptions of the methods of preparation of compounds of Formula V-H. These detailed descriptions fall within the scope and are presented for illustrative purposes only and are not intended as a restriction on the scope of the invention. All parts are by weight and temperatures are Degrees centigrade unless otherwise indicated.

EXAMPLE 1

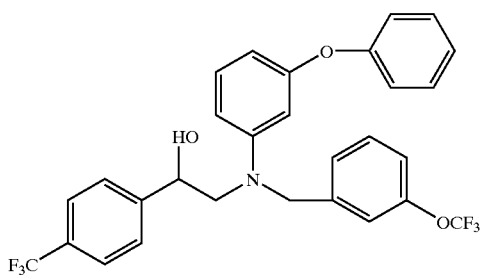

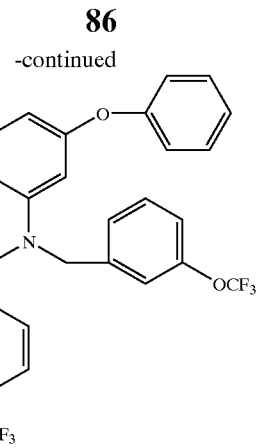

2-[(3-phenoxy)phenyl[[3-trifluoromethoxy)phenyl]methyl]amino]-1-[(4-trifluoromethyl)phenyl]ethanol and
2-[(3-phenoxy)phenyl[[3-trifluoromethoxy)phenyl]methyl]amino]-2-[(4-trifluoromethyl)phenyl]ethanol To a methylene chloride (5 mL) solution of 4-(trifluoromethyl)-styrene oxide (0.70 g, 3.7 mmol) and N-(3-phenoxyphenyl)-N-[[(3-trifluoromethoxy)phenyl]methyl]amine (1.34 g, 3.7 mmol) was added Yb(OTf)$_3$ (461 mg, 0.74 mmol). The resulting slurry was stirred for 18 h at room temperature under nitrogen. Diethyl ether (50 mL) was added to the reaction mixture, and the mixture was washed with water (50 mL) and brine (50 mL). The organic layer was dried over MgSO$_4$ and evaporated to give a pale green oil. Thin-layer chromatography of the isolated oil suggested two major products. Separation and purification of the products was accomplished by flash-column chromatography over silica gel (60 g), eluting with 15% ethyl acetate in hexanes. Fractions were collected containing pure fraction of the two products separately. The fractions containing the more mobile, less polar band were evaporated to an oil. The oil was taken up in ethanol, evaporated and dried in vacuo for 24 h to give 230 mg (10%) of the desired EX-1A, 2-[(3-phenoxy)phenyl[[(3-trifluoromethoxy)phenyl]-methyl]amino]-1-[(4-trifluoromethyl)phenyl]ethanol, as an oil. MS: m/z=548 [M+H]$^+$, Anal. calcd. for C$_{29}$H$_{23}$O$_3$NF$_6$.0.16 EtOH: C, 63.62; H, 4.23; N, 2.56. Found: C, 63.46; H, 4.26; N, 2.54. Structure confirmed by $^1$H NMR (C$_6$D$_6$) in which the OH signal at 1.31 ppm appears as a doublet and pcosy NMR.

The fractions containing the less mobile, more polar band were evaporated to an oil. The oil was taken up in ethanol, evaporated and dried in vacuo for 24 h to give 910 mg (45%) of the desired EX-1B, 2-[(3-phenoxy)phenyl[[(3-trifluoromethoxy)phenyl]-methyl]amino]-2-[(4-trifluoromethyl)phenyl]ethanol, as an oil. MS: m/z=548 [M+H]$^+$, Anal. calcd. for C$_{29}$H$_{23}$O$_3$NF$_6$.0.40 EtOH: C, 63.28; H, 4.46; N, 2.52. Found: C, 63.17; H, 4.41; N, 2.44. Structure confirmed by $^1$H NMR (C$_6$D$_6$) in which the OH signal at 0.84 ppm appears as a triplet and pcosy NMR.

Additional substituted 2-[(N-aryl)[N-arylmethyl]amino]alkanols and 2-[(N-aralkyl)[N-arylmethyl]amino]alkanols can be prepared by one skilled in the art using similar methods with the appropriate epoxide and amine, as shown in Example Tables 1 and 2, respectively. Additional substituted 2-[(N-aryl)[N-arylmethyl]amino]cycloalkanols can also be prepared by one skilled in the art using similar methods with the appropriate epoxide and amine, as shown in Example Table 3.

Example Table 1. Substituted 2-[(N-aryl)[N-arylmethyl]amino]alkanols.

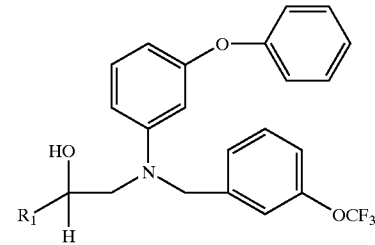

| Ex. No. | R$_1$ | Calculated Mass [M + H]$^+$ | Observed Mass [M + H]$^+$ |
|---|---|---|---|
| 2 | n-propyl | 446.1943 | 446.1940 |
| 3 | phenyl | 480.1786 | 480.1792 |
| 4 | ethenyl | 430.1630 | 430.1621 |
| 5 | benzyl | 494.1943 | 494.1935 |
| 6 | (p-Cl-phenoxy)-methyl | 544.1502 | 544.1507 |
| 7 | (2-furylmethoxy)-methyl | 514.1841 | 514.1797 |

| Ex. No. | R$_1$ | R$_2$ | R$_3$ | Calculated Mass [M + H]$^+$ | Observed Mass [M + H]$^+$ |
|---|---|---|---|---|---|
| 8 | H | H | 3-CF$_3$-phenyl | 548.1660 | 548.1676 |
| 9 | CO$_2$CH$_3$ | CH$_3$ | H | 476.1685 | 476.1702 |

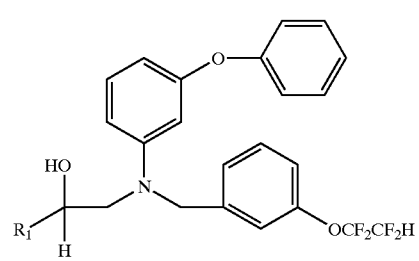

| Ex. No. | R$_1$ | Calculated Mass [M + H]$^+$ | Observed Mass [M + H]$^+$ |
|---|---|---|---|
| 10 | phenyl | 512.1848 | 512.1833 |

Example Table 2. Substituted 2-[(N-aralkyl)[N-arylmethyl]amino]alkanols.

| Ex. No. | R$_1$ | Calculated Mass [M + H]$^+$ | Observed Mass [M + H]$^+$ |
|---|---|---|---|
| 11 | n-propyl | 452.1660 | 452.1669 |
| 12 | benzyl | 500.1660 | 500.1648 |
| 13 | methoxymethyl | 454.1453 | 454.1488 |
| 14 | methyl | 424.1347 | 424.1344 |
| 15 | carboethoxy | 482.1402 | 482.1421 |
| 16 | hydroxymethyl | 440.1296 | 440.1288 |
| 17 | phenoxymethyl | 516.1609 | 516.1631 |
| 18 | (p-Cl-phenoxy)-methyl | 550.1220 | 550.1210 |
| 19 | N-morpholinyl-methyl | 509.1875 | 509.1874 |
| 20 | N-phthalimido-methyl | 569.1510 | 569.1521 |
| 21 | (p-CH$_3$O-phenoxy)-methyl | 546.1714 | 546.1724 |

| Ex. No. | R$_3$ | Calculated Mass [M + H]$^+$ | Observed Mass [M + H]$^+$ |
|---|---|---|---|
| 22 | CH$_3$ | 500.1660 | 500.1613 |
| 23 | phenyl | 562.1817 | 562.1768 |
| 24 | carboethoxy | 558.1715 | 558.1720 |

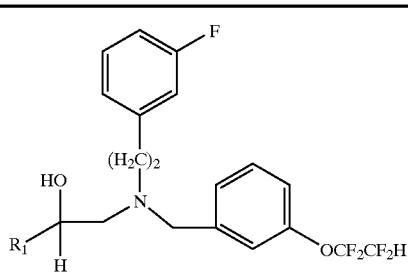

| Ex. No. | R$_1$ | Calculated Mass [M + H]$^+$ | Observed Mass [M + H]$^+$ |
|---|---|---|---|
| 25 | n-hexyl | 474.2431 | 474.2446 |

Example Table 3. Substituted
2-[(N-aryl)[N-arylmethyl]amino]cyclohexanols.

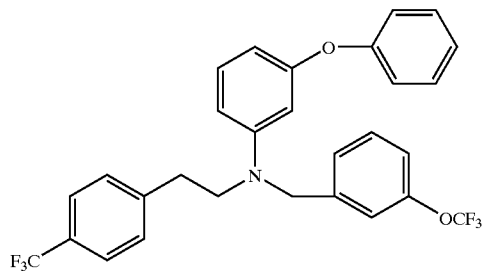

| Ex. No. | R₂ + R₃ | Calculated Mass [M + H]⁺ | Observed Mass [M + H]⁺ |
|---|---|---|---|
| 26 | (CH₂)₄ | 458.1943 | 458.1958 |

EXAMPLE 27

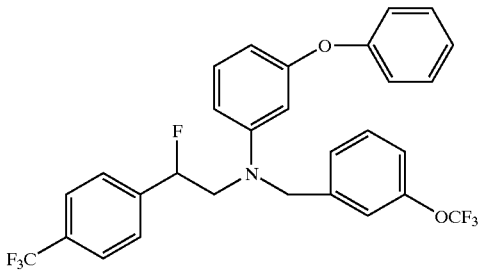

N-[(3-phenoxy)phenyl]-N-[[(3-trifluoromethoxy)phenyl]methyl]-
2-[(4-trifluoromethyl)phenyl]ethanamine EX-27A) To a $CH_2Cl_2$ (10 mL) solution of 4-trifluoromethylphenylacetic acid (0.714 g, 3.5 mmol) and pyridine (0.281 mL, 3.5 mmol) at 0° C. was added cyanuric fluoride (0.62 g, 4.6 mmol) dropwise causing the formation of a precipitate. The slurry was stirred at 0° C. for 1 h, and then the reaction mixture was quenched with ice water (30 mL). The mixture was extracted with $CH_2Cl_2$ (2×30 mL), dried (MgSO₄), filtered and concentrated to approx. 10 mL. The resulting yellow solution of the acid fluoride was added to a $CH_2Cl_2$ (10 mL) solution of N-(3-phenoxyphenyl)-[[3-(trifluoromethoxy)-phenyl]methyl]amine (1.00 g, 2.79 mmol) and triethylamine (0.425 mL, 3.05 mmol). This reaction mixture was stirred at room temperature for 3 hours, diluted with $CH_2Cl_2$ (30 mL) and washed with 1 N HCl, saturated NaHCO₃ and brine. Concentration of the organic layer yielded 1.41 g of the desired amide, N-[(3-phenoxy)phenyl-N-(3-tri-fluoromethoxy)phenyl]methyl]-2-[(4-trifluoromethyl)phenyl]ethanamide, as a red oil which was used without further purification.

To a THF (10 mL) solution of the crude amide (1.41 g, 2.58 mmol) from EX-27A at 0° C. was added dropwise a THF solution of LiAlH₄ (5.0 mL, 1.0 M, 5.0 mmol). The reaction mixture was allowed to warm to room temperature and stirred for 1 h. The reaction was quenched by the slow addition of water (0.15 mL), 2.5 N NaOH (0.15 mL) and water (0.45 mL). The resulting slurry was filtered through celite, and the filtrate was dried (MgSO₄), filtered and evaporated to a yellow oil. Purification by flash column chromatography on silica gel eluting with 5% ethyl acetate in hexane gave 32 mg (2%) of the desired pure N-[(3-phenoxy)phenyl]-N-[[(3-trifluoromethoxy)-phenyl]methyl]-2-[(4-trifluoromethyl)phenyl]ethanamine as an oil. HRMS calcd. for $C_{29}H_{24}NO_2F_6$ 532.1711 [M+H]⁺, found 532.1686. ¹H NMR (CDCl₃) δ2.40 (t, 2H), 3.02 (t, 2H), 3.79 (s, 2H), 6.21 (dd, 1H), 6.43 (m, 2H), 6.56 (d, 2H), 6.64 (m, 1H), 6.78 (m, 4H), 7.0 (m, 5H), 7.24 (d, 2H).

EXAMPLE 28

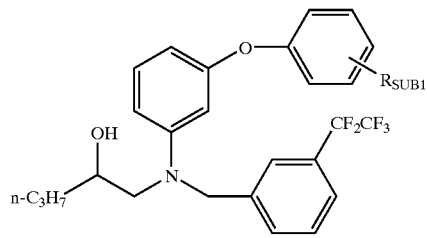

N-[(3-phenoxy)phenyl]-N-[[(3-trifluoromethoxy)phenyl]methyl]-
2-[(4-trifluoromethyl)phenyl]-2-fluoro-ethanamine To a $CH_2Cl_2$ (2 mL) solution of EX-1A (153 mg, 0.28 mmol) at −78° C. was added (diethylamino)sulfur trifluoride (40 mL, 0.30 mmol). The solution was stirred for 15 min at −78° C. and allowed to reach room temperature. After 1 h at room temperature, the solution was diluted with $CH_2Cl_2$ (20 mL) and then washed with water and brine. The organic layer was dried (MgSO₄), filtered and evaporated to an oil. Purification by flash column chromatography on silica gel eluting with 20% ethyl acetate in hexane gave 21 mg (14%) of the desired pure N-[(3-phenoxy)phenyl]-N-[[(3-trifluoromethoxy)phenyl]methyl]-2-[(4-trifluoromethyl)phenyl]-2-fluoro-ethanamine as an oil. HRMS calcd. for $C_{29}H_{23}NO_2F_7$ 550.1617 [M+H]⁺, found 3078550.1652. ¹⁹F NMR (CDCl₃) δ−57.9 (s, 3F), −62.7 (s, 3F), −184.3 (m, 1F). ¹H NMR (CDCl₃) δ3.13 (m, 2H), 4.09 (s, 2H), 5.35 (m, 1H), 6.2 (d, 1H), 6.4 (t, 1H), 6.5 (d, 1H), 6.6–7.0 (m, 12H), 7.2 (d, 2H).

Based on the preceding procedures, additional substituted 2-[(N-aryl)[N-arylmethyl]amino]alkanols and additional substituted 2-[(N-aryl)[N-aralkyl]amino]cycloalkanols are prepared by one skilled in the art using similar methods, as shown in Example Tables 4 and 5, respectively.

Example Table 4.
Substituted 2-[(N-aryl)[N-arylmethyl]amino]alkanols.

| Ex. No. | R_SUB1 |
|---|---|
| 29 | 3-isopropyl |
| 30 | 2-Cl, 3-Cl |
| 31 | 3-CF₃O |
| 32 | 4-F |
| 33 | 4-CH₃ |
| 34 | 2-F, 5-Br |
| 35 | 3-CF₃CF₂ |

Example Table 4.
Substituted 2-[(N-aryl)[N-arylmethyl]amino]alkanols.

| | |
|---|---|
| 36 | 3-CH$_3$CH2 |
| 37 | 3-CH$_3$, 5-CH$_3$ |
| 38 | 3-(CH$_3$)$_3$C |
| 39 | 4-Cl, 3-CH$_3$CH$_2$ |
| 40 | 3-Cl, 4-Cl |
| 41 | 3,4-(CH$_2$)4 |
| 42 | 3-HCF$_2$CF$_2$O |
| 43 | 3-CHF$_2$O |
| 44 | 3-(CH$_3$)$_2$N |
| 45 | 3-cyclopropyl |
| 46 | 3-(2-furyl) |
| 47 | 3-CF$_3$CF$_2$ |
| 48 | 4-NH$_2$ |
| 49 | 4CH$_3$CH$_2$CH$_2$O |

Structure: 3-R$_{SUB2}$-phenyl-N(CH$_2$CH(OH)-n-C$_3$H$_7$)-CH$_2$-(3-CF$_2$CF$_3$-phenyl)

| Ex. No. | R$_{SUB2}$ |
|---|---|
| 50 | 3-CF$_3$O-benzyloxy |
| 51 | 3-CF$_3$-benzyloxy |
| 52 | 3-F, 5-F-benzyloxy |
| 53 | cyclohexylmethyleneoxy |
| 54 | benzyloxy |
| 55 | 3-CF$_3$, 5-CF$_3$-benzyloxy |
| 56 | 4-CF$_3$O-benzyloxy |
| 57 | 4-CH$_3$CH$_2$-benzyloxy |
| 58 | isopropoxy |
| 59 | 3-CF$_3$-benzyl |
| 60 | isopropylthio |
| 61 | cyclopentoxy |
| 62 | 3-Cl-5-pyridinyloxy |
| 63 | 3-CF$_3$S-benzyloxy |
| 64 | 4-NO$_2$-phenylthio |
| 65 | 2-F, 3-CF$_3$-benzyloxy |
| 66 | 4-CH$_3$O-phenylamino |
| 67 | cyclopropoxy |
| 68 | 1-phenylethoxy |
| 69 | 4-F, 3-CH3-benzoyl |
| 70 | 3-CF$_3$-phenyl |

Structure: 3-(4-R$_{SUB1}$-phenoxy)-phenyl-N(CH$_2$CH(OH)-n-C$_3$H$_7$)-CH$_2$-(3-OCF$_2$CF$_2$H-phenyl)

| Ex. No. | R$_{SUB1}$ |
|---|---|
| 71 | 3-isopropyl |
| 72 | 2-Cl, 3-Cl |
| 73 | 3-CF$_3$O |
| 74 | 4-F |
| 75 | 4-CH$_3$ |
| 76 | 2-F, 5-Br |
| 77 | 3-CF$_3$CF$_2$ |
| 78 | 3-CH$_3$CH$_2$ |
| 79 | 3-CH$_3$, 5-CH$_3$ |
| 80 | 3-(CH$_3$)$_3$C |
| 81 | 4-Cl, 3-CH$_3$CH$_2$ |
| 82 | 4-CH$_3$CH$_2$CH$_2$O |

Example Table 4.
Substituted 2-[(N-aryl)[N-arylmethyl]amino]alkanols.

| | |
|---|---|
| 83 | 3,4-(CH$_2$)4 |
| 84 | 3-HCF$_2$CF$_2$O |
| 85 | 3-CHF$_2$O |
| 86 | 3-(CH$_3$)$_2$N |
| 87 | 3-cyclopropyl |
| 88 | 3-(2-furyl) |
| 89 | 3-CF$_3$CF$_2$ |
| 90 | 4-NH$_2$ |

Structure: 3-R$_{SUB2}$-phenyl-N(CH$_2$CH(OH)-n-C$_3$H$_7$)-CH$_2$-(3-OCF$_2$CF$_2$H-phenyl)

| Ex. No. | R$_{SUB2}$ |
|---|---|
| 91 | 3-CF$_3$O-benzyloxy |
| 92 | 3-CF$_3$-benzyloxy |
| 93 | 3-F, 5-F-benzyloxy |
| 94 | cyclohexylmethyleneoxy |
| 95 | benzyloxy |
| 96 | 3-CF$_3$, 5-CF$_3$-benzyloxy |
| 97 | 4-CF$_3$O-benzyloxy |
| 98 | 4-CH$_3$CH$_2$-benzyloxy |
| 99 | isopropoxy |
| 100 | 3-CF$_3$-benzyl |
| 101 | isopropylthio |
| 102 | cyclopentoxy |
| 103 | 3-Cl-5-pyridinyloxy |
| 104 | 3-CF$_3$S-benzyloxy |
| 105 | 4-NO2-phenylthio |
| 106 | 3-CF$_3$-phenyl |
| 107 | 4-CH$_3$O-phenylamino |
| 108 | cyclopropoxy |
| 109 | 1-phenylethoxy |
| 110 | 4-F, 3-CH$_3$-benzoyl |

Structure: 3-(4-R$_{SUB1}$-phenoxy)-phenyl-N(CH$_2$CH(OH)-i-C$_3$H$_7$)-CH$_2$-(3-OCF$_2$CF$_2$H-phenyl)

| Ex. No. | R$_{SUB1}$ |
|---|---|
| 111 | 3-isopropyl |
| 112 | 2-Cl, 3-Cl |
| 113 | 3-CF$_3$O |
| 114 | 4-F |
| 115 | 4-CH$_3$ |
| 116 | 2-F, 5-Br |
| 117 | 3-CF$_3$CF$_2$ |
| 118 | 3-CH$_3$CH$_2$ |
| 119 | 3-CH$_3$, 5-CH$_3$ |
| 120 | 3-(CH$_3$)$_3$C |
| 121 | 4-Cl, 3-CH$_3$CH$_2$ |
| 122 | 4-CH$_3$CH$_2$CH$_2$O |
| 123 | 3,4-(CH$_2$)4 |
| 124 | 3-HCF$_2$CF$_2$O |
| 125 | 3-CHF$_2$O |
| 126 | 3-(CH$_3$)$_2$N |
| 127 | 3-cyclopropyl |
| 128 | 3-(2-furyl) |

-continued

Example Table 4.
Substituted 2-[(N-aryl)[N-arylmethyl]amino]alkanols.

| Ex. No. | |
|---|---|
| 129 | 3-CF$_3$CF$_2$ |
| 130 | 4-NH$_2$ |

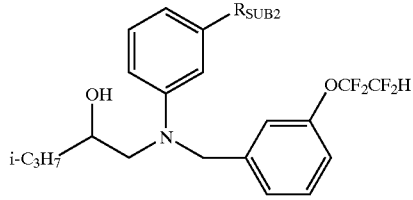

| Ex. No. | R$_{SUB2}$ |
|---|---|
| 131 | 3-CF$_3$O-benzyloxy |
| 132 | 3-CF$_3$-benzyloxy |
| 133 | 3-F, 5-F-benzyloxy |
| 134 | cyclohexylmethyleneoxy |
| 135 | benzyloxy |
| 136 | 3-CF$_3$, 5-CF$_3$-benzyloxy |
| 137 | 4-CF$_3$O-benzyloxy |
| 138 | 4-CH$_3$CH$_2$-benzyloxy |
| 139 | isopropoxy |
| 140 | 3-CF$_3$-benzyl |
| 141 | isopropylthio |
| 142 | cyclopentoxy |
| 143 | 3-Cl-5-pyridinyloxy |
| 144 | 3-CF$_3$S-benzyloxy |
| 145 | 4-NO$_2$-phenylthio |
| 146 | 3-CF$_3$-phenyl |
| 147 | 4-CH$_3$O-phenylamino |
| 148 | cyclopropoxy |
| 149 | 1-phenylethoxy |
| 150 | 4-F, 3-CH$_3$-benzoyl |

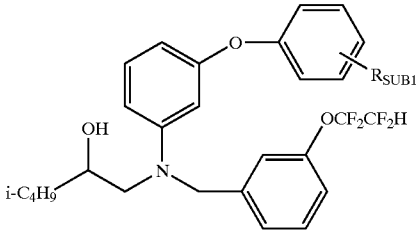

| Ex. No. | R$_{SUB1}$ |
|---|---|
| 151 | 3-isopropyl |
| 152 | 2-Cl, 3-Cl |
| 153 | 3-CF$_3$O |
| 154 | 4-F |
| 155 | 4-CH$_3$ |
| 156 | 2-F, 5-Br |
| 157 | 3-CF$_3$CF$_2$ |
| 158 | 3-CH$_3$CH$_2$ |
| 159 | 3-CH$_3$, 5-CH$_3$ |
| 160 | 3-(CH$_3$)$_3$C |
| 161 | 4-Cl, 3-CH$_3$CH$_2$ |
| 162 | 4-CH$_3$CH$_2$CH$_2$O |
| 163 | 3,4-(CH$_2$)$_4$ |
| 164 | 3-HCF$_2$CF$_2$O |
| 165 | 3-CHF$_2$O |
| 166 | 3-(CH$_3$)$_2$N |
| 167 | 3-cyclopropyl |
| 168 | 3-(2-furyl) |
| 169 | 3-CF$_3$CF$_2$ |
| 170 | 4-NH$_2$ |

-continued

Example Table 4.
Substituted 2-[(N-aryl)[N-arylmethyl]amino]alkanols.

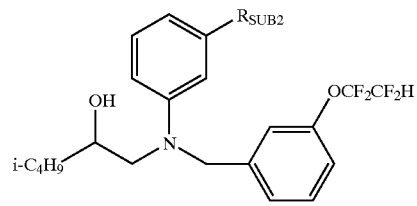

| Ex. No. | R$_{SUB2}$ |
|---|---|
| 171 | 3-CF$_3$O-benzyloxy |
| 172 | 3-CF$_3$-benzyloxy |
| 173 | 3-F, 5-F-benzyloxy |
| 174 | cyclohexylmethyleneoxy |
| 175 | benzyloxy |
| 176 | 3-CF$_3$, 5-CF$_3$-benzyloxy |
| 177 | 4-CF$_3$O-benzyloxy |
| 178 | 4-CH$_3$CH$_2$-benzyloxy |
| 179 | isopropoxy |
| 180 | 3-CF$_3$-benzyl |
| 181 | isopropylthio |
| 182 | cyclopentoxy |
| 183 | 3-Cl-5-pyridinyloxy |
| 184 | 3-CF$_3$S-benzyloxy |
| 185 | 4-NO$_2$-phenylthio |
| 186 | 3-CF$_3$-phenyl |
| 187 | 4-CH$_3$O-phenylamino |
| 188 | cyclopropoxy |
| 189 | 1-phenylethoxy |
| 190 | 4-F, 3-CH$_3$-benzoyl |

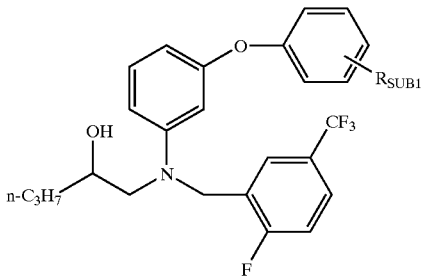

| Ex. No. | R$_{SUB1}$ |
|---|---|
| 191 | 3-isopropyl |
| 192 | 2-Cl, 3-Cl |
| 193 | 3-CF$_3$O |
| 194 | 4-F |
| 195 | 4-CH$_3$ |
| 196 | 2-F, 5-Br |
| 197 | 3-CF$_3$CF$_2$ |
| 198 | 3-CH$_3$CH$_2$ |
| 199 | 3-CH$_3$, 5-CH$_3$ |
| 200 | 3-(CH$_3$)$_3$C |
| 201 | 4-Cl, 3-CH$_3$CH$_2$ |
| 202 | 4-CH$_3$CH$_2$CH$_2$O |
| 203 | 3,4-(CH$_2$)$_4$ |
| 204 | 3-HCF$_2$CF$_2$O |
| 205 | 3-CHF$_2$O |
| 206 | 3-(CH$_3$)$_2$N |
| 207 | 3-cyclopropyl |
| 208 | 3-(2-furyl) |
| 209 | 3-CF$_3$CF$_2$ |
| 210 | 4-NH$_2$ |

-continued

Example Table 4.
Substituted 2-[(N-aryl)[N-arylmethyl]amino]alkanols.

| Ex. No. | $R_{SUB2}$ |
|---|---|
| 211 | 3-CF$_3$O-benzyloxy |
| 212 | 3-CF$_3$-benzyloxy |
| 213 | 3-F, 5-F-benzyloxy |
| 214 | cyclohexylmethyleneoxy |
| 215 | benzyloxy |
| 216 | 3-CF$_3$, 5-CF$_3$-benzyloxy |
| 217 | 4-CF$_3$O-benzyloxy |
| 218 | 4-CH$_3$CH$_2$-benzyloxy |
| 219 | isopropoxy |
| 220 | 3-CF$_3$-benzyl |
| 221 | isopropylthio |
| 222 | cyclopentoxy |
| 223 | 3-Cl-5-pyridinyloxy |
| 224 | 3-CF$_3$S-benzyloxy |
| 225 | 4-NO$_2$-phenylthio |
| 226 | 3-CF$_3$-phenyl |
| 227 | 4-CH$_3$O-phenylamino |
| 228 | cyclopropoxy |
| 229 | 1-phenylethoxy |
| 230 | 4-F, 3-CH$_3$-benzoyl |

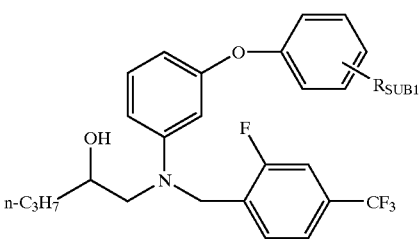

| Ex. No. | $R_{SUB1}$ |
|---|---|
| 231 | 3-isopropyl |
| 232 | 2-Cl, 3-Cl |
| 233 | 3-CF$_3$O |
| 234 | 4-F |
| 235 | 4-CH$_3$ |
| 236 | 2-F, 5-Br |
| 237 | 3-CF$_3$CF$_2$ |
| 238 | 3-CH$_3$CH$_2$ |
| 239 | 3-CH$_3$, 5-CH$_3$ |
| 240 | 3-(CH$_3$)$_3$C |
| 241 | 4-Cl, 3-CH$_3$CH$_2$ |
| 242 | 4-CH$_3$CH$_2$CH$_2$O |
| 243 | 3,4-(CH$_2$)$_4$ |
| 244 | 3-HCF$_2$CF$_2$O |
| 245 | 3-CHF$_2$O |
| 246 | 3-(CH$_3$)$_2$N |
| 247 | 3-cyclopropyl |
| 248 | 3-(2-furyl) |
| 249 | 3-CF$_3$CF$_2$ |
| 250 | 4-NH$_2$ |

-continued

Example Table 4.
Substituted 2-[(N-aryl)[N-arylmethyl]amino]alkanols.

| Ex. No. | $R_{SUB2}$ |
|---|---|
| 251 | 3-CF$_3$O-benzyloxy |
| 252 | 3-CF$_3$-benzyloxy |
| 253 | 3-F, 5-F-benzyloxy |
| 254 | cyclohexylmethyleneoxy |
| 255 | benzyloxy |
| 256 | 3-CF$_3$, 5-CF$_3$-benzyloxy |
| 257 | 4-CF$_3$O-benzyloxy |
| 258 | 4-CH$_3$CH$_2$-benzyloxy |
| 259 | isopropoxy |
| 260 | 3-CF$_3$-benzyl |
| 261 | isopropylthio |
| 262 | cyclopentoxy |
| 263 | 3-Cl-5-pyridinyloxy |
| 264 | 3-CF$_3$S-benzyloxy |
| 265 | 4-NO$_2$-phenylthio |
| 266 | 3-CF$_3$-phenyl |
| 267 | 4-CH$_3$O-phenylamino |
| 268 | cyclopropoxy |
| 269 | 1-phenylethoxy |
| 270 | 4-F, 3-CH$_3$-benzoyl |

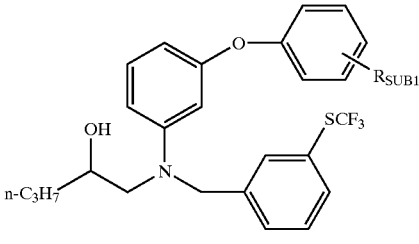

| Ex. No. | $R_{SUB1}$ |
|---|---|
| 271 | 3-isopropyl |
| 272 | 2-Cl, 3-Cl |
| 273 | 3-CF$_3$O |
| 274 | 4-F |
| 275 | 4-CH$_3$ |
| 276 | 2-F, 5-Br |
| 277 | 3-CF$_3$CF$_2$ |
| 278 | 3-CH$_3$CH$_2$ |
| 279 | 3-CH$_3$, 5-CH$_3$ |
| 280 | 3-(CH$_3$)$_3$C |
| 281 | 4-Cl, 3-CH$_3$CH$_2$ |
| 282 | 4-CH$_3$CH$_2$CH$_2$O |
| 283 | 3,4-(CH$_2$)$_4$ |
| 284 | 3-HCF$_2$CF$_2$O |
| 285 | 3-CHF$_2$O |
| 286 | 3-(CH$_3$)$_2$N |
| 287 | 3-cyclopropyl |
| 288 | 3-(2-furyl) |
| 289 | 3-CF$_3$CF$_2$ |
| 290 | 4-NH$_2$ |

-continued

Example Table 4.
Substituted 2-[(N-aryl)[N-arylmethyl]amino]alkanols.

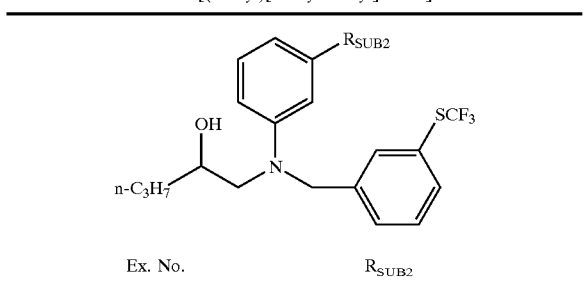

| Ex. No. | $R_{SUB2}$ |
|---|---|
| 291 | 3-$CF_3$O-benzyloxy |
| 292 | 3-$CF_3$-benzyloxy |
| 293 | 3-F, 5-F-benzyloxy |
| 294 | cyclohexylmethyleneoxy |
| 295 | benzyloxy |
| 296 | 3-$CF_3$, 5-$CF_3$-benzyloxy |
| 297 | 4-$CF_3$O-benzyloxy |
| 298 | 4-$CH_3CH_2$-benzy-oxy |
| 299 | isopropoxy |
| 300 | 3-$CF_3$-benzyl |
| 301 | isopropylthio |
| 302 | cyclopentoxy |
| 303 | 3-Cl-5-pyridinyloxy |
| 304 | 3-$CF_3$S-benzyloxy |
| 305 | 4-$NO_2$-phenylthio |
| 306 | 3-$CF_3$-phenyl |
| 307 | 4-$CH_3$O-phenylamino |
| 308 | cyclopropoxy |
| 309 | 1-phenylethoxy |
| 310 | 4-F, 3-$CH_3$-benzoyl |

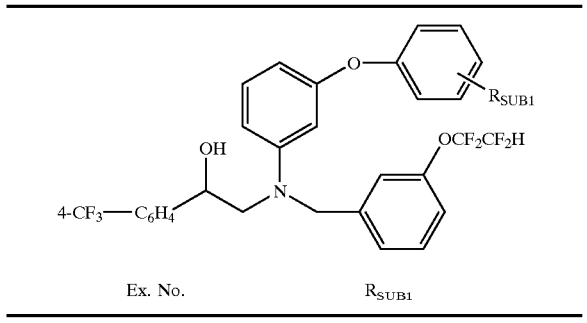

| Ex. No. | $R_{SUB1}$ |
|---|---|
| 311 | 3-isopropyl |
| 312 | 2-Cl, 3-Cl |
| 313 | 3-$CF_3$O |
| 314 | 4-F |
| 315 | 4-$CH_3$ |
| 316 | 2-F, 5-Br |
| 317 | 3-$CF_3CF_2$ |
| 318 | 3-$CH_3CH_2$ |
| 319 | 3-$CH_3$, 5-$CH_3$ |
| 320 | 3-$(CH_3)_3$C |
| 321 | 4-Cl, 3-C-3$CH_2$ |
| 322 | 4-$CH_3CH_2CH_2$O |
| 323 | 3,4-$(CH_2)_4$ |
| 324 | 3-$HCF_2CF_2$O |
| 325 | 3-$CHF_2$O |
| 326 | 3-$(CH_3)_2$N |
| 327 | 3-cyclopropyl |
| 328 | 3-(2-furyl) |
| 329 | 3-$CF_3CF_2$ |
| 330 | 4-$NH_2$ |

-continued

Example Table 4.
Substituted 2-[(N-aryl)[N-arylmethyl]amino]alkanols.

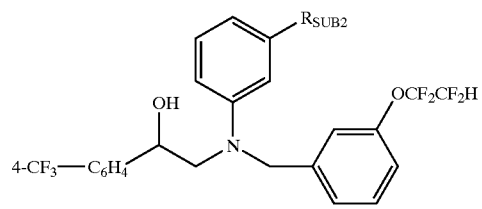

| Ex. No. | $R_{SUB2}$ |
|---|---|
| 331 | 3-$CF_3$O-benzyloxy |
| 332 | 3-$CF_3$-benzyloxy |
| 333 | 3-F, 5-F-benzyloxy |
| 334 | cyclohexylmethyleneoxy |
| 335 | benzyloxy |
| 336 | 3-$CF_3$, 5-$CF_3$-benzyloxy |
| 337 | 4-$CF_3$O-benzyloxy |
| 338 | 4-$CH_3CH_2$-benzyloxy |
| 339 | isopropoxy |
| 340 | 3-$CF_3$-benzyl |
| 341 | isopropylthio |
| 342 | cyclopentoxy |
| 343 | 3-Cl-5-pyridinyloxy |
| 344 | 3-$CF_3$S-benzyloxy |
| 345 | 4-$NO_2$-phenylthio |
| 346 | 3-$CF_3$-phenyl |
| 347 | 4-$CH_3$O-phenylamino |
| 348 | cyclopropoxy |
| 349 | 1-phenylethoxy |
| 350 | 4-F, 3-$CH_3$-benzoyl |

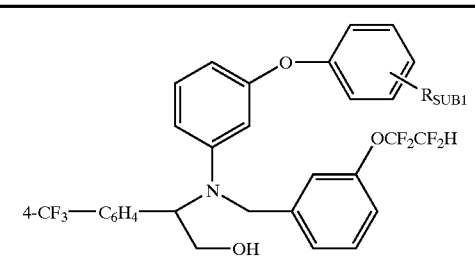

| Ex. No. | $R_{SUB1}$ |
|---|---|
| 351 | 3-isopropyl |
| 352 | 2-Cl, 3-Cl |
| 353 | 3-$CF_3$O |
| 354 | 4-F |
| 355 | 4-$CH_3$ |
| 356 | 2-F, 5-Br |
| 357 | 3-$CF_3CF_2$ |
| 358 | 3-$CH_3CH_2$ |
| 359 | 3-$CH_3$, 5-$CH_3$ |
| 360 | 3-$(CH_3)_3$C |
| 361 | 4-Cl, 3-$CH_3CH_2$ |
| 362 | 4-$CH_3CH_2CH_2$O |
| 363 | 3,4-$(CH_2)_4$ |
| 364 | 3-$HCF_2CF_2$O |
| 365 | 3-$CHF_2$O |
| 366 | 3-$(CH_3)_2$N |
| 367 | 3-cyclopropyl |
| 368 | 3-(2-furyl) |
| 369 | 3-$CF_3CF_2$ |
| 370 | 4-$NH_2$ |

-continued

Example Table 4.
Substituted 2-[(N-aryl)[N-arylmethyl]amino]alkanols.

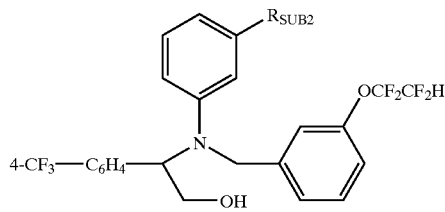

| Ex. No. | R$_{SUB2}$ |
|---|---|
| 371 | 3-CF$_3$O-benzyloxy |
| 372 | 3-CF$_3$-benzyloxy |
| 373 | 3-F, 5-F-benzyloxy |
| 374 | cyclohexylmethyleneoxy |
| 375 | benzyloxy |
| 376 | 3-CF$_3$, 5-CF$_3$-benzyloxy |
| 377 | 4-CF$_3$O-benzyloxy |
| 378 | 4-CH$_3$CH$_2$-benzyloxy |
| 379 | isopropoxy |
| 380 | 3-CF$_3$-benzyl |
| 381 | isopropyithio |
| 382 | cyclopentoxy |
| 383 | 3-Cl-5-pyridinyloxy |
| 384 | 3-CF$_3$S-benzyloxy |
| 385 | 4-NO$_2$-phenylthio |
| 386 | 3-CF$_3$-phenyl |
| 387 | 4-CH$_3$O-phenylamino |
| 388 | cyclopropoxy |
| 389 | 1-phenylethoxy |
| 390 | 4-F, 3-CH$_3$-benzoyl |

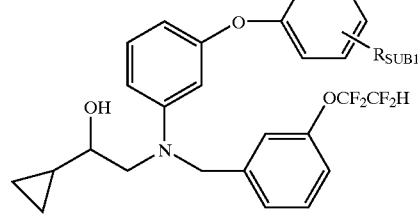

| Ex. No. | R$_{SUB1}$ |
|---|---|
| 391 | 3-isopropyl |
| 392 | 2-Cl, 3-Cl |
| 393 | 3-CF$_3$O |
| 394 | 4-F |
| 395 | 4-CH$_3$ |
| 396 | 2-F, 5-Br |
| 397 | 3-CF$_3$CF$_2$ |
| 398 | 3-CH$_3$CH$_2$ |
| 399 | 3-CH$_3$, 5-CH$_3$ |
| 400 | 3-(CH$_3$)$_3$C |
| 401 | 4-Cl, 3-CH$_3$CH$_2$ |
| 402 | 4-CH$_3$CH$_2$CH$_2$O |
| 403 | 3,4-(CH$_2$)$_4$ |
| 404 | 3-HCF$_2$CF$_2$O |
| 405 | 3-CHF$_2$O |
| 406 | 3-(CH$_3$)$_2$N |
| 407 | 3-cyclopropyl |
| 408 | 3-(2-furyl) |
| 409 | 3-CF$_3$CF$_2$ |
| 410 | 4-NH$_2$ |

-continued

Example Table 4.
Substituted 2-[(N-aryl)[N-arylmethyl]amino]alkanols.

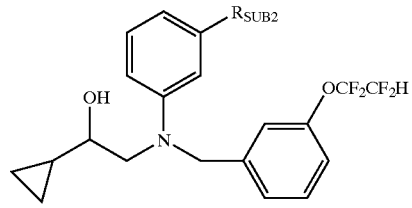

| Ex. No. | R$_{SUB2}$ |
|---|---|
| 411 | 3-CF$_3$O-benzyloxy |
| 412 | 3-CF$_3$-benzyloxy |
| 413 | 3-F, 5-F-benzyloxy |
| 414 | cyclohexylmethyleneoxy |
| 415 | benzyloxy |
| 416 | 3-CF$_3$, 5-CF$_3$-benzyloxy |
| 417 | 4-CF$_3$O-benzyloxy |
| 418 | 4-CH$_3$CH$_2$-benzyloxy |
| 419 | isopropoxy |
| 420 | 3-CF$_3$-benzyl |
| 421 | isopropylthio |
| 422 | cyclopentoxy |
| 423 | 3-Cl-5-pyridinyloxy |
| 424 | 3-CF$_3$S-benzyloxy |
| 425 | 4-NO2-phenylthio |
| 426 | 3-CF$_3$-phenyl |
| 427 | 4-CH$_3$O-phenylamino |
| 428 | cyclopropoxy |
| 429 | 1-phenylethoxy |
| 430 | 4-F, 3-CH$_3$-benzoyl |

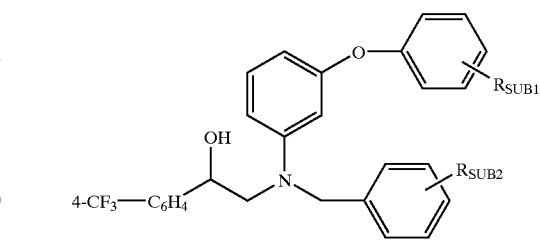

| Ex. No. | R$_{SUB1}$ | R$_{SUB2}$ |
|---|---|---|
| 431 | 4-chloro-3-ethylphenoxy | 3-CF$_3$O |
| 432 | 4-chloro-3-ethylphenoxy | 3-CF$_3$CF$_2$ |
| 433 | 4-chloro-3-ethylphenoxy | 2-F, 4-CF$_3$ |
| 434 | 4-chloro-3-ethylphenoxy | 2-F, 5-CF$_3$ |
| 435 | 4-chloro-3-ethylphenoxy | 3-CF$_3$S |
| 436 | 3-ethylphenoxy | 3-CF$_3$CF$_2$ |
| 437 | 3-ethylphenoxy | 2-F, 4-CF$_3$ |
| 438 | 3-ethylphenoxy | 2-F, 5-CF$_3$ |
| 439 | 3-ethylphenoxy | 3-CF$_3$S |
| 440 | 3-isopropylphenoxy | 3-CF$_3$CF$_2$ |
| 441 | 3-isopropylphenoxy | 2-F, 4-CF$_3$ |
| 442 | 3-isopropylphenoxy | 2-F, 5-CF$_3$ |
| 443 | 3-isopropylphenoxy | 3-CF$_3$S |
| 444 | 3-CF$_3$O-phenoxy | 3-CF$_3$CF$_2$ |
| 445 | 3-CF$_3$O-phenoxy | 2-F, 4-CF$_3$ |
| 446 | 3-CF$_3$O-phenoxy | 2-F, 5-CF$_3$ |
| 447 | 3-CF$_3$O-phenoxy | 3-CF$_3$S |
| 448 | 2,3-dichlorophenoxy | 3-CF$_3$CF$_2$ |
| 449 | 2,3-dichlorophenoxy | 2-F, 4-CF$_3$ |
| 450 | 2,3-dichlorophenoxy | 2-F, 5-CF$_3$ |
| 451 | 2,3-dichlorophenoxy | 3-CF$_3$S |
| 452 | 3-CF$_3$-benzyloxy | 3-CF$_3$CF$_2$ |
| 453 | 3-CF$_3$-benzyloxy | 2-F, 4-CF$_3$ |
| 454 | 3-CF$_3$-benzyloxy | 2-F, 5-CF$_3$ |
| 455 | 3-CF$_3$-benzyloxy | 3-CF$_3$S |
| 456 | 3-CF$_3$O-benzyloxy | 3-CF$_3$CF$_2$ |
| 457 | 3-CF$_3$O-benzyloxy | 2-F, 4-CF$_3$ |

-continued

Example Table 4.
Substituted 2-[(N-aryl)[N-arylmethyl]amino]alkanols.

| Ex. No. | | |
|---|---|---|
| 458 | 3-CF$_3$O-benzyloxy | 2-F, 5-CF$_3$ |
| 459 | 3-CF$_3$O-benzyloxy | 3-CF$_3$S |

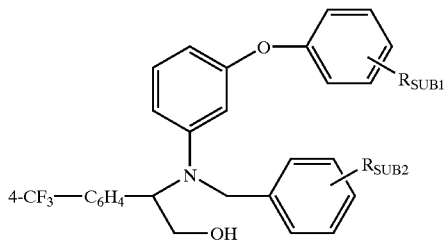

| Ex. No. | R$_{SUB1}$ | R$_{SUB2}$ |
|---|---|---|
| 460 | 4-chloro-3-ethylphenoxy | 3-CF$_3$O |
| 461 | 4-chloro-3-ethylphenoxy | 3-CF$_3$CF$_2$ |
| 462 | 4-chloro-3-ethylphenoxy | 2-F, 4-CF$_3$ |
| 463 | 4-chloro-3-ethylphenoxy | 2-F, 5-CF$_3$ |
| 464 | 4-chloro-3-ethylphenoxy | 3-CF$_3$S |
| 465 | 3-ethylphenoxy | 3-CF$_3$CF$_2$ |
| 466 | 3-ethylphenoxy | 2-F, 4-CF$_3$ |
| 467 | 3-ethylphenoxy | 2-F, 5-CF$_3$ |
| 468 | 3-ethylphenoxy | 3-CF$_3$S |
| 469 | 3-isopropylphenoxy | 3-CF$_3$CF$_2$ |
| 470 | 3-isopropylphenoxy | 2-F, 4-CF$_3$ |
| 471 | 3-isopropylphenoxy | 2-F, 5-CF$_3$ |
| 472 | 3-isopropylphenoxy | 3-CF$_3$S |
| 473 | 3-CF$_3$O-phenoxy | 3-CF$_3$CF$_2$ |
| 474 | 3-CF$_3$O-phenoxy | 2-F, 4-CF$_3$ |
| 475 | 3-CF$_3$O-phenoxy | 2-F, 5-CF$_3$ |
| 476 | 3-CF$_3$O-phenoxy | 3-CF$_3$S |
| 477 | 2,3-dichlorophenoxy | 3-CF$_3$CF$_2$ |
| 478 | 2,3-dichlorophenoxy | 2-F, 4-CF$_3$ |
| 479 | 2,3-dichlorophenoxy | 2-F, 5-CF$_3$ |
| 480 | 2,3-dichlorophenoxy | 3-CF$_3$S |
| 481 | 3-CF$_3$-benzyloxy | 3-CF$_3$CF$_2$ |
| 482 | 3-CF$_3$-benzyloxy | 2-F, 4-CF$_3$ |
| 483 | 3-CF$_3$-benzyloxy | 2-F, 5-CF$_3$ |
| 484 | 3-CF$_3$-benzyloxy | 3-CF$_3$S |
| 485 | 3-CF$_3$O-benzyloxy | 3-CF$_3$CF$_2$ |
| 486 | 3-CF$_3$O-benzyloxy | 2-F, 4-CF$_3$ |
| 487 | 3-CF$_3$O-benzyloxy | 2-F, 5-CF$_3$ |
| 488 | 3-CF$_3$O-benzyloxy | 3-CF$_3$S |

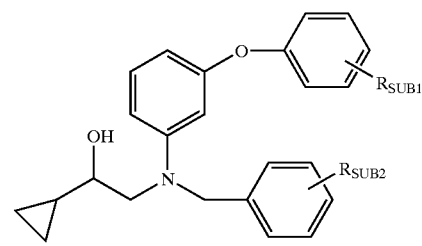

| Ex. No. | R$_{SUB1}$ | R$_{SUB2}$ |
|---|---|---|
| 489 | 4-chloro-3-ethylphenoxy | 3-CF$_3$O |
| 490 | 4-chloro-3-ethylphenoxy | 3-CF$_3$CF$_2$ |
| 491 | 4-chloro-3-ethylphenoxy | 2-F, 4-CF$_3$ |
| 492 | 4-chloro-3-ethylphenoxy | 2-F, 5-C F3 |
| 493 | 4-chloro-3-ethylphenoxy | 3-CF$_3$S |
| 494 | 3-ethylphenoxy | 3-CF$_3$CF$_2$ |
| 495 | 3-ethylphenoxy | 2-F, 4-CF$_3$ |
| 496 | 3-ethylphenoxy | 2-F, 5-CF$_3$ |
| 497 | 3-ethylphenoxy | 3-CF$_3$S |
| 498 | 3-isopropylphenoxy | 3-CF$_3$CF$_2$ |
| 499 | 3-isopropylphenoxy | 2-F, 4-CF$_3$ |
| 500 | 3-isopropylphenoxy | 2-F, 5-CF$_3$ |
| 501 | 3-isopropylphenoxy | 3-CF$_3$S |
| 502 | 3-CF$_3$O-phenoxy | 3-CF$_3$CF$_2$ |

-continued

Example Table 4.
Substituted 2-[(N-aryl)[N-arylmethyl]amino]alkanols.

| | | |
|---|---|---|
| 503 | 3-CF$_3$O-phenoxy | 2-F, 4-CF$_3$ |
| 504 | 3-CF$_3$O-phenoxy | 2-F, 5-CF$_3$ |
| 505 | 3-CF$_3$O-phenoxy | 3-CF$_3$S |
| 506 | 2,3-dichlorophenoxy | 3-CF$_3$CF$_2$ |
| 507 | 2,3-dichlorophenoxy | 2-F, 5-CF$_3$ |
| 508 | 2,3-dichlorophenoxy | 2-F, 5-CF$_3$ |
| 509 | 2,3-dichlorophenoxy | 3-CF$_3$S |
| 510 | 3-CF$_3$-benzyloxy | 3-CF$_3$CF$_2$ |
| 511 | 3-CF$_3$-benzyloxy | 2-F, 4-CF$_3$ |
| 512 | 3-CF$_3$-benzyloxy | 2-F, 5-CF$_3$ |
| 513 | 3-CF$_3$-benzyloxy | 3-CF$_3$S |
| 514 | 3-CF$_3$O-benzyloxy | 3-CF$_3$CF$_2$ |
| 515 | 3-CF$_3$O-benzyloxy | 2-F, 4-CF$_3$ |
| 516 | 3-CF$_3$O-benzyloxy | 2-F, 5-CF$_3$ |
| 517 | 3-CF$_3$O-benzyloxy | 3-CF$_3$S |

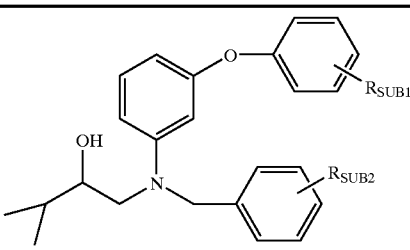

| Ex. No. | R$_{SUB1}$ | R$_{SUB2}$ |
|---|---|---|
| 518 | 4-chloro-3-ethylphenoxy | 3-CF$_3$O |
| 519 | 4-chloro-3-ethylphenoxy | 3-CF$_3$CF$_2$ |
| 520 | 4-chloro-3-ethylphenoxy | 2-F, 4-CF$_3$ |
| 521 | 4-chloro-3-ethylphenoxy | 2-F, 5-CF$_3$ |
| 522 | 4-chloro-3-ethylphenoxy | 3-CF$_3$S |
| 523 | 3-ethylphenoxy | 3-CF$_3$CF$_2$ |
| 524 | 3-ethylphenoxy | 2-F, 4-CF$_3$ |
| 525 | 3-ethylphenoxy | 2-F, 5-CF$_3$ |
| 526 | 3-ethylphenoxy | 3-CF$_3$S |
| 527 | 3-isopropylphenoxy | 3-CF$_3$CF$_2$ |
| 528 | 3-isopropylphenoxy | 2-F, 4-CF$_3$ |
| 529 | 3-isopropylphenoxy | 2-F, 5-CF$_3$ |
| 530 | 3-isopropylphenoxy | 3-CF$_3$S |
| 531 | 3-CF$_3$O-phenoxy | 3-CF$_3$CF$_2$ |
| 532 | 3-CF$_3$O-phenoxy | 2-F, 4-CF$_3$ |
| 533 | 3-CF$_3$O-phenoxy | 2-F, 5-CF$_3$ |
| 534 | 3-CF$_3$O-phenoxy | 3-CF$_3$S |
| 535 | 2,3-dichlorophenoxy | 3-CF$_3$CF$_2$ |
| 536 | 2,3-dichlorophenoxy | 2-F, 4-CF$_3$ |
| 537 | 2,3-dichlorophenoxy | 2-F, 5-CF$_3$ |
| 538 | 2,3-dichlorophenoxy | 3-CF$_3$S |
| 539 | 3-CF$_3$-benzyloxy | 3-CF$_3$CF$_2$ |
| 540 | 3-CF$_3$-benzyloxy | 2-F, 4-CF$_3$ |
| 541 | 3-CF$_3$-benzyloxy | 2-F, 5-CF$_3$ |
| 542 | 3-CF$_3$-benzyloxy | 3-CF$_3$S |
| 543 | 3-CF$_3$O-benzyloxy | 3-CF$_3$CF$_2$ |
| 544 | 3-CF$_3$O-benzyloxy | 2-F, 4CF$_3$ |
| 545 | 3-CF$_3$O-benzyloxy | 2-F, 5-CF$_3$ |
| 546 | 3-CF$_3$O-benzyloxy | 3-CF$_3$S |

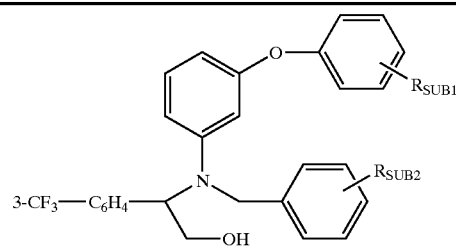

| Ex. No. | R$_{SUB1}$ | R$_{SUB2}$ |
|---|---|---|
| 547 | 4-chloro-3-ethylphenoxy | 3-CF$_3$O |
| 548 | 4-chloro-3-ethylphenoxy | 3-CF$_3$CF$_2$ |

-continued

Example Table 4.
Substituted 2-[(N-aryl)[N-arylmethyl]amino]alkanols.

| Ex. No. | | |
|---|---|---|
| 549 | 4-chloro-3-ethylphenoxy | 2-F, 4-CF$_3$ |
| 550 | 4-chloro-3-ethylphenoxy | 2-F, 5-CF$_3$ |
| 551 | 4-chloro-3-ethylphenoxy | 3-CF$_3$S |
| 552 | 3-ethylphenoxy | 3-CF$_3$CF$_2$ |
| 553 | 3-ethylphenoxy | 2-F, 4-CF$_3$ |
| 554 | 3-ethylphenoxy | 2-F, 5-CF$_3$ |
| 555 | 3-ethylphenoxy | 3-CF$_3$S |
| 556 | 3-isopropylphenoxy | 3-CF$_3$CF$_2$ |
| 557 | 3-isopropylphenoxy | 2-F, 4-CF$_3$ |
| 558 | 3-isopropylphenoxy | 2-F, 5-CF$_3$ |
| 559 | 3-isopropylphenoxy | 3-CF$_3$S |
| 560 | 3-CF$_3$O-phenoxy | 3-CF$_3$CF$_2$ |
| 561 | 3-CF$_3$O-phenoxy | 2-F, 4-CF$_3$ |
| 562 | 3-CF$_3$O-phenoxy | 2-F, 5-CF$_3$ |
| 563 | 3-CF$_3$O-phenoxy | 3-CF$_3$S |
| 564 | 2,3-dichlorophenoxy | 3-CF$_3$CF$_2$ |
| 565 | 2,3-dichlorophenoxy | 2-F, 4-CF$_3$ |
| 566 | 2,3-dichlorophenoxy | 2-F, 5-CF$_3$ |
| 567 | 2,3-dichlorophenoxy | 3-CF$_3$S |
| 568 | 3-CF$_3$-benzyloxy | 3-CF$_3$CF$_2$ |
| 569 | 3-CF$_3$-benzyloxy | 2-F, 4-CF$_3$ |
| 570 | 3-CF$_3$-benzyloxy | 2-F, 5-CF$_3$ |
| 571 | 3-CF$_3$-benzyloxy | 3-CF$_3$S |
| 572 | 3-CF$_3$O-benzyloxy | 3-CF$_3$CF$_2$ |
| 573 | 3-CF$_3$O-benzyloxy | 2-F, 4-CF$_3$ |
| 574 | 3-CF$_3$O-benzyloxy | 2-F, 5-CF$_3$ |
| 575 | 3-CF$_3$O-benzyloxy | 3-CF$_3$S |
| 576 | 4-chloro-3-ethylphenoxy | 3-OCF$_2$CF$_2$H |
| 577 | 3-CF$_3$O-phenoxy | 3-OCF$_2$CF$_2$H |
| 578 | 2,3-dichlorophenoxy | 3-OCF$_2$CF$_2$H |
| 579 | 3-ethylphenoxy | 3-OCF$_2$CF$_2$H |
| 580 | 3-isopropylphenoxy | 3-OCF$_2$CF$_2$H |
| 581 | 3-CF$_3$-benzyloxy | 3-OCF$_2$CF$_2$H |
| 582 | 3-CF$_3$O-benzyloxy | 3-OCF$_2$CF$_2$H |

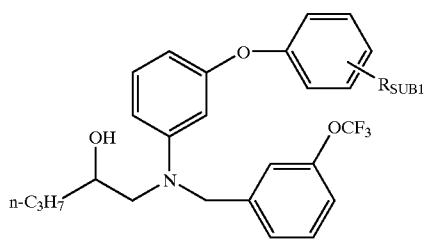

| Ex. No. | R$_{SUB1}$ |
|---|---|
| 583 | 3-isopropyl |
| 584 | 2-Cl, 3-Cl |
| 585 | 3-CF$_3$O |
| 586 | 4-F |
| 587 | 4-CH$_3$ |
| 588 | 2-F, 5-Br |
| 589 | 3-CF$_3$CF$_2$ |
| 590 | 3-CH$_3$CH$_2$ |
| 591 | 3-CH$_3$, 5-CH$_3$ |
| 592 | 3-(CH$_3$)$_3$C |
| 593 | 4-Cl, 3-CH$_3$CH$_2$ |
| 594 | 4-CH$_3$CH$_2$CH$_2$O |
| 595 | 3,4-(CH$_2$)$_4$ |
| 596 | 3-HCF$_2$CF$_2$O |
| 597 | 3-CHF$_2$O |
| 598 | 3-(CH$_3$)$_2$N |
| 599 | 3-cyclopropyl |
| 600 | 3-(2-furyl) |
| 601 | 3-CF$_3$CF$_2$ |
| 602 | 4-NH$_2$ |

-continued

Example Table 4.
Substituted 2-[(N-aryl)[N-arylmethyl]amino]alkanols.

| Ex. No. | R$_{SUB2}$ |
|---|---|
| 603 | 3-CF$_3$O-benzyloxy |
| 604 | 3-CF$_3$-benzyloxy |
| 605 | 3-F, 5-F-benzyloxy |
| 606 | cyclohexylmethyleneoxy |
| 607 | benzyloxy |
| 608 | 3-CF$_3$, 5-CF$_3$-benzyloxy |
| 609 | 4-CF$_3$O-benzyloxy |
| 610 | 4-CH$_3$CH$_2$-benzyloxy |
| 611 | isopropoxy |
| 612 | 3-CF$_3$-benzyl |
| 613 | isopropylthio |
| 614 | cyclopentoxy |
| 615 | 3-Cl-5-pyridinyloxy |
| 616 | 3-CF$_3$S-benzyloxy |
| 617 | 4-NO$_2$-phenylthio |
| 618 | 3-CF$_3$-phenyl |
| 619 | 4-CH$_3$O-phenylamino |
| 620 | cyclopropoxy |
| 621 | 1-phenylethoxy |
| 622 | 4-F, 3-CH$_3$-benzoyl |

| Ex. No. | R$_{SUB1}$ |
|---|---|
| 623 | 3-isopropyl |
| 624 | 2-Cl, 3-Cl |
| 625 | 3-CF$_3$O |
| 626 | 4-F |
| 627 | 4-CH$_3$ |
| 628 | 2-F, 5-Br |
| 629 | 3-CF$_3$CF$_2$ |
| 630 | 3-CH$_3$CH$_2$ |
| 631 | 3-CH$_3$, 5-CH$_3$ |
| 632 | 3-(CH$_3$)$_3$C |
| 633 | 4-Cl, 3-CH$_3$CH$_2$ |
| 634 | 4-CH$_3$CH$_2$CH$_2$O |
| 635 | 3,4-(CH$_2$)$_4$ |
| 636 | 3-HCF$_2$CF$_2$O |
| 637 | 3-CHF$_2$O |
| 638 | 3-(CH$_3$)$_2$N |
| 639 | 3-cyclopropyl |
| 640 | 3-(2-furyl) |
| 641 | 3-CF$_3$CF$_2$ |
| 642 | 4-NH$_2$ |

Example Table 4.
Substituted 2-[(N-aryl)[N-arylmethyl]amino]alkanols.

| Ex. No. | R$_{SUB2}$ |
|---|---|
| 643 | 3-CF$_3$O-benzyloxy |
| 644 | 3-CF$_3$-benzyloxy |
| 645 | 3-F, 5-F-benzyloxy |
| 646 | cyclohexylmethyleneoxy |
| 647 | benzyloxy |
| 648 | 3-CF$_3$, 5-CF$_3$-benzyloxy |
| 649 | 4CF$_3$O-benzyloxy |
| 650 | 4-CH$_3$CH$_2$-benzyloxy |
| 651 | isopropoxy |
| 652 | 3-CF$_3$-benzyl |
| 653 | isopropylthio |
| 654 | cyclopentoxy |
| 655 | 3-Cl-5-pyridinyloxy |
| 656 | 3-CF$_3$S-benzyloxy |
| 657 | 4-NO$_2$-phenylthio |
| 658 | 3-CF$_3$-phenyl |
| 659 | 4-CH$_3$O-phenylamino |
| 660 | cyclopropoxy |
| 661 | 1-phenylethoxy |
| 662 | 4-F, 3-CH$_3$-benzoyl |

Example Table 5. Substituted 2-[(N-aryl)[N-aralkyl]amino]cycloalkanols.

| Ex. No. | R$_{SUB1}$ | Ex. No. | R$_{SUB2}$ |
|---|---|---|---|
| 663 | 3-isopropyl | 683 | 3-CF$_3$O-benzyloxy |
| 664 | 2-Cl, 3-Cl | 684 | 3-CF$_3$-benzyloxy |
| 665 | 3-CF$_3$O | 685 | 3-F, 5-F-benzyloxy |
| 666 | 4-F | 686 | cyclohexylmethyleneoxy |
| 667 | 4-CH$_3$ | 687 | benzyloxy |
| 668 | 2-F, 5-Br | 688 | 3-CF$_3$, 5-CF$_3$-benzyloxy |
| 669 | 3-CF$_3$CF$_2$ | 689 | 4-CF$_3$O-benzyloxy |
| 670 | 3-CH$_3$CH$_2$ | 690 | 4-CH$_3$CH$_2$-benzyloxy |
| 671 | 3-CH$_3$, 5-CH$_3$ | 691 | isopropoxy |
| 672 | 3-(CH$_3$)$_3$C | 692 | 3-CF$_3$-benzyl |
| 673 | 4-Cl, 3-CH$_3$CH$_2$ | 693 | isopropylthio |
| 674 | 4-CH$_3$CH$_2$CH$_2$O | 694 | cyclopentoxy |
| 675 | 3,4-(CH$_2$)$_4$ | 695 | 3-Cl-5-pyridinyloxy |
| 676 | 3-HCF$_2$CF$_2$O | 696 | 3-CF$_3$S-benzyloxy |
| 677 | 3-CHF$_2$O | 697 | 4-NO$_2$-phenylthio |
| 678 | 3-(CH$_3$)$_2$N | 698 | 3-CF$_3$-phenyl |
| 679 | 3-cyclopropyl | 699 | 4-CH$_3$O-phenylamino |
| 680 | 3-(2-furyl) | 700 | cyclopropoxy |
| 681 | 3-CF$_3$CF$_2$ | 701 | 1-phenylethoxy |
| 682 | 4-NH$_2$ | 702 | 4F, 3-CH$_3$-benzoyl |

-continued

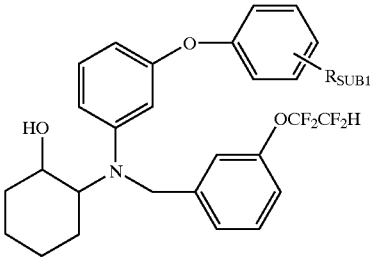

| Ex. No. | R$_{SUB1}$ | Ex. No. | R$_{SUB2}$ |
|---|---|---|---|
| 703 | 3-isopropyl | 723 | 3-CF$_3$O-benzyloxy |
| 704 | 2-Cl, 3-Cl | 724 | 3-CF$_3$-benzyloxy |
| 705 | 3-CF$_3$O | 725 | 3-F, 5-F-benzyloxy |
| 706 | 4-F | 726 | cyclohexylmethyleneoxy |
| 707 | 4-CH$_3$ | 727 | benzyloxy |
| 708 | 2-F, 5-Br | 728 | 3-CF$_3$, 5-CF$_3$-benzyloxy |
| 709 | 3-CF$_3$CF$_2$ | 729 | 4-CF$_3$O-benzyloxy |
| 710 | 3-CH$_3$CH$_2$ | 730 | 4-CH$_3$CH$_2$-benzyloxy |
| 711 | 3-CH$_3$, 5-CH$_3$ | 731 | isopropoxy |
| 712 | 3-(CH$_3$)$_3$C | 732 | 3-CF$_3$-benzyl |
| 713 | 4-Cl, 3-CH$_3$CH$_2$ | 733 | isopropylthio |
| 714 | 4-CH$_3$CH$_2$CH$_2$O | 734 | cyclopentoxy |
| 715 | 3,4-(CH$_2$)$_4$ | 735 | 3-Cl-5-pyridinyloxy |
| 716 | 3-HCF$_2$CF$_2$O | 736 | 3-CF$_3$S-benzyloxy |
| 717 | 3-CHF$_2$O | 737 | 4-NO$_2$-phenylthio |
| 718 | 3-(CH$_3$)$_2$N | 738 | 3-CF$_3$-phenyl |
| 719 | 3-cyclopropyl | 739 | 4-CH$_3$O-phenylamino |
| 720 | 3-(2-furyl) | 740 | cyclopropoxy |
| 721 | 3-CF$_3$CF$_2$ | 741 | 1-phenylethoxy |
| 722 | 4-NH$_2$ | 742 | 4-F, 3-CH$_3$-benzoyl |

Bioassays
CETP Activity in Vitro
Assay of CETP Inhibition Using Purified Components (Reconstituted Buffer Assay)

The ability of compounds to inhibit CETP activity was assessed using an in vitro assay that measured the rate of transfer of radiolabeled cholesteryl ester ([$^3$H]CE) from HDL donor particles to LDL acceptor particles. Details of the assay are provided by Glenn, K. C. et al. (Glenn and Melton, "Quantification of Cholesteryl Ester Transfer Protein (CETP): A) CETP Activity and B) Immunochemical Assay of CETP Protein," Meth. Enzymol., 263, 339–351 (1996)). Human recombinant CETP can be obtained from the serum-free conditioned medium of CHO cells transfected with a cDNA for CETP and purified as described by Wang, S. et al. (J. Biol. Chem. 267, 17487–17490 (1992)). To measure CETP activity, [3H]CE-labeled-HDL, LDL, CETP and assay buffer (50 mM tris(hydroxymethyl) aminomethane, pH 7.4; 150 mM sodium chloride; 2 mM ethylenediamine-tetraacetic acid (EDTA); 1% bovine serum albumin) were incubated in a final volume of 200 μL, for 2 hours at 37° C. in 96 well plates. Inhibitors were included in the assay by diluting from a 10 mM DMSO stock solution into 16% (v/v) aqueous DMSO so that the final concentration of inhibitor was 800 μM. The inhibitors were then diluted 1:1 with CETP in assay buffer, and then 25 μL of that solution was mixed with 175 μL of lipoprotein pool for assay. Following incubation, LDL was differentially precipitated by the addition of 50 μL of 1% (w/v) dextran sulfate/0.5 M magnesium chloride, mixed by vortex, and incubated at room temperature for 10 minutes. A potion of the solution (200 μL) was transferred to a filter plate (Millipore). After filtration, the radioactivity present in the precipitated LDL was measured by liquid scintillation counting. Correction for non-specific transfer or precipitation was made by including samples that do not contain CETP. The rate of [$^3$H]CE transfer using this assay was linear with respect to time and CETP concentration, up to 25–30% of [$^3$H]CE transferred.

The potency of test compounds was determined by performing the above described assay in the presence of varying concentrations of the test compounds and determining the concentration required for 50% inhibition of transfer of [$^3$H]CE from HDL to LDL. This value was defined as the IC$_{50}$. The IC$_{50}$ values determined from this assay are accurate when the IC$_{50}$ is greater than 10 nM. In the case where compounds have greater inhibitory potency, accurate measurements of IC$_{50}$ may be determined using longer incubation times (up to 18 hours) and lower final concentrations of CETP (<50 nM).

Examples of IC$_{50}$ values determined by these methods are specified in Table 6.

TABLE 6

Inhibition of CETP Activity by Examples in Reconstituted Buffer Assay.

| Ex. No. | IC$_{50}$ (μM) |
|---|---|
| 2 | 3.6 |
| 1B | 6 |
| 8 | 7 |
| 12 | 14 |
| 26 | 15 |

TABLE 6-continued

Inhibition of CETP Activity by Examples in
Reconstituted Buffer Assay.

| Ex. No. | IC$_{50}$ (µM) |
|---|---|
| 1A | 18 |
| 9 | 24 |
| 11 | 30 |
| 3 | 44 |
| 4 | >50 |
| 5 | >50 |
| 22 | 50 |
| 10 | 57 |
| 25 | 80 |
| 13 | 80 |
| 14 | 90 |
| 28 | >100.0 |
| 6 | >100.0 |
| 7 | >100.0 |
| 15 | >100.0 |
| 16 | >100.0 |
| 17 | >100.0 |
| 18 | >100.0 |
| 19 | >100.0 |
| 20 | >100.0 |
| 23 | >100.0 |
| 21 | >100.0 |
| 24 | >100.0 |
| 27 | >100.0 |

What we claim is:

1. A method of treating or preventing a CETP-mediated disorder in a subject by administering a therapeutically effective amount of a compound or a pharmaceutically acceptable salt thereof, said compound being of Formula I:

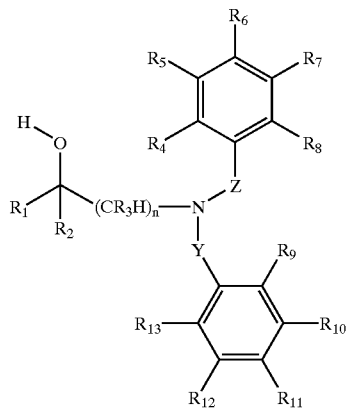

(I)

wherein;

n is 1 or 2;

R$_1$ is selected from the group consisting of hydrogen, methyl, isopropyl, isobutyl, propyl, benzyl, 4-trifluoromethylphenyl, methoxycarbonyl, vinyl, methoxymethyl, cyclopropyl, cyclopropylmethyl, 3-trifluoromethylphenyl, and 4-trifluoromethylcyclohexyl;

R$_2$ is selected from the group consisting of hydrogen, methyl, ethyl, hydroxymethyl, 1-hydroxyethyl, propyl, vinyl, methoxycarbonyl, benzyl, 3-trifluoromethylphenyl, and 4-trifluoromethylphenyl;

R$_3$ is selected from the group consisting of hydrogen, methyl, ethyl, propyl, cyclopropyl, cyclopropylmethyl, cyclobutyl, cyclobutylmethyl, cyclopentyl, cyclopentylmethyl, cyclohexyl, cyclohexylmethyl, phenyl, 4-trifluoromethylphenyl, trifluoromethyl, chloromethyl, fluoromethyl, difluoromethyl, chlorodifluoromethyl, pentafluoroethyl, 2,2,3,3,3-pentafluoropropyl, heptafluoropropyl, pentafluorophenyl, and 3-trifluoromethylphenyl;

Y is selected from the group consisting of methylene, ethylene, and ethylidene;

Z is a bond or methylene;

R$_4$, R$_8$, R$_9$, and R$_{13}$ are independently hydrogen or fluoro;

R$_5$ and R$_{10}$ are independently selected from the group consisting of 4-aminophenoxy, benzoyl, benzyl, benzyloxy, 5-bromo-2-fluorophenoxy, 4-bromo-3-fluorophenoxy, 4-bromo-2-nitrophenoxy, 3-bromobenzyloxy, 4-bromobenzyloxy, 4-bromophenoxy, 5-bromopyrid-2-yloxy, 4-butoxyphenoxy, chloro, 3-chlorobenzyl, 2-chlorophenoxy, 4-chlorophenoxy, 4-chloro-3-ethylphenoxy, 3-chloro-4-fluorobenzyl, 3-chloro-4-fluorophenyl, 3-chloro-2-fluorobenzyloxy, 3-chlorobenzyloxy, 4-chlorobenzyloxy, 4-chloro-3-methylphenoxy, 2-chloro-4-fluorophenoxy, 4-chloro-2-fluorophenoxy, 4-chlorophenoxy, 3-chloro-4-ethylphenoxy, 3-chloro-4-methylphenoxy, 3-chloro-4-fluorophenoxy, 4-chloro-3-fluorophenoxy, 4-chlorophenylamino, 5-chloropyrid-3-yloxy, 2-cyanopyrid-3-yloxy, 4-cyanophenoxy, cyclobutoxy, cyclobutyl, cyclohexoxy, cyclohexylmethoxy, cyclopentoxy, cyclopentyl, cyclopentylcarbonyl, cyclopropyl, cyclopropylmethoxy, cyclopropoxy, 2,3-dichlorophenoxy, 2,4-dichlorophenoxy, 2,4-dichlorophenyl, 3,5-dichlorophenyl, 3,5-dichlorobenzyl, 3,4-dichlorophenoxy, 3,4-difluorophenoxy, 2,3-difluorobenzyloxy, 2,4-difluorobenzyloxy, 3,4-difluorobenzyloxy, 2,5-difluorobenzyloxy, 3,5-difluorophenoxy, 3,4-difluorophenyl, 3,5-difluorobenzyloxy, 4-difluoromethoxybenzyloxy, 2,3-difluorophenoxy, 2,4-difluorophenoxy, 2,5-difluorophenoxy, 3,5-dimethoxyphenoxy, 3-dimethylaminophenoxy, 3,5-dimethylphenoxy, 3,4-dimethylphenoxy, 3,4-dimethylbenzyl, 3,4-dimethylbenzyloxy, 3,5-dimethylbenzyloxy, 2,2-dimethylpropoxy, 1,3-dioxan-2-yl, 1,4-dioxan-2-yl, 1,3-dioxolan-2-yl, ethoxy, 4-ethoxyphenoxy, 4-ethylbenzyloxy, 3-ethylphenoxy, 4-ethylaminophenoxy, 3-ethyl-5-methylphenoxy, fluoro, 4-fluoro-3-methylbenzyl, 4-fluoro-3-methylphenyl, 4-fluoro-3-methylbenzoyl, 4-fluorobenzyloxy, 2-fluoro-3-methylphenoxy, 3-fluoro-4-methylphenoxy, 3-fluorophenoxy, 3-fluoro-2-nitrophenoxy, 2-fluoro-3-trifluoromethylbenzyloxy, 3-fluoro-5-trifluoromethylbenzyloxy, 4-fluoro-2-trifluoromethylbenzyloxy, 4-fluoro-3-trifluoromethylbenzyloxy, 2-fluorophenoxy, 4-fluorophenoxy, 2-fluoro-3-trifluoromethylphenoxy, 2-fluorobenzyloxy, 4-fluorophenylamino, 2-fluoro-4-trifluoromethylphenoxy, 4-fluoropyrid-2-yloxy, 2-furyl, 3-furyl, heptafluoropropyl, 1,1,1,3,3,3-hexafluoropropyl, 2-hydroxy-3,3,3-trifluoropropoxy, 3-iodobenzyloxy, isobutyl, isobutylamino, isobutoxy, 3-isoxazolyl, 4-isoxazolyl, 5-isoxazolyl, isopropoxy, isopropyl, 4-isopropylbenzyloxy, 3-isopropylphenoxy, 4-isopropylphenoxy, isopropylthio, 4-isopropyl-3-methylphenoxy, 3-isothiazolyl, 4-isothiazolyl, 5-isothiazolyl, 3-methoxybenzyl, 4-methoxycarbonylbutoxy, 3-methoxycarbonylprop-2- enyloxy, 4-methoxyphenyl, 3-methoxyphenylamino, 4-methoxyphenylamino, 3-methylbenzyloxy, 4-methylbenzyloxy, 3-methylphenoxy, 3-methyl-4-methylthiophenoxy, 4-methylphenoxy, 1-methylpropoxy, 2-methylpyrid-5-yloxy, 4-methylthiophenoxy, 2-naphthyloxy, 2-nitrophenoxy, 4-nitrophenoxy, 3-nitrophenyl, 4-nitrophenylthio, 2-oxazolyl, 4-oxazolyl, 5-oxazolyl, pentafluoroethyl, pentafluoroethylthio, 2,2,3,3,3-pentafluoropropyl, 1,1,3,3,3-pentafluoropropyl, 1,1,2,2,3-pentafluoropropyl, phenoxy, phenylamino, 1-phenylethoxy, phenylsulfonyl, 4-propanoylphenoxy, propoxy, 4-propylphenoxy, 4-propoxyphenoxy, thiophen-3-yl, sec-butyl, 4-sec-butylphenoxy, tert-butoxy, 3-tert-butylphenoxy, 4-tert-butylphenoxy, 1,1,2,2-tetrafluoroethoxy, tetrahydrofuran-2-yl, 2-(5,6,7,8-tetrahydronaphthyloxy), thiazol-2-yl, thiazol-4-yl, thiazol-5-yl, thiophen-2-yl, 2,3,5-trifluorobenzyloxy, 2,2,2-trifluoroethoxy, 2,2,2-trifluoroethyl, 3,3,3-trifluoro-2-hydroxypropyl, trifluoromethoxy, 3-trifluoromethoxybenzyloxy, 4-trifluoromethoxybenzyloxy, 3-trifluoromethoxyphenoxy, 4-trifluoromethoxyphenoxy, trifluoromethyl, 3-trifluoromethylbenzyloxy, 4-trifluoromethylbenzyloxy, 2,4-bis-trifluoromethylbenzyloxy, 1,1-bis-trifluoromethyl-1-hydroxymethyl, 3-trifluoromethylbenzyl, 3,5-bis-trifluoromethylbenzyloxy, 4-trifluoromethylphenoxy, 3-trifluoromethylphenoxy, 3-trifluoromethylphenyl, 3-trifluoromethylthiobenzyloxy, 4-trifluoromethylthiobenzyloxy, 2,3,4-trifluorophenoxy, 2,3,4-trifluorophenyl, 2,3,5-trifluorophenoxy, 3,4,5-trimethylphenoxy, 3-difluoromethoxyphenoxy, 3-pentafluoroethylphenoxy, 3-(1,1,2,2-tetrafluoroethoxy)phenoxy, 3-trifluoromethylthiophenoxy, and trifluoromethylthio;

$R_6$ and $R_{11}$ are independently selected from the group consisting of chloro, fluoro, hydrogen, pentafluoroethyl, 1,1,2,2-tetrafluoroethoxy, trifluoromethyl, and trifluoromethoxy;

$R_7$ and $R_{12}$ are independently selected from the group consisting of hydrogen, fluoro, and trifluoromethyl.

2. The method of claim 1, wherein said compound is of Formula I, wherein;

n is 1;

$R_1$ is selected from the group consisting of hydrogen, isopropyl, isobutyl, propyl, benzyl, cyclopropyl, cyclopropylmethyl, and 4-trifluoromethylphenyl;

$R_2$ is selected from the group consisting of hydrogen, methyl, ethyl, hydroxymethyl, 1-hydroxyethyl, propyl, benzyl, 3-trifluoromethylphenyl, and 4-trifluoromethylphenyl;

$R_3$ is selected from the group consisting of hydrogen, methyl, trifluoromethyl, difluoromethyl, chlorodifluoromethyl, cyclopropyl, cyclopropylmethyl, 3-trifluoromethylphenyl, and 4-trifluoromethylphenyl;

Y is methylene;

Z is a bond;

$R_4$, $R_5$, $R_9$, and $R_{13}$ are independently hydrogen or fluoro;

$R_5$ and $R_{10}$ are independently selected from the group consisting of benzyloxy, 5-bromo-2fluorophenoxy, 4-bromo-3-fluorophenoxy, 3-bromobenzyloxy, 4-bromophenoxy, 4-butoxyphenoxy, 3-chlorobenzyloxy, 2-chlorophenoxy, 4-chloro-3ethylphenoxy, 4-chloro-3-methylphenoxy, 2-chloro-4-fluorophenoxy, 4-chloro-2-fluorophenoxy, 4-chlorophenoxy, 3-chloro-4-ethylphenoxy, 3-chloro-4-methylphenoxy, 3-chloro-4-fluorophenoxy, 4-chloro-3-fluorophenoxy, 4-chlorophenylamino, 5-chloropyrid-3-yloxy, cyclobutoxy, cyclobutyl, cyclohexylmethoxy, cyclopentoxy, cyclopentyl, cyclopentylcarbonyl, cyclopropylmethoxy, 2,3-dichlorophenoxy, 2,4-dichlorophenoxy, 2,4-dichlorophenyl, 3,5-dichlorophenyl, 3,5-dichlorobenzyl, 3,4-dichlorophenoxy, 3,4-difluorophenoxy, 2,3-difluorobenzyloxy, 3,5-difluorobenzyloxy, difluoromethoxy, 3,5-difluorophenoxy, 3,4-difluorophenyl, 2,3-difluorophenoxy, 2,4-difluorophenoxy, 2,5-difluorophenoxy, 3,5-dimethoxyphenoxy, 3-dimethylaminophenoxy, 3,4-dimethylbenzyloxy, 3,5-dimethylbenzyloxy, 3,5-dimethylphenoxy, 3,4-dimethylphenoxy, 1,3-dioxolan-2-yl, 3-ethylbenzyloxy, 3-ethylphenoxy, 4-ethylaminophenoxy, 3-ethyl-5-methylphenoxy, 4-fluoro-3-methylbenzyl, 4-fluorobenzyloxy, 2-fluoro-3-methylphenoxy, 3-fluoro-4-methylphenoxy, 3-fluorophenoxy, 3-fluoro-2-nitrophenoxy, 2-fluoro-3-trifluoromethylbenzyloxy, 3-fluoro-5-trifluoromethylbenzyloxy, 2-fluorophenoxy, 4-fluorophenoxy, 2-fluoro-3-trifluoromethylphenoxy, 2-fluorobenzyloxy, 4-fluorophenylamino, 2-fluoro-4-trifluoromethylphenoxy, 2-furyl, 3-furyl, heptafluoropropyl, 1,1,1,3,3,3-hexafluoropropyl, 2-hydroxy-3,3,3-trifluoropropoxy, isobutoxy, isobutyl, 3-isoxazolyl, 4-isoxazolyl, 5-isoxazolyl, isopropoxy, 3-isopropylbenzyloxy, 3-isopropylphenoxy, isopropylthio, 4-isopropyl-3-methylphenoxy, 3-isothiazolyl, 4-isothiazolyl, 5-isothiazolyl, 3-methoxybenzyl, 4-methoxyphenylamino, 3-methylbenzyloxy, 4-methylbenzyloxy, 3-methylphenoxy, 3-methyl-4-methylthiophenoxy, 4-methylphenoxy, 1-methylpropoxy, 2-methylpyrid-5-yloxy, 4-methylthiophenoxy, 2-naphthyloxy, 2-nitrophenoxy, 4-nitrophenoxy, 3-nitrophenyl, 2-oxazolyl, 4-oxazolyl, 5-oxazolyl, pentafluoroethyl, pentafluoroethylthio, 2,2,3,3,3-pentafluoropropyl, 1,1,3,3,3-pentafluoropropyl, 1,1,2,2,3-pentafluoropropyl, phenoxy, phenylamino, 1-phenylethoxy, 4-propylphenoxy, 4-propoxyphenoxy, thiophen-3-yl, tert-butoxy, 3-tert-butylphenoxy, 4-tert-butylphenoxy, 1,1,2,2-tetrafluoroethoxy, tetrahydrofuran-2-yl, 2-(5,6,7,8-tetrahydronaphthyloxy), thiazol-2-yl, thiazol-4-yl, thiazol-5-yl, thiophen-2-yl, 2,2,2-trifluoroethoxy, 2,2,2-trifluoroethyl, 3,3,3-trifluoro-2-hydroxypropyl, trifluoromethoxy, 3-trifluoromethoxybenzyloxy, 4-trifluoromethoxybenzyloxy, 4-trifluoromethoxyphenoxy, 3-trifluoromethoxyphenoxy, trifluoromethyl, 3-trifluoromethylbenzyloxy, 1,1-bis-trifluoromethyl-1-hydroxymethyl, 3-trifluoromethylbenzyl, 3,5-bis-trifluoromethylbenzyloxy, 4-trifluoromethylphenoxy, 3-trifluoromethylphenoxy, 3-trifluoromethylphenyl, 2,3,4-trifluorophenoxy, 2,3,5-trifluorophenoxy, 3,4,5-trimethylphenoxy, 3-difluoromethoxyphenoxy, 3-pentafluoroethylphenoxy, 3-(1,1,2,2-tetrafluoroethoxy)phenoxy, 3-trifluoromethylthiophenoxy, 3-trifluoromethylthiobenzyloxy, and trifluoromethylthio;

$R_6$ and $R_{11}$ are independently selected from the group consisting of chloro, fluoro, hydrogen, pentafluoroethyl, 1,1,2,2-tetrafluoroethoxy, and trifluoromethyl;

$R_7$ and $R_{12}$ are independently selected from the group consisting of hydrogen, fluoro, and trifluoromethyl.

3. The method of claim 1, wherein said compound is of Formula II:

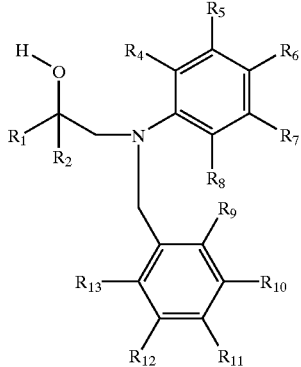

(II)

wherein;

$R_1$ is selected from the group consisting of hydrogen, isopropyl, propyl, benzyl, cyclopropyl, cyclopropylmethyl, 3-trifluoromethylphenyl, and 4-trifluoromethylphenyl;

$R_2$ is selected from the group consisting of hydrogen, methyl, ethyl, and hydroxymethyl;

$R_4$, $R_8$, $R_9$, and $R_{13}$ are independently hydrogen or fluoro;

$R_5$ is selected from the group consisting of phenoxy, 5-bromo-2-fluorophenoxy, 4-chloro-3-ethylphenoxy, 2,3-dichlorophenoxy, 3,4-dichlorophenoxy, 3-difluoromethoxyphenoxy, 3,5-dimethylphenoxy, 3,4-dimethylphenoxy, 3-ethylphenoxy, 3-ethyl-5-methylphenoxy, 4-fluoro-3-methylphenoxy, 4-fluorophenoxy, 3-isopropylphenoxy, 3-methylphenoxy, 3-pentafluoroethylphenoxy, 3-tert-butylphenoxy, 3-(1,1,2,2-tetrafluoroethoxy)phenoxy, 2-(5,6,7,8-tetrahydronaphthyloxy), 3-trifluoromethoxybenzyloxy, 3-trifluoromethoxyphenoxy, 3-trifluoromethylbenzyloxy, and 3-trifluoromethylthiophenoxy;

$R_{10}$ is selected from the group consisting of cyclopentyl, 1,1,2,2-tetrafluoroethoxy, 2-furyl, 1,1-bis-trifluoromethyl-1-hydroxymethyl, pentafluoroethyl, trifluoromethoxy, trifluoromethyl, and trifluoromethylthio;

$R_6$ and $R_{11}$ are independently fluoro or hydrogen;

$R_7$ and $R_{12}$ are independently hydrogen or fluoro.

4. The method of claim 3, wherein said compound is of Formula II, wherein;

$R_1$ is selected from the group consisting of hydrogen, isopropyl, propyl, cyclopropyl, cyclopropylmethyl, benzyl, 3-trifluoromethylphenyl, and 4-trifluoromethylphenyl;

$R_2$ is hydrogen;

$R_4$, $R_8$, $R_9$, and $R_{13}$ are independently hydrogen or fluoro;

$R_5$ is selected from the group consisting of phenoxy, 5-bromo-2-fluorophenoxy, 4-chloro-3-ethylphenoxy, 2,3-dichlorophenoxy, 3,4-dichlorophenoxy, 3-difluoromethoxyphenoxy, 3,5-dimethylphenoxy, 3,4-dimethylphenoxy, 3-ethylphenoxy, 3-ethyl-5-methylphenoxy, 4-fluoro-3-methylphenoxy, 4-fluorophenoxy, 3-isopropylphenoxy, 3-methylphenoxy, 3-pentafluoroethylphenoxy, 3-tert-butylphenoxy, 3-(1,1,2,2-tetrafluoroethoxy)phenoxy, 2-(5,6,7,8-tetrahydronaphthyloxy), 3-trifluoromethoxybenzyloxy, 3-trifluoromethoxyphenoxy, 3-trifluoromethylbenzyloxy, and 3-trifluoromethylthiophenoxy;

$R_{10}$ is selected from the group consisting of 1,1,2,2,-tetrafluoroethoxy, pentafluoroethyl, and trifluoromethyl;

$R_6$ and $R_{11}$ are independently selected from the group consisting of fluoro and hydrogen;

$R_7$ and $R_{12}$ are independently selected from the group consisting of hydrogen and fluoro.

5. The method of claim 1, wherein said compound is selected from the group consisting of:

1-[(3-phenoxy)phenyl[[3-trifluoromethoxyphenyl]methyl] amino]-2-pentanol;

2-[(3-phenoxy)phenyl[[(3-trifluoromethoxy)phenyl]methyl] amino]-1-[(4-trifluoromethyl)phenyl]ethanol;

2-[[3-(4-chloro-3-ethylphenoxy)phenyl][[(3-trifluoromethoxy)phenyl]methyl]-amino]-1-[(4-trifluoromethyl)phenyl]ethanol;

2-[[3-(4-chloro-3-ethylphenoxy)phenyl][[3-(1,1,2,2-tetrafluoroethoxy)phenyl]-methyl]amino]-1-[(4-trifluoromethyl)phenyl]ethanol;

2-[[3-(4-chloro-3-ethylphenoxy )phenyl][[3-(pentafluoroethyl)phenyl]methyl]-amino]-1-[(4-trifluoromethyl)phenyl]ethanol;

2-[[3-(4-chloro-3-ethylphenoxy)phenyl][[2-fluoro-4-(trifluoromethyl)phenyl]methyl]amino]-1-[(4-trifluoromethyl)phenyl]ethanol;

2-[[3-(4-chloro-3-ethylphenoxy)phenyl][[2-fluoro-5-(trifluoromethyl)phenyl]-methyl]amino]-1-[(4-trifluoromethyl)phenyl]ethanol;

2-[[3-(4-chloro-3-ethylphenoxy)phenyl][[(3-trifluoromethylthio)phenyl]-methyl]amino]-1-[(4-trifluoromethyl)phenyl]ethanol;

2-[[3-(4-chloro-3-ethylphenoxy)phenyl][[(3-trifluoromethylthio)phenyl]-methyl]amino]-1-[(4-trifluoromethyl)phenyl]ethanol;

2-[[3-(3-ethylphenoxy)phenyl][[3-(1,1,2,2-tetrafluoroethoxy)phenyl]methyl]-amino]1-[(4-trifluoromethyl)phenyl]ethanol;

2-[[3-(3-ethylphenoxy)phenyl][[3-(pentafluoroethyl)phenyl]methyl]amino]-1-[(4-trifluoromethyl)phenyl]ethanol;

2-[[3-(3-ethylphenoxy)phenyl][[2-fluoro-4-(trifluoromethyl)phenyl]methyl]-amino]-1-[(4-trifluoromethyl)phenyl]ethanol;

2-[[3-(3-ethylphenoxy)phenyl][[2-fluoro-5-(trifluoromethyl)phenyl]methyl]-amino]-1-[(4-trifluoromethyl)phenyl]ethanol;

2-[[3-(3-ethylphenoxy)phenyl][[(3-trifluoromethylthio) phenyl]methyl]amino]-1-[(4-trifluoromethyl)phenyl] ethanol;

2-[[3-(3-isopropylphenoxy)phenyl][[3-(1,1,2,2-tetrafluoroethoxy)phenyl]-methyl]amino]-1-[(4-trifluoromethyl)phenyl]ethanol;

2-[[3-(3-isopropylphenoxy)phenyl][[3-(pentafluoroethyl) phenyl]methyl]-amino]-1-[(4-trifluoromethyl)phenyl] ethanol;

2-[[3-(3-isopropylphenoxy)phenyl][[2-fluoro-4-(trifluoromethyl)phenyl]-methyl]-amino]-1-[(4-trifluoromethyl)phenyl]ethanol;

2-[[3-(3-isopropylphenoxy)phenyl][[2-fluoro-5-(trifluoromethyl)phenyl]-methyl]amino]-1-[(4-trifluoromethyl)phenyl]ethanol;

2-[[3-(3-isopropylphenoxy)phenyl]][(3-trifluoromethylthio)phenyl]-methyl]amino]-1-[(4-trifluoromethyl)phenyl]ethanol;

2-[[3-(3-trifluoromethoxyphenoxy)phenyl]][3-(1,1,2,2-tetrafluoroethoxy)-phenyl]methyl]amino]-1-[(4-trifluoromethyl)phenyl]ethanol;

2-[[3-(3-trifluoromethoxyphenoxy)phenyl]][3-(pentafluoroethyl)phenyl]-methyl]amino]-1-[(4-trifluoromethyl)phenyl]ethanol;

2-[[3-(3-trifluoromethoxyphenoxy)phenyl]][[2-fluoro-4-(trifluoromethyl)-phenyl]methyl]amino]-1-[(4-trifluoromethyl)phenyl]ethanol;

2-[[3-(3-trifluoromethoxyphenoxy)phenyl]][[2-fluoro-5-(trifluoromethyl)-phenyl]methyl]amino]-1-[(4-trifluoromethyl)phenyl]ethanol;

2-[[3-(3-trifluoromethoxyphenoxy)phenyl]][[(3-trifluoromethylthio)phenyl]-methyl]amino]-1-[(4-trifluoromethyl)phenyl]ethanol;

2-[[3-(2,3-dichlorophenoxy)phenyl]][3-(1,1,2,2-tetrafluoroethoxy)phenyl]-methyl]amino]-1-[(4-trifluoromethyl)phenyl]ethanol;

2-[[3-(2,3-dichlorophenoxy)phenyl]][3-(pentafluoroethyl)phenyl]methyl]-amino]-1-[(4-trifluoromethyl)phenyl]ethanol;

2-[[3-(2,3-dichlorophenoxy)phenyl]][[2-fluoro-4-(trifluoromethyl)phenyl]-methyl]amino]-1-[(4-trifluoromethyl)phenyl]ethanol;

2-[[3-(2,3-dichlorophenoxy)phenyl]][[2-fluoro-5-(trifluoromethyl)phenyl]-methyl]amino]-1-[(4-trifluoromethyl)phenyl]ethanol;

2-[[3-(2,3-dichlorophenoxy)phenyl]][[(3-trifluoromethylthio)phenyl]-methyl]amino]-1-[(4-trifluoromethyl)phenyl]ethanol;

2-[[3-(3-trifluoromethylbenzyloxy)phenyl]][3-(1,1,2,2-tetrafluoroethoxy)-phenyl]methyl]amino]-1-[(4-trifluoromethyl)phenyl]ethanol;

2-[[3-(3-trifluoromethylbenzyloxy)phenyl]][3-(pentafluoroethyl)phenyl]-methyl]amino]-1-[(4-trifluoromethyl)phenyl]ethanol;

2-[[3-(3-trifluoromethylbenzyloxy)phenyl]][[2-fluoro-4-(trifluoromethyl)-phenyl]methyl]amino]-1-[(4-trifluoromethyl)phenyl]ethanol;

2-[[3-(3-trifluoromethylbenzyloxy)phenyl]][[2-fluoro-5-(trifluoromethyl)-phenyl]methyl]amino]-1-[(4-trifluoromethyl)phenyl]ethanol;

2-[[3-(3-trifluoromethylbenzyloxy)phenyl]][[(3-trifluoromethylthio)phenyl]-methyl]amino]-1-[(4-trifluoromethyl)phenyl]ethanol;

2-[[3-(3-trifluoromethoxybenzyloxy)phenyl]][3-(1,1,2,2-tetrafluoroethoxy)-phenyl]methyl]amino]-1-[(4-trifluoromethyl)phenyl]ethanol;

2-[[3-(3-trifluoromethoxybenzyloxy)phenyl]][3-(pentafluoroethyl)phenyl]-methyl]amino]-1-[(4-trifluoromethyl)phenyl]ethanol;

2-[[3-(3-trifluoromethoxybenzyloxy)phenyl]][[2-fluoro-4-(trifluoromethyl)-phenyl]methyl]amino]-1-[(4-trifluoromethyl)phenyl]ethanol;

2-[[3-(3-trifluoromethoxybenzyloxy)phenyl]][[2-fluoro-5-(trifluoromethyl)-phenyl]methyl]amino]-1-[(4-trifluoromethyl)phenyl]ethanol;

2-[[3-(3-trifluoromethoxybenzyloxy)phenyl]][[(3-trifluoromethylthio)phenyl]-methyl]amino]-1-[(4-trifluoromethyl)phenyl]ethanol;

2-[(3-phenoxy)phenyl][[(3-trifluoromethoxy)phenyl]methyl]amino]-2-[(4-trifluoromethyl)phenyl]ethanol;

2-[[3-(4-chloro-3-ethylphenoxy)phenyl]][[(3-trifluoromethoxy)phenyl]methyl]-amino]-2-[(4-trifluoromethyl)phenyl]ethanol;

2-[[3-(4-chloro-3-ethylphenoxy)phenyl]][3-(1,1,2,2-tetrafluoroethoxy)phenyl]-methyl]amino]-2-[(4-trifluoromethyl)phenyl]ethanol;

2-[[3-(4-chloro-3-ethylphenoxy)phenyl]][3-(pentafluoroethyl)phenyl]methyl]-amino]-2-[(4-trifluoromethyl)phenyl]ethanol;

2-[[3-(4-chloro-3-ethylphenoxy)phenyl]][[2-fluoro-4-(trifluoromethyl)phenyl]-methyl]amino]-2-[(4-trifluoromethyl)phenyl]ethanol;

2-[[3-(4-chloro-3-ethylphenoxy)phenyl]][[2-fluoro-5-(trifluoromethyl)phenyl]-methyl]amino]-2-[(4-trifluoromethyl)phenyl]ethanol;

2-[[3-(4-chloro-3-ethylphenoxy)phenyl]][[(3-trifluoromethylthio)phenyl]-methyl]amino]-2-[(4-trifluoromethyl)phenyl]ethanol;

2-[[3-(3-ethylphenoxy)phenyl]][3-(1,1,2,2-tetrafluoroethoxy)phenyl]methyl]-amino]-2-[(4-trifluoromethyl)phenyl]ethanol;

2-[[3-(3-ethylphenoxy)phenyl]][3-(pentafluoroethyl)phenyl]methyl]amino]-2-[(4-trifluoromethyl)phenyl]ethanol;

2-[[3-(3-ethylphenoxy)phenyl]][[2-fluoro-4-(trifluoromethyl)phenyl]methyl]-amino]-2-[(4-trifluoromethyl)phenyl]ethanol;

2-[[3-(3-ethylphenoxy)phenyl]][[2-fluoro-5-(trifluoromethyl)phenyl]methyl]-amino]-2-[(4-trifluoromethyl)phenyl]ethanol;

2-[[3-(3-ethylphenoxy)phenyl]][[(3-trifluoromethylthio)phenyl]methyl]amino]-2-[(4-trifluoromethyl)phenyl]ethanol;

2-[[3-(3-isopropylphenoxy)phenyl]][3-(1,1,2,2-tetrafluoroethoxy)phenyl]-methyl]amino]-2-[(4-trifluoromethyl)phenyl]ethanol;

2-[[3-(3-isopropylphenoxy)phenyl]][3-(pentafluoroethyl)phenyl]methyl]-amino]-2-[(4-trifluoromethyl)phenyl]ethanol;

2-[[3-(3-isopropylphenoxy)phenyl]][[2-fluoro-4-(trifluoromethyl)phenyl]-methyl]amino]-2-[(4-trifluoromethyl)phenyl]ethanol;

2-[[3-(3-isopropylphenoxy)phenyl]][[2-fluoro-5-(trifluoromethyl)phenyl]-methyl]amino]-2-[(4-trifluoromethyl)phenyl]ethanol;

2-[[3-(3-isopropylphenoxy)phenyl]][[(3-trifluoromethylthio)phenyl]methyl]-amino]-2-[(4-trifluoromethyl)phenyl]ethanol;

2-[[3-(3-trifluoromethoxyphenoxy)phenyl]][3-(1,1,2,2-tetrafluoroethoxy)-phenyl]methyl]amino]-2-[(4-trifluoromethyl)phenyl]ethanol;

2-[[3-(3-trifluoromethoxyphenoxy)phenyl]][3-(pentafluoroethyl)phenyl]-methyl]amino]-2-[(4-trifluoromethyl)phenyl]ethanol;

2-[[3-(3-trifluoromethoxyphenoxy)phenyl]][[2-fluoro-4-(trifluoromethyl)-phenyl]methyl]amino]-2-[(4-trifluoromethyl)phenyl]ethanol;

2-[[3-(3-trifluoromethoxyphenoxy)phenyl]][[2-fluoro-5-(trifluoromethyl)-phenyl]methyl]amino]-2-[(4-trifluoromethyl)phenyl]ethanol;

2-[[3-(3-trifluoromethoxyphenoxy)phenyl]][[(3-trifluoromethylthio)phenyl]-methyl]amino]-2-[(4-trifluoromethyl)phenyl]ethanol;

2-[[3-(2,3-dichlorophenoxy)phenyl]][3-(1,1,2,2-tetrafluoroethoxy)phenyl]-methyl]amino]-2-[(4-trifluoromethyl)phenyl]ethanol;

2-[[3-(2,3-dichlorophenoxy)phenyl]][3-(pentafluoroethyl)phenyl]methyl]-amino]-2-[(4-trifluoromethyl)phenyl]ethanol;

2-[[3-(2,3-dichlorophenoxy)phenyl]][[2-fluoro-4-(trifluoromethyl)phenyl]-methyl]amino]-2-[(4-trifluoromethyl)phenyl]ethanol;

2-[[3-(2,3-dichlorophenoxy)phenyl][[2-fluoro-5-(trifluoromethyl)phenyl]-methyl]amino]-2-[(4-trifluoromethyl)phenyl]ethanol;

2-[[3-(2,3-dichlorophenoxy)phenyl][[(3-trifluoromethylthio)phenyl]-methyl]amino]-2-[(4-trifluoromethyl)phenyl]ethanol;

2-[[3-(3-trifluoromethylbenzyloxy)phenyl][[3-(1,1,2,2-tetrafluoroethoxy)-phenyl]methyl]amino]-2-[(4-trifluoromethyl)phenyl]ethanol;

2-[[3-(3-trifluoromethylbenzyloxy)phenyl][[3-(pentafluoroethyl)phenyl]-methyl]-amino]-2-[(4-trifluoromethyl)phenyl]ethanol;

2-[[3-(3-trifluoromethylbenzyloxy)phenyl][[2-fluoro-4-(trifluoromethyl)-phenyl]methyl]amino]-2-[(4-trifluoromethyl)phenyl]ethanol;

2-[[3-(3-trifluoromethylbenzyloxy)phenyl][[2-fluoro-5-(trifluoromethyl)-phenyl]methyl]amino]-2-[(4-trifluoromethyl)phenyl]ethanol;

2-[[3-(3-trifluoromethylbenzyloxy)phenyl][[(3-trifluoromethylthio)phenyl]-methyl]amino]-2-[(4-trifluoromethyl)phenyl]ethanol;

2-[[3-(3-trifluoromethoxybenzyloxy)phenyl][[3-(1,1,2,2-tetrafluoroethoxy)-phenyl]methyl]amino]-2-[(4-trifluoromethyl)phenyl]ethanol;

2-[[3-(3-trifluoromethoxybenzyloxy)phenyl][[3-(pentafluoroethyl)phenyl]-methyl]amino]-2-[(4-trifluoromethyl)phenyl]ethanol;

2-[[3-(3-trifluoromethoxybenzyloxy)phenyl][[2-fluoro-4-(trifluoromethyl)-phenyl]methyl]amino]-2-[(4-trifluoromethyl)phenyl]ethanol;

2-[[3-(3-trifluoromethoxybenzyloxy)phenyl][[2-fluoro-5-(trifluoromethyl)-phenyl]methyl]amino]-2-[(4-trifluoromethyl)phenyl]ethanol;

2-[[3-(3-trifluoromethoxybenzyloxy)phenyl][[(3-trifluoromethylthio)phenyl]-methyl]amino]-2-[(4-trifluoromethyl)phenyl]ethanol;

2-[(3-phenoxy)phenyl[[(3-trifluoromethoxy)phenyl]methyl]amino]-2-[(3-trifluoromethyl)phenyl]ethanol;

2-[[3-(4-chloro-3-ethylphenoxy)phenyl][[(3-trifluoromethoxy)phenyl]methyl]-amino]-2-[(3-trifluoromethyl)phenyl]ethanol;

2-[[3-(4-chloro-3-ethylphenoxy)phenyl][[3-(1,1,2,2-tetrafluoroethoxy)phenyl]methyl]amino]-2-[(3-trifluoromethyl)phenyl]ethanol;

2-[[3-(4-chloro-3-ethylphenoxy)phenyl][[3-(pentafluoroethyl)phenyl]methyl]-amino]-2-[(3-trifluoromethyl)phenyl]ethanol;

2-[[3-(4-chloro-3-ethylphenoxy)phenyl][[2-fluoro-4-(trifluoromethyl)phenyl]-methyl]amino]-2-[(3-trifluoromethyl)phenyl]ethanol;

2-[[3-(4-chloro-3-ethylphenoxy)phenyl][[2-fluoro-5-(trifluoromethyl)phenyl]-methyl]amino]-2-[(3-trifluoromethyl)phenyl]ethanol;

2-[[3-(4-chloro-3-ethylphenoxy)phenyl][[(3-trifluoroethylthio)phenyl]-methyl]amino-2-[(3-trifluoromethyl)phenyl]ethanol;

2-[[3-(3-ethylphenoxy)phenyl][[3-(1,1,2,2-tetrafluoroethoxy)phenyl]methyl]amino]-2-[(3-trifluoromethyl)phenyl]ethanol;

2-[[3-(3-ethylphenoxy)phenyl][[3-(pentafluoroethyl)phenyl]methyl]amino]-2-[(3-trifluoromethyl)phenyl]ethanol;

2-[[3-(3-ethylphenoxy)phenyl][[2-fluoro-4-(trifluoromethyl)phenyl]methyl]amino]-2-[(3-trifluoromethyl)phenyl]ethanol;

2-[[3-(3-ethylphenoxy)phenyl][[2-fluoro-5-(trifluoromethyl)phenyl]methyl]amino]-2-[(3-trifluoromethyl)phenyl]ethanol;

2-[[3-(3-ethylphenoxy)phenyl][[(3-trifluoromethylthio)phenyl]methyl]amino]-2-[(3-trifluoromethyl)phenyl]ethanol;

2-[[3-(3-isopropylphenoxy)phenyl][[3-(1,1,2,2-tetrafluoroethoxy)phenyl]-methyl]amino]-2-[(3-trifluoromethyl)phenyl]ethanol;

2-[[3-(3-isopropylphenoxy)phenyl][[3-(pentafluoroethyl)phenyl]methyl]-amino]-2-[(3-trifluoromethyl)phenyl]ethanol;

2-[[3-(3-isopropylphenoxy)phenyl][[2-fluoro-4-(trifluoromethyl)phenyl]-methyl]amino]-2-[(3-trifluoromethyl)phenyl]ethanol;

2-[[3-(3-isopropylphenoxy)phenyl][[2-fluoro-5-(trifluoromethyl)phenyl]-methyl]amino]-2-[(3-trifluoromethyl)phenyl]ethanol;

2-[[3-(3-isopropylphenoxy)phenyl][[(3-trifluoromethylthio)phenyl]methyl]-amino]-2-[(3-trifluoromethyl)phenyl]ethanol;

2-[[3-(3-trifluoromethoxyphenoxy)phenyl][[3-(1,1,2,2-tetrafluoroethoxy)-phenyl]methyl]amino]-2-[(3-trifluoromethyl)phenyl]ethanol;

2-[[3-(3-trifluoromethoxyphenoxy)phenyl][[3-(pentafluoroethyl)phenyl]-methyl]amino]-2-[(3-trifluoromethyl)phenyl]ethanol;

2-[[3-(3-trifluoromethoxyphenoxy)phenyl][[2-fluoro-4-(trifluoromethyl)-phenyl]methyl]amino]-2-[(3-trifluoromethyl)phenyl]ethanol;

2-[[3-(3-trifluoromethoxyphenoxy)phenyl][[2-fluoro-5-(trifluoromethyl)-phenyl]methyl]amino]-2-[(3-trifluoromethyl)phenyl]ethanol;

2-[[3-(3-trifluoromethoxyphenoxy)phenyl][[(3-trifluoromethylthio)phenyl]-methyl]amino]-2-[(3-trifluoromethyl)phenyl]ethanol;

2-[[3-(2,3-dichlorophenoxy)phenyl][[3-(1,1,2,2-tetrafluoroethoxy)-phenyl]methyl]amino]-2-[(3-trifluoromethyl)phenyl]ethanol;

2-[[3-(2,3-dichlorophenoxy)phenyl][[3-(pentafluoroethyl)phenyl]methyl]-amino]-2-[(3-trifluoromethyl)phenyl]ethanol;

2-[[3-(2,3-dichlorophenoxy)phenyl][[2-fluoro-4-(trifluoromethyl)phenyl]-methyl]amino]-2-[(3-trifluoromethyl)phenyl]ethanol;

2-[[3-(2,3-dichlorophenoxy)phenyl][[2-fluoro-5-(trifluoromethyl)phenyl]-methyl]amino]-2-[(3-trifluoromethyl)phenyl]ethanol;

2-[[3-(2,3-dichlorophenoxy)phenyl][[(3-trifluoromethylthio)phenyl]methyl]-amino]-2-[(3-trifluoroethyl)phenyl]ethanol;

2-[[3-(3-trifluoromethylbenzyloxy)phenyl][[3-(1,1,2,2-tetrafluoroethoxy)-phenyl]methyl]amino]-2-[(3-trifluoromethyl)phenyl]ethanol;

2-[[3-(3-trifluoromethylbenzyloxy)phenyl][[3-(pentafluoroethyl)phenyl]-methyl]amino]-2-[(3-trifluoromethyl)phenyl]ethanol;

2-[[3-(3-trifluoromethylbenzyloxy)phenyl][[2-fluoro-4-(trifluoromethyl)-phenyl]methyl]amino]-2-[(3-trifluoromethyl)phenyl]ethanol];

2-[[3-(3-trifluoromethylbenzyloxy)phenyl][[2-fluoro-5-(trifluoromethyl)-phenyl]methyl]amino]-2-[(3-trifluoromethyl)phenyl]ethanol;

2-[[3-(3-trifluoromethylbenzyloxy)phenyl][[(3-trifluoromethylthio)phenyl]-methyl]amino]-2-[(3-trifluoromethyl)phenyl]ethanol;

2-[[3-(3-trifluoromethoxybenzyloxy)phenyl][[3-(1,1,2,2-tetrafluoroethoxy)-phenyl]methyl]amino]-2-[(3-trifluoromethyl)phenyl]ethanol;

2-[[3-(3-trifluoromethoxybenzyloxy)phenyl][[3-(pentafluoroethyl)phenyl]-methyl]amino]-2-[(3-trifluoromethyl)phenyl]ethanol;

2-[[3-(3-trifluoromethoxybenzyloxy)phenyl][[2-fluoro-4-(trifluoromethyl)-phenyl]methyl]amino]-2-[(3-trifluoromethyl)phenyl]ethanol;

2-[[3-(3-trifluoromethoxybenzyloxy)phenyl][[2-fluoro-5-(trifluoromethyl)-phenyl]methyl]amino]-2-[(3-trifluoromethyl)phenyl]ethanol;

2-[[3-(3-trifluoromethoxybenzyloxy)phenyl][[(3-trifluoromethylthio)phenyl]-methyl]amino]-2-[(3-trifluoromethyl)phenyl]ethanol;

2-[(3-phenoxy)phenyl[[(3-trifluoromethoxy)phenyl]methyl]amino]-1-(cyclopropyl)ethanol;

2-[[3-(4-chloro-3-ethylphenoxy)phenyl][[(3-trifluoromethoxy)phenyl]methyl]-amino]-1-(cyclopropyl)ethanol;

2-[[3-(4-chloro-3-ethylphenoxy)phenyl][3-(1,1,2,2-tetrafluoroethoxy)phenyl]-methyl]amino]-1-(cyclopropyl)ethanol;

2-[[3-(4-chloro-3-ethylphenoxy)phenyl][3-(pentafluoroethyl)phenyl]methyl]-amino]-1-(cyclopropyl)ethanol;

2-[[3-(4-chloro-3-ethylphenoxy)phenyl][[2-fluoro-4-(trifluoromethyl)phenyl]-methyl]amino]-1-(cyclopropyl)ethanol;

2-[[3-(4-chloro-3-ethylphenoxy)phenyl][[2-fluoro-5-(trifluoromethyl)phenyl]-methyl]amino]-1-(cyclopropyl)ethanol;

2-[[3-(4-chloro-3-ethylphenoxy)phenyl][[(3-trifluoromethylthio)phenyl]-methyl]amino]-1-(cyclopropyl)ethanol;

2-[[3-(3-ethylphenoxy)phenyl][[3-(1,1,2,2-tetrafluoroethoxy)phenyl]methyl]-amino]-1-(cyclopropyl)ethanol;

2-[[3-(3-ethylphenoxy)phenyl][[3-(pentafluoroethyl)phenyl]methyl]amino]-1-(cyclopropyl)ethanol;

2-[[3-(3-ethylphenoxy)phenyl][[2-fluoro-4-(trifluoromethyl)phenyl]methyl]-amino]-1-(cyclopropyl)ethanol;

2-[[3-(3-ethylphenoxy)phenyl][[2-fluoro-5-(trifluoromethyl)phenyl]methyl]-amino]-1-(cyclopropyl)ethanol;

2-[[3-(3-ethylphenoxy)phenyl][[(3-trifluoromethylthio)phenyl]methyl]amino]-1-(cyclopropyl)ethanol;

2-[[3-(3-isopropylphenoxy)phenyl][[3-(1,1,2,2-tetrafluoroethoxy)phenyl]-methyl]amino]-1-(cyclopropyl)ethanol;

2-[[3-(3-isopropylphenoxy)phenyl][[3-(pentafluoroethyl)phenyl]methyl]-amino]-1-(cyclopropyl)ethanol;

2-[[3-(3-isopropylphenoxy)phenyl][[2-fluoro-4-(trifluoromethyl)phenyl]-methyl]amino]-1-(cyclopropyl)ethanol;

2-[[3-(3-isopropylphenoxy)phenyl][[2-fluoro-5-(trifluoromethyl)phenyl]-methyl]amino]-1-(cyclopropyl)ethanol;

2-[[3-(3-isopropylphenoxy)phenyl][[(3-trifluoromethylthio)phenyl]-methyl]amino]-1-(cyclopropyl)ethanol;

2-[[3-(3-trifluoromethoxyphenoxy)phenyl][[3-(1,1,2,2-tetrafluoroethoxy)phenyl]methyl]amino]-1-(cyclopropyl)ethanol;

2-[[3-(3-trifluoromethoxyphenoxy)phenyl][3-(pentafluoroethyl)phenyl]-methyl]amino]-1-(cyclopropyl)ethanol;

2-[[3-(3-trifluoromethoxyphenoxy)phenyl][[2-fluoro)-4-(trifluoromethyl)-phenyl]methyl]amino]-1-(cyclopropyl)ethanol;

2-[[3-(3-trifluoromethoxyphenoxy)phenyl][[2-fluoro-5-(trifluoromethyl)-phenyl]methyl]amino]-1-(cyclopropyl)ethanol;

2-[[3-(3-trifluoromethoxyphenoxy)phenyl][[(3-trifluoromethylthio)phenyl]-methyl]amino]-1-(cyclopropyl)ethanol;

2-[[3-(2,3-dichlorophenoxy)phenyl][[3-(1,1,2,2-tetrafluoroethoxy)phenyl]-methyl]amino]-1-(cyclopropyl)ethanol;

2-[[3-(2,3-dichlorophenoxy)phenyl][3-(pentafluoroethyl)phenyl]methyl]-amino]-1-(cyclopropyl)ethanol;

2-[[3-(2,3-dichlorophenoxy)phenyl][[2-fluoro-4-(trifluoromethyl)phenyl]-methyl]amino]-1-(cyclopropyl)ethanol;

2-[[3-(2,3-dichlorophenoxy)phenyl][[2-fluoro-5-(trifluoromethyl)phenyl]-methyl]amino]-1-(cyclopropyl)ethanol;

2-[[3-(2,3-dichlorophenoxy)phenyl][[(3-trifluoromethylthio)phenyl]-methyl]amino]-1-(cyclopropyl)ethanol;

2-[[3-(3-trifluoromethylbenzyloxy)phenyl][[3-(1,1,2,2-tetrafluoroethoxy)-phenyl]methyl]amino]-1-(cyclopropyl)ethanol;

2-[[3-(3-trifluoromethylbenzyloxy)phenyl][[3-(pentafluoroethyl)phenyl]-methyl]amino]-1-(cyclopropyl)ethanol;

2-[[3-(3-trifluoromethylbenzyloxy)phenyl][[2-fluoro-4-(trifluoromethyl)-phenyl]methyl]amino]-1-(cyclopropyl)ethanol;

2-[[3-(3-trifluoromethylbenzyloxy)phenyl][[2-fluoro-5-(trifluoromethyl)-phenyl]methyl]amino]-1-(cyclopropyl)ethanol;

2-[[3-(3-trifluoromethylbenzyloxy)phenyl][[(3-trifluoromethylthio)phenyl]-methyl]amino]-1-(cyclopropyl)ethanol;

2-[[3-(3-trifluoromethoxybenzyloxy)phenyl][[3-(1,1,2,2-tetrafluoroethoxy)-phenyl]methyl]amino]-1-(cyclopropyl)ethanol;

2-[[3-(3-trifluoromethoxybenzyloxy)phenyl][[3-(pentafluoroethyl)phenyl]-methyl]amino]-1-(cyclopropyl)ethanol;

2-[[3-(3-trifluoromethoxybenzyloxy)phenyl][[2-fluoro-4-(trifluoromethyl)-phenyl]methyl]amino]-1-(cyclopropyl)ethanol;

2-[[3-(3-trifluoromethoxybenzyloxy)phenyl][[2-fluoro-5-(trifluoromethyl)-phenyl]methyl]amino]-1-(cyclopropyl)ethanol;

2-[[3-(3-trifluoromethoxybenzyloxy)phenyl][[(3-trifluoromethylthio)phenyl]-methyl]amino]-1-(cyclopropyl)ethanol;

1-[[3-(4-chloro-3-ethylphenoxy)phenyl][[(3-trifluoromethoxy)phenyl]methyl]-amino]-2-pentanol;

1-[[3-(4-chloro-3-ethylphenoxy)phenyl][[3-(1,1,2,2-tetrafluoroethoxy)phenyl]-methyl]amino]-2-pentanol;

1-[[3-(4-chloro-3-ethylphenoxy)phenyl][[3-(pentafluoroethyl)phenyl]methyl]-amino]-2-pentanol;

1-[[3-(4-chloro-3-ethylphenoxy)phenyl][[2-fluoro-4-(trifluoromethyl)phenyl]-methyl]amino]-2-pentanol;

1-[[3-(4-chloro-3-ethylphenoxy)phenyl][[2-fluoro-5-(trifluoromethyl)phenyl]-methyl]amino]-2-pentanol;

1-[[3-(4-chloro-3-ethylphenoxy)phenyl][[(3-trifluoromethylthio)phenyl]-methyl]amino]-2-pentanol;

1-[[3-(3-ethylphenoxy)phenyl][[3-(1,1,2,2-tetrafluoroethoxy)phenyl]methyl]-amino]-2-pentanol;

1-[[3-(3-ethylphenoxy)phenyl][[3-(pentafluoroethyl)phenyl]methyl]amino]-2-pentanol;

1-[[3-(3-ethylphenoxy)phenyl][[2-fluoro-4-(trifluoromethyl)phenyl]methyl]-amino]-2-pentanol;

1-[[3-(3-ethylphenoxy)phenyl][[2-fluoro-5-(trifluoromethyl)phenyl]methyl]-amino]-2-pentanol;

1-[[3-(3-ethylphenoxy)phenyl][[(3-trifluoromethylthio)phenyl]methyl]amino]-2-pentanol;
1-[[3-(3-isopropylphenoxy)phenyl][[3-(1,1,2,2-tetrafluoroethoxy)phenyl]-methyl]amino]-2-pentanol;
1-[[3-(3-isopropylphenoxy)phenyl][[3-(pentafluoroethyl)phenyl]methyl-amino]-2-pentanol;
1-[[3-(3-isopropylphenoxy)phenyl][[2-fluoro-4-(trifluoromethyl)phenyl]-methyl]amino]-2-pentanol;
1-[[3-(3-isopropylphenoxy)phenyl][[2-fluoro-5-(trifluoromethyl)phenyl]-methyl]amino]-2-pentanol;
1-[[3-(3-isopropylphenoxy)phenyl][[(3-trifluoromethylthio)phenyl]-methyl]amino]-2-pentanol;
1-[[3-(3-trifluoromethoxyphenoxy)phenyl][[3-(1,1,2,2-tetrafluoroethoxy)phenyl]methyl]amino]-2-pentanol;
1-[[3-(3-trifluoromethoxyphenoxy)phenyl][[3-(pentafluoroethyl)phenyl]-methyl]amino]-2-pentanol;
1-[[3-(3-trifluoromethoxyphenoxy)phenyl][[2-fluoro-4-(trifluoromethyl)-phenyl]methyl]amino]-2-pentanol;
1-[[3-(3-trifluoromethoxyphenoxy)phenyl][[2-fluoro-5-(trifluoromethyl)-phenyl]methyl]amino]-2-pentanol;
1-[[3-(3-trifluoromethoxyphenoxy)phenyl][[(3-trifluoromethylthio)phenyl]methyl]amino]-2-pentanol;
1-[[3-(2,3-dichlorophenoxy)phenyl][[3-(1,1,2,2-tetrafluoroethoxy)phenyl]-methyl]amino]-2-pentanol;
1-[[3-(2,3-dichlorophenoxy)phenyl][[3-(pentafluoroethyl)phenyl]methyl-amino]-2-pentanol;
1-[[3-(2,3-dichlorophenoxy)phenyl][[2-fluoro-4-(trifluoromethyl)phenyl]-methyl]amino]-2-pentanol;
1-[[3-(2,3-dichlorophenoxy)phenyl][[2-fluoro-5-(trifluoromethyl)phenyl]-methyl]amino]-2-pentanol;
1-[[3-(2,3-dichlorophenoxy)phenyl][[(3-trifluoromethylthio)phenyl]-methyl]amino]-2-pentanol;
1-[[3-(3-trifluoromethylbenzyloxy)phenyl][[3-(1,1,2,2-tetrafluoroethoxy)phenyl]-methyl]amino]-2-pentanol;
1-[[3-(3-trifluoromethylbenzyloxy)phenyl][[3-(pentafluoroethyl)phenyl]methyl]-amino]-2-pentanol;
1-[[3-(3-trifluoromethylbenzyloxy)phenyl][[2-fluoro-4-(trifluoromethyl)phenyl]methyl]amino]-2-pentanol;
1-[[3-(3-trifluoromethylbenzyloxy)phenyl][[2-fluoro-5-(trifluoromethyl)phenyl]methyl]amino]-2-pentanol;
1-[[3-(3-trifluoromethylbenzyloxy)phenyl][[(3-trifluoromethylthio)phenyl]-methyl]amino]-2-pentanol;
1-[[3-(3-trifluoromethoxybenzyloxy)phenyl][[3-(1,1,2,2-tetrafluoroethoxy)phenyl]methyl]amino]-2-pentanol;
1-[[3-(3-trifluoromethoxybenzyloxy)phenyl][[3-(pentafluoroethyl)-phenyl]methyl]amino]-2-pentanol;
1-[[3-(3-trifluoromethoxybenzyloxy)phenyl][[2-fluoro-4-(trifluoromethyl)phenyl]methyl]amino]-2-pentanol;
1-[[3-(3-trifluoromethoxybenzyloxy)phenyl][[2-fluoro-5-(trifluoromethyl)phenyl]methyl]amino]-2-pentanol;
1-[[3-(3-trifluoromethoxybenzyloxy)phenyl][[(3-trifluoromethylthio)phenyl]-methyl]amino]-2-pentanol;
1-[[3-(4-chloro-3-ethylphenoxy)phenyl][[(3-trifluoromethoxy)phenyl]methyl-amino]-3-methyl-2-butanol;
1-[[3-(4-chloro-3-ethylphenoxy)phenyl][[3-(1,1,2,2-tetrafluoroethoxy)phenyl]-methyl]amino]-3-methyl-2-butanol;
1-[[3-(4-chloro-3-ethylphenoxy)phenyl][[3-(pentafluoroethyl)phenyl]methyl]-amino]-3-methyl-2-butanol;
1-[[3-(4-chloro-3-ethylphenoxy)phenyl][[2-fluoro-4-(trifluoromethyl)phenyl]-methyl]amino]-3-methyl-2-butanol;
1-[[3-(4-chloro-3-ethylphenoxy)phenyl][[2-fluoro-5-(trifluoromethyl)phenyl]-methyl]amino]-3-methyl-2-butanol;
1-[[3-(4-chloro-3-ethylphenoxy)phenyl][[(3-trifluoromethylthio)phenyl]-methyl]amino]-3-methyl-2-butanol;
1-[[3-(3-ethylphenoxy)phenyl][[3-(1,1,2,2-tetrafluoroethoxy)phenyl]methyl]-amino]-3-methyl-2-butanol;
1-[[3-(3-ethylphenoxy)phenyl][[3-(pentafluoroethyl)phenyl]methyl]amino]-3-methyl-2-butanol;
1-[[3-(3-ethylphenoxy)phenyl][[2-fluoro-4-(trifluoromethyl)phenyl]methyl]-amino]-3-methyl-2-butanol;
1-[[3-(3-ethylphenoxy)phenyl][[2-fluoro-5-(trifluoromethyl)phenyl]methyl]-amino]-3-methyl-2-butanol;
1-[[3-(3-ethylphenoxy)phenyl][[(3-trifluoromethylthio)phenyl]methyl]amino]-3-methyl-2-butanol;
1-[[3-(3-isopropylphenoxy)phenyl][[3-(1,1,2,2-tetrafluoroethoxy)phenyl]-methyl]amino]-3-methyl-2-butanol;
1-[[3-(3-isopropylphenoxy)phenyl][[3-(pentafluoroethyl)phenyl]methyl-amino]-3-methyl-2-butanol;
1-[[3-(3-isopropylphenoxy)phenyl][[2-fluoro-4-(trifluoromethyl)phenyl]-methyl]amino]-3-methyl-2-butanol;
1-[[3-(3-isopropylphenoxy)phenyl][[2-fluoro-5-(trifluoromethyl)phenyl]-methyl]amino]-3-methyl-2-butanol;
1-[[3-(3-isopropylphenoxy)phenyl][[(3-trifluoromethylthio)phenyl]-methyl]amino]-3-methyl-2-butanol;
1-[[3-(3-trifluoromethoxyphenoxy)phenyl][[3-(1,1,2,2-tetrafluoroethoxy)phenyl]methyl]amino]-3-methyl-2-butanol;
1-[[3-(3-trifluoromethoxyphenoxy)phenyl][[3-(pentafluoroethyl)phenyl]methyl]amino]-3-methyl-2-butanol;
1-[[3-(3-trifluoromethoxyphenoxy)phenyl][[2-fluoro-4-(trifluoromethyl)-phenyl]methyl]amino]-3-methyl-2-butanol;
1-[[3-(3-trifluoromethoxyphenoxy)phenyl][[2-fluoro-5-(trifluoromethyl)-phenyl]methyl]amino]-3-methyl-2-butanol;
b 1-[[3-(3-trifluoromethoxyphenoxy)phenyl][[(3-trifluoromethylthio)phenyl]-methyl]amino]-3-methyl-2-butanol;
1-[[3-(2,3-dichlorophenoxy)phenyl][[3-(1,1,2,2-tetrafluoroethoxy)phenyl]-methyl]amino]-3-methyl-2-butanol;
1-[[3-(2,3-dichlorophenoxy)phenyl][[3-(pentafluoroethyl)phenyl]methyl-amino]-3-methyl-2-butanol;
1-[[3-(2,3-dichlorophenoxy)phenyl][[2-fluoro-4-(trifluoromethyl)phenyl]-methyl]amino]-3-methyl-2-butanol;
1-[[3-(2,3-dichlorophenoxy)phenyl][[2-fluoro-5-(trifluoromethyl)phenyl]-methyl]amino]-3-methyl-2-butanol;
1-[[3-(2,3-dichlorophenoxy)phenyl][[(3-trifluoromethylthio)phenyl]-methyl]amino]-3-methyl-2-butanol;
1-[[3-(3-trifluoromethylbenzyloxy)phenyl][[3-(1,1,2,2-tetrafluoroethoxy)phenyl]-methyl]amino]-3-methyl-2-butanol;
1-[[3-(3-trifluoromethylbenzyloxy)phenyl][[3-(pentafluoroethyl)phenyl]methyl]-amino]-3-methyl-2-butanol;
1-[[3-(3-trifluoromethylbenzyloxy)phenyl][[2-fluoro-4-(trifluoromethyl)phenyl]-methyl]amino]-3-methyl-2-butanol;

1-[[3-(3-trifluoromethylbenzyloxy)phenyl][[2-fluoro-5-(trifluoromethyl)phenyl]-methyl]amino]-3-methyl-2-butanol;

1-[[3-(3-trifluoromethylbenzyloxy)phenyl][[(3-trifluoromethylthio)phenyl]-methyl]amino]-3-methyl-2-butanol;

1-[[3-(3-trifluoromethoxybenzyloxy)phenyl][[3-(1,1,2,2-tetrafluoroethoxy)phenyl]methyl]amino]-3-methyl-2-butanol;

1-[[3-(3-trifluoromethoxybenzyloxy)phenyl][[3-(pentafluoroethyl)phenyl]methyl]amino]-3-methyl-2-butanol;

1-[[3-(3-trifluoromethoxybenzyloxy)phenyl][[2-fluoro-4-(trifluoromethyl)-phenyl]methyl]amino]-3-methyl-2-butanol;

1-[[3-(3-trifluoromethoxybenzyloxy)phenyl][[2-fluoro-5-(trifluoromethyl)-phenyl]methyl]amino]-3-methyl-2-butanol; and 1-[[3-(3-trifluoromethoxybenzyloxy)phenyl][[(3-trifluoromethylthio)phenyl]-methyl]amino]-3-methyl-2-butanol.

1-[[3-(4-chloro-3-ethylphenoxy)phenyl][[3-(1,1,2,2-tetrafluoroethoxy)phenyl]-methyl]amino]-4-methyl-2-pentanol;

1-[[3-(3-isopropylphenoxy)phenyl][[3-(1,1,2,2-tetrafluoroethoxy)phenyl]-methyl]amino]-4-methyl-2-pentanol;

1-[[3-(4-chloro-3-ethylphenoxy)phenyl][[3-(1,1,2,2-tetrafluoroethoxy)phenyl]-methyl]amino]-3-phenyl-2-propanol; and 1-[[3-(3-isopropylphenoxy)phenyl][[3-(1,1,2,2-tetrafluoroethoxy)phenyl]-methyl]amino]-3-phenyl-2-propanol.

6. The method of claim 1 further characterized by treating coronary artery disease in a subject by administering a therapeutically effective amount of a compound of claim 1 or a pharmaceutically acceptable salt thereof.

7. The method of claim 1 further characterized by preventing coronary artery disease in a subject by administering a therapeutically effective amount of a compound of claim 1 or a pharmaceutically acceptable salt thereof.

8. The method of claim 1 further characterized by preventing cerebral vascular accident (CVA) in a subject by administering a therapeutically effective amount of a compound of claim 1 or a pharmaceutically acceptable salt thereof.

9. The method of claim 1 further characterized by treating or preventing dyslipidemia in a subject by administering a therapeutically effective amount of a compound of claim 1 or a pharmaceutically acceptable salt thereof.

* * * * *